United States Patent
Yang et al.

(10) Patent No.: US 7,863,271 B2
(45) Date of Patent: Jan. 4, 2011

(54) 2-AMINOBENZOXAZOLE CARBOXAMIDES AS 5HT3 MODULATORS

(75) Inventors: Zhicai Yang, Schenectady, NY (US); David D. Manning, Duanesburg, NY (US)

(73) Assignee: Albany Molecular Research, Inc., Albany, NY (US)

( * ) Notice: Subject to any disclaimer, the term of this patent is extended or adjusted under 35 U.S.C. 154(b) by 429 days.

(21) Appl. No.: 11/835,178

(22) Filed: Aug. 7, 2007

(65) Prior Publication Data

US 2008/0255114 A1 Oct. 16, 2008

Related U.S. Application Data

(60) Provisional application No. 60/821,646, filed on Aug. 7, 2006.

(51) Int. Cl.
| | |
|---|---|
| A61K 31/5377 | (2006.01) |
| A61K 31/439 | (2006.01) |
| A61K 31/496 | (2006.01) |
| A61P 1/08 | (2006.01) |
| A61P 25/00 | (2006.01) |
| C07D 453/02 | (2006.01) |
| C07D 413/14 | (2006.01) |

(52) U.S. Cl. ............... 514/235.2; 514/253.04; 514/305; 544/127; 544/362; 546/133

(58) Field of Classification Search .......... None
See application file for complete search history.

(56) References Cited

U.S. PATENT DOCUMENTS

| | | | |
|---|---|---|---|
| 5,260,303 | A | 11/1993 | Becker et al. |
| 5,631,257 | A | 5/1997 | Iwamatsu et al. |
| 7,307,094 | B2 | 12/2007 | Fairfax et al. |
| 7,553,846 | B2 | 6/2009 | Yang et al. |
| 2009/0298809 | A1 | 12/2009 | Manning et al. |

FOREIGN PATENT DOCUMENTS

| | | |
|---|---|---|
| EP | 0621271 A1 | 10/1994 |
| EP | 0975327 B1 | 2/2000 |
| WO | WO03037896 A1 | 5/2003 |
| WO | WO2006089100 A1 | 8/2006 |
| WO | WO2008019363 A2 | 2/2008 |
| WO | WO2008019372 A2 | 2/2008 |

OTHER PUBLICATIONS

PCT International Search Report for PCT/US2007/075355 dated Feb. 7, 2008.
PCT International Search Report for PCT/US2007/075378 dated Feb. 26, 2008.
PCT International Search Report for PCT/US2006/005605 dated Jul. 4, 2006.
PCT International Preliminary Report on Patentability (Jun. 13, 2007) and Written Opinion (Jul. 4, 2006) for PCT/US2006/005605.
PCT International Preliminary Report on Patentability (Feb. 10, 2009) and Written Opinion (Feb. 26, 2008) for PCT/US2007/075378.
PCT International Preliminary Report on Patentability (Sep. 5, 2008) and Written Opinion (Feb. 7, 2008) for PCT/US2007/075355.

*Primary Examiner*—Kamal A Saeed
(74) *Attorney, Agent, or Firm*—Nixon Peabody LLP

(57) ABSTRACT

Compounds of formulae I, II and III:

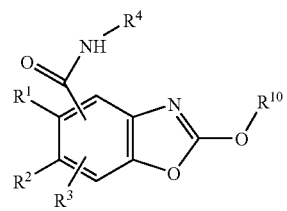

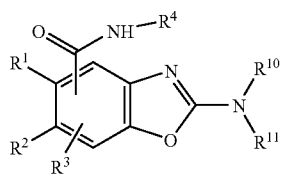

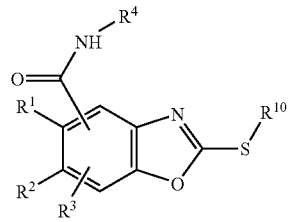

are disclosed as 5-HT3 inhibitors. The compounds are useful in treating CINV, IBS-D and other diseases and conditions.

37 Claims, No Drawings

2-AMINOBENZOXAZOLE CARBOXAMIDES AS 5HT3 MODULATORS

CROSS-REFERENCE TO RELATED APPLICATIONS

This application clams priority from U.S. Provisional Application Ser. No. 60/821,646, filed Aug. 7, 2006, the entire contents of which are incorporated herein by reference.

FIELD OF THE INVENTION

The invention relates to a genus of 2-aminobenzoxazole carboxamides that are useful in treating chemotherapy-induced nausea and vomiting (CINV) and in treating diarrhea-predominant Irritable Bowel Syndrome (IBS-D).

BACKGROUND OF THE INVENTION

Nausea and vomiting caused by chemotherapy remain among the most distressing side effects for patients undergoing treatment for cancer. Depending upon the chemotherapy agents or regimens given, up to 90% of patients may suffer from some form of chemotherapy-induced nausea and vomiting (CINV). Symptoms from CINV can be severely debilitating and often result in patients refusing further courses of chemotherapy, with obviously unfavorable consequences with respect to progression of the cancer. Furthermore, CINV is burdensome on the medical system, consuming time from the healthcare staff, who could otherwise attend to other patients or medical issues.

CINV is divided into two main categories: acute CINV and delayed CINV. Acute CINV occurs within the first 24 hours of treatment; delayed CINV occurs from 24 hours to 120 hours following treatment. Delayed CINV remains a highly undertreated side effect in patients undergoing chemotherapy, as healthcare providers tend to underestimate the number of patients who suffer from delayed CINV. Furthermore, delayed CINV greatly impairs patients' ability to provide care to themselves once they have been discharged.

Compounds that inhibit serotonin receptors are currently the most effective anti-emetics; they constitute the single greatest advance in the management of nausea and vomiting in patients with cancer and have had additional application in radiation-induced nausea and vomiting (RINV) and post-operative nausea and vomiting (PONV). Blocking the 5-HT3 receptor from the serotonin signal produced from chemotherapy-induced damage to the gut's enterochromaffin cells, which house the majority of the body's serotonin reserves, via either a peripheral or central mechanism appears to prevent acute emesis. Except for palonosetron (Aloxi®), 5-HT3 inhibitors have been approved for and most effective against the treatment of acute CINV. Palonosetron, which must be given intravenously, is the only 5-HT3 inhibitor currently approved for the prevention of both acute and delayed CINV. The efficacy of palonosetron against delayed emesis has been postulated to be due to its long serum half-life. Therefore persons of skill in the art accept that 5-HT3 inhibitors that have long serum half-lives will be effective therapeutic agents for both acute and delayed CINV, while those that have short half-lives will be useful to treat acute CINV. In addition, the combination of palonosetron, a 5-HT3 inhibitor, and aprepitant (EMEND®), a neurokinin antagonist, has been shown to be highly effective in preventing both acute and delayed CINV following a variety of moderately to highly emetogenic chemotherapy regimens in clinical trials. Notably, combination therapy of either NK1 antagonists or 5-HT3 antagonists with corticosteroids such as dexamethasone, improve the performance of these drugs against acute or delayed emesis. To that point, EMEND® labeling indicates that the drug is dosed with a corticosteroid and a 5-HT3 antagonist.

Irritable Bowel Syndrome (IBS) generally occurs in three types: diarrhea predominant (IBS-D), constipation predominant (IBS-C) and IBS with alternating symptoms termed IBS-A or mixed-mode (IBS-M). Diarrhea predominant Irritable Bowel Syndrome is a debilitating, though seldom fatal, disease. The typical sufferer of IBS-D exhibits primary symptoms including multiple and daily explosive diarrhea attacks and severe daily abdominal cramps. The most common secondary side effects include panic attacks, depression, withdrawal from social and family activities and malnutrition.

At present, compounds that inhibit 5-HT3 receptors are the only effective treatment for IBS-D. The only drug currently approved for IBS-D is alosetron, which was introduced by Glaxo, withdrawn by the FDA because it appeared to cause ischemic colitis, then reinstated by the FDA because the demand was so great for some treatment for IBS-D. In 2002, the US Food and Drug Administration approved alosetron hydrochloride (LOTRONEX®) tablets under restricted conditions for women in whom the medical benefits outweigh the risks. The restrictions on the approval reflect the serious gastrointestinal adverse events that have been reported with the use of alosetron. A second structurally related 5-HT3 inhibitor, cilansetron, had been making its way through clinical trials and recently received a non-approvable letter from the FDA. New, structurally unrelated 5-HT3 inhibitors may be useful for the treatment of IBS-D.

Clearly there is a need for improved therapy for both CINV and IBS-D.

SUMMARY OF THE INVENTION

It has now been found that compounds of formulae I, II and III are potent and selective inhibitors of the 5-HT3 receptor:

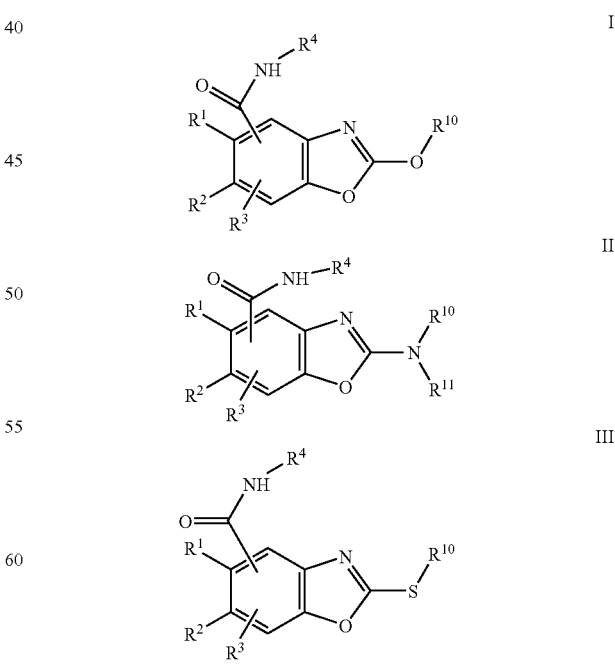

In these compounds $R_1$, $R_2$, and $R_3$ are independently selected from hydrogen, halogen, cyano, alkyl or aryl sulfoxide, alkyl or aryl sulfone, amino, alkylamino, dialkylamino, acylamino, morpholinyl, —O-loweralkyl, hydroxy, loweralkyl, fluoroloweralkyl, O lowerfluoroalkyl, methylenedioxy, ethylenedioxy, alkoxy-loweralkyl and hydroxyloweralkyl.

$R_4$ is a saturated nitrogen heterocycle or methyl-substituted saturated nitrogen heterocycle, in which said nitrogen is tertiary, said heterocycle containing at least one 5 or 6-membered ring;

$R_{10}$ is chosen from the group consisting of
  (i) hydrogen;
  (ii) $(C_1-C_{10})$alkyl;
  (iii) substituted $(C_1-C_{10})$alkyl;
  (iv) heterocyclyl;
  (v) substituted heterocyclyl;
  (vi) aryl; and
  (vii) substituted aryl;

$R_{11}$ is chosen from the group consisting of hydrogen and $(C_1-C_{10})$alkyl; or taken together $R_{10}$, $R_{11}$, and the nitrogen to which they are attached form a nitrogenous heterocyle or substituted nitrogenous heterocycle.

In another aspect, the invention relates to pharmaceutical compositions comprising a pharmaceutically acceptable carrier and a therapeutically effective amount of a compound of formula I, II, or III. The compositions may comprise an additional antiemetic agent, particularly a neurokinin antagonist. The compositions may also comprise a corticosteroid.

In another aspect, the invention relates to a method of treating a disorder arising from inappropriate activity of the serotonin type 3 receptor or dependent upon modulation of the serotonin type 3 receptor. The method comprises administering a therapeutically effective amount of a compound of formula I, II, or III. Exemplary disorders arising from inappropriate activity of the serotonin type 3 receptor or dependent upon modulation of the serotonin type 3 receptor include emesis, particularly CINV, IBS-D, post-operative induced nausea and vomiting and radiation induced nausea and vomiting. Other such disorders include psychological disorders, obesity, substance abuse disorders, dementia associated with a neurodegenerative disease, cognition loss, pain, fibromyalgia syndrome and chronic fatigue syndrome (see US published application 2004/0204467). Serotonin type 3 receptor antagonists are also known to be useful for the prevention and treatment of bronchial asthma, bulimia nervosa, sleep apnea, pruritis and migraine (see Costall and Naylor, Current Drug Targets—CNS & Neurological Disorders, 2004:3 27-37 and Israili, Current Med. Chem.—CNS Agents, 2001:1 171-199). Serotonin type 3 receptor antagonists are also known to be useful for the prevention and treatment of epilepsy. Application of such compounds for the treatment of epilepsy has been demonstrated in International Application Number PCT/GB2006/002733.

DETAILED DESCRIPTION OF THE INVENTION

Throughout this specification the substituents are defined when introduced and retain their definitions.

In a first aspect the invention relates to compounds of formula I, II, or III:

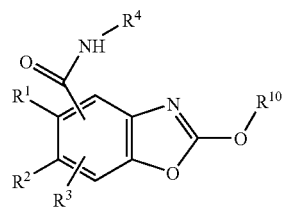

I

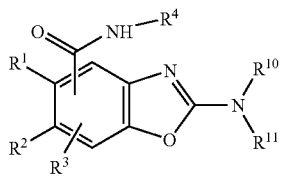

II

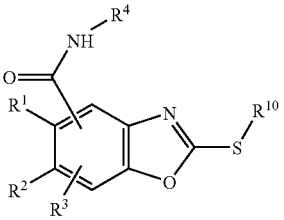

III

In general, it has been found that compounds of the foregoing formulae are potent and selective inhibitors of the 5-HT3 receptor. Each of the three genera may be divided into two subgenera: the 4-carboxamides (Ia, IIa, and IIIa) and the 7-carboxamides (Ib, IIb, and IIIb):

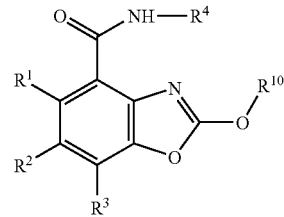

Ia

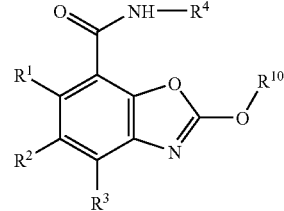

Ib

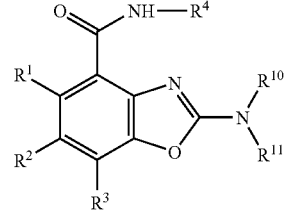

IIa

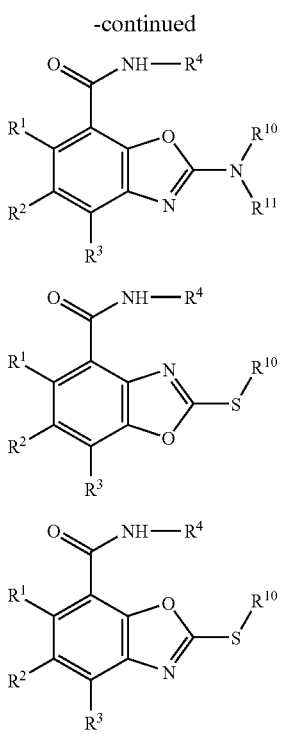

In these compounds, $R_4$ represents a saturated nitrogen heterocycle or methyl-substituted saturated nitrogen heterocycle, in which the nitrogen is tertiary. A nitrogen heterocycle (also referred to as a nitrogenous heterocycle) is a heterocycle containing at least one nitrogen in the ring; it may contain additional nitrogens, as well as other heteroatoms. Nitrogenous heterocycles include piperidine, methylpiperidine, tropane, 9-azabicyclo[3.3.1]nonan-3-one, and

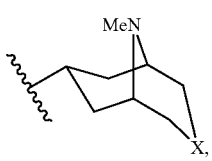

in which X is $NCH_3$, O, S, SO or $SO_2$. In some embodiments, $R_4$ is

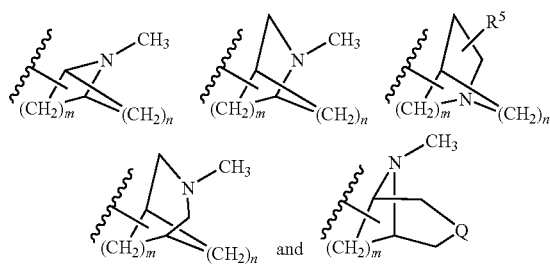

in which m is 1, 2, 3 or 4; n is 0, 1, 2, 3 or 4; Q is $N(CH_3)$ or —O—; and $R_5$ is hydrogen or methyl. For example, $R_4$ may be quinuclidine, tropane, azabicyclo[3.3.1]nonane, methyl azabicyclo[3.3.1]nonane, dimethyl diazabicyclo[3.3.1]nonane, methylpiperidine or methyl-3-oxa-9-azabicyclo [3.3.1]nonane.

In some embodiments, $R_1$, $R_2$, and $R_3$ are hydrogen; in others one of $R_1$, $R_2$, and $R_3$ is halogen.

In some embodiments of the parent genus, $R_{10}$ is chosen from the group consisting of hydrogen and ($C_1$ to $C_3$)alkyl. In other embodiments of the genus II, $R_{11}$ is H or $CH_3$ and $R_{10}$ is chosen from the group consisting of phenyl, substituted phenyl, ($C_1$-$C_6$)alkyl, 4 to 7-membered monocyclic nitrogenous heterocycle, 4 to 10 carbon bicyclic nitrogenous heterocycle, 4 to 7-membered monocyclic nitrogenous heterocycle substituted with one or more ($C_1$-$C_6$)alkyl, 4 to 10 carbon bicyclic nitrogenous heterocycle substituted with one or more ($C_1$-$C_6$) alkyl, dimethylamino($C_1$-$C_6$)alkyl, 4 to 7-membered monocyclic nitrogenous heterocyclyl($C_1$-$C_6$)alkyl, ($C_1$-$C_6$)alkoxy ($C_1$-$C_6$)alkyl, hydroxy($C_1$-$C_6$)alkyl, and dialkylaminocarbonyl($C_1$-$C_6$)alkyl.

In other embodiments, $R_{10}$ and $R_{11}$, taken together, form a nitrogenous heterocycle or substituted nitrogenous heterocycle. Examples include morpholine, piperazine, piperidine, diazepam, tetrahydroquinoxaline, azabicyclo[3.3.1]nonane, triazolopyrazine, diazabicyclo[2.2.1]heptane, or any of the foregoing substituted with one, two or three substituents chosen independently from ($C_1$-$C_6$)alkyl, ($C_1$-$C_6$)haloalkyl, ($C_1$-$C_6$)alkoxy phenyl, heteroaryl, substituted heteroaryl, heterocyclyl, and substituted heterocyclyl.

Compounds falling within the foregoing parent genus and its subgenera are useful as 5-HT3 inhibitors. It may be found upon examination that compounds that are not presently excluded from the claims are not patentable to the inventors in this application. In that case, the exclusion of species and genera in applicants' claims are to be considered artifacts of patent prosecution and not reflective of the inventors' concept or description of their invention. The invention, in a composition aspect, is all compounds of formulae I, II and III, except (a) those compounds that are in the public's possession, and (b) the single species of example 55, falling within the subgenus IIa, in which $R_{10}$, $R_{11}$ and nitrogen form a morpholine ring and $R_4$ appears (based on NMR data) to be endo 3,9-dimethyl-3,9-diazabicyclo[3.3.1]nonan-7-yl. This compound has not exhibited the level of potency established as the threshold for the screen.

DEFINITIONS

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like. Certain moieties require explicit mention. The statement that alkyl is intended to include linear, branched, or cyclic hydrocarbon structures and combinations thereof means that the following combination of linear and cyclic structural elements

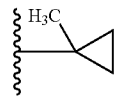

(and similar combinations) is considered an "alkyl" group. $C_1$ to $C_{20}$ hydrocarbon includes alkyl, cycloalkyl, alkenyl, alkynyl, aryl and combinations thereof. Examples include phenethyl, cyclohexylmethyl, camphoryl and naphthylethyl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Loweralkoxy refers to groups containing one to four carbons.

Oxyalkyl refers to alkyl residues in which one or more carbons has been replaced by oxygen. Examples include methoxypropoxy, 3,6,9-trioxadecyl and the like.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl (Ac), benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl refers to a residue in which an aryl moiety is attached to the parent through an alkyl. Examples are benzyl, phenethyl and the like. Tolyl is not arylalkyl; tolyl is alkylaryl. Heteroarylalkyl means a heteroaryl residue attached to the parent via alkyl. Examples include, e.g., pyridinylmethyl, pyrimidinylethyl and the like.

Heterocycle means a cycloalkyl or aryl residue of one to three rings in which from one to four carbons is replaced by a heteroatom selected from the group consisting of N, O and S. The nitrogen and sulfur heteroatoms may optionally be oxidized, and the nitrogen heteroatom may optionally be quaternized. Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. Nitrogen heterocycles are heterocycles containing at least one nitrogen. They may additionally include other heteroatoms and multiple nitrogens. Examples include quinuclidine, tropane, piperidine, piperazine, morpholine, quinoline, benzo[b][1,4]oxazine, 1,2,4-triazolo[4,3-a]pyrazine, perhydroquinoxaline and thiazole. It is to be noted that heteroaryl is a subset of heterocycle in which the heterocycle is aromatic. Dihydroheteroaryl are, as the name implies, hetearyl residues formally reduced by one mole of hydrogen. An example of a dihydroheteroaryl residue is 2,3-dihydrobenzofuran.

Substituted alkyl, aryl, cycloalkyl, heterocyclyl etc. refer to alkyl, aryl, cycloalkyl, or heterocyclyl wherein up to four H atoms in each residue are replaced with halogen, haloalkyl, hydroxy, loweralkoxy, carboxy, alkoxycarbonyl (COOR), oxo, carboxamido (—$CONR_2$), sulfonamido (—$SO_2NR_2$), cyano, carbonyl, nitro, amino, alkylamino, dialkylamino, mercapto, alkylthio, sulfoxide, sulfone, acylamino, amidino, phenyl, benzyl, heterocyclyl, heterocycylylcarbonyl, phenoxy, benzyloxy, or heteroaryloxy. In the foregoing listing, R is hydrogen or alkyl.

The term "halogen" means fluorine, chlorine, bromine or iodine.

Some of the compounds described herein may contain one or more asymmetric centers and may thus give rise to enantiomers, diastereomers, and other stereoisomeric forms that may be defined, in terms of absolute stereochemistry, as (R)— or (S)—. The present invention is meant to include all such possible isomers, as well as, their racemic and optically pure forms. Optically active (R)— and (S)— isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration; thus a carbon-carbon double bond depicted arbitrarily herein as trans may be Z, E or a mixture of the two in any proportion.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, chlorine and iodine include $^{3}H$, $^{14}C$, $^{35}S$, $^{18}F$, $^{36}Cl$ and $^{125}I$, respectively. Compounds that contain those radioisotopes and/or other radioisotopes of other atoms are within the scope of this invention. Tritiated, i.e. $^{3}H$, and carbon-14, i.e., $^{14}C$, radioisotopes are particularly preferred for their ease in preparation and detectability. Radiolabeled compounds of this invention can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

Terminology related to "protecting", "deprotecting" and "protected" functionalities occurs throughout this application. Such terminology is well understood by persons of skill in the art and is used in the context of processes, which involve sequential treatment with a series of reagents. In that context, a protecting group refers to a group, which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

The term "preventing" as used herein refers to administering a medicament beforehand to forestall or obtund an attack.

The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended herein. Indeed, the 2006 edition of the Physician's Desk Reference, which is the standard text in the field, employs the term "prevent", or "prevention" not less than 10 times in its description of the indications for palonosetron.

The graphic representations of racemic, ambiscalemic and scalemic or enantiomerically pure compounds used herein are taken from Maehr J. Chem. Ed. 62, 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. A simple solid line implies nothing about stereochemistry. For example, a solid line is shown in the graphic for example 2 in the table below, but the compound of the example is actually a single enantiomer of the S configuration and could have been accurately depicted as

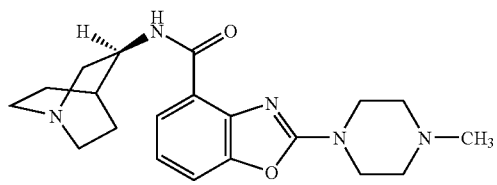

As used herein, and as would be understood by the person of skill in the art, the recitation of "a compound" is intended to include salts, solvates and inclusion complexes of that compound. The term "solvate" refers to a compound of Formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Inclusion complexes are described in Remington: The Science and Practice of Pharmacy 19th Ed. (1995) volume 1, page 176-177, which is incorporated herein by reference. The most commonly employed inclusion complexes are those with cyclodextrins, and all cyclodextrin complexes, natural and synthetic, are specifically encompassed within the claims.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine.

A comprehensive list of abbreviations utilized by organic chemists appears in the first issue of each volume of the Journal of Organic Chemistry. The list, which is typically presented in a table entitled "Standard List of Abbreviations" is incorporated herein by reference.

Generalized Synthetic Schemes are Presented Below:
General Procedures for Modifying the Benzoxazole Core

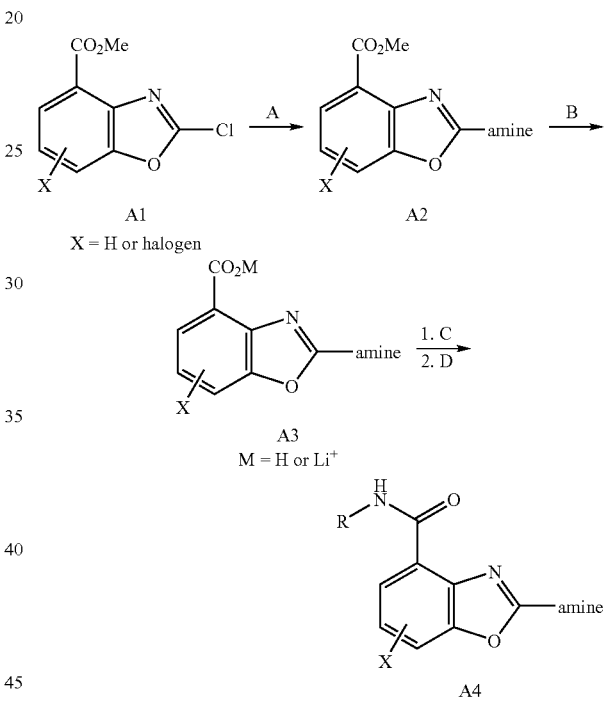

Conditions: A) amine, solvent; B) hydroxide base C) amine, EDCI, HOBt, DMF or HBTU, DMF; D) HCl, MeOH or Et$_2$O General Procedure (GP-A) for the Amination of the Benzoxazole Core:

A mixture of an appropriate 2-chlorobenzoxazole, A1 (1 eq), and appropriate amine (2 eq) and optional base (e.g. K$_2$CO$_3$, triethylamine, disopropylamine, 1,8-diazabicyclo [5.4.0]undecene, or sodium hydride) in THF (or DME, DMF) was heated in the range of 20 to 80° C. up to 24 h. After cooling to room temperature, the reaction mixture was concentrated under reduced pressure. The crude product was purified by silica gel column chromatography (typical eluents include 9:1 dichloromethane/methanol, ethyl acetate, hexanes) to afford the desired product 2-aminobenzoxazole. Product structure was confirmed by $^1$H NMR or by mass analysis.

General Procedure (GP-B1) for the Hydrolysis of the Methyl Ester:

A mixture of the methyl ester A2 in 2 N NaOH and THF was stirred at room temperature for 12 h. The reaction mixture was neutralized by 2 N HCl, and then extracted with dichloromethane. The combined organics were dried (Na$_2$SO$_4$), filtered and concentrated to afford the desired carboxylic acid A3. Product structure was confirmed either by $^1$H NMR or by mass analysis.

General Procedure (GP-B2) for the Hydrolysis of the Methyl Ester (Lithium Carboxylate Salt):

A mixture of the methyl ester A2 and lithium hydroxide monohydrate (1-3 eq) in methanol/water (3:1) was stirred at room temperature until the reaction was complete by LC-MS. The solvent was removed in vacuum and the crude lithium salt A3 was dried under high vacuum and subsequently used without further purification. The product structure was confirmed by $^1$H NMR or by mass analysis.

General Procedure (GP-B3) for the Hydrolysis of the Methyl Ester:

A mixture of the methyl ester A2, lithium hydroxide monohydrate (1-3 eq) and a mixture of methanol/water or THF/water (3:1 to 5:1) was stirred at room temperature until the reaction was complete by LC-MS. The reaction mixture was concentrated under reduced pressure. The resulting residue was diluted in water, acidified (pH 1-5) with 3 N hydrochloric acid and concentrated to dryness. The solid was triturated in dichloromethane, and the filtrate was concentrated under reduced pressure to afford the desired carboxylic acid A3. The product structure was confirmed either by $^1$H NMR or by mass analysis.

General Procedure (GP-C1) for Amidation:

A mixture of the carboxylic acid or lithium carboxylate salt A3 (1 eq), appropriate amine (e.g. endo-3-amino-9-methyl-9-azabicyclo[3.3.1]nonane dihydrochloride (1 eq), 1-ethyl-3-(3-dimethylaminopropyl)carbodiimide hydrochloride) (2 eq) and 1-hydroxybenzotriazole (2 eq) in DMF was stirred at room temperature for 5 min, then triethylamine (2 to 4 eq) was added. The resulting reaction mixture was stirred at room temperature for 12 h. The mixture was diluted with dichloromethane, and then washed with a saturated solution of sodium bicarbonate. The aqueous layer was further extracted with dichloromethane. The combined organics were dried (Na$_2$SO$_4$), filtered and concentrated. The crude material was purified by silica gel chromatography (typical eluents ethyl acetate/hexanes, ethyl acetate/methanol, dichloromethane, dichloromethane/methanol or dichloromethane/methanol/concentrated ammonium hydroxide) to afford the desired carboxamide A4. The product structure was verified by $^1$H NMR.

General Procedure (GP-C2) for Amidation:

A mixture of the carboxylic acid or lithium carboxylate salt A3 (1 eq), an appropriate amine (e.g. endo-3-amino-9-methyl-9-azabicyclo[3.3.1]nonane dihydrochloride) (1 eq), and HBTU (1.3-2 eq) in DMF was stirred at room temperature for 5 min, then triethylamine (2 to 4 eq) was added. The resulting reaction mixture was stirred at room temperature for 12 h. The mixture was diluted with dichloromethane, and then washed with a saturated solution of sodium bicarbonate. The aqueous layer was further extracted with dichloromethane. The combined organics were dried (Na$_2$SO$_4$), filtered and concentrated. The crude material was purified by silica gel chromatography (typical eluents ethyl acetate/hexanes, ethyl acetate/methanol, dichloromethane, dichloromethane/methanol or dichloromethane/methanol/concentrated ammonium hydroxide) to afford the desired carboxamide A4. The product structure was verified by $^1$H NMR.

General Procedure (GP-D1) for Conversion to the HCl Salt:

To an ice-cold solution of the carboxamide A4 (1 eq) in dichloromethane and ethyl ether was added hydrogen chloride (2 eq) in methanol. The mixture was stirred at room temperature for 5 min, and then diluted with anhydrous ethyl ether. The mixture was left at room temperature for 2 h, and then the resulting precipitate was collected by filtration and washed with ethyl ether. The solid was dried under vacuum to afford the desired A4 hydrochloride salt. The product was verified by mass analysis and $^1$H NMR.

General Procedure (GP-D2) for Conversion to the HCl Salt:

An ice-cold solution of the Boc-protected carboxamide from GP-C (1 eq) was treated with an excess of either TFA or HCl (in diethyl ether, dioxane or methanol) in dichloromethane. The crude salt was diluted with methanol and loaded onto a cation exchange resin (Isolute SCX-2, 10 g Column). The column was washed with methanol (50 mL) and the product then eluted with 2 N ammonium hydroxide in methanol (50 mL). The solution was concentrated under reduced pressure. The crude material was purified by silica gel chromatography (typical eluents dichloromethane/methanol, dichloromethane/methanol/concentrated ammonium hydroxide) to afford the desired carboxamide. The carboxamide was subsequently treated with HCl (1-2 equivalents) in dichloromethane and concentrated under reduced pressure. The amorphous hydrochloride salt was lyophilized from acetonitrile/water (6:1) to afford the desired A4 hydrochloride salt. The product was verified by mass analysis and $^1$H NMR.

General Procedure (GP-E) for Acylation of endo-N-(9-methyl-9-azabicyclo[3.3.1]nonan-3-yl)-2-((2S,6S)-2,6-dimethyl-piperazin-1-yl)benzoxazole-4-carboxamide:

To an ice-cold mixture of endo-N-(9-methyl-9-azabicyclo[3.3.1]nonan-3-yl)-2-((2S,6S)-2,6-dimethylpiperazin-1-yl)benzoxazole-4-carboxamide and triethylamine in CH$_2$Cl$_2$ was added the appropriate acyl chloride, chloroformate, or sulfonyl chloride. The mixture was allowed to warm to ambient temperature and then stirred for up to an additional 24 h. The reaction was quenched with CH$_3$OH/brine and the resulting mixture extracted with dichloromethane (2×). The combined organic layers were washed successively with 10% citric acid and brine, then dried (Na$_2$SO$_4$), filtered, and concentrated under reduced pressure. Purification by column chromatography (silica gel, 9:1 CH$_2$Cl$_2$/CH$_3$OH to 90:9:1 CH$_2$Cl$_2$/CH$_3$OH/NH$_4$OH) afforded the corresponding endo-N-(9-methyl-9-azabicyclo[3.3.1]nonan-3-yl)-2-((2S,6S)-2,6-dimethyl-4-acylpiperazin-1-yl)benzoxazole-4-carboxamide.

Preparation of methyl 2-chlorobenzoxazole-4-carboxylate

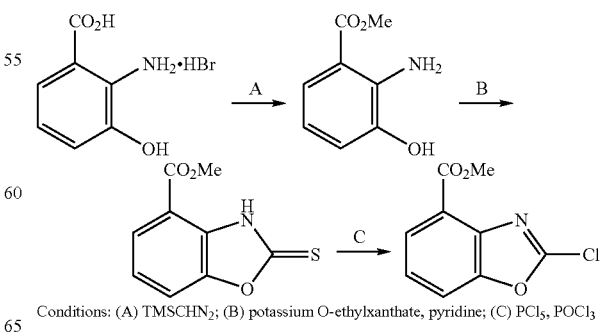

Conditions: (A) TMSCHN$_2$; (B) potassium O-ethylxanthate, pyridine; (C) PCl$_5$, POCl$_3$ Step A: To an ice-cold suspension of 2-amino-3-hydroxybenzoic acid hydrobromide (3.0 g, 12.8 mmol) in toluene (30 mL) and methanol (30 mL) was added (trimethylsilyl)diazomethane (16.0 mL, 2 M solution in ethyl ether, 32.0 mmol) slowly, then the mixture was stirred at 0° C. for 20 min. Acetic acid (5 mL) was added into the reaction mixture at 0° C., then the mixture was stirred at room temperature for 0.5 h. The reaction mixture was concentrated under reduced pressure, and then the crude was dissolved in ethyl acetate and washed with a saturated solution of sodium bicarbonate and brine. The organic layer was dried ($Na_2SO_4$), filtered and concentrated. The crude product was purified by column chromatography (silica gel, 1:1 hexanes/ethyl acetate) to afford the desired ester (2.04 g, 95%) as a light brown solid: $^1$H NMR (500 MHz, $CDCl_3$) δ 7.48 (dd, J 8.0, 1.5 Hz, 1H), 6.81 (dd, J 7.5, 1.5 Hz, 1H), 6.50 (t, J=8.0 Hz, 1H), 5.80 (br s, 2H), 3.87 (s, 3H); MS (ESI+) m/z 168 (M+H).

Step B: A mixture of methyl 2-amino-3-hydroxybenzoate from Step A (2.04 g, 12.2 mmol) and potassium O-ethylxanthate (1.37 g, 8.56 mmol) in pyridine (8 mL) was heated to reflux for 2 h, then cooled to room temperature and poured into a mixture of ice-water (45 mL) and conc. HCl (4.8 mL). The resulting precipitate was collected by filtration and washed with water, dried on vacuum to give methyl 2-thioxo-2,3-dihydrobenzoxazole-4-carboxylate (1.33 g, 52%) as a light brown solid: $^1$H NMR (500 MHz, $CDCl_3$) δ 10.40 (br s, 1H), 7.82 (dd, J 8.0, 1.0 Hz, 1H), 7.49 (dd, J 8.0, 1.0 Hz, 1H), 7.28 (t, J=8.0 Hz, 1H), 4.01 (s, 3H); MS (ESI+) m/z 210 (M+H).

Step C: A mixture of the thione from Step B (0.65 g, 3.11 mmol) and phosphorus pentachloride (0.65 g, 3.11 mmol) in phosphorus oxychloride (6 mL) was heated to 95° C. for 2.5 h. After cooling to room temperature, the reaction mixture was concentrated and dried on vacuum to give methyl 2-chlorobenzoxazole-4-carboxylate (0.66 g, quantitative) as a brown solid: $^1$H NMR (300 MHz, $CDCl_3$) δ 8.05 (dd, J 8.1, 1.2 Hz, 1H), 7.72 (dd, J 8.1, 1.2 Hz, 1H), 7.45 (t, J=8.1 Hz, 1H), 4.04 (s, 3H); MS (ESI+) m/z 212 (M+H).

Preparation of methyl
2,6-dichlorobenzoxazole-4-carboxylate

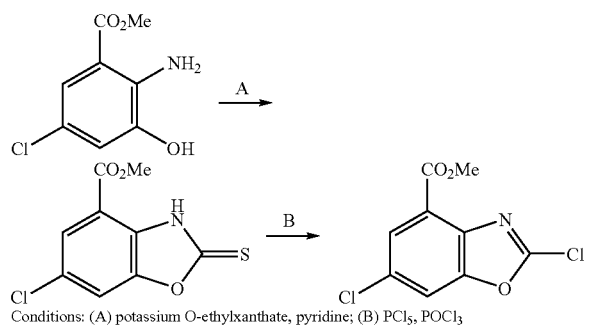

Conditions: (A) potassium O-ethylxanthate, pyridine; (B) PCl$_5$, POCl$_3$

Step A: To a mixture of methyl 2-amino-5-chloro-3-hydroxybenzoate (4.00 g, 19.84 mmol) in anhydrous pyridine (30 mL) was added potassium-O-ethylxanthate (3.50 g, 21.82 mmol), and the reaction mixture heated to 125° C. for 3 h under nitrogen atmosphere. The warm solution was poured into a mixture of concentrated HCl (12 mL) and ice (120 mL), the resulting precipitate filtered, and dried under vacuum to provide methyl 6-chloro-2-thioxo-2,3-dihydrobenzoxazole-4-carboxylate (4.80 g, 99%) as a yellow solid: $^1$H NMR (300 MHz, $CDCl_3$) δ 8.10 (s, 1H), 7.81 (d, J=1.9 Hz, 1H), 7.48 (d, J=1.9 Hz, 1H), 4.01 (s, 3H); MS (ESI+) m/z 244 (M+H).

Step B: A mixture of the product from Step A (2.00 g, 8.20 mmol), POCl3 (1.26 g, 8.21 mmol), and PCl$_5$ (1.71 g, 8.21 mmol) was heated to 125° C. for 2.5 hours. The reaction mixture was dried under high vacuum for 24 hours to afford methyl 2,6-dichlorobenzoxazole-4-carboxylate (2.00 g, 99%) as a brown solid: $^1$H NMR (300 MHz, $CDCl_3$) δ 8.04 (d, J=2.0 Hz, 1H), 7.72 (d, J=2.0 Hz, 1H), 4.04 (s, 3H); MS (ESI+) m/z 247 (M+H).

Preparation of methyl
2-chloro-7-fluoro-benzoxazole-4-carboxylate

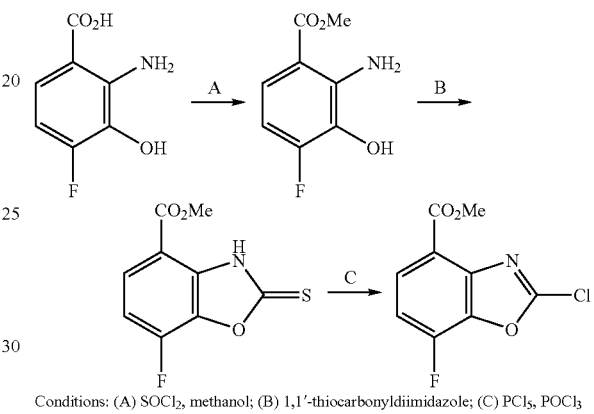

Conditions: (A) SOCl$_2$, methanol; (B) 1,1'-thiocarbonyldiimidazole; (C) PCl$_5$, POCl$_3$ Step A: To a solution of 2-amino-4-fluoro-3-hydroxybenzoic acid (2.44 g, 9.7 mmol) in methanol (200 mL) was added thionyl chloride (3.8 mL, 50 mmol) at −78° C. The mixture was stirred in the boiling solvent for 17 h. The solvent was removed under reduced pressure; the residue was dissolved in methanol (200 mL). The solution was cooled to −78° C. and treated with thionyl chloride (8 mL, 100 mmol). The mixture was stirred in boiling solvent for 48 h. The solvent was removed under reduced pressure and the crude material was purified by column chromatography (silica gel, 0 to 70% ethyl acetate in hexanes) to afford methyl 2-amino-4-fluoro-3-hydroxybenzoate (1.5 g, 44%) as off-white solid. $^1$H NMR (300 MHz, $CDCl_3$) δ 7.48-7.43 (m, 1H), 6.40 (t, J=9.3 Hz, 1H), 3.87 (s, 3H); MS (ESI+) m/z 186 (M+H).

Step B: A mixture of methyl 2-amino-4-fluoro-3-hydroxybenzoate (1.5 g, 8.11 mmol) and 1,1'-thiocarbonyldiimidazole (1.46 g, 8.2 mmol) in THF (30 mL) was stirred at ambient temperature overnight, and at 50° C. for 6 h. The reaction mixture was cooled to ambient temperature and the solvent was removed under reduced pressure. The residue was washed with ether (3×50 mL) and dried to afford methyl 7-fluoro-2-thioxo-2,3-dihydrobenzoxazole-4-carboxylate (1.3 g, 70%) as a yellow solid. $^1$H NMR (500 MHz, $CDCl_3$) δ 7.82-7.78 (m, 1H), 6.40 (t, J=9.0 Hz, 1H), 4.00 (s, 3H); (ESI+) m/z 228 (M+H).

Step C: A mixture of methyl 7-fluoro-2-thioxo-2,3-dihydrobenzoxazole-4-carboxylate (1.3 g, 5.72 mmol) and phosphorus pentachloride (1.2 g, 5.72 mmol) in phosphorus oxychloride (2.6 mL, 10.25 mmol) was heated to 95° C. for 3.5 h. After cooling to room temperature, the reaction mixture was concentrated and dried under vacuum to afford methyl 2-chloro-7-fluorobenzoxazole-4-carboxylate (1.3 g, quantitative) as a brown solid. $^1$H NMR (300 MHz, CDCl$_3$) δ 8.08-8.04 (m, 1H), 7.21 (t, J=9.3 Hz, 1H), 4.02 (s, 3H); MS (ESI+) m/z 229 (M+H).

In other embodiments where X is not hydrogen or halogen, the method of preparation of the foregoing is similar to those presented in U.S. Patent Application 2006/183769, the entire contents of which are herein incorporated by reference. In situations where an inconsistency in nomenclature between the foregoing application and the present application may exist, the nomenclature and definitions of the present application take precedence.

EXAMPLE 1

Preparation of Endo-N-(9-Methyl-9-azabicyclo [3.3.1]non-3-yl)-2-(4-methylpiperazin-1-yl)benzoxazole-4-carboxamide Dihydrochloride Step A: Following general procedure GP-A, methyl 2-chlorobenzoxazole-4-carboxylate and 1-methylpiperazine were converted to methyl 2-(4-methylpiperazin-1-yl)benzoxazole-4-carboxylate. $^1$H NMR and MS consistent.

Step B: Following general procedure GP-B1, methyl 2-(4-methylpiperazin-1-yl)benzoxazole-4-carboxylate was converted to 2-(4-methylpiperazin-1-yl)benzoxazole-4-carboxylic acid. $^1$H NMR and MS consistent.

Step C: Following general procedure GP-C$_1$, a mixture of methyl 2-(4-methylpiperazin-1-yl)benzoxazole-4-carboxylate was converted to 2-(4-methylpiperazin-1-yl)benzoxazole-4-carboxylic acid. The acid and endo-3-amino-9-methyl-9-azabicyclo[3.3.1]nonane dihydrochloride were then coupled to provide endo-N-(9-methyl-9-azabicyclo[3.3.1] non-3-yl)-2-(4-methylpiperazin-1-yl)benzoxazole-4-carboxamide, which was converted to the dihydrochloride salt following general procedure GP-D1. $^1$H NMR and MS consistent.

EXAMPLE 2

Preparation of (S)—N-(quinuclidine-8-yl)-2-(4-methylpiperazin-1-yl)benzoxazole-4-carboxamide Dihydrochloride Following the general procedure GP-C1,2-(4-methylpiperazin-1-yl)benzoxazole-4-carboxylic acid and (S)-(−)-3-aminoquinuclidine dihydrochloride were coupled to provide (S)—N-(quinuclidine-8-yl)-2-(4-methylpiperazin-1-yl)benzoxazole-4-carboxamide, which was converted to the dihydrochloride salt following general procedure GP-D1. $^1$H-NMR and MS consistent.

EXAMPLE 3

Preparation of Endo-N-(9-Methyl-9-azabicyclo [3.3.1]non-3-yl)-2-(piperidin-1-yl)benzoxazole-4-carboxamide Hydrochloride Step A: Methyl 2-(piperidin-1-yl)benzoxazole-4-carboxylate was synthesized following general procedure GP-A. $^1$H NMR and MS consistent.

Step B: 2-(piperidin-1-yl)benzoxazole-4-carboxylic acid was synthesized following general procedure GP-B1 except that the reaction was heated to 50° C. for 12 h. $^1$H NMR and MS consistent.

Step C: Following general procedure GP-C$_1$, a mixture of 2-(piperidin-1-yl)benzoxazole-4-carboxylic acid and endo-3-amino-9-methyl-9-azabicyclo[3.3.1]nonane dihydrochloride were coupled to provide endo-N-(9-methyl-9-azabicyclo [3.3.1]non-3-yl)-2-(piperidin-1-yl)benzoxazole-4-carboxamide, which was converted to the dihydrochloride salt following general procedure GP-D1. $^1$H NMR and MS consistent.

EXAMPLE 4

Preparation of (S)—N-(quinuclidine-8-yl)-2-(piperidin-1-yl)benzoxazole-4-carboxamide hydrochloride Step A: Following general procedure GP-C$_1$, a mixture of 2-(piperidin-1-yl)benzoxazole-4-carboxylic acid and (S)-(−)-3-aminoquinuclidine dihydrochloride were coupled to provide (S)—N-(quinuclidine-8-yl)-2-(piperidin-1-yl)benzoxazole-4-carboxamide which was converted to the hydrochloride salt following general procedure GP-D1. $^1$H NMR and MS consistent.

EXAMPLE 5

Preparation of Endo-N-(9-Methyl-9-azabicyclo [3.3.1]non-3-yl)-2-(phenylamino)benzoxazole-4-carboxamide Hydrochloride Step A: Methyl 2-(phenylamino)benzoxazole-4-carboxylate was synthesized following general procedure GP-A. $^1$H NMR and MS consistent.

Step B: 2-(phenylamino)benzoxazole-4-carboxylic acid was synthesized following general procedure GP-B1 except that the reaction was heated to 50° C. for 12 h. $^1$H NMR and MS consistent.

Step C: Following general procedure GP-C$_1$, a mixture of 2-(phenylamino)benzoxazole-4-carboxylic acid and endo-3-amino-9-methyl-9-azabicyclo[3.3.1]nonane dihydrochloride were coupled to provide endo-N-(9-methyl-9-azabicyclo [3.3.1]non-3-yl)-2-(phenylamino)benzoxazole-4-carboxamide, which was converted to the hydrochloride salt following general procedure GP-D1. $^1$H NMR and MS consistent.

EXAMPLE 6

Preparation of (S)—N-(quinuclidine-8-yl)-2-(phenylamino) benzoxazole-4-carboxamide Hydrochloride Following general procedure GP-C$_1$, A mixture of 2-(phenylamino)benzoxazole-4-carboxylic acid and (S)-(−)-3-aminoquinuclidine dihydrochloride were coupled to provide (S)—N-(quinuclidine-8-yl)-2-(phenylamino) benzoxazole-4-carboxamide, which was converted to the hydrochloride salt following general procedure GP-D1. $^1$H NMR and MS consistent.

EXAMPLE 7

Preparation of Endo-N-(9-Methyl-9-azabicyclo [3.3.1]non-3-yl)-2-(dimethylamino)benzoxazole-4-carboxamide Hydrochloride Step A: Methyl 2-(dimethylamino)benzoxazole-4-carboxylate was synthesized by following general procedure GP-A. $^1$H NMR and MS consistent.

Step B: 2-(dimethylamino)benzoxazole-4-carboxylic acid was synthesized by following general procedure GP-B1. $^1$H NMR and MS consistent.

Step C: Following general procedure GP-C1, A mixture of 2-(dimethylamino)benzoxazole-4-carboxylic acid and endo- 3-amino-9-methyl-9-azabicyclo[3.3.1]nonane dihydrochloride were coupled to provide endo-N-(9-methyl-9-azabicyclo[3.3.1]non-3-yl)-2-(dimethylamino)benzoxazole-4-carboxamide, which was converted to the hydrochloride salt following general procedure GP-D1. $^1$H-NMR and MS consistent.

EXAMPLE 8

Preparation of (S)—N-(quinuclidine-8-yl)-2-(dimethylamino)benzoxazole-4-carboxamide Hydrochloride Step A: Following general procedure GP-C$_1$, a mixture of 2-(dimethylamino)benzoxazole-4-carboxylic acid and (S)-(–)-3-aminoquinuclidine dihydrochloride were coupled to provide (S)—N-(quinuclidine-8-yl)-2-(dimethylamino)benzoxazole-4-carboxamide, which was converted to the hydrochloride salt following general procedure GP-D1. $^1$H NMR and MS consistent.

EXAMPLE 9

Preparation of Endo-N-(9-Methyl-9-azabicyclo[3.3.1]non-3-yl)-2-morpholinobenzoxazole-4-carboxamide Hydrochloride Step A: Methyl 2-morpholinobenzoxazole-4-carboxylate was synthesized by following general procedure GP-A. $^1$H NMR and MS consistent.

Step B: 2-morpholinobenzoxazole-4-carboxylic acid was synthesized by following general procedure GP-B1. $^1$H NMR and MS consistent.

Step C: Following general procedure GP-C$_1$, a mixture of 2-morpholinobenzoxazole-4-carboxylic acid and endo-3-amino-9-methyl-9-azabicyclo[3.3.1]nonane dihydrochloride were coupled to provide endo-N-(9-methyl-9-azabicyclo[3.3.1]non-3-yl)-2-morpholinobenzoxazole-4-carboxamide, which was converted to the hydrochloride salt following general procedure GP-D1. $^1$H NMR and MS consistent.

EXAMPLE 10

Preparation of (S)—N-(quinuclidine-8-yl)-2-morpholino-benzoxazole-4-carboxamide Hydrochloride Following general procedure GP-C$_1$, a mixture of 2-morpholinobenzoxazole-4-carboxylic acid and (S)-(–)-3-aminoquinuclidine dihydrochloride were coupled to provide (S)—N-(quinuclidine-8-yl)-2-morpholino-benzoxazole-4-carboxamide, which was converted to the hydrochloride salt following general procedure GP-D1. $^1$H NMR and MS consistent.

EXAMPLE 11

Preparation of Endo-N-(9-Methyl-9-azabicyclo[3.3.1]non-3-yl)-2-(4-methyl-1,4-diazepam-1-yl)benzoxazole-4-carboxamide Dihydrochloride Step A: Methyl 2-(4-methyl-1,4-diazepam-1-yl)benzoxazole-4-carboxylate was synthesized by following general procedure GP-A. $^1$H NMR and MS consistent.

Step B: 2-(4-methyl-1,4-diazepam-1-yl)benzoxazole-4-carboxylic acid was synthesized by following general procedure GP-B1. $^1$H NMR and MS consistent.

Step C: Following general procedure GP-C$_1$, a mixture of 2-(4-methyl-1,4-diazepam-1-yl)benzoxazole-4-carboxylic acid and endo-3-amino-9-methyl-9-azabicyclo[3.3.1]nonane dihydrochloride were coupled to provide endo-N-(9-methyl-9-azabicyclo[3.3.1]non-3-yl)-2-(4-methyl-1,4-diazepam-1-yl)benzoxazole-4-carboxamide, which was converted to the dihydrochloride salt following general procedure GP-D1. $^1$H NMR and MS consistent.

EXAMPLE 12

Preparation of (S)—N-(quinuclidine-8-yl)-2-(4-methyl-1,4-diazepam-1-yl)benzoxazole-4-carboxamide Dihydrochloride Following general procedure GP-C1, a mixture of 2-(4-methyl-1,4-diazepam-1-yl)benzoxazole-4-carboxylic acid and (S)-(–)-3-aminoquinuclidine dihydrochloride were coupled to provide (S)—N-(quinuclidine-8-yl)-2-(4-methyl-1,4-diazepam-1-yl)benzoxazole-4-carboxamide, which was converted to the dihydrochloride salt following general procedure GP-D1. $^1$H NMR and MS consistent.

EXAMPLE 13

Preparation of Endo-N-(9-Methyl-9-azabicyclo[3.3.1]non-3-yl)-2-methylthiobenzoxazole-4-carboxamide Hydrochloride Step A: To a solution of methyl 2-thioxo-2,3-dihydrobenzoxazole-4-carboxylate (1.5 g, 7.2 mmol) in acetone (150 mL) was added potassium carbonate (4.00 g, 28.7 mmol) followed by iodomethane (0.89 mL, 14.0 mmol), then the mixture was stirred at room temperature for 12 h. The reaction mixture was filtered through diatomaceous earth and washed with acetone, then concentrated under reduced pressure. The crude product was purified by column chromatography (silica gel, 3:1 hexanes/EtOAc) to afford the desired product (1.4 g, 86%) as a light yellow solid: $^1$H NMR and MS consistent.

Step B: 2-(methylthio)benzoxazole-4-carboxylic acid was synthesized by following general procedure GP-B1. $^1$H NMR and MS consistent.

Step C: Following general procedure GP-C$_1$, a mixture of 2-(methylthio)benzoxazole-4-carboxylic acid and endo-3-amino-9-methyl-9-azabicyclo[3.3.1]nonane dihydrochloride were coupled to provide endo-N-(9-methyl-9-azabicyclo[3.3.1]non-3-yl)-2-methylthiobenzoxazole-4-carboxamide, which was converted to the hydrochloride salt following general procedure GP-D1. $^1$H NMR and MS consistent.

EXAMPLE 14

Preparation of (S)—N-(quinuclidine-8-yl)-2-(methylthio)benzoxazole-4-carboxamide Hydrochloride Following general procedure GP-C1, a mixture of 2-(methylthio)benzoxazole-4-carboxylic acid and (S)-(–)-3-aminoquinuclidine dihydrochloride were coupled to provide (S)—N-(quinuclidine-8-yl)-2-(methylthio)benzoxazole-4-carboxamide, which was converted to the hydrochloride salt following general procedure GP-D1. $^1$H NMR and MS consistent.

EXAMPLE 15

Preparation of Endo-N-(1-Methylpiperidin-4-yl)-2-morpholinobenzoxazole-4-carboxamide Hydrochloride Following general procedure GP-C$_1$, a mixture of 2-morpholinobenzoxazole-4-carboxylic acid and 4-amino-1-methylpiperidine were coupled to provide N-(1-methylpiperidin-4-yl)-2-morpholinobenzoxazole-4-carboxamide, which was converted to the hydrochloride salt following general procedure GP-D1. $^1$H NMR and MS consistent.

EXAMPLE 16

Preparation of Endo-N-(9-Methyl-9-azabicyclo[3.3.1]non-3-yl)-2-(azetidin-3-ylamino)benzoxazole-4-carboxamide Dihydrochloride Step A: Methyl 2-(1-(tert-butoxycarbonyl)azetidin-3-ylamino)benzoxazole-4-carboxylate was synthesized by following general procedure GP-A. $^1$H NMR and MS consistent.

Step B: 2-(1-(tert-butoxycarbonyl)azetidin-3-ylamino)benzoxazole-4-carboxylic acid was synthesized by following general procedure GP-B1. $^1$H NMR and MS consistent.

Step C: Following general procedure GP-C$_1$, a mixture of 2-(1-(tert-butoxycarbonyl)azetidin-3-ylamino)benzoxazole-4-carboxylic acid and endo-3-amino-9-methyl-9-azabicyclo[3.3.1]nonane dihydrochloride were coupled to provide tert-butyl 3-(4-(9-methyl-9-azabicyclo[3.3.1]nonan-3-ylcarbamoyl)benzoxazol-2-ylamino)azetidine-1-carboxylate. $^1$H NMR and MS consistent.

Step D: To an ice-cold solution of tert-butyl 3-(4-(9-methyl-9-azabicyclo[3.3.1]nonan-3-ylcarbamoyl)benzoxazol-2-ylamino)azetidine-1-carboxylate (69 mg, 0.15 mmol) in CH$_2$Cl$_2$ (5 mL) was added TFA(0.12 mL, 1.5 mmol). The reaction mixture was stirred at room temperature for 12 h, and then concentrated under reduced pressure. Following general procedure GP-D1, the resulting TFA salt (73 mg, 0.15 mmol) was converted to endo-N-(9-methyl-9-azabicyclo[3.3.1]non-3-yl)-2-(azetidin-3-ylamino)benzoxazole-4-carboxamide dihydrochloride. $^1$H NMR and MS consistent.

EXAMPLE 17

Preparation of Endo-N-(9-Methyl-9-azabicyclo[3.3.1]non-3-yl)-2-[(2S,6R)-2,6-dimethylmorpholino]benzoxazole-4-carboxamide Hydrochloride Step A: Methyl 2-[(2S,6R)-2,6-dimethylmorpholino]benzoxazole-4-carboxylate was synthesized by following general procedure GP-A. $^1$H NMR and MS consistent.

Step B: 2-[(2S,6R)-2,6-dimethylmorpholino]benzoxazole-4-carboxylic acid was synthesized by following general procedure GP-B1. $^1$H NMR and MS consistent.

Step C: Following general procedure GP-C1, A mixture of 2-[(2S,6R)-2,6-dimethylmorpholino]benzoxazole-4-carboxylic acid and endo-3-amino-9-methyl-9-azabicyclo[3.3.1]nonane dihydrochloride were coupled to provide endo-N-(9-methyl-9-azabicyclo[3.3.1]non-3-yl)-2-[(2S,6R)-2,6-dimethylmorpholino]benzoxazole-4-carboxamide, which was converted to the hydrochloride salt following general procedure GP-D1. $^1$H NMR and MS consistent.

EXAMPLE 18

Preparation of (S)—N-(quinuclidine-8-yl)-2-((2S,6R)-2,6-dimethylmorpholino)benzoxazole-4-carboxamide Hydrochloride Following general procedure GP-C1, a mixture of 2-[(2S,6R)-2,6-dimethylmorpholino]benzoxazole-4-carboxylic acid and (S)-(−)-3-aminoquinuclidine dihydrochloride were coupled to provide (S)—N-(quinuclidine-8-yl)-2-((2S,6R)-2,6-dimethylmorpholino)benzoxazole-4-carboxamide, which was converted to the hydrochloride salt following general procedure GP-D1. $^1$H NMR and MS consistent.

EXAMPLE 19

Preparation of Endo-N-(9-Methyl-9-azabicyclo[3.3.1]non-3-yl)-2-(3-phenylmorpholino)benzoxazole-4-carboxamide Hydrochloride Step A: Methyl 2-(3-phenylmorpholino)benzoxazole-4-carboxylate was synthesized by following general procedure GP-A using triethylamine (1.5 eq) as the optional base. $^1$H NMR and MS consistent.

Step B: 2-(3-phenylmorpholino)benzoxazole-4-carboxylic acid was synthesized by following general procedure GP-B1. $^1$H NMR and MS consistent.

Step C: Following general procedure GP-C1, A mixture of 2-(3-phenylmorpholino)benzoxazole-4-carboxylic acid and endo-3-amino-9-methyl-9-azabicyclo[3.3.1]nonane dihydrochloride were coupled to provide endo-N-(9-methyl-9-azabicyclo[3.3.1]non-3-yl)-2-(3-phenylmorpholino)benzoxazole-4-carboxamide, which was converted to a hydrochloride salt following general procedure GP-D1 and isolated as a mixture of enantiomers. $^1$H NMR and MS consistent.

EXAMPLE 20

Preparation of (S)—N-(quinuclidine-8-yl)-2-(3-phenylmorpholino)benzoxazole-4-carboxamide Hydrochloride Following general procedure GP-C1, a mixture of 2-(3-phenylmorpholino)benzoxazole-4-carboxylic acid and (S)-(−)-3-aminoquinuclidine dihydrochloride were coupled to provide (S)—N-(quinuclidine-8-yl)-2-(3-phenylmorpholino)benzoxazole-4-carboxamide which was converted to the hydrochloride salt following general procedure GP-D1. $^1$H NMR and MS consistent.

EXAMPLE 21

Preparation of Endo-N-(9-Methyl-9-azabicyclo[3.3.1]non-3-yl)-2-(piperazin-1-yl)benzoxazole-4-carboxamide Dihydrochloride Step A: Methyl 2-(4-(tert-butoxycarbonyl)piperazin-1-yl)benzoxazole-4-carboxylate was synthesized by following general procedure GP-A except that the reaction was conducted at room temperature for 1 h prior to concentration. $^1$H NMR and MS consistent.

Step B: 2-[4-(tert-butoxycarbonyl)piperazin-1-yl]benzoxazole-4-carboxylic acid was synthesized by following general procedure GP-B1. $^1$H NMR and MS consistent.

Step C: Following general procedure GP-C$_1$, a mixture of 2-(1-(tert-butoxycarbonyl)azetidin-3-ylamino)benzoxazole- 4-carboxylic acid and endo-3-amino-9-methyl-9-azabicyclo[3.3.1]nonane dihydrochloride were coupled to provide tert-butyl 4-(4-(9-methyl-9-azabicyclo[3.3.1]nonan-3-ylcarbamoyl)benzoxazol-2-yl)piperazine-1-carboxylate. $^1$H NMR and MS consistent.

Step D: To an ice-cold solution of tert-butyl 4-(4-(9-methyl-9-azabicyclo[3.3.1]nonan-3-ylcarbamoyl)benzoxazol-2-yl)piperazine-1-carboxylate (73 mg, 0.15 mmol) in CH$_2$Cl$_2$ (5 mL) was added TFA (0.16 mL, 2.0 mmol). The reaction mixture was stirred at room temperature for 12 h, and then concentrated under reduced pressure. Following general procedure GP-D1, the resulting TFA salt (92 mg, 0.15 mmol) was converted to endo-N-(9-methyl-9-azabicyclo[3.3.1]non-3-yl)-2-(piperazin-1-yl)benzoxazole-4-carboxamide dihydrochloride. $^1$H NMR and MS consistent.

EXAMPLE 22

Preparation of (S)—N-(quinuclidine-8-yl)-2-(piperazin-1-yl)benzoxazole-4-carboxamide Dihydrochloride Following general procedure GP-C1, A mixture of 2-[4-(tert-butoxycarbonyl)piperazin-1-yl]benzoxazole-4-carboxylic acid and (S)-(−)-3-aminoquinuclidine dihydrochloride were coupled to provide tert-butyl 4-[4-(quinuclidine-8-ylcarbamoyl]benzoxazol-2-yl)piperazine-1-carboxylate (85 mg, 0.19 mmol) to which was added TFA (0.17 mL, 2.3 mmol). The reaction mixture was stirred at room temperature for 12 h, and then concentrated under reduced pressure. The TFA salt was converted to the dihydrochloride salt following general procedure GP-D1. $^1$H NMR and MS consistent.

EXAMPLE 23

Preparation of Endo-N-(9-Methyl-9-azabicyclo[3.3.1]non-3-yl)-2-(4-methyl-2-phenylpiperazin-1-yl)benzoxazole-4-carboxamide Dihydrochloride Step A: Following general procedure GP-A, methyl 2-chlorobenzoxazole-4-carboxylate and 1-methyl-3-phenylpiperazine were converted to methyl 2-(4-methyl-2-phenylpiperazin-1-yl)benzoxazole-4-carboxylate except that the reaction was conducted at room temperature for 1.5 h prior to concentration. $^1$H NMR and MS consistent.

Step B: 2-(4-methyl-2-phenylpiperazin-1-yl)benzoxazole-4-carboxylic acid was synthesized by following general procedure GP-B1. $^1$H NMR and MS consistent.

Step C: Following general procedure GP-C$_1$, a mixture of 2-(4-methyl-2-phenylpiperazin-1-yl)benzoxazole-4-carboxylic acid and endo-3-amino-9-methyl-9-azabicyclo[3.3.1]nonane dihydrochloride were coupled to provide endo-N-(9-methyl-9-azabicyclo[3.3.1]non-3-yl)-2-(4-methyl-2-phenylpiperazin-1-yl)benzoxazole-4-carboxamide which was converted the dihydrochloride salt following general procedure GP-D1 and isolated as a mixture of enantiomers. $^1$H NMR and MS consistent.

EXAMPLE 24

Preparation of (S)—N-(quinuclidine-8-yl)-2-(4-methyl-2-phenylpiperazin-1-yl)benzoxazole-4-carboxamide Dihydrochloride Following general procedure GP-C1, a mixture of 2-[4-(tert-butoxycarbonyl)piperazin-1-yl]benzoxazole-4-carboxylic acid and (S)-(−)-3-aminoquinuclidine dihydrochloride were coupled to provide (S)—N-(quinuclidine-8-yl)-2-(4-methyl-2-phenylpiperazin-1-yl)benzoxazole-4-carboxamide which was converted to the dihydrochloride salt following general procedure GP-D1 and isolated as a mixture of diastereomers. $^1$H NMR and MS consistent.

EXAMPLE 25

Preparation of Endo-N-(9-Methyl-9-azabicyclo[3.3.1]non-3-yl)-2-(2-methylpiperazin-1-yl)benzoxazole-4-carboxamide Dihydrochloride Step A: Methyl 2-[4-(tert-butoxycarbonyl)-2-methylpiperazin-1-yl]benzoxazole-4-carboxylate was synthesized by following general procedure GP-A. $^1$H NMR and MS consistent.

Step B: 2-[4-(tert-butoxycarbonyl)-2-methylpiperazin-1-yl]benzoxazole-4-carboxylic acid was synthesized by following general procedure GP-B1. $^1$H NMR and MS consistent.

Step C: Following general procedure GP-C1, 2-[4-(tert-butoxycarbonyl)-2-methylpiperazin-1-yl]benzoxazole-4-carboxylic acid and endo-3-amino-9-methyl-9-azabicyclo[3.3.1]nonane dihydrochloride were coupled to provide tert-butyl 3-methyl-4-(endo-N-(9-methyl-9-azabicyclo[3.3.1]nonan-3-ylcarbamoyl)benzoxazole-2-yl)piperazine-1-carboxylate. $^1$H NMR and MS consistent.

Step D: To an ice-cold solution of tert-butyl 3-methyl-4-(endo-N-(9-methyl-9-azabicyclo[3.3.1]nonan-3-ylcarbamoyl)benzoxazole-2-yl)piperazine-1-carboxylate (120 mg, 0.24 mmol) in CH$_2$Cl$_2$ (5 mL) was added TFA (0.29 mL, 3.6 mmol). The reaction mixture was stirred at room temperature for 12 h, and then concentrated under reduced pressure. The resulting TFA salt was converted to endo-N-(9-methyl-9-azabicyclo[3.3.1]non-3-yl)-2-(2-methylpiperazin-1-yl)benzoxazole-4-carboxamide dihydrochloride following general procedure GP-D1. $^1$H NMR and MS consistent.

EXAMPLE 26

Preparation of (S)—N-(quinuclidine-8-yl)-2-(2-methylpiperazin-1-yl)benzoxazole-4-carboxamide Dihydrochloride Step A: Following general procedure GP-C1, 2-[4-(tert-butoxycarbonyl)-2-methylpiperazin-1-yl]benzoxazole-4-carboxylic acid and (S)-(−)-3-aminoquinuclidine dihydrochloride were coupled to provide of tert-butyl 3-methyl-4-(4-(quinuclidine-8-ylcarbamoyl)benzoxazole-2-yl)piperazine-1-carboxylate. $^1$H NMR and MS consistent.

Step B: To an ice-cold solution of tert-butyl 3-methyl-4-(4-(quinuclidine-8-ylcarbamoyl)benzoxazole-2-yl)piperazine-1-carboxylate. (90 mg, 0.19 mmol) in CH$_2$Cl$_2$ (5 mL) was added TFA(0.25 mL, 3.2 mmol). The reaction mixture was stirred at room temperature for 12 h, and then concentrated under reduced pressure. The resulting TFA salt was converted to (S—N-(quinuclidine-8-yl)-2-(2-methylpiperazin-1-yl)benzoxazole-4-carboxamide dihydrochloride following GP-D1. $^1$H NMR and MS consistent.

EXAMPLE 27

Preparation of Endo-N-(9-Methyl-9-azabicyclo[3.3.1]non-3-yl)-2-(pyridine-4-ylamino)benzoxazole-4-carboxamide Dihydrochloride Step A: A mixture of methyl 2-chlorobenzoxazole-4-carboxylate (350 mg, 1.65 mmol), 4-aminopyridine (233 mg, 2.48 mmol), palladium(II) acetate (7.4 mg, 0.033 mmol), 2-dicyclohexylphosphino-2',4',6'-triisopropylbiphenyl (39 mg, 0.083 mmol), $K_2CO_3$ (570 mg, 4.13 mmol) and t-BuOH (4 mL) was heated to 90° C. for 40 min. After cooling to room temperature, the reaction mixture was filtered through diatomaceous earth and concentrated. The crude product was purified by column chromatography (silica gel, 9:1 $CH_2Cl_2/CH_3OH$) to afford methyl 2-(pyridin-4-ylamino)benzoxazole-4-carboxylate. $^1H$ NMR and MS consistent.

Step B: 2-(pyridin-4-ylamino)benzoxazole-4-carboxylic acid was synthesized by following general procedure GP-B1. $^1H$ NMR and MS consistent.

Step C: Following general procedure GP-$C_1$, a mixture of 2-(pyridin-4-ylamino)benzoxazole-4-carboxylic acid and endo-3-amino-9-methyl-9-azabicyclo[3.3.1]nonane dihydrochloride were coupled to provide endo-N-(9-methyl-9-azabicyclo[3.3.1]non-3-yl)-2-(pyridine-4-ylamino)benzoxazole-4-carboxamide, which was converted to the dihydrochloride salt following general procedure GP-D1. $^1H$ NMR and MS consistent.

EXAMPLE 28

Preparation of (S)—N-(quinuclidine-8-yl)-2-(pyridin-4-ylamino)benzoxazole-4-carboxamide Dihydrochloride Following general procedure GP-C1, a mixture of 2-(pyridin-4-ylamino)benzoxazole-4-carboxylic acid and (S)-(−)-3-aminoquinuclidine dihydrochloride were coupled to provide (S)—N-(quinuclidine-8-yl)-2-(pyridin-4-ylamino)benzoxazole-4-carboxamide, which was converted to the dihydrochloride salt following general procedure GP-D1. $^1H$ NMR and MS consistent.

EXAMPLE 29

Preparation of Endo-N-(9-Methyl-9-azabicyclo[3.3.1]non-3-yl)-2-(3,4-dihydroquinoxaline-1(2H)-yl)benzoxazole-4-carboxamide Dihydrochloride Step A: Methyl-2-(3,4-dihydroquinoxaline-1(2H)-yl)benzoxazole-4-carboxylate was synthesized by following general procedure GP-A. $^1H$ NMR and MS consistent.

Step B: 2-(3,4-dihydroquinoxaline-1(2H)-yl)benzoxazole-4-carboxylic acid was synthesized by following general procedure GP-B3. $^1H$ NMR and MS consistent.

Step C: Following general procedure GP-C1a mixture of 2-(3,4-dihydroquinoxaline-1(2H)-yl)benzoxazole-4-carboxylic acid and endo-3-amino-9-methyl-9-azabicyclo[3.3.1]nonane dihydrochloride were coupled to provide endo-N-(9-methyl-9-azabicyclo[3.3.1]non-3-yl)-2-(3,4-dihydroquinoxaline-1(2H)-yl)benzoxazole-4-carboxamide, which was converted to the dihydrochloride salt following general procedure GP-D1. $^1H$ NMR and MS consistent.

EXAMPLE 30

Preparation of Endo-N-(9-methyl-3-oxa-9-azabicyclo[3.3.1]non-7-yl)-2-(dimethylamino)benzoxazole-4-carboxamide Hydrochloride Following general procedure GP-C1, a mixture of 2-(dimethylamino) benzoxazole-4-carboxylic acid and endo-7-amino-9-methyl-3-oxa-9-azabicyclo[3.3.1]nonane dihydrochloride were coupled to provide endo-N-(9-methyl-3-oxa-9-azabicyclo[3.3.1]non-7-yl)-2-(dimethylamino)benzoxazole-4-carboxamide, which was converted to the hydrochloride salt following general procedure GP-D1. $^1H$ NMR and MS consistent.

EXAMPLE 31

Preparation of Endo-N-(9-methyl-9-azabicyclo[3.3.1]nonan-3-yl)-2-((2-(dimethylamino)ethyl)(methyl)amino)benzoxazole-4-carboxamide hydrochloride Step A: Methyl 2-((2-(dimethylamino)ethyl)(methyl)amino)benzoxazole-4-carboxylate was synthesized by following general procedure GP-A. $^1H$ NMR and MS consistent.

Step B: A solution of methyl 2-((2-(dimethylamino)ethyl)(methyl)amino)benzoxazole-4-carboxylate (620 mg, 1.4 mmol) and lithium hydroxide monohydrate (130 mg, 3.0 mmol) in $H_2O$ (2.5 mL) and THF (15 mL) was stirred at room temperature for 17 h. The THF was removed under reduced pressure and the residue was diluted with $H_2O$ to 150 mL and then loaded onto an anion exchange column (Bio Rad AG 1-X8 Cl-form, 2.6 meq/g (dry), 5.5 g resin (wet)). The column was washed with $H_2O$ and then eluted with 0.1 N HCl (aq). The product fractions were combined and concentrated. The residue was concentrated with $CH_3OH$ (3×15 mL) and then lyophilized to afford 2-((2-(dimethylamino)ethyl)(methyl)amino)benzoxazole-4-carboxylic acid dihydrochloride (273 mg, 58% (2 steps)) as a tan solid. $^1H$ NMR and MS consistent.

Step C: Following general procedure GP-C1, a mixture of 2-[(2-(dimethylamino)ethyl)(methyl)amino]benzoxazole-4-carboxylic acid dihydrochloride and endo-3-amino-9-methyl-9-azabicyclo[3.3.1]nonane dihydrochloride were coupled to provide endo-N-(9-methyl-9-azabicyclo[3.3.1]nonan-3-yl)-2-[(2-(dimethylamino)ethyl)(methyl)amino]benzoxazole-4-carboxamide, which was converted to the hydrochloride salt following general procedure GP-D1. $^1H$ NMR and MS consistent.

EXAMPLE 32

Preparation of Endo-N-(9-Methyl-9-azabicyclo[3.3.1]nonan-3-yl)-2-(2-(dimethylamino)ethylamino)benzoxazole-4-carboxamide Trihydrochloride Step A: Methyl 2-(2-(dimethylamino)ethylamino)benzoxazole-4-carboxylate was synthesized by following general procedure GP-A. $^1H$ NMR and MS consistent.

Step B: A solution of methyl 2-(2-(dimethylamino)ethylamino)benzoxazole-4-carboxylate (570 mg, 1.4 mmol) and lithium hydroxide monohydrate (130 mg, 3.0 mmol) in $H_2O$ (2.5 mL) and THF (15 mL) was stirred at room temperature for 17 h. The THF was removed under reduced pressure, the residue diluted with $H_2O$ to 150 mL and then loaded onto an anion exchange column (Bio Rad AG 1-X8 Cl- form, 2.6 meq/g (dry), 3.5 g resin (wet)). The column was washed with $H_2O$ and then eluted with 0.1 N HCl(aq). The product fractions were combined and concentrated. The residue was concentrated with $CH_3OH$ (3×15 mL) and then lyophilized to afford 2-(2-(dimethylamino)ethylamino)benzoxazole-4-carboxylic acid dihydrochloride (270 mg, 60% (2 steps)) as a tan solid. $^1H$ NMR and MS consistent.

Step C: Following general procedure GP-C1,2-(2-(dimethylamino)ethylamino)benzoxazole-4-carboxylic acid dihydrochloride and endo-3-amino-9-methyl-9-azabicyclo

[3.3.1]nonane dihydrochloride were coupled to provide endo-N-(9-methyl-9-azabicyclo[3.3.1]nonan-3-yl)-2-(2-(dimethylamino)ethylamino)benzoxazole-4-carboxamide, which was converted to the trihydrochloride salt following general procedure GP-D1. $^1$H NMR and MS consistent.

EXAMPLE 33

Preparation of Endo-N-(9-Methyl-9-azabicyclo[3.3.1]nonan-3-yl)-2-(2-morpholinoethylamino)benzoxazole-4-carboxamide Trihydrochloride Step A: Methyl 2-(2-morpholinoethylamino)benzoxazole-4-carboxylate was synthesized by following general procedure GP-A. $^1$H NMR and MS consistent.

Step C: A solution of methyl 2-(2-morpholinoethylamino)benzoxazole-4-carboxylate (220 mg, 0.72 mmol) and lithium hydroxide monohydrate (60 mg, 1.44 mmol) in H2O (1 mL) and THF (10 mL) was stirred at room temperature for 17 h. The THF was removed under reduced pressure and the residue diluted to 150 mL with $H_2O$ and then loaded onto an anion exchange column (Bio Rad AG 1-X8 $C_1$-form, 2.6 meq/g (dry), 2.5 g resin (wet)). The column was washed with $H_2O$ and then eluted with 0.1 N HCl(aq). The product fractions were combined and concentrated. The residue was concentrated with $CH_3OH$ (3×15 mL) and then lyophilized to afford 2-(2-morpholinoethylamino)benzoxazole-4-carboxylic acid hydrochloride (230 mg, 98%) as an off-white solid. $^1$H NMR and MS consistent.

Step D: Following general procedure GP-C1, a mixture of 2-(2-morpholinoethylamino)benzoxazole-4-carboxylic acid hydrochloride and endo-3-amino-9-methyl-9-azabicyclo[3.3.1]nonane dihydrochloride were coupled to provide endo-N-(9-methyl-9-azabicyclo[3.3.1]nonan-3-yl)-2-(2-morpholinoethylamino)benzoxazole-4-carboxamide, which was converted to the trihydrochloride salt following general procedure GP-D1. $^1$H NMR and MS consistent.

EXAMPLE 34

Preparation of Endo-N-(9-Methyl-9-azabicyclo[3.3.1]non-3-yl)-2-(methylamino)benzoxazole-4-carboxamide Hydrochloride Step A: Following general procedure GP-A, a mixture of methyl 2-chlorobenzoxazole-4-carboxylate and methylamine was heated to 80° C. in a sealed tube for 4 h to provide methyl 2-(methylamino-4-yl)benzoxazole-4-carboxylate. $^1$H NMR and MS consistent.

Step B: 2-(methylamino)benzoxazole-4-carboxylic acid was synthesized by following general procedure GP-B1. $^1$H NMR and MS consistent.

Step C: Following general procedure GP-C1, a mixture of 2-(methylamino)benzoxazole-4-carboxylic acid and endo-3-amino-9-methyl-9-azabicyclo[3.3.1]nonane dihydrochloride were coupled to provide endo-N-(9-methyl-9-azabicyclo[3.3.1]non-3-yl)-2-(methylamino)benzoxazole-4-carboxamide, which was converted to the hydrochloride salt following general procedure GP-D1. $^1$H NMR and MS consistent

EXAMPLE 35

Preparation of Endo-N-(9-Methyl-9-azabicyclo[3.3.1]non-3-yl)-2-aminobenzoxazole-4-carboxamide Hydrochloride Step A: To a solution of imidazole (13.63 g, 200 mmol) in $CH_2Cl_2$ (750 mL) was added cyanogen bromide at room temperature and the resulting mixture was heated to reflux for 45 min. The reaction mixture was cooled to room temperature and the solid obtained was isolated by filtration. The filtrate was concentrated to afford di(1H-imidazole-1-yl)methanamine as a white solid (10.5 g, 97%). $^1$H NMR and MS consistent.

Step B: Synthesis of methyl 2-aminobenzoxazole-4-carboxylate: To a solution of di(1H-imidazole-1-yl)methanamine (2.05 g, 12.26 mmol) in THF (60 mL) was added methyl-2-amino-3-hydroxybenzoate (1.98 g, 12.26 mmol) at room temperature and the resulting reaction mixture was heated to reflux for 17 h. The reaction mixture was cooled to room temperature, diluted with EtOAc (100 mL) and washed with $H_2O$ (3×100 mL), saturated ammonium chloride (2×100 mL), dried ($Na_2SO_4$), filtered and concentrated under reduced pressure. The crude material was purified by recrystallization from diethyl ether to afford methyl 2-aminobenzoxazole-4-carboxylate (1.10 g, 50%) as a brown solid. $^1$H NMR and MS consistent.

Step C: A mixture of methyl 2-aminobenzoxazole-4-carboxylate (750 mg, 3.9 mmol) and di-tert-butyldicarbonate (936 mg, 4.29 mmol) in $CH_2Cl_2$ (50 mL) was stirred at room temperature for 17 h. The reaction was quenched with a saturated $NaHCO_3$ (25 mL), and then extracted with $CH_2Cl_2$ (3×100 mL). The combined organic phase was washed with $H_2O$ (2×75 μL), brine (1×50 mL), and dried ($Na_2SO_4$), filtered and concentrated under reduced pressure. The crude material was purified by column chromatography (silica gel, 9:1, $CH_2Cl_2/CH_3OH$) to afford methyl 2-(tert-butoxycarbonylamino-4-yl)benzoxazole-4-carboxylate (930 mg, 82%) as a light yellow solid. $^1$H NMR and MS consistent.

Step D: 2-(tert-butoxycarbonylamino-4-yl)benzoxazole-4-carboxylic acid was synthesized by following general procedure GP-B1. $^1$H NMR and MS consistent.

Step E: Following general procedure GP-C1,2-(tert-butoxycarbonylamino-4-yl)benzoxazole-4-carboxylic acid and endo-3-amino-9-methyl-9-azabicyclo[3.3.1]nonane dihydrochloride were coupled to provide endo-N-(9-methyl-9-azabicyclo[3.3.1]non-3-yl)-2-aminobenzoxazole-4-carboxamide. $^1$H NMR and MS consistent.

Step F: A solution of endo-N-(9-methyl-9-azabicyclo[3.3.1]non-3-yl)-2-aminobenzoxazole-4-carboxamide (0.20 g, 0.48 mmol), in $CH_2Cl_2$ (5 mL) was added TFA(4 mL) and stirred at room temperature for 2 h. The reaction mixture was concentrated and the crude material was purified by preparative TLC (90:9:1 $CH_2Cl_2/CH_3OH$/concentrated $NH_4OH$) to afford endo-N-(9-methyl-9-azabicyclo[3.3.1]non-3-yl)-2-aminobenzoxazole-4-carboxamide (45 mg, 30%), which was converted to the hydrochloride salt following general procedure GP-D1. $^1$H NMR and MS consistent.

EXAMPLE 36

Preparation of Endo-N-(9-Methyl-9-azabicyclo[3.3.1]nonan-3-yl)-2-((S)-3-ethylmorpholine)benzoxazole-4-carboxamide Hydrochloride Step A: To an ice cold, stirred suspension of sodium hydride (60% in oil, 1.6 g, 39.0 mmol) in toluene (50 mL) was added dropwise a solution of (S)-2-aminobutan-1-ol (1.5 g, 17.0 mmol) in toluene (36 mL). After the addition was completed, the reaction mixture was warmed to room temperature and a solution of ethyl chloroacetate (2.3 g, 19.0 mmol) in toluene (9 mL) was added in a dropwise manner. The resulting mixture was then stirred at reflux for 20 h, cooled to room temperature, and solid ammonium chloride (2.0 g, 38.7 mmol) added to the reaction. The mixture was stirred for 20 min and then concentrated under reduced pressure. The crude material was purified by column chromatography (silica gel, 95:5 CH$_2$Cl$_2$/CH$_3$OH) to give (S)-5-ethylmorpholine-3-one (1.9 g, 88%) as an off-white semi-solid. $^1$H NMR consistent.

Step B: To ice-cold THF (10 mL) was added lithium aluminum hydride (29.0 mL, 1.0 M solution in THF). Once the addition was complete, a solution of (S)-5-ethylmorpholine-3-one (1.9 g, 15 mmol) in THF (10 mL) was added dropwise over 20 min. Once the addition was completed, the ice bath was removed and the reaction mixture stirred at reflux for 20 h. The reaction was cooled in an ice-bath and slowly, added dropwise (in a sequential manner) was H$_2$O (1.2 mL), a 15% solution of sodium hydroxide (1.2 mL), and H$_2$O (1.2 mL). The resulting mixture was stirred at room temperature for 1 h and then filtered washing the solid with EtOAc (50 mL). The filtrate was concentrated at room temperature under reduced pressure to provide (S)-3-ethylmorpholine (1.6 g, 94%) as a clear, colorless oil. $^1$H NMR consistent.

Step C: (S)-methyl-2-(3-ethyl morpholino)benzoxazole-4-carboxylate synthesized by following general procedure GP-A. $^1$H NMR and MS consistent.

Step D: (S)-2-(3-ethylmorpholino)benzoxazole-4-carboxylic acid was synthesized by following general procedure GP-B3. $^1$H NMR consistent.

Step E: Following general procedure GP-C2, a mixture of (S)-2-(3-ethylmorpholino)benzoxazole-4-carboxylic acid and endo-3-amino-9-methyl-9-azabicyclo[3.3.1]nonane dihydrochloride were coupled to provide endo-N-(9-methyl-9-azabicyclo[3.3.1]nonan-3-yl)-2-((S)-3-ethylmorpholino)benzoxazole-4-carboxamide, which was converted to the hydrochloride salt following general procedure GP-D1. $^1$H NMR and MS consistent

EXAMPLE 37

Preparation of Endo-N-(9-Methyl-9-azabicyclo [3.3.1]nonan-3-yl)-2-(9-Methyl-9-azabicyclo[3.3.1] non-3-ylamino)benzoxazole-4-carboxamide Trihydrochloride Step A: Methyl-2-(3-amino-9-methyl-9-azabicyclo[3.3.1] nonan-3-ylamino) benzoxazole-4-carboxylate was synthesized by following general procedure GP-A. $^1$H NMR and MS consistent.

Step B: A mixture of methyl-2(3-amino-9-methyl-9-azabicyclo[3.3.1]nonanylamino)benzoxazole-4-carboxylate (0.43 g, 1.74 mmol), lithium hydroxide monohydrate (252 mg, 5.96 mmol) and THF/H$_2$O (2:1, 15 mL) was stirred at room temperature for 17 h. The reaction mixture was adjusted to pH 10 with 6 N NaOH. A precipitate formed which was filtered to afford sodium-2-(3-amino-9-methyl-9-azabicyclo[3.3.1] nonanylamino)benzoxazole-4-carboxylate. $^1$H NMR and MS consistent.

Step C: Following general procedure GP-C$_1$, endo-3-amino-9-methyl-9-azabicyclo[3.3.1]nonane dihydrochloride and sodium-2-(3-amino-9-methyl-9-azabicyclo[3.3.1]nonanylamino)benzoxazole-4-carboxylate was coupled with endo-3-amino-9-methyl-9-azabicyclo[3.3.1]nonane dihydrochloride to provide endo-N-(9-methyl-9-azabicyclo [3.3.1]nonan-3-yl)-2-(9-methyl-9-azabicyclo[3.3.1]nonan-3-ylamino)benzoxazole-4-carboxamide, which was converted to the trihydrochloride salt following general procedure GP-D1. $^1$H NMR and MS consistent.

EXAMPLE 38

Preparation of Endo-N-(9-Methyl-9-azabicyclo [3.3.1]nonan-3-yl)-2-(2-methoxyethylamino)benzoxazole-4-carboxamide Hydrochloride Step A: Methyl-2-(2-methoxyethylamino)benzoxazole-4-carboxylate was synthesized by following general procedure GP-A. $^1$H NMR and MS consistent.

Step B: A mixture of methyl-2-(2-methoxyethylamino) benzoxazole-4-carboxylate (0.30 g, 1.19 mmol), potassium trimethylsilanolate (330 mg, 2.63 mmol) and THF (15 mL) was stirred at room temperature for 48 h, additional potassium trimethylsilanolate (75 mg, 0.59 mmol) was added and the mixture heated to reflux for 6 h. The reaction mixture was cooled to 0° C. and treated with HCl (1.0 M solution in diethyl ether, 3.57 mL, 3.57 mmol). The solvent was removed under vacuum and the crude 2-(2-methoxyethylamino)benzoxazole-4-carboxylic acid directly elaborated without further purification: MS consistent.

Step C: Following general procedure GP-C$_1$, a mixture of 2-(2-methoxyethylamino)benzoxazole-4-carboxylic acid and endo-3-amino-9-methyl-9-azabicyclo[3.3.1]nonane dihydrochloride were coupled to provide endo-N-(9-methyl-9-azabicyclo[3.3.1]nonan-3-yl)-2-(2-methoxyethylamino) benzoxazole-4-carboxamide, which was converted to the hydrochloride salt following general procedure GP-D1. $^1$H NMR and MS consistent.

EXAMPLE 39

Preparation of Endo-N-(9-Methyl-9-azabicyclo [3.3.1]nonan-3-yl)-2-(3-methoxypropylamino)benzoxazole-4-carboxamide Hydrochloride Step A: Methyl 2-chlorobenzoxazole-4-carboxylate and 3-methoxypropylamine were converted to methyl-2-(3-methoxypropylamino)benzoxazole-4-carboxylate. $^1$H NMR and MS consistent.

Step B: A mixture of methyl-2-(3-methoxypropylamino) benzoxazole-4-carboxylate (0.30 g, 1.13 mmol), potassium trimethylsilanolate (323 mg, 2.52 mmol) and THF (15 mL) was stirred at room temperature for 17 h, additional potassium trimethylsilanolate (72 mg, 0.56 mmol) was added and the mixture heated to reflux for 6 h. The reaction mixture was cooled to 0° C. and treated with HCl (1.0 M solution in diethyl ether, 3.39 mL, 3.39 mmol). The solvent was removed under vacuum and the crude 2-(3-methoxypropylamino)benzoxazole-4-carboxylic acid directly elaborated without further purification: MS consistent.

Step C: Following general procedure GP-C$_1$, a mixture of 2-(3-methoxypropylamino)benzoxazole-4-carboxylic acid and endo-3-amino-9-methyl-9-azabicyclo[3.3.1]nonane dihydrochloride coupled to provide endo-N-(9-methyl-9-azabicyclo[3.3.1]nonan-3-yl)-2-(3-methoxypropylamino) benzoxazole-4-carboxamide, which was converted to the hydrochloride salt following general procedure GP-D1. $^1$H NMR and MS consistent.

EXAMPLE 40

Preparation of Endo-N-(9-Methyl-9-azabicyclo [3.3.1]nonan-3-yl)-2-(3-hydroxypropylamino)benzoxazole-4-carboxamide Hydrochloride Step A: Methyl-2-(3-hydroxypropylamino)benzoxazole-4-carboxylate was synthesized by following general procedure GP-A. $^1$H NMR and MS consistent.

Step B: 2-(3-hydroxypropylamino)benzoxazole-4-carboxylic acid was synthesized by following general procedure GP-B3. MS consistent.

Step C: Following general procedure GP-C$_1$, a mixture of methyl-2-(3-hydroxypropylamino)benzoxazole-4-carboxylate and endo-3-amino-9-methyl-9-azabicyclo[3.3.1]nonane dihydrochloride coupled to provide endo-N-(9-methyl-9-azabicyclo[3.3.1]nonan-3-yl)-2-(3-hydroxypropylamino)benzoxazole-4-carboxamide, which was converted to the hydrochloride salt following general procedure GP-D1. $^1$H NMR and MS consistent.

EXAMPLE 41a and 41b

Preparation of Endo-N-(9-Methyl-9-azabicyclo [3.3.1]nonan-3-yl)-2-[(S)-2-methylpiperazin-1-yl] benzoxazole-4-carboxamide Hydrochloride and Endo-N-(9-Methyl-9-azabicyclo[3.3.1]nonan-3-yl)-2-[(R)-2-methylpiperazin-1-yl]benzoxazole-4-carboxamide Hydrochloride Step A: (S) or (R)-methyl 2-(4-(tert-butoxycarbonyl)-2-methylpiperazin-1-yl)benzoxazole-4-carboxylate were synthesized by following general procedure GP-A. $^1$H NMR and MS consistent.

Step B: (S) or (R)-2-(4-(tert-butoxycarbonyl)-2-methylpiperazin-1-yl)benzoxazole-4-carboxylic acid were synthesized by following general procedure GP-B3. $^1$H NMR and MS consistent.

Step C: Following general procedure GP-C1, a mixture of(S) or (R)-2-(4-(tert-butoxycarbonyl)-2-methylpiperazin-1-yl)benzoxazole-4-carboxylic acid. and endo-N-(9-methyl)-9-azabicyclo[3.3.1]nonan-3-amine dihydrochloride salt was coupled to provide (3S) or (3R)-tert-butyl 3-methyl-4-(4-(9-methyl-9-azabicyclo[3.3.1]nonan-3-ylcarbamoyl) benzoxazole-2-yl)piperazine-1-carboxylate. A solution of this material in CH$_2$Cl$_2$ (44 mL) at 0° C. was treated with TFA (3.53 mL, 46 mmol) and stirred at room temperature for 12 hours. The mixture was made basic with 2 N NaOH and the aqueous layer extracted with CH$_2$Cl$_2$ (3×150 mL). The combined organics were dried (MgSO$_4$), filtered, and concentrated. The crude material was purified by column chromatography (silica gel, 90:10:1 CH$_2$Cl$_2$/CH$_3$OH/concentrated NH$_4$OH) to provide endo-N-(9-methyl-9-azabicyclo[3.3.1] nonan-3-yl)-2-[(S)-2-methylpiperazin-1-yl]benzoxazole-4-carboxamide and endo-N-(9-methyl-9-azabicyclo[3.3.1] nonan-3-yl)-2-[(R)-2-methylpiperazin-1-yl]benzoxazole-4-carboxamide. Both enantiomers were converted to the respective hydrochloride salts following general procedure GP-D1. $^1$H NMR and MS consistent.

EXAMPLE 42

Preparation of Endo-N-(9-Methyl-9-azabicyclo [3.3.1]nonan-3-yl)-2-(4-(pyrimidin-2-yl)piperazin-1-yl)benzoxazole-4-carboxamide Hydrochloride Step A: Methyl 2-(4-(pyrimidin-2-yl)piperazin-1-yl)benzoxazole-4-carboxylate was synthesized by following general procedure GP-A. $^1$H NMR and MS consistent.

Step B: 2-(4-(pyrimidin-2-yl)piperazin-1-yl)benzoxazole-4-carboxylic acid was synthesized by following general procedure GP-B3. $^1$H NMR and MS consistent.

Step C: Following general procedure GP-C1, a mixture of 2-(4-(pyrimidin-2-yl)piperazin-1-yl)benzoxazole-4-carboxylic acid and endo-N-(9-methyl)-9-azabicyclo[3.3.1] nonan-3-amine hydrochloride coupled to provide endo-N-(9-methyl-9-azabicyclo[3.3.1]nonan-3-yl)-2-(4-(pyrimidin-2-yl)piperazin-1-yl)benzoxazole-4-carboxamide, which was converted to the hydrochloride salt following general procedure GP-D1. $^1$H NMR and MS consistent.

EXAMPLE 43

Preparation of Exo-N-(3,9-Dimethyl-3,9-diazabicyclo[3.3.1]nonan-7-yl)-2-morpholinobenzoxazole-4-carboxamide Hydrochloride Following general procedure GP-C1, a mixture of 2-morpholinobenzoxazole-4-carboxylic acid and endo-3,9-dimethyl-3,9-diazabicyclo[3.3.1]nonan-7-amine hydrochloride salt were coupled to provide N-(3,9-dimethyl-3,9-diazabicyclo[3.3.1]nonan-7-yl)-2-morpholinobenzoxazole-4-carboxamide, which was converted to the hydrochloride salt following general procedure GP-D1. $^1$H NMR and MS consistent.

EXAMPLE 44

Preparation of Endo-N-(9-Methyl-3-oxa-9-azabicyclo[3.3.1]nonan-7-yl)-2-morpholinobenzoxazole-4-carboxamide Hydrochloride Following general procedure GP-C$_1$, a mixture of 2-morpholinobenzoxazole-4-carboxylic acid and endo-9-methyl-3-oxa-9-azabicyclo[3.3.1]nonan-7-amine hydrochloride were coupled to provide N-(9-methyl-3-oxa-9-azabicyclo [3.3.1]nonan-7-yl)-2-morpholinobenzoxazole-4-carboxamide, which was converted to the hydrochloride salt following general procedure GP-D1. $^1$H NMR and MS consistent.

EXAMPLE 45

Preparation of Endo-N-(9-Methyl-3-oxa-9-azabicyclo[3.3.1]nonan-7-yl)-2-(phenylamino)benzoxazole-4-carboxamide Hydrochloride Following general procedure GP-C$_1$, a mixture of 2-(phenylamino)benzoxazole-4-carboxylic acid and endo-9-methyl-3-oxa-9-azabicyclo[3.3.1]nonan-7-amine hydrochloride salt coupled to provide endo-N-(9-methyl-3-oxa-9-azabicyclo[3.3.1]nonan-7-yl)-2-(phenylamino) benzoxazole-4-carboxamide, which was converted to the hydrochloride salt following general procedure GP-D1. $^1$H NMR and MS consistent.

EXAMPLE 46

Preparation of Endo-N-(9-Methyl-9-azabicyclo [3.3.1]nonan-3-yl)-2-((3aS,6aS)-hexahydropyrrolo [3,4-b]pyrrol-5(1H)-yl)benzoxazole-4-carboxamide Hydrochloride Step A: Following general procedure GP-A, a mixture of methyl 2-chlorobenzoxazole-4-carboxylate and (3S),(4S)-5-tert-butoxycarbonyl-2,5-diazabicyclo[2.2.1]heptane was converted to methyl 2-((1S),(4S)-5-(tert-butoxycarbonyl)-2,5-diazabicyclo[2.2.1]heptan-2-yl)benzoxazole-4-carboxylate. $^1$H NMR and MS consistent.

Step B: 2-((1S), (4S)-5-(tert-butoxycarbonyl)-2,5-diazabi-cyclo[2.2.1]heptan-2-yl)benzoxazole-4-carboxylic acid was synthesized by following general procedure GP-B3. $^1$H NMR and MS consistent.

Step C: Following general procedure GP-C1, a mixture of 2-((1S), (4S)-5-(tert-butoxycarbonyl)-2,5-diazabicyclo [2.2.1]heptan-2-yl)benzoxazole-4-carboxylic acid and endo-3-amino-9-methyl-9-azabicyclo[3.3.1]nonane dihydrochloride coupled to provide endo-N-(9-methyl-9-azabicyclo [3.3.1]nonan-3-yl)-2-((3aS,6aS)-hexahydropyrrolo[3,4-b] pyrrol-5(1H)-yl)benzoxazole-4-carboxamide, which was converted to the hydrochloride salt following general procedure GP-D1. $^1$H NMR and MS consistent.

EXAMPLE 47

Preparation of Endo-N-(9-Methyl-9-azabicyclo [3.3.1]nonan-3-yl)-2-(2-(dimethylamino)-2-oxoethylamino)benzoxazole-4-carboxamide Dihydrochloride Step A: Following general procedure GP-A, a mixture of methyl 2-chlorobenzoxazole-4-carboxylate and 2-amino-N, N-dimethylacetamide provided methyl 2-(2-(dimethylamino)-2-oxoethylamino)benzoxazole-4-carboxylate. $^1$H NMR and MS consistent.

Step B: A solution of methyl 2-(2-(dimethylamino)-2-oxoethylamino)benzoxazole-4-carboxylate (465 mg, 1.68 mmol) and lithium hydroxide monohydrate (106 mg, 2.52 mmol) in H$_2$O (3 mL) and THF (15 mL) was stirred at room temperature for 17 h. The THF was removed under reduced pressure; the residue diluted H$_2$O to 150 mL and then loaded onto an anion exchange cartridge (Isolute SAX 10 g). The cartridge was washed with H$_2$O and then eluted with 0.1 N HCl. The product fractions were combined and concentrated. The residue was concentrated with CH$_3$OH (3×15 mL) and then lyophilized from H$_2$O to afford 2-(2-(dimethylamino)-2-oxoethylamino)benzoxazole-4-carboxylic acid hydrochloride (280 mg, 56%). $^1$H NMR and MS consistent.

Step C: Following general procedure GP-C$_1$, a mixture of 2-(2-(dimethylamino)-2-oxoethylamino)benzoxazole-4-carboxylic acid hydrochloride and endo-3-amino-9-methyl-9-azabicyclo[3.3.1]nonane dihydrochloride coupled to provide endo-N-(9-methyl-9-azabicyclo[3.3.1]nonan-3-yl)-2-(2-(dimethylamino)-2-oxoethylamino)benzoxazole-4-carboxamide, which was converted to the dihydrochloride salt following general procedure GP-D1. $^1$H NMR and MS consistent.

EXAMPLE 48

Preparation of Endo-N-(9-Methyl-9-azabicyclo [3.3.1]nonan-3-yl)-2-((S)-3-isopropylmorpholino) benzoxazole-4-carboxamide Hydrochloride Step A: To an ice cold, stirred suspension of sodium hydride (60% in oil, 1.3 g, 34.0 mmol) in toluene (45 mL) was added dropwise a solution of (S)-2-amino-3-methylbutan-1-ol (1.5 g, 15.0 mmol) in toluene (30 mL). After the addition was complete, the reaction mixture was warmed to room temperature and a solution of ethyl chloroacetate (2.0 g, 16.0 mmol) in toluene (8 mL) was added in a dropwise manner. The resulting mixture was then stirred at reflux for 20 h, cooled to room temperature, and solid ammonium chloride (1.8 g, 34.0 mmol) added to the reaction. The mixture was stirred for 20 min and then concentrated under reduced pressure. The crude material was purified by column chromatography (silica gel, 95:5 CH$_2$Cl$_2$/CH$_3$OH) to give (S)-5-isopropylmorpholin-3-one (1.4 g, 67%) as a light yellow solid. $^1$H NMR and MS consistent.

Step B: To ice-cold THF (6 mL) was added lithium aluminum hydride (1.0 M solution in THF, 18.0 mL, 18.0 mmol). Once the addition was complete, a solution of (S)-5-isopropylmorpholin-3-one (1.3 g, 9.0 mmol) in THF (6 mL) was added dropwise over 20 min. Once the addition was completed, the ice bath was removed and the reaction mixture stirred at reflux for 18 h. The reaction was cooled in an ice-bath and to this was slowly added H$_2$O (0.75 mL), then a 15% aqueous solution of NaOH (0.75 mL), and then H$_2$O (0.75 mL). The resulting mixture was stirred at room temperature for 1 h and then filtered washing the solid with EtOAc (50 mL). The filtrate was concentrated at room temperature under reduced pressure to provide (S)-3-isopropylmorpholine (0.96 g, 83%) as a clear, colorless oil. $^1$H NMR and MS consistent.

Step C: Following general procedure GP-A, (S)-methyl-2-(3-isopropylmorpholino)benzoxazole-4-carboxylate and methyl 2-chlorobenzoxazole-4-carboxylate were converted to (S)-methyl-2-(3-isopropylmorpholino)benzoxazole-4-carboxylate. $^1$H NMR and MS consistent.

Step D: (S)-2-(3-isopropylmorpholino)benzoxazole-4-carboxylic acid was synthesized by following general procedure GP-B3. $^1$H NMR and MS consistent.

Step E: Following general procedure GP-C2, a mixture of (S)-2-(3-isopropylmorpholino)benzoxazole-4-carboxylic acid and endo-3-amino-9-methyl-9-azabicyclo[3.3.1]nonane dihydrochloride were coupled to provide of endo-N-(9-methyl-9-azabicyclo[3.3.1]nonan-3-yl)-2-((S)-3-isopropylmorpholino)benzoxazole-4-carboxamide, which was converted to the hydrochloride salt following general procedure GP-D1. $^1$H NMR and MS consistent.

EXAMPLE 49

Preparation of Endo-N-(9-Methyl-9-azabicyclo [3.3.1]nonan-3-yl)-2-((S)-3-methylmorpholino)benzoxazole-4-carboxamide Hydrochloride Step A: A solution of (S)-(+)-2-amino-1-propanol (5.0 g, 67.0 mmol) in toluene (60 mL) was added dropwise at 0° C. to a stirred suspension of NaH (60% in mineral oil, 6.2 g, 145 mmol) in toluene (150 mL). The cooling bath was removed and the reaction mixture was stirred at room temperature for 30 min. A solution of ethyl chloroacetate (8.0 mL, 73.8 mmol) in toluene (60 mL) was then added dropwise at room temperature and the resulting reaction mixture heated at reflux for 20 h. The reaction was cooled to room temperature and solid NH$_4$Cl (5 g, 96.7 mmol) added to the reaction. The reaction mixture was stirred for 20 min, filtered and the filtrate concentrated under reduced pressure. Purification by column chromatography (silica gel, 94.5:5:0.5 CH$_2$Cl$_2$/CH$_3$OH/ NH$_4$OH) afforded (S)-5-methylmorpholine-3-one (6.5 g, 84%) as an off-white semi-solid. $^1$H NMR and MS consistent.

Step B: A solution of (S)-5-methylmorpholine-3-one (6.9 g, 59.9 mmol) in THF (40 mL) was added dropwise at 0° C. to a solution of LiAlH$_4$ (1.0 M solution in THF, 120.0 mL, 120 mmol) in THF (40 mL). The ice bath was removed and the reaction mixture was heated at reflux for 18 h. The reaction was cooled in an ice-bath and excess hydride reagent was quenched by careful, dropwise addition of H$_2$O (5 mL), 15% aqueous NaOH (5 mL) and H$_2$O (15 mL). The resulting mixture was stirred at room temperature for 1 h and the reaction mixture was filtered through a pad of diatomaceous earth and the pad rinsed with EtOAc (100 mL). The filtrate was washed with saturated brine solution, dried over $Na_2SO_4$, filtered and concentrated under reduced pressure to provide (S)-3-methylmorpholine as a red oil. Due to the products suspected high volatility, the (S)-3-methylmorpholine was used in the next step without further isolation or purification.

Step C: (S)-methyl-2-(3-methylmorpholino)benzoxazole-4-carboxylate was synthesized by following general procedure GP-A. $^1$H NMR and MS consistent.

Step D: A solution of (S)-methyl 2-(3-methylmorpholino)benzoxazole-4-carboxylate (0.58 g, 2.1 mmol) in 1,4-dioxane/$CH_3OH/H_2O$ (2:2:1, 8.5 mL) containing lithium hydroxide monohydrate (150 mg, 6.30 mmol) was stirred at room temperature 24 h. The reaction mixture was concentrated under reduced pressure and residual $H_2O$ was azeotropically removed with benzene (2×100 mL) to yield lithium (S)-2-(3-methylmorpholino)benzoxazole-4-carboxylate as a white solid which was used in the next step without further isolation or purification.

Step E: Following general procedure GP-C2, a mixture of lithium (S)-2-(3-methylmorpholino)benzoxazole-4-carboxylate and endo-3-amino-9-methyl-9-azabicyclo[3.3.1]nonane dihydrochloride were coupled to provide endo-N-(9-methyl-9-azabicyclo[3.3.1]nonan-3-yl)-2-((S)-3-methylmorpholino)benzoxazole-4-carboxamide, which was converted to the hydrochloride salt following general procedure GP-D1. $^1$H NMR and MS consistent.

EXAMPLE 50

Preparation of Endo-N-(9-Methyl-9-azabicyclo[3.3.1]nonan-3-yl)-2-((2S*,6R*)-2,6-dimethylpiperazin-1-yl)benzoxazole-4-carboxamide Hydrochloride Step A: To an ice-cold solution of cis-2,6-dimethylpiperazine (1.50 g, 13.13 mmol), di-tert-butyldicarbonate (3.15 g, 14.45 mmol) and 4-dimethylaminopyridine (1.60 g, 13.13 mmol) in $CH_2Cl_2$ (20 mL) was added diisopropylethylamine (2.17 mL, 13.13 mmol). The mixture was stirred for 10 min then allowed to warm to room temperature for 4 h. The reaction was quenched with saturated $NaHCO_3$. The aqueous phase was further extracted with $Et_2O$ (2×20 mL). The combined organic phase was washed with brine, dried ($Na_2SO_4$), filtered and concentrated under reduced pressure. The crude product was purified by column chromatography (silica gel, 0 to 10% $CH_3OH$ in $CH_2Cl_2$) to afford (3S*,5R*)-tert-butyl 3,5-dimethylpiperazine-1-carboxylate (2.18 g, 77%) as a clear oil. $^1$H NMR and MS consistent.

Step B: Methyl 2-((2S*,6R*)-4-(tert-butoxycarbonyl)-2,6-dimethylpiperazin-1-yl)benzoxazole-4-carboxylate was synthesized by following general procedure GP-A. $^1$H NMR and MS consistent.

Step C: Lithium 2-((2S*,6R*)-4-(tert-butoxycarbonyl)-2,6-dimethylpiperazin-1-yl)benzoxazole-4-carboxylate was synthesized by following general procedure Gp-B2. MS consistent.

Step D: Following general procedure GP-C1, lithium 2-((2S*,6R*)-4-(tert-butoxycarbonyl)-2,6-dimethylpiperazin-1-yl)benzoxazole-4-carboxylate (109 mg, 0.28 mmol), and endo-3-amino-9-methyl-9-azabicyclo[3.3.1]nonane dihydrochloride were coupled to provide endo-(3 S*,5R*)-tert-butyl 3,5-dimethyl-4-(4-(9-methyl-9-azabicyclo[3.3.1]nonan-3-ylcarbamoyl)benzoxazol-2-yl)piperazine-1-carboxylate, which was converted to the hydrochloride salt following general procedure GP-D1. $^1$H NMR and MS consistent.

EXAMPLES 51 and 52

Preparation of Exo-N-(3,9-Dimethyl-3,9-diazabicyclo[3.3.1]nonan-7-yl)-2-(phenylamino)benzoxazole-4-carboxamide Hydrochloride and Endo-N-(3,9-Dimethyl-3,9-diazabicyclo[3.3.1]nonan-7-yl)-2-(phenylamino)benzoxazole-4-carboxamide Hydrochloride Following general procedure GP-C1, 2-(phenylamino)benzoxazole-4-carboxylic acid (140 mg, 0.551 mmol) and 3,9-dimethyl-3,9-diazabicyclo[3.3.1]nonan-7-amine hydrochloride salt (214 mg, 0.767 mmol) were coupled to provide exo-N-(3,9-dimethyl-3,9-diazabicyclo[3.3.1]nonan-7-yl)-2-(phenylamino)benzoxazole-4-carboxamide hydrochloride and endo-N-(3,9-dimethyl-3,9-diazabicyclo[3.3.1]nonan-7-yl)-2-(phenylamino)benzoxazole-4-carboxamide, which were converted to their hydrochloride salts following general procedure GP-D1. $^1$H NMR and MS consistent.

EXAMPLE 53

Preparation of Endo-N-(9-Methyl-9-azabicyclo[3.3.1]non-3-yl)-2-((S)-2-carbamoylpyrrolidin-1-yl)benzoxazole-4-carboxamide Hydrochloride Step A: Following general procedure GP-A, methyl 2-chlorobenzoxazole-4-carboxylate and (S)-prolinamide were converted to (S)-methyl 2-(2-carbamoylpyrrolidin-1-yl)benzoxazole-4-carboxylate. $^1$H NMR and MS consistent.

Step B: To an ice cold slurry of endo-3-amino-9-methyl-9-azabicyclo[3.3.1]nonane dihydrochloride (93 mg, 0.41 mmol) in $CH_2Cl_2$ (3 mL) was added trimethylaluminum (2 N in toluene, 0.17 mL, 0.34 mmol) and stirred for 1 h at room temperature. To the reaction mixture was added (S)-methyl 2-(2-carbamoylpyrrolidin-1-yl)benzoxazole-4-carboxylate (50 mg, 0.17 mmol) and the resulting reaction mixture was stirred at room temperature for 4 days. The reaction was quenched with $CH_3OH$ (1 mL), adjusted to pH 7 with 6 N HCl and concentrated under reduced pressure. The crude material was purified by preparative TLC (80:12:1.5 $CH_2Cl_2/CH_3OH$/concentrated $NH_4OH$) to afford endo-N-(9-methyl-9-azabicyclo[3.3.1]non-3-yl)-2-(S)-2-carbamoylpyrrolidin-1-yl)benzoxazole-4-carboxamide (35 mg, 50%) as a white solid, which was converted to the hydrochloride salt following general procedure GP-D1. $^1$H NMR and MS consistent.

EXAMPLE 54

Preparation of Endo-N-(9-Methyl-9-azabicyclo[3.3.1]nonan-3-yl)-2-(3-(trifluoromethyl)-5,6-dihydro-[1,2,4]triazolo[4,3-a]pyrazin-7(8H)-yl)benzoxazole-4-carboxamide Hydrochloride Step A: Following general procedure GP-A except using sodium hydride as base, 3-(trifluoromethyl)-5,6,7,8-tetrahydro-[1,2,4]triazolo[4,3-a]pyrazine and methyl 2-chlorobenzoxazole-4-carboxylate (243 mg, 1.15 mmol) were converted to methyl 2-(3-(trifluoromethyl)-5,6-dihydro-[1,2,4]triazolo[4,3-a]pyrazin-7(8H)-yl)benzoxazole-4-carboxylate. $^1$H NMR and MS consistent.

Step B: Lithium 2-(3-(trifluoromethyl)-5,6-dihydro-[1,2,4]triazolo[4,3-a]pyrazin-7(8H)-yl)benzoxazole-4-carboxylate was synthesized by following general procedure GP-B2. MS consistent.

Step C: Following general procedure GP-$C_1$, lithium 2-(3-(trifluoromethyl)-5,6-dihydro-[1,2,4]triazolo[4,3-a]pyrazin- 7(8H)-yl)benzoxazole-4-carboxylate and endo-3-amino-9-methyl-9-azabicyclo[3.3.1]nonane dihydrochloride were coupled to provide endo-N-(9-methyl-9-azabicyclo[3.3.1]nonan-3-yl)-2-(3-(trifluoromethyl)-5,6-dihydro-[1,2,4]triazolo[4,3-a]pyrazin-7(8H)-yl)benzoxazole-4-carboxamide, which was converted to the hydrochloride salt following general procedure GP-D1. $^1$H NMR and MS consistent.

EXAMPLE 55

Preparation of Endo-N-(9-Methyl-9-azabicyclo[3.3.1]nonan-3-yl)-2-((S)-2,4-dimethylpiperazin-1-yl)benzoxazole-4-carboxamide Hydrochloride Step A: (S)-methyl 2-(4-(tert-butoxycarbonyl)-2-methylpiperazin-1-yl)benzoxazole-4-carboxylate was synthesized by following general procedure GP-A. $^1$H NMR and MS consistent.

Step B: (R)-2-(4-(tert-butoxycarbonyl)-2-methylpiperazin-1-yl)benzoxazole-4-carboxylic acid was synthesized by following general procedure GP-B3. $^1$H NMR and MS consistent.

Step C: Following general procedure GP-C$_1$, (R)-2-(4-(tert-butoxycarbonyl)-2-methylpiperazin-1-yl)benzoxazole-4-carboxylic acid and endo-3-amino-9-methyl-9-azabicyclo[3.3.1]nonane dihydrochloride were coupled to provide of endo-N-(9-methyl-9-azabicyclo[3.3.1]nonan-3-yl)-(3S)-(tert-butylbenzoxazole-2-yl)piperazine-1-carboxylate. A solution of this intermediate in CH$_2$Cl$_2$ (44 mL) at 0° C. was treated with TFA (3.53 mL, 46 mmol) and stirred at room temperature for 12 h. The mixture was made basic with 2 N NaOH and the aqueous layer extracted with CH$_2$Cl$_2$ (3×150 mL). The combined organics were dried (MgSO$_4$), filtered, and concentrated under reduced pressure. The crude material was purified by column chromatography (silica gel, 90:10:1 CH$_2$Cl$_2$/CH$_3$OH/concentrated NH$_4$OH), to afford endo-N-(9-methyl-9-azabicyclo[3.3.1]nonan-3-yl)-2-((S)-2-methylpiperazin-1-yl)benzoxazole-4-carboxamide. $^1$H NMR and MS consistent.

Step D: A mixture of endo-N-(9-methyl-9-azabicyclo[3.3.1]nonan-3-yl)-2-((S)-2-methylpiperazin-1-yl)benzoxazole-4-carboxamide (44 mg, 0.11 mmol), formaldehyde (37% aqueous solution, 4 mL, 49 mmol), acetic acid (0.5 mL, 8.73 mmol), and sodium cyanoborohydride (14 mg, 0.22 mmol) in CH$_3$OH (5 mL) was stirred at room temperature for 12 hours. The mixture was concentrated to dryness, rendered basic to pH 12 with 2 N NaOH and extracted with CH$_2$Cl$_2$ (2×50 mL). The combined organics were washed with brine (5 mL), dried (MgSO$_4$), filtered, and concentrated under reduced pressure. The crude material was purified by column chromatography (silica gel, 90:10:1 CH$_2$Cl$_2$/CH$_3$OH/concentrated NH$_4$OH), to afford endo-N-(9-methyl-9-azabicyclo[3.3.1]nonan-3-yl)-2-((S)-2,4-dimethylpiperazin-1-yl)benzoxazole-4-carboxamide as an oil (45 mg, 99%). $^1$H NMR and MS consistent.

Step E: Following general procedure GP-D1, endo-N-(9-methyl-9-azabicyclo[3.3.1]nonan-3-yl)-2-((S)-2,4-dimethylpiperazin-1-yl)benzoxazole-4-carboxamide was converted to the hydrochloride salt. $^1$H NMR and MS consistent.

EXAMPLE 56

Preparation of Endo-N-(9-Methyl-9-azabicyclo[3.3.1]nonan-3-yl)-2-oxo-2,3-dihydrobenzoxazole-4-carboxamide Hydrochloride Step A: To a solution of methyl 2-chlorobenzoxazole-4-carboxylate (100 mg, 0.47 mmol) in THF (6 mL) was added a solution of lithium hydroxide monohydrate (29.7 mg, 0.71 mmol) in H$_2$O (3 mL). The reaction mixture was stirred at room temperature for 18 h and then concentrated to dryness to afford lithium 2-oxo-2,3-dihydrobenzoxazole-4-carboxylate (130 mg, 100%) as a yellow solid that was directly used in the next step without purification. MS consistent Step B: Following general procedure GP-C1, lithium 2-oxo-2,3-dihydrobenzoxazole-4-carboxylate and endo-3-amino-9-methyl-9-azabicyclo[3.3.1]nonane dihydrochloride were coupled to afford endo-N-(9-methyl-9-azabicyclo[3.3.1]nonan-3-yl)-2-oxo-2,3-dihydrobenzoxazole-4-carboxamide, which was converted to the hydrochloride salt following general procedure GP-D1. $^1$H NMR and MS consistent.

EXAMPLE 57

Preparation of Endo-N-(9-methyl-9-azabicyclo[3.3.1]nonan-3-yl)-6-chloro-2-((S)-2-methylpiperazin-1-yl)benzoxazole-4-carboxamide Hydrochloride Step A: (S)-methyl 2-(4-(tert-butoxycarbonyl)-2-methylpiperazin-1-yl)-6-chlorobenzoxazole-4-carboxylate was synthesized by following general procedure GP-A. $^1$H NMR and MS consistent.

Step B: (S)-2-(4-(tert-butoxycarbonyl)-2-methylpiperazin-1-yl)-6-chlorobenzoxazole-4-carboxylic acid was synthesized by following general procedure GP-B3. $^1$H NMR and MS consistent.

Step C: Following general procedure GP-C1, (S)-2-(4-(tert-butoxycarbonyl)-2-methylpiperazin-1-yl)-6-chlorobenzoxazole-4-carboxylic acid and endo-3-amino-9-methyl-9-azabicyclo[3.3.1]nonane dihydrochloride were coupled to afford endo-N-(3,9-dimethyl-3,9-diazabicyclo[3.3.1]nonan-7-ylcarbamoyl)benzoxazol-2-yl)-(3S)-tert-butyl 4-(6-chloro-4-(3-methylpiperazine)-1-carboxylate. The intermediate (410 mg, 0.79 mmol) was dissolved in CH$_2$Cl$_2$ (10 mL) and treated with TFA (609 mL, 7.9 mmol) at 0° C. The mixture stirred at room temperature for 12 h. The mixture was made basic with 2 N NaOH and the aqueous layer extracted with CH$_2$Cl$_2$ (3×150 mL). The combined organics were dried (MgSO$_4$), filtered, and concentrated. The crude material was purified by column chromatography (silica gel, 90:10:1 CH$_2$Cl$_2$/CH$_3$OH/concentrated NH$_4$OH) to afford endo-N-(9-methyl-9-azabicyclo[3.3.1]nonan-3-yl)-6-chloro-2-((S)-2-methylpiperazin-1-yl)benzoxazole-4-carboxamide, which was converted to the hydrochloride salt following general procedure GP-D1. $^1$H NMR and MS consistent.

EXAMPLE 58

Preparation of Endo-N-(9-methyl-9-azabicyclo[3.3.1]nonan-3-yl)-6-chloro-2-(4-methylpiperazin-1-yl)benzoxazole-4-carboxamide Hydrochloride Step A: Methyl 6-chloro-2-(4-methylpiperazin-1-yl)benzoxazole-4-carboxylate was synthesized by following general procedure GP-A except that the reaction was conducted at ambient temperature for 12 h. $^1$H NMR and MS consistent.

Step B: 6-chloro-2-(4-methylpiperazin-1-yl)benzoxazole-4-carboxylic acid was synthesized by following general procedure GP-B3. $^1$H NMR and MS consistent.

Step C: Following general procedure GP-C1,6-chloro-2-(4-methylpiperazin-1-yl)benzoxazole-4-carboxylic acid and endo-3-amino-9-methyl-9-azabicyclo[3.3.1]nonane dihydrochloride were coupled provide endo N-(9-methyl-9-azabicyclo[3.3.1]nonan-3-yl)-6-chloro-2-(4-methylpiperazin-1-yl)benzoxazole-4-carboxamide, which was converted to the hydrochloride salt following general procedure GP-D1. $^1$H NMR and MS consistent.

EXAMPLE 59

Preparation of Endo-N-(9-methyl-9-azabicyclo[3.3.1]nonan-3-yl)-2-(4-methoxyphenylamino)benzoxazole-4-carboxamide Hydrochloride Step A: Methyl 2-(4-methoxyphenylamino)benzoxazole-4-carboxylate oil was synthesized by following general procedure GP-A. $^1$H NMR and MS consistent.

Step B: 2-(4-methoxyphenylamino)benzoxazole-4-carboxylic acid was synthesized by following general procedure GP-B3. $^1$H NMR and MS consistent.

Step C: Following general procedure GP-C1 2-(4-methoxyphenylamino)benzoxazole-4-carboxylic acid and endo-3-amino-9-methyl-9-azabicyclo[3.3.1]nonane dihydrochloride were coupled to afford endo-N-(9-methyl-9-azabicyclo[3.3.1]nonan-3-yl)-2-(4-methoxyphenylamino)benzoxazole-4-carboxamide, which was converted to the hydrochloride salt following general procedure GP-D1. $^1$H NMR and MS were consistent.

EXAMPLE 60

Preparation of Endo N-(9-Methyl-9-azabicyclo[3.3.1]nonan-3-yl)-2-((2S*,5R*)-2,5-dimethylpiperazin-1-yl)benzoxazole-4-carboxamide Hydrochloride Step A: Following general procedure GP-A, methyl 2-chlorobenzoxazole-4-carboxylate and (i) trans-1-allyl-2,5-dimethylpiperazine were converted to methyl 2-(4-allyl-(2R*,5S*)-dimethylpiperazin-1-yl)benzoxazole-4-carboxylate. $^1$H NMR and MS consistent.

Step B: 2-(4-allyl-(2R*,5S*)-dimethylpiperazin-1-yl)benzoxazole-4-carboxylic acid was synthesized by following general procedure GP-B3. MS consistent.

Step C: Following general procedure GP-C1 2-(4-Allyl-(2R*,5S*)-dimethylpiperazin-1-yl)benzoxazole-4-carboxylic acid and 3-amino-9-methyl-9-azabicyclo[3.3.1]nonane dihydrochloride were coupled to afford endo N-(9-methyl-9-azabicyclo[3.3.1]nonan-3-yl)-2-((2S*,5R*)-4-allyl-2,5-dimethylpiperazin-1-yl)benzoxazole-4-carboxamide. $^1$H NMR and MS were consistent.

Step D: A solution of endo N-(9-methyl-9-azabicyclo[3.3.1]nonan-3-yl)-2-((2S*,5R*)-)-4-allyl-2,5-dimethylpiperazin-1-yl)benzoxazole-4-carboxamide (200 mg, 0.44 mmol), barbituric acid (337 mg, 2.64 mmol) and tetrakis(triphenylphosphine)palladium(0) (25 mg/0.022 mmol, 5 mol %) in the mixture of THF/DMF (2:1, 30mL) was stirred for 17 h at 60° C. under an atmosphere of argon. The mixture was poured into saturated NaHCO$_3$ (100 mL) and extracted with EtOAc (3×50 mL). The combined organic phase was washed sequentially with brine (100 mL), H$_2$O (100 mL), dried (Na$_2$SO$_4$), filtered and concentrated. The crude material was purified twice by column chromatography (silica gel, 100% CH$_2$Cl$_2$ to 20:76.5:3.5 CH$_2$Cl$_2$/CH$_3$OH/NH$_4$OH) to afford endo-N-(9-methyl-9-azabicyclo[3.3.1]nonan-3-yl)-2-((2S*,5R*)-2,5-dimethylpiperazin-1-yl)benzoxazole-4-carboxamide (34 mg, 17%) as a yellow film. $^1$H NMR and MS consistent.

Step E: Endo N-(9-methyl-9-azabicyclo[3.3.1]nonan-3-yl)-2-((2S*,5R*)-2,5-dimethylpiperazin-1-yl)benzoxazole-4-carboxamide was converted into the dihydrochloride salt following general procedure GP-D1. $^1$H NMR and MS consistent.

EXAMPLE 61

Preparation of Endo-N-(9-methyl-9-azabicyclo[3.3.1]nonan-3-yl)-2-(3-hydroxybutylamino)benzoxazole-4-carboxamide Hydrochloride Step A: To a solution of 2-hydroxybutylamine (4.00 g, 44.87 mmol) in anhydrous DMF (25 mL) was added tert-butyldiphenylsilylchloride (16.9 mL, 66.19 mmol) and imidazole (9.16 g, 13.46 mmol). The reaction mixture was stirred at room temperature for 2 days, then concentrated under reduced pressure, and diluted with CH$_2$Cl$_2$ (150 mL). The organics were washed with 5% aqueous NaHCO$_3$ solution (50 mL), brine (50 mL), dried (MgSO$_4$), filtered, and concentrated. The crude material was purified by column chromatography (0 to 100% EtOAc in hexane) to give 3-(tert-butyldiphenylsilyloxy)butan-1-amine (8.00 g, 54%) as a white solid. $^1$H NMR and MS consistent.

Step B: Methyl 2-(3-(tert-butyldiphenylsilyloxy)butylamino)benzoxazole-4-carboxylate was synthesized by following general procedure GP-A. $^1$H NMR and MS consistent.

Step C: 2-(3-(tert-butyldiphenylsilyloxy)butylamino)benzoxazole-4-carboxylic acid was synthesized by following general procedure GP-B3. $^1$H NMR and MS consistent.

Step D: Following general procedure GP-C1,2-(3-(tert-Butyldiphenylsilyloxy)butylamino)benzoxazole-4-carboxylic acid and endo-9-methyl-9-azabicyclo[3.3.1]nonan-3-amine hydrochloride salt were coupled to afford endo-N-(9-methyl-9-azabicyclo[3.3.1]nonan-3-yl)-2-(3-(tert-butyldiphenylsilyloxy)butylamino-benzoxazole-4-carboxamide. $^1$H NMR and MS consistent.

Step E: To a solution endo-N-(9-methyl-9-azabicyclo[3.3.1]nonan-3-yl)-2-(3-(tert-butyldiphenylsilyloxy)butylamino-benzoxazole-4-carboxamide (553 mg, 0.89 mmol) in THF (10 mL) was added a 1M solution TBAF in diethylether (2.65 mL, 2.65 mmol). The reaction mixture stirred at room temperature for 24 h, then concentrated and diluted with CH$_2$Cl$_2$ (250 mL). The organics were washed with saturated NH$_4$Cl (50 mL) and brine (50 mL), dried (MgSO$_4$), filtered, and concentrated under reduced pressure. The crude material was purified by column chromatography (silica gel, 90:10:1 CH$_2$Cl$_2$/CH$_3$OH/concentrated NH$_4$OH) to afford endo-N-(9-methyl-9-azabicyclo[3.3.1]nonan-3-yl)-2-(3-hydroxybutylamino)benzoxazole-4-carboxamide (342 mg, 99%) as a white solid. $^1$H NMR and MS consistent.

Step F: endo-N-2-(9-methyl-9-azabicyclo[3.3.1]nonan-3-yl)-(3-hydroxybutylamino)benzoxazole-4-carboxamide was converted into the hydrochloride salt following general procedure GP-D1. $^1$H NMR and MS consistent.

EXAMPLE 62

Preparation of Endo-N-(9-Methyl-9-azabicyclo[3.3.1]nonan-3-yl)-6-chloro 2-((S-3-ethylmorpholino)benzoxazole-4-carboxamide Hydrochloride Step A: To an ice cold, stirred suspension of NaH(60% in oil, 1.6 g, 39.0 mmol) in toluene (50 mL) was added dropwise a solution of (S)-2-aminobutan-1-ol (1.5 g, 17.0 mmol) in toluene (36 mL). After the addition was completed, the reaction mixture was warmed to room temperature and a solution of ethyl chloroacetate (2.3 g, 19.0 mmol) in toluene (9 mL) was added in a dropwise manner. The resulting mixture was then stirred at reflux for 20 h, cooled to room temperature, and solid NH$_4$Cl (2.0 g, 38.7 mmol) was added to the reaction. The mixture was stirred for 20 min and then concentrated under reduced pressure. The crude material was purified by column chromatography (silica gel, 95:5 methylene chloride/CH$_3$OH) to give (S)-5-ethylmorpholine-3-one (1.9 g, 88%) as an off-white semi-solid: $^1$H NMR and MS consistent.

Step B: To ice-cold THF (10 mL) was added LiAlH$_4$ (29.0 mL, 1.0 M solution in THF). Once the addition was complete, a solution of (S)-5-ethylmorpholine-3-one (1.9 g, 15 mmol) in THF (10 mL) was added dropwise over 20 min. Once the addition was completed, the ice bath was removed and the reaction mixture stirred at reflux for 20 h. The reaction was cooled in an ice-bath and slowly, added dropwise (in a sequential manner) was H$_2$O (1.2 mL), a 15% solution of sodium hydroxide (1.2 mL), and H2O (1.2 mL). The resulting mixture was stirred at room temperature for 1 h and then filtered washing the solid with EtOAc (50 mL). The filtrate was concentrated at room temperature under reduced pressure to provide (S)-3-ethylmorpholine (1.6 g, 94%) as a clear, colorless oil: $^1$H NMR and MS consistent.

Step C: Following general procedure GP-A, (S)-3-ethylmorpholine and methyl 2,6-dichlorobenzoxazole-4-carboxylate were coupled to provide (S)-methyl 6-chloro-2-(3-ethylmorpholino)benzoxazole-4-carboxylate. MS consistent.

Step D: (S)-6-chloro-2-(3-ethylmorpholino)benzoxazole-4-carboxylic acid was synthesized by following general procedure GP-B3. MS consistent.

Step E: Following general procedure GP-C2, (S)-6-chloro-2-(3-ethylmorpholino)benzoxazole-4-carboxylic acid and endo-3-amino-9-methyl-9-azabicyclo[3.3.1]nonane dihydrochloride were coupled to provide-endo-N-(9-methyl-9-azabicyclo[3.3.1]nonan-3-yl)-6-chloro-2-((S-3-ethylmorpholino)benzoxazole-4-carboxamide, which was converted to the hydrochloride salt following general procedure GP-D1. $^1$H NMR and MS consistent

EXAMPLE 63

Preparation of Endo-N-(9-methyl-9-azabicyclo[3.3.1]nonan-3-yl)-6-chloro-2-((S-2,4-dimethylpiperazin-1-yl)benzoxazole-4-carboxamide Hydrochloride Step A: Following general procedure GP-A, methyl 2,6-dichlorobenzoxazole-4-carboxylate and N-Boc-(S)-4-methylpiperazine were converted to (S)-methyl 2-(4-(tert-butoxycarbonyl)-2-methylpiperazin-1-yl)-6-chlorobenzoxazole-4-carboxylate. $^1$H NMR and MS were consistent.

Step B: (S)-2-(4-(tert-butoxycarbonyl)-2-methylpiperazin-1-yl)-6-chlorobenzoxazole-4-carboxylic acid was synthesized by following general procedure GP B3. $^1$H NMR and MS consistent.

Step C: Following general procedure GP-C2, (S)-2-(4-(tert-butoxycarbonyl)-2-methylpiperazin-1-yl)-6-chlorobenzoxazole-4-carboxylic acid and endo-9-methyl-9-azabicyclo[3.3.1]nonan-3-amine hydrochloride salt were coupled to provide endo-N-(3,9-dimethyl-3,9-diazabicyclo[3.3.1]nonan-7-ylcarbamoyl)benzoxazol-2-yl)-(3S)-tert-butyl 4-(6-chloro-4-(3-methylpiperazine)-1-carboxylate. This material (410 mg, 0.79 mmol) was dissolved in CH$_2$Cl$_2$ (10 mL) at 0° C., treated with TFA (609 mL, 7.9 mmol) and stirred at room temperature for 12 h. The mixture was made basic with 2 N NaOH and the aqueous layer extracted with CH$_2$Cl$_2$ (3×150 mL). The combined organics were dried (MgSO$_4$), filtered, and concentrated. The crude material was purified by column chromatography (silica gel, 90:10:1 CH$_2$Cl$_2$/CH$_3$OH/concentrated NH$_4$OH) to afford endo-N-(9-methyl-9-azabicyclo[3.3.1]nonan-3-yl)-6-chloro-2-((S)-2-methylpiperazin-1-yl)benzoxazole-4-carboxamide. $^1$H NMR and MS were consistent.

Step D: A mixture of endo-N-(9-methyl-9-azabicyclo[3.3.1]nonan-3-yl)-6-chloro-2-((S)-2-methylpiperazin-1-yl)benzoxazole-4-carboxamide (60 mg, 0.14 mmol), formaldehyde (37% aqueous solution, 4 mL, 49 mmol), HOAc (0.5 mL, 8.73 mmol), and NaCNBH3 (17 mg, 0.28 mmol) in CH$_3$OH (5 mL) was stirred at room temperature for 12 h. The mixture was concentrated to dryness, made basic to pH 12 with 2 N NaOH, and extracted with CH$_2$Cl$_2$ (2×70 mL). The combined organics were washed with brine (5 mL), dried (MgSO$_4$), filtered, and concentrated under reduced pressure. The crude material was purified by column chromatography (silica gel, 90:10:1 CH$_2$Cl$_2$/CH$_3$OH/concentrated NH$_4$OH), to afford endo-N-(9-methyl-9-azabicyclo[3.3.1]nonan-3-yl)-6-chloro-2-((S-2,4-dimethylpiperazin-1-yl)benzoxazole-4-carboxamide which was converted to the hydrochloride salt following general procedure GP-D1. $^1$H NMR and MS consistent.

EXAMPLE 64

Preparation of Endo-N-(9-methyl-9-azabicyclo[3.3.1]nonan-3-yl)-2-(2-methoxyphenylamino)benzoxazole-4-carboxamide Hydrochloride Step A: Methyl 2-(2-methoxyphenylamino)benzoxazole-4-carboxylate was synthesized by following general procedure GP-A. $^1$H NMR and MS consistent.

Step B: 2-(2-methoxyphenylamino)benzoxazole-4-carboxylic acid was synthesized by following general procedure GP-B3.

Step C: Following general procedure GP-C1, 2-(2-methoxyphenylamino)benzoxazole-4-carboxylic acid and endo-9-methyl-9-azabicyclo[3.3.1]nonan-3-amine dihydrochloride were coupled to provide endo-N-9-methyl-9-azabicyclo[3.3.1]nonan-3-yl)-2-(2-methoxyphenylamino) benzoxazole-4-carboxamide, which was converted to the hydrochloride salt following general procedure GP-D1. $^1$H NMR and MS consistent.

EXAMPLE 65

Preparation of Endo-N-(9-Methyl-9-azabicyclo[3.3.1]nonan-3-yl)-2-((R)-3-methylmorpholino)benzoxazole-4-carboxamide Step A: Glacial HOAc (1.5 mL) was added dropwise at room temperature to a well stirred solution of (R)-(+)-2-amino-1-propanol (10.0 g, 133 mmol) and benzaldehyde (13.5 mL, 133 mmol) in CH$_3$OH (260 mL). The reaction mixture was stirred at room temperature for 1.5 h followed by addition of NaCNBH$_3$ (12.6 g, 200 mmol) and the reaction stirred at room temperature overnight. The reaction was concentrated under reduced pressure and the recovered solids dissolved in EtOAc (500 mL) and then washed with saturated bicarbonate (2×250 mL), H$_2$O (250 mL) and saturated brine (250 mL). The organic phase was then dried over Na$_2$SO$_4$, filtered and concentrated to yield (R)-2-(benzylamino)propan-1-ol (19.8 g, 94%) as a colorless oil: MS consistent.

Step B: Chloroacetyl chloride (11.6 mL, 120 mmol) was added dropwise at 0° C. to a solution of (R)-2-(benzylamino)propan-1-ol (19.9 g, 120 mmol) and triethylamine (30.5 mL) in toluene (600 mL). The cooling bath was removed and the reaction mixture was stirred at room temperature for 18 h. The reaction was concentrated under reduced pressure and the recovered solids dissolved in EtOAc (500 mL) and then washed with saturated bicarbonate (2×250 mL), H$_2$O (250 mL) and saturated brine (250 mL). The organic phase was then dried (Na$_2$SO$_4$), filtered and concentrated to afford (R)-2-(2-(benzylamino)propoxy)acetyl chloride: MS consistent.

Step C: (R)-2-(2-(benzylamino)propoxy)acetyl chloride was dissolved in tert-butanol (500 mL). Sodium tert-butoxide (14.0 g, 125 mmol) was then added in one portion and the reaction mixture heated at reflux for 18 h. The reaction was cooled and concentrated under reduced pressure to remove the solvent. The residue was dissolved in diethyl ether (300 mL) and then washed with 2 N HCl (150 mL), H$_2$O (150 mL) and saturated brine (100 mL). The organic phase was then dried (Na$_2$SO$_4$), filtered, and concentrated under reduced pressure to afford a light yellow oil. Purification by column chromatography (silica gel, 10-50% EtOAc in heptanes) afforded (R)-4-benzyl-5-methylmorpholine-3-one (17.2 g, 63%) as a light yellow oil. $^1$H NMR and MS consistent.

Step D: A solution of (R)-4-benzyl-5-methylmorpholine-3-one (3.0 g, 14.22 mmol) in THF (10 mL) was added dropwise at 0° C. to a solution of lithium aluminum hydride (1.0 M solution in THF, 28.5 mL, 28.5 mmol) in THF (10 mL). The ice bath was removed and the reaction mixture was heated at reflux for 18 h. The reaction was cooled in an ice-bath and excess hydride reagent was quenched by careful, dropwise addition of H2O (5 mL), 15% sodium hydroxide (5 mL) and H$_2$O (15 mL). The resulting mixture was stirred at room temperature for 1 h and the reaction mixture was filtered through a pad of Celite and the pad rinsed with EtOAc (100 mL). The filtrate was washed with saturated brine solution, dried (Na$_2$SO$_4$), filtered and concentrated under reduced pressure to provide (R)-4-benzyl-3-methylmorpholine (2.66 g, 95%) as a red oil. $^1$H NMR and MS consistent.

Step E: To a solution of (R)-4-benzyl-3-methylmorpholine (1.0 g, 5.07 mmol) in EtOAc (40 mL) containing a catalytic amount of HCl (4 M solution in 1,4-dioxane, 2 drops) was added 10% palladium on carbon (400 mg) and the solution agitated in a Parr apparatus under an atmosphere of hydrogen (40 psi) for 18 h. The reaction mixture was filtered through a pad of Celite and the filter cake washed with additional EtOAc. Careful concentration of the filtrate under reduced pressure afforded (R)-3-methylmorpholine as a yellow oil, which was used in the next step without further isolation or purification.

Step F: Synthesis of (R)-methyl-2-(3-methylmorpholino)benzoxazole-4-carboxylate: Following general procedure GP-A except using triethylamine as base, (R)-3-methylmorpholine and methyl 2-chlorobenzoxazole-4-carboxylate were converted to (R)-methyl-2-(3-methylmorpholino)benzoxazole-4-carboxylate. $^1$H NMR and MS consistent.

Step G: Synthesis of lithium (R)-2-(3-methylmorpholino)benzoxazole-4-carboxylate: Following general procedure GP-B2, (R)-methyl 2-(3-methylmorpholino)benzoxazole-4-carboxylate was converted to lithium (R)-2-(3-methylmorpholino)benzoxazole-4-carboxylate, which was used without further isolation or purification. MS consistent.

Step H: Following general procedure GP-C2, lithium (R)-2-(3-methylmorpholino)benzoxazole-4-carboxylate and endo-3-amino-9-methyl-9-azabicyclo[3.3.1]nonane dihydrochloride (0.856 g, 3.76 mmol) were coupled to provide endo-N-(9-methyl-9-azabicyclo[3.3.1]nonan-3-yl)-2-((R)-3-methylmorpholino)benzoxazole-4-carboxamide. MS consistent.

Step I: To a solution of endo-N-(9-methyl-9-azabicyclo[3.3.1]nonan-3-yl)-2-((R)-3-methylmorpholino)benzoxazole-4-carboxamide (0.070 g, 0.175 mmol) in 1,4-dioxane (15 mL) was added HCl (4.0 M solution in 1,4-dioxane 5.0 mL, 5.0 mmol) in a dropwise manner. The resulting mixture was stirred at room temperature for 3 h and then filtered. The recovered hydroscopic solid was then dissolved in acetonitrile/H$_2$O (1:10, 10 mL) and lyophilized 3 times to afford a viscous oil. This material was then dried under high vacuum for 72 h at 60° C. in the presence of phosphorous pentoxide to afford a brown glassy solid which, when scratched from the sides of the flask, afforded endo-N-(9-methyl-9-azabicyclo[3.3.1]nonan-3-yl)-2-((R)-3-methylmorpholino)benzoxazole-4-carboxamide hydrochloride (0.050 g, 95%) as a hydroscopic brown solid. $^1$H NMR and MS consistent.

EXAMPLE 66

Preparation of Endo-N-(9-Methyl-9-azabicyclo[3.3.1]nonan-3-yl)-2-((S)-3-propylmorpholino)benzoxazole-4-carboxamide Hydrochloride Step A: To an ice cold, stirred suspension of NaH (60% in oil, 1.9 g, 46.0 mmol) in toluene (62 mL) was added dropwise a solution of (S)-2-aminopentan-1-ol (2.1 g, 20.0 mmol) in toluene (44 mL). After the addition was completed, the reaction mixture was warmed to room temperature and a solution of ethyl chloroacetate (2.7 g, 22.0 mmol) in toluene (12 mL) was added in a dropwise manner. The resulting mixture was then stirred at reflux for 20 h, cooled to room temperature, and solid ammonium chloride (2.5 g, 46.0 mmol) was added to the reaction. The mixture was stirred for 20 min and then concentrated under reduced pressure. The crude material was purified by column chromatography (silica gel, 98:2 CH$_2$Cl$_2$/CH$_3$OH to 95:5 CH$_2$Cl$_2$/CH$_3$OH) to give (S)-5-propylmorpholin-3-one (2.2 g, 76%) as a yellow oil. To ice-cold THF (10 mL) was added lithium aluminum hydride (1.0 M solution in THF, 30 mL, 30 mmol). Once the addition was complete, a solution of (S)-5-propylmorpholin-3-one (2.2 g, 15 mmol) in THF (10 mL) was added dropwise over 20 min. Once the addition was completed, the ice bath was removed and the reaction mixture stirred at reflux for 20 h. The reaction was cooled in an ice-bath and to this was slowly added H$_2$O (1.2 mL), then 15% aqueous solution of sodium hydroxide (1.2 mL), and then H$_2$O (1.2 mL). The resulting mixture was stirred at room temperature for 1.5 h and then filtered washing the solid with EtOAc (50 mL). The filtrate was concentrated at room temperature under reduced pressure to provide (S)-3-propylmorpholine (1.9 g, 98%) as a light yellow oil. $^1$H NMR and MS consistent.

Step B: (S)-methyl-2-(3-propylmorpholino)benzoxazole-4-carboxylate was synthesized by following general procedure GP-A. MS consistent.

Step C: (S)-2-(3-propylmorpholino)benzoxazole-4-carboxylic acid was synthesized by following general procedure GP-B3. MS consistent.

Step D: Following general procedure GP-C3, (S)-2-(3-propylmorpholino)benzoxazole-4-carboxylic acid and endo-3-amino-9-methyl-9-azabicyclo[3.3.1]nonane dihydrochloride were coupled to provide endo-N-(9-methyl-9-azabicyclo[3.3.1]nonan-3-yl)-2-((S)-3-propylmorpholino)benzoxazole-4-carboxamide, which was converted to the hydrochloric acid salt following general procedure GP-D1. $^1$H NMR and MS consistent.

EXAMPLE 67

Preparation of Endo-N-(9-Methyl-9-azabicyclo[3.3.1]nonan-3-yl)-2-((S)-3-isobutylmorpholino)benzoxazole-4-carboxamide Hydrochloride Step A: To an ice cold, stirred suspension of NaH (60% in oil, 1.6 g, 39.0 mmol) in toluene (53 mL) was added dropwise a solution of (S)-2-amino-4-methylpentan-1-ol (2.0 g, 17.0 mmol) in toluene (37 mL). After the addition was completed, the reaction mixture was warmed to room temperature and a solution of ethyl chloroacetate (2.3 g, 19.0 mmol) in toluene (10 mL) was added in a dropwise manner. The resulting mixture was then stirred at reflux for 20 h, cooled to room temperature, and solid ammonium chloride (2.1 g, 39.0 mmol) was added to the reaction. The mixture was stirred for 20 min and then concentrated under reduced pressure. The crude material was purified by column chromatography (silica gel, 98:2 $CH_2Cl_2/CH_3OH$ to 95:5 $CH_2Cl_2/CH_3OH$) to give (S)-5-iso-butylmorpholin-3-one (1.9 g, 70%) as a light yellow oil. To ice-cold THF (8 mL) was added lithium aluminum hydride (1.0 M solution in THF, 23.0 mL, 23.0 mmol). Once the addition was complete, a solution of (S)-5-iso-butylmorpholin-3-one (1.8 g, 12.0 mmol) in THF (7.0 mL) was added dropwise over 20 min. Once the addition was completed, the ice bath was removed and the reaction mixture stirred at reflux for 20 h. The reaction was cooled in an ice-bath and to this was slowly added $H_2O$ (1.2 mL), then 15% aqueous solution of sodium hydroxide (1.2 mL), and then $H_2O$ (1.2 mL). The resulting mixture was stirred at room temperature for 1.5 h and then filtered washing the solids with EtOAc (50 mL). The filtrate was concentrated at room temperature under reduced pressure to provide (S)-3-iso-butylmorpholine (1.6 g, 95%) as a light yellow oil. $^1H$ NMR and MS consistent.

Step B: Following general method GP-A, (S)-3-iso-butylmorpholine (0.38 g, 2.6 mmol) and methyl 2-chlorobenzoxazole-4-carboxylate were converted to (S)-methyl-2-(3-iso-butylmorpholino)benzoxazole-4-carboxylate. MS consistent.

Step C: (S)-2-(3-iso-butylmorpholino)benzoxazole-4-carboxylic acid was synthesized by following general method GP-B3. MS consistent.

Step D: Following general method GP-C1, (S)-2-(3-iso-butylmorpholino)benzoxazole-4-carboxylic acid and endo-3-amino-9-methyl-9-azabicyclo[3.3.1]nonane dihydrochloride were coupled to provide endo-N-(9-methyl-9-azabicyclo[3.3.1]nonan-3-yl)-2-((S)-3-iso-butylmorpholino)benzoxazole-4-carboxamide, which was converted to the hydrochloride salt following general procedure GP-D1. $^1H$ NMR and MS consistent.

EXAMPLE 68

Preparation of Endo-N-(9-Methyl-9-azabicyclo[3.3.1]nonan-3-yl)-2-((S)-3-tert-butylmorpholino)benzoxazole-4-carboxamide Hydrochloride Step A: To an ice cold, stirred suspension of NaH (60% in oil, 1.6 g, 39.0 mmol) in toluene (53 mL) was added dropwise a solution of (S)-2-amino-4,5-dimethylpentan-1-ol (2.0 g, 17.0 mmol) in toluene (37 mL). After the addition was completed, the reaction mixture was warmed to room temperature and a solution of ethyl chloroacetate (2.3 g, 19.0 mmol) in toluene (10 mL) was added in a dropwise manner. The resulting mixture was then stirred at reflux for 20 h, cooled to room temperature, and solid ammonium chloride (2.1 g, 39.0 mmol) was added to the reaction. The mixture was stirred for 20 min and then concentrated under reduced pressure. The crude material was purified by column chromatography (silica gel, 98:2 $CH_2Cl_2/CH_3OH$ to 95:5 $CH_2Cl_2/CH_3OH$) to give (S)-5-tert-butylmorpholin-3-one (2.0 g, 74%) as a light yellow solid. To ice-cold THF (9 mL) was added $LiAlH_4$ (1.0 M solution in THF, 26.0 mL, 26.0 mmol). Once the addition was complete, a solution of (S)-5-tert-butylmorpholin-3-one (2.0 g, 13.0 mmol) in THF (8.0 mL) was added dropwise over 20 min. Once the addition was completed, the ice bath was removed and the reaction mixture stirred at reflux for 20 h. The reaction was cooled in an ice-bath and to his was slowly added $H_2O$ (1.2 mL), then 15% aqueous solution of sodium hydroxide (1.2 mL), and then $H_2O$ (1.2 mL). The resulting mixture was stirred at room temperature for 1.5 h and then filtered washing the solids with EtOAc (50 mL). The filtrate was concentrated at room temperature under reduced pressure to provide (S)-3-tert-butylmorpholine (1.7 g, 97%) as a light yellow oil. $^1H$ NMR and MS consistent.

Step B: Following general procedure GP-A, (S)-3-tert-butylmorpholine (0.38 g, 2.6 mmol and methyl 2-chlorobenzoxazole-4-carboxylate (0.28 g, 1.3 mmol) were converted to (S)-methyl-2-(3-tert-butylmorpholino)benzoxazole-4-carboxylate. MS consistent.

Step C: (S)-2-(3-tert-butylmorpholino)benzoxazole-4-carboxylic acid was synthesized by following general procedure GP-B3. MS consistent.

Step D: Following general procedure GP-$C_1$, (S)-2-(3-tert-butylmorpholino)benzoxazole-4-carboxylic acid and endo-3-amino-9-methyl-9-azabicyclo[3.3.1]nonane dihydrochloride were coupled to provide endo-N-(9-methyl-9-azabicyclo[3.3.1]nonan-3-yl)-2-((S)-3-tert-butylmorpholino)benzoxazole-4-carboxamide, which was converted to the hydrochloride salt following general procedure GP-D1. $^1H$ NMR and MS consistent.

EXAMPLE 69

Preparation of Endo-N-(9-Methyl-9-azabicyclo[3.3.1]nonan-3-yl)-2-((2R,6R)-2,6-dimethylpiperazin-1-yl)benzoxazole-4-carboxamide Hydrochloride Step A: To a solution of (2R,6R)-2,6-dimethylpiperazine dihydrochloride (1.60 g, 8.55 mmol), in $CH_2Cl_2$ (15 mL) at room temperature was added triethylamine (2.50 mL, 17.95 mmol) followed by di-tert butyldicarbonate (2.05 g, 9.40 mmol) and the reaction mixture was allowed to stir at room temperature 48 h. The reaction mixture was partitioned between EtOAc (20 mL) and saturated $NaHCO_3$ (20 mL). The aqueous phase was further extracted with EtOAc (2×20 mL). The combined organic phase was washed with brine (20 mL) and dried ($Na_2SO_4$). The crude product was purified by column chromatography (silica gel, 3 to 10% $CH_3OH$ in $CH_2Cl_2$) to afford (3R,5R)-tert-butyl 3,5-dimethylpiperazine-1-carboxylate (1.17 g, 64%) as a clear oil. $^1H$ NMR and MS consistent.

Step B: Following general procedure GP-A except that the reaction was heated in DMF at 40° C., (3R,5R)-tert-butyl 3,5-dimethylpiperazine-1-carboxylate (500 mg, 2.33 mmol) and methyl 2-chlorobenzoxazole-4-carboxylate were converted to methyl 2-((2R,6R)-4-(tert-butoxycarbonyl)-2,6-dimethylpiperazin-1-yl)benzoxazole-4-carboxylate. $^1H$ NMR and MS consistent.

Step C: Following general procedure GP-B2, methyl 2-((2R,6R)-4-(tert-butoxycarbonyl)-2,6-dimethylpiperazin-1-yl)benzoxazole-4-carboxylate was converted to lithium 2-((2R,6R)-4-(tert-butoxycarbonyl)-2,6-dimethylpiperazin-1-yl)benzoxazole-4-carboxylate. MS consistent.

Step D: Following general procedure GP-C2 at 40° C., lithium 2-((2R,6R)-4-(tert-butoxycarbonyl)-2,6-dimethylpiperazin-1-yl)benzoxazole-4-carboxylate and endo-3-amino-9-methyl-9-azabicyclo[3.3.1]nonane dihydrochloride were coupled to provide endo-N-(9-methyl-9-azabicyclo[3.3.1]nonan-3-yl)-2-((2R,6R)-4-(tert-butoxycarbonyl)-2,6-dimethylpiperazin-1-yl)benzoxazole-4-carboxylate. $^1$H NMR and MS consistent.

Step E: To solution of endo-N-(9-methyl-9-azabicyclo[3.3.1]nonan-3-yl)-2-((2R,6R)-4-(tert-butoxycarbonyl)-2,6-dimethylpiperazin-1-yl)benzoxazole-4-carboxylate (387 mg, 0.756 mmol) in $CH_2Cl_2$/dioxane/$CH_3OH$ (2:1:1, 8 mL) was added HCl (4 M in dioxane, 3.78 mL, 15.12 mmol) and the mixture was stirred at room temperature for 24 h then concentrated under reduced pressure. The amorphous solid was lyophilized from acetonitrile/$H_2O$ (10:1, 22 mL) to afford endo-N-(9-methyl-9-azabicyclo[3.3.1]nonan-3-yl)-2-((2R,6R)-2,6-dimethylpiperazin-1-yl)benzoxazole-4-carboxamide dihydrochloride (361 mg, 98%) as a brown solid. $^1$H NMR and MS consistent.

EXAMPLE 70

Preparation of Endo-N-(9-Methyl-9-azabicyclo[3.3.1]nonan-3-yl)-2-(cyclohexylamino)benzoxazole-4-carboxamide Hydrochloride Step A: Following general procedure GP-A, methyl 2-chlorobenzoxazole-4-carboxylate and cyclohexylamine and were converted to methyl 2-(cyclohexylamino)benzoxazole-4-carboxylate. $^1$H NMR and MS consistent.

Step B: Methyl 2-(cyclohexylamino)benzoxazole-4-carboxylate (220 mg, 0.80 mmol), lithium hydroxide monohydrate (50 mg, 1.20 mmol) and a mixture of THF and $H_2O$ (10:1, 11 mL) was stirred at room temperature for 17 h. The mixture was diluted with $H_2O$ and loaded onto an anion exchange resin (Isolute SAX, 10 g Column). The column was washed with $H_2O$ (50 mL) and eluted with 0.1 N aqueous HCl (50 mL). The solvent was removed under reduced pressure to afford 2-(cyclohexylamino)benzoxazole-4-carboxylic acid hydrochloride (188 mg, 79%) as a pink solid. $^1$H NMR and MS consistent.

Step C: Following general procedure GP-C1, 2-(cyclohexylamino)benzoxazole-4-carboxylic acid hydrochloride and endo-3-amino-9-methyl-9-azabicyclo[3.3.1]nonane dihydrochloride were coupled to provide endo N-(9-methyl-9-azabicyclo[3.3.1]nonan-3-yl)-2-(cyclohexylamino)benzoxazole-4-carboxamide, which was converted to the hydrochloride salt following general procedure GP-D1. $^1$H NMR and MS consistent.

EXAMPLE 71

Preparation of Endo-N-(9-Methyl-9-azabicyclo[3.3.1]nonan-3-yl)-2-((2S)-2-isobutyl-4-benzylpiperazin-1-yl)benzoxazole-4-carboxamide Hydrochloride Step A: To a solution of (2S)-4-benzyl-2-isobutylpiperazine (100 mg, 0.52 mmol) in 1,2-dimethoxyethane (DME) (10 mL) at room temperature, was added NaH (21 mg, 0.52 mmol, 60% suspension in mineral oil) and the mixture was stirred for 1 h. Methyl 2-chlorobenzoxazole-4-carboxylate (110 mg, 0.52 mmol) was added to the reaction mixture and the reaction was stirred at room temperature for 17 h. The reaction mixture was quenched with $CH_3OH$ (10 mL), silica gel (15 mL) was added, and solvent removed under reduced pressure. The mixture was purified by column chromatography (silica gel, 0 to 100% EtOAc in hexanes) to afford (S)-methyl 2-(4-benzyl-2-isobutylpiperazine-1-yl)benzoxazole-4-carboxylate (133 mg, 62%) as a pale yellow oil. $^1$H NMR and MS consistent.

Step B: (S)-2-(4-benzyl-2-isobutylpiperazine-1-yl)benzoxazole-4-carboxylic acid was synthesized by following general procedure GP-B3. MS consistent.

Step C: Following general procedure GP-$C_1$, (S)-2-(4-benzyl-2-isobutylpiperazine-1-yl)benzoxazole-4-carboxylic acid and endo-3-amino-9-methyl-9-azabicyclo[3.3.1]nonane dihydrochloride were coupled were coupled to provide endo-N-(9-methyl-9-azabicyclo[3.3.1]nonan-3-yl)-2-((2S)-2-isobutyl-4-benzylpiperazin-1-yl)benzoxazole-4-carboxamide, which was converted to the hydrochloride salt following general procedure GP-D1. $^1$H NMR and MS consistent.

EXAMPLE 72

Preparation of Endo N-(9-methyl-9-azabicyclo[3.3.1]nonan-3-yl)-2-thioxo-2,3-dihydrobenzoxazole-4-carboxamide Hydrochloride Step A: To a solution of methyl 2-thioxo-2,3-dihydrobenzoxazole-4-carboxylate (150 mg, 0.72 mmol) in THF (6 mL) was added a solution of lithium hydroxide monohydrate (45.1 mg, 1.08 mmol) in $H_2O$ (3 mL). The reaction mixture was heated to 75° C. with stirring for 3 days, cooled down to room temperature and concentrated under reduced pressure to afford the lithium 2-thioxo-2,3-dihydrobenzoxazole-4-carboxylate (135 mg, 96.5%) as a yellow solid. MS consistent Step B: Following general procedure GP-C1, lithium 2-thioxo-2,3-dihydrobenzoxazole-4-carboxylate and endo-3-amino-9-methyl-9-azabicyclo[3.3.1]nonane dihydrochloride were coupled to provide endo N-(9-methyl-9-azabicyclo[3.3.1]nonan-3-yl)-2-thioxo-2,3-dihydrobenzoxazole-4-carboxamide, which was converted to the hydrochloride salt following general procedure GP-D1. $^1$H NMR and MS consistent.

EXAMPLE 73

Preparation of Endo-N-(9-Methyl-9-azabicyclo[3.3.1]nonan-3-yl)-2-((2S,6S)-2,6-dimethylpiperazin-1-yl)benzoxazole-4-carboxamide Hydrochloride Step A: To a solution of (2S,6S)-2,6-dimethylpiperazine dihydrochloride (0.30 g, 1.63 mmol), in $CH_2Cl_2$ (10 mL) at room temperature was added triethylamine (0.48 mL, 3.42 mmol) followed by di-tert butyldicarbonate (0.39 g, 1.79 mmol) and the reaction mixture was allowed to stir at room temperature 48 h. The reaction mixture was partitioned between EtOAc (20 mL) and saturated $NaHCO_3$ (20 mL). The aqueous phase was further extracted with EtOAc (2×20 mL). The combined organic phase was washed with brine (20 mL) and dried ($Na_2SO_4$). The crude product was purified by column chromatography (silica gel, 3 to 10% $CH_3OH$ in $CH_2Cl_2$) to afford (3S,5S)-tert-butyl 3,5-dimethylpiperazine-1-carboxylate (0.34 g, 52%) as a clear oil. $^1$H NMR and MS consistent.

Step B: Following general procedure GP-A except in DMF at 40° C., (3S,5S)-tert-butyl 3,5-dimethylpiperazine-1-carboxylate (500 mg, 2.33 mmol) and methyl 2-chlorobenzoxazole-4-carboxylate were converted to methyl 2-((2S,6S)-4-

(tert-butoxycarbonyl)-2,6-dimethylpiperazin-1-yl) benzoxazole-4-carboxylate. $^1$H NMR and MS consistent.

Step C: Lithium 2-((2S,6S)-4-(tert-butoxycarbonyl)-2,6-dimethylpiperazin-1-yl)benzoxazole-4-carboxylate was synthesized by following general procedure GP-B2. MS consistent.

Step D: Following general procedure GP-C2 at 40° C., lithium 2-((2S,6S)-4-(tert-butoxycarbonyl)-2,6-dimethylpiperazin-1-yl)benzoxazole-4-carboxylate and endo-3-amino-9-methyl-9-azabicyclo[3.3.1]nonane dihydrochloride were coupled to provide endo-N-(9-methyl-9-azabicyclo[3.3.1]nonan-3-yl)-2-((2S,6S)-4-(tert-but oxycarbonyl)-2,6-dimethylpiperazin-1-yl)benzoxazole-4-carboxylate, which was converted to the hydrochloride salt following general procedure GP-D2. $^1$H NMR and MS consistent.

EXAMPLE 74

Preparation of Endo-N-(9-Methyl-9-azabicyclo [3.3.1]nonan-3-yl)-2-((3S)-3-isobutylpiperazine-1-yl)benzoxazole-4-carboxamide Hydrochloride Step A: To a solution of 1-tert-butyloxycarbonyl-(2S)-2-isobutylpiperazine (384 mg, 1.6 mmol) in DME (10 mL) was added NaH (70 mg of 60% suspension in mineral oil, 1.6 mmol) and the mixture was stirred for 1 h at room temperature. Methyl 2-chlorobenzoxazole-4-carboxylate (368 mg, 1.6 mmol) was added to the reaction mixture and suspension formed was stirred at room temperature for 17 h. The reaction mixture was quenched with $CH_3OH$ (10 mL), silica gel (15 mL) was added, and solvent removed under reduced pressure. The mixture was purified by column chromatography ((silica gel, 0 to 80% EtOAc in $CH_2Cl_2$) to afford methyl 2-(4-(tert-butoxycarbonyl)-(3S)-3-isobutylpiperazine-1-yl)benzoxazole-4-carboxylate (219 mg, 32%) as a clear oil: $^1$H NMR and MS consistent.

Step B: Following general method GP-B3, methyl 2-(4-(tert-butoxycarbonyl)-(3S)-3-isobutylpiperazine-1-yl)benzoxazole-4-carboxylate was converted to 2-(4-(tert-butoxycarbonyl)-(3S)-3-isobutylpiperazine-1-yl)benzoxazole-4-carboxylic acid. MS consistent.

Step C: Following general procedure GP-C1,2-(4-(tert-butoxycarbonyl)-(3S)-3-isobutylpiperazine-1-yl)benzoxazole-4-carboxylic acid and endo-3-amino-9-methyl-9-azabicyclo[3.3.1]nonane dihydrochloride were coupled to provide endo-N-(9-methyl-9-azabicyclo[3.3.1]nonan-3-yl)-2-(3S)-3-isobutyl-4-tert-butoxycarbonylpiperazin-1-yl)benzoxazole-4-carboxamide, which was converted to the hydrochloride salt following general procedure GP-D2. $^1$H NMR and MS consistent.

EXAMPLE 75

Preparation of Endo-N-(9-Methyl-9-azabicyclo [3.3.1]nonan-3-yl)-2-((3S,5S)-3,5-dimethylmorpholino)benzoxazole-4-carboxamide Hydrochloride Step A: To a solution of (3S,5S)-dimethylmorpholine (209 mg, 1.82 mmol) in 1,2-dimethoxyethane (10 mL) was added NaH(60% suspension in mineral oil, 146 mg, 3.64 mmol). After 10 min the reaction mixture was cooled to 0° C. and methyl 2-chlorobenzoxazole-4-carboxylate (500 mg, 2.36 mmol) was added portion-wise over 5 min. After 10 min, the reaction mixture was warmed to ambient temperature and allowed to stir for 3 days. The reaction mixture was quenched with $CH_3OH$ (10 mL) and then dry loaded onto silica gel (4.5 g). Purification by chromatography (silica gel, 0 to 20% EtOAc in hexanes) gave a 1:1 mixture of methyl 2-((3S,5S)-3,5-dimethylmorpholino)benzoxazole-4-carboxylate and methyl 2-oxo-2,3-dihydrobenzoxazole-4-carboxylate (312 mg, 59%) as an off-white solid. MS consistent.

Step B: Lithium 2-((3S,5S)-3,5-dimethylmorpholino)benzoxazole-4-carboxylate was synthesized by following general procedure GP-B2 which was directly elaborated without purification.

Step C: Following general procedure GP-C1, lithium 2-((3S,5S)-3,5-dimethylmorpholino)benzoxazole-4-carboxylate and endo-3-amino-9-methyl-9-azabicyclo[3.3.1] nonane dihydrochloride were coupled to provide endo-N-(9-methyl-9-azabicyclo[3.3.1]nonan-3-yl)-2-((3S,5S)-3,5-dimethylmorpholino)benzoxazole-4-carboxamide, which was converted to the hydrochloride salt following general procedure GP-D1. $^1$H NMR and MS consistent.

EXAMPLE 76

Preparation of Endo-N-(9-Methyl-9-azabicyclo [3.3.1]nonan-3-yl)-2-((S)-2-isopropylpiperazin-1-yl) benzoxazole-4-carboxamide Hydrochloride Step A: To a solution of (2S)-4-benzyl-2-isopropylpiperazine (363 mg, 1.66 mmol) in 1,2-dimethoxyethane (10 mL) at room temperature, was added NaH (80 mg, 1.66 mmol, 60% suspension in mineral oil) and the mixture was stirred for 1 h. Methyl 2-chlorobenzoxazole-4-carboxylate (351 mg, 1.66 mmol) was added to the reaction mixture and the reaction was stirred at room temperature for 17 h. The reaction mixture was quenched with $CH_3OH$ (10 mL), silica gel (15 mL) was added, and solvent removed under reduced pressure. The mixture was purified by column chromatography (silica gel, 0 to 100% EtOAc in hexanes) to afford (S)-methyl 2-(4-benzyl-2-isopropylpiperazin-1-yl)benzoxazole-4-carboxylate (355 mg, 54%) as a pale yellow oil. MS consistent.

Step B: (S)-2-(4-benzyl-2-isopropylpiperazin-1-yl)benzoxazole-4-carboxylic acid was synthesized following general procedure GP-B2. MS consistent.

Step C: Following general procedure GP-C$_1$, a mixture of (S)-2-(4-benzyl-2-isopropylpiperazin-1-yl)benzoxazole-4-carboxylic acid and endo-3-amino-9-methyl-9-azabicyclo [3.3.1]nonane dihydrochloride were coupled to provide endo-N-(9-methyl-9-azabicyclo[3.3.1]nonan-3-yl)-2-((4-benzyl-(S)-2-isopropylpiperazin-1-yl)benzoxazole-4-carboxamide except the material was purified by column chromatography (silica gel, 100% $CH_2Cl_2$ to 20:76.5:3.5 $CH_2Cl_2$/$CH_3OH$/$NH_4OH$). $^1$H NMR and MS consistent.

Step D: To a solution of endo-N-(9-methyl-9-azabicyclo [3.3.1]nonan-3-yl)-2-((4-benzyl-(S)-2-isopropylpiperazin-1-yl)benzoxazole-4-carboxamide (0.230 g, 0.44 mmol) in 1,2-dichloroethane (2 mL) was added 1-chloroethylchloroformate (0.12 mL, 1.10 mmol) and the mixture was stirred for 10 h at room temperature and for 10 h at 55° C. Additional 1-chloroethylchloroformate (0.1 mL, 0.8 mmol) was added and heating was continued for 6 h at 55° C. The solvent was removed under reduced pressure, and the residue consecutively purified by column chromatography (silica gel, 10:1: 0.1 $CH_2Cl_2$/$CH_3OH$/concentrated $NH_4OH$) and preparative HPLC (Luna C18(2), 10% $CH_3CN$/0.05% TFA in $H_2O$/0.05% TFA to 100% $CH_3CN$/0.05% TFA over 20 min, hold for 15 min, l=223 nm). The fractions containing desired product were combined and concentrated. The residue was

49 converted to the hydrochloride salt following general procedure GP-D2. ¹H NMR and MS consistent.

EXAMPLE 77

Preparation of Endo-N-(9-Methyl-9-azabicyclo[3.3.1]nonan-3-yl)-2-((S)-2-isobutylpiperazine-1-yl)benzoxazole-4-carboxamide Hydrochloride Step A: To a solution of (S)-1-tert-butoxycarbonyl-2-isobutylpiperazine (973 mg, 4.0 mmol) in DME (15 mL) was added sodium hydride (o 60% suspension in mineral oil, 160 mg, 4.0 mmol) and the mixture was stirred for 45 min at room temperature. A solution of allyl bromide (0.35 mL, 4.0 mmol) in DMF (5 ml) was added to the reaction mixture and suspension formed was stirred at room temperature for 3 days. The solvent was removed under reduced pressure to afford a dark oil (1.06 g). The oil obtained was dissolved in $CH_2Cl_2$ (10 mL) and treated with TFA (5 mL). The resulting solution was stirred at room temperature for 18 h. The solvent was removed under reduced pressure; the residue was dissolved in $CH_2Cl_2$ and extracted with a saturated aqueous $NaHCO_3$ solution. The organic phase was washed with brine, $H_2O$, dried over $Na_2SO_4$, and concentrated. The residue was dissolved to $CH_3OH$ (5 mL) and passed through ion exchange SCX-2 column to afford (3S)-1-allyl-3-isobutylpiperazine (0.44 g, 60%). ¹H NMR and MS consistent.

Step B: To a solution of (S)-1-allyl-3-isobutylpiperazine (442 mg, 2.42 mmol) in DME (10 mL) at room temperature, was added NaH (60% suspension in mineral oil, 100 mg, 2.42 mmol) and the mixture was stirred for 45 min. Methyl 2-chlorobenzoxazole-4-carboxylate (510 mg, 2.42 mmol) was added to the reaction mixture and the reaction was stirred at room temperature for 17 h. The reaction mixture was quenched with $CH_3OH$ (10 mL), silica gel (15 mL) was added, and solvent removed under reduced pressure. The mixture was purified by column chromatography (silica gel, 10:1:0.1 $CH_2Cl_2/CH_3OH$/concentrated $NH_4OH$) to afford methyl 2-(4-allyl-(S)-2-isobutylpiperazine-1-yl)benzoxazole-4-carboxylate (372 mg, 43%) as a yellow oil. ¹H NMR and MS consistent.

Step C: 2-(4-allyl-(S)-2-isobutylpiperazine-1-yl)benzoxazole-4-carboxylic acid was synthesized by following general procedure GP-B3. MS consistent.

Step D: Following general procedure GP-C₁, a mixture of 2-(4-allyl-(S)-2-isobutylpiperazine-1-yl)benzoxazole-4-carboxylic acid and endo-3-amino-9-methyl-9-azabicyclo[3.3.1]nonane dihydrochloride were coupled to provide endo-N-(9-methyl-9-azabicyclo[3.3.1]nonan-3-yl)-2-((S)-2-isobutyl-4-allylpiperazin-1-yl)benzoxazole-4-carboxamide. MS consistent.

Step E: A solution of endo-N-(9-methyl-9-azabicyclo[3.3.1]nonan-3-yl)-2-((S)-2-isobutyl-4-allylpiperazin-1-yl)benzoxazole-4-carboxamide (180 mg, 0.37 mmol), barbituric acid (284 mg, 1.2 mmol) and tetrakis(triphenylphosphine)palladium(0) (40 mg, 0.037 mmol, 10 mol %) in DMF (8 mL) was stirred for 17 h at 60° C. in argon atmosphere. The mixture was poured into saturated $NaHCO_3$ (100 mL) and extracted with $CH_2Cl_2$ (3×50 mL). The combined organic phase was washed sequentially with brine (100 mL), H2O (100 mL), dried ($Na_2SO_4$), filtered and concentrated. The crude material was purified by preparative TLC (silica gel, 10:1:0.1 $CH_2Cl_2/CH_3OH$/concentrated $NH_4OH$) to afford endo-N-(9-methyl-9-azabicyclo[3.3.1]nonan-3-yl)-2-((S)-2-isobutylpiperazine-1-yl)benzoxazole-4-carboxamide (62

50 mg, 3 8%), which was converted to the hydrochloride salt following general procedure GP-D1. ¹H NMR and MS consistent.

EXAMPLE 78

Preparation of Endo-N-(9-Methyl-9-azabicyclo[3.3.1]nonan-3-yl)-2-((S)-3-propylpiperazin-1-yl)benzoxazole-4-carboxamide Hydrochloride Step A: To a solution of 1-tert-butyloxycarbonyl-(S)-2-isopropylpiperazine (384 mg, 1.7 mmol) in DME (10 mL) was added NaH (70 mg of 60% suspension in mineral oil, 1.6 mmol) and the mixture was stirred for 1 h at room temperature. Methyl 2-chlorobenzoxazole-4-carboxylate (368 mg, 1.6 mmol) was added to the reaction mixture and suspension formed was stirred at room temperature for 17 h. The reaction mixture was quenched with $CH_3OH$ (10 mL), silica gel (15 mL) was added, and solvent removed under reduced pressure. The mixture was purified by column chromatography (silica gel, 0 to 80% EtOAc in $CH_2Cl_2$) to afford methyl 2-(4-(tert-butoxycarbonyl)-(S)-3-isopropylpiperazin-1-yl)benzoxazole-4-carboxylate (255 mg, 39%) as a white foam. ¹H NMR and MS consistent.

Step B: 2-(4-(tert-butoxycarbonyl)-(S)-3-isopropylpiperazin-1-yl)benzoxazole-4-carboxylic acid was synthesized by following general procedure GP-B2, methyl 2-(4-(tert-butoxycarbonyl)-(S)-3-propylpiperazin-1-yl)benzoxazole-4-carboxylate was converted to. MS consistent.

Step C: Following general procedure GP-C₁, a mixture of 2-(4-(tert-butoxycarbonyl)-(S)-3-isopropylpiperazin-1-yl)benzoxazole-4-carboxylic acid and endo-3-amino-9-methyl-9-azabicyclo[3.3.1]nonane dihydrochloride were coupled to provide endo-N-(9-methyl-9-azabicyclo[3.3.1]nonan-3-yl)-2-((S)-3-isopropyl-4-tert-butoxycarbonylpiperazin-1-yl)benzoxazole-4-carboxamide. ¹H NMR and MS consistent.

Step D: A solution of endo-N-(9-methyl-9-azabicyclo[3.3.1]nonan-3-yl)-2-((S)-3-isopropyl-4-tert-butoxycarbonylpiperazin-1-yl)benzoxazole-4-carboxamide (230 mg, 0.43 mmol) in $CH_2Cl_2$ was treated with TFA (0.33 mL, 4.3 mmol). The mixture was stirred at room temperature for 17 h. The solvent was removed under vacuum, and the residue was neutralized by ion-exchange chromatography (SCX-2 column, 5 g) to afford endo-N-(9-methyl-9-azabicyclo[3.3.1]nonan-3-yl)-2-((S)-3-isopropylpiperazin-1-yl)benzoxazole-4-carboxamide which was converted to the hydrochloride salt following general procedure GP-D1. ¹H NMR and MS consistent.

EXAMPLE 79

Preparation of Endo-N-(9-Methyl-9-azabicyclo[3.3.1]nonan-3-yl)-2-(5,6-dihydroimidazo[1,2-a]pyrazin-7(8H)-yl)benzoxazole-4-carboxamide Hydrochloride Step A: To a solution of NaH (60% dispersion in mineral oil, 0.130 g, 3.25 mmol) in THF (10 mL) was added 5,6,7,8-tetrahydroimidazo[1,2-a]pyrazine (0.33 g, 2.71 mmol) and the reaction mixture stirred for 10 min. Methyl 2-chlorobenzoxazole-4-carboxylate (478 mg, 2.26 mmol), in THF (10 mL) was added and the reaction mixture was allowed to stir at room temperature 17 h. The reaction mixture was quenched with $CH_3OH$ (3 mL), and adsorbed onto silica gel (2 g). The crude product was purified by column chromatography (silica gel, 0.5 to 10% $CH_3OH$ in $CH_2Cl_2$) to afford methyl 2-(5,6- dihydroimidazo[1,2-a]pyrazin-7(8H)-yl)benzoxazole-4-carboxylate (251 mg, 37%) as an orange oil. $^1$H NMR and MS consistent.

Step B: Lithium 2-(5,6-dihydroimidazo[1,2-a]pyrazin-7(8H)-yl)benzoxazole-4-carboxylate was synthesized by following general procedure GP-B2. MS consistent.

Step C: Following general procedure GP-C1, a mixture of lithium 2-(5,6-dihydroimidazo[1,2-a]pyrazin-7(8H)-yl)benzoxazole-4-carboxylate (243 mg, 0.84 mmol) and endo-3-amino-9-methyl-9-azabicyclo[3.3.1]nonane dihydrochloride (229 mg, 1.01 mmol) were coupled to provide endo-N-(9-methyl-9-azabicyclo[3.3.1]nonan-3-yl)-2-(5,6-dihydroimidazo[1,2-a]pyrazin-7(8H)-yl)benzoxazole-4-carboxamide which was converted to the hydrochloride salt following general procedure GP-D1. $^1$H NMR and MS consistent.

EXAMPLE 80

Preparation of Endo N-(9-Methyl-9-azabicyclo[3.3.1]nonan-3-yl)-2-((S)-3-tert-butylmorpholino)-6-chloro-benzoxazole-4-carboxamide Hydrochloride Step A: To an ice cold, stirred suspension of NaH (60% in oil, 1.6 g, 39.0 mmol) in toluene (53 mL) was added drop wise a solution of (S)-2-amino-4,5-dimethylpentan-1-ol (2.0 g, 17.0 mmol) in toluene (37 mL). After the addition was completed, the reaction mixture was warmed to room temperature and a solution of ethyl chloroacetate (2.3 g, 19.0 mmol) in toluene (10 mL) was added in a drop wise manner. The resulting mixture was then stirred at reflux for 20 h, cooled to room temperature, and solid ammonium chloride (2.1 g, 39.0 mmol) was added to the reaction. The mixture was stirred for 20 min and then concentrated under reduced pressure. The crude material was purified by column chromatography (silica gel, 98:2 $CH_2Cl_2/CH_3OH$ to 95:5 $CH_2Cl_2/CH_3OH$) to give (S)-5-tert-butylmorpholin-3-one (2.0 g, 74%) as a light yellow solid. To ice-cold THF (9 mL) was added lithium aluminum hydride (1.0 M solution in THF, 26.0 mL, 26.0 mmol). Once the addition was complete, a solution of (S)-5-tert-butylmorpholin-3-one (2.0 g, 13.0 mmol) in THF (8.0 mL) was added drop wise over 20 min. Once the addition was completed, the ice bath was removed and the reaction mixture stirred at reflux for 20 h. The reaction was cooled in an ice-bath and to his was slowly added $H_2O$ (1.2 mL), then 15% aqueous solution of NaOH (1.2 mL), and then $H_2O$ (1.2 mL). The resulting mixture was stirred at room temperature for 1.5 h and then filtered washing the solids with EtOAc (50 mL). The filtrate was concentrated at room temperature under reduced pressure to provide (S)-3-tert-butylmorpholine (1.7 g, 97%) as a light yellow oil. $^1$H NMR consistent.

Step B: To a solution of methyl 2,6-dichlorobenzoxazole-4-carboxylate (515 mg, 2.09 mmol) in THF (15 mL) was added (S)-3-tert-butylmorpholine (600 mg, 4.19 mmol). The mixture was stirred at room temperature for 5 days. The reaction mixture was concentrated to dryness. The crude material was purified by column chromatography (silica gel, 2% EtOAc in hexane) to afford the desired methyl(S)-methyl 2-(3-tert-butylmorpholino)-6-chlorobenzoxazole-4-carboxylate (149 mg, 20.2%) as yellow solid. MS consistent.

Step C: Following general procedure GP-B2, (S)-methyl 2-(3-tert-butylmorpholino)-6-chlorobenzoxazole-4-carboxylate was converted to lithium (S)-2-(3-tert-butylmorpholino)-6-chlorobenzoxazole-4-carboxylate. MS consistent.

Step D: Following general procedure GP-C$_1$, a mixture of lithium (S)-2-(3-tert-butylmorpholino)-6-chlorobenzoxazole-4-carboxylate and 9-methyl-9-azabicyclo[3.3.1]nonan-3-amine dihydrochloride were coupled to afford endo N-(9-methyl-9-azabicyclo[3.3.1]nonan-3-yl)-2-((S)-3-tert-butylmorpholino)benzoxazole-4-carboxamide which was converted to the hydrochloride salt following general procedure GP-D1. $^1$H NMR and MS consistent.

EXAMPLE 81

Preparation of Endo-N-(9-Azabicyclo[3.3.1]nonan-3-yl)-2-((3S,5S)-3,5-dimethylmorpholino)benzoxazole-4-carboxamide Hydrochloride To endo-N-(9-methyl-9-azabicyclo[3.3.1]nonan-3-yl)-2-((3S,5S)-3,5-dimethylmorpholino)benzoxazole-4-carboxamide (107 mg, 0.24 mmol) in $CH_2Cl_2$ (3 ml), at 0° C., was added 1,8-bis(dimethylamino)naphthalene (10 mg, 0.048 mmol) and 1-chloroethyl chloroformate (0.21 mL, 1.90 mmol). After stirring at 0° C. for 0.5 h, the reaction mixture was heated to reflux. After 2 h, additional 1,8-bis(dimethylamino)naphthalene (10 mg, 0.048 mmol) was added. After another 0.5 h, more 1,8-bis(dimethylamino)naphthalene (10 mg, 0.048 mmol) and 1-chloroethyl chloroformate (0.21 mL, 1.90 mmol) were added. After 3 h, the reaction mixture was cooled to ambient temperature and stirred overnight. Next, additional 1,8-bis(dimethylamino)-naphthalene (20 mg, 0.096 mmol) and 1-chloroethyl chloroformate (0.21 mL, 1.90 mmol) were added and the reaction mixture was heated to reflux. After 7.5 h, more 1-chloroethyl chloroformate (0.21 mL, 1.90 mmol) was added and the reaction mixture was refluxed overnight. The reaction mixture was cooled to ambient temperature and concentrated under reduced pressure. $CH_3OH$ (5 mL) was added and the solution was heated to reflux. After 1.5 h, the reaction mixture was concentrated and the resulting residue was dissolved in $CH_2Cl_2$ (20 mL). The organic layer was washed with saturated $NaHCO_3$ (10 mL), brine (10 mL), dried ($Na_2SO_4$) and concentrated under reduced pressure. The crude material was purified by column chromatography (silica gel, 9:1 $CH_2Cl_2/CH_3OH$ to 90:9:1 $CH_2Cl_2/CH_3OH$/concentrated $NH_4OH$) to afford endo-N-(9-azabicyclo[3.3.1]nonan-3-yl)-2-((3 S,5S)-3,5-dimethylmorpholino)benzoxazole-4-carboxamide (62 mg). This material was dissolved in acetonitrile/$H_2O$ (1:4, 10 mL) and HCl (1 N in diethyl ether, 0.31 mL, 0.31 mmol) was added. The solution was lyophilized to afford endo-N-(9-azabicyclo[3.3.1]nonan-3-yl)-2-((3S,5S)-3,5-dimethylmorpholino)benzoxazole-4-carboxamide hydrochloride (71 mg, 68%) as a white powder. $^1$H NMR and MS consistent.

EXAMPLE 82

Preparation of Endo-N-(9-Methyl-9-azabicyclo[3.3.1]nonan-3-yl)-2-(thiomorpholine 1,1-dioxide)benzoxazole-4-carboxamide Hydrochloride Step A: A solution of methyl 2-chlorobenzoxazole-4-carboxylate (1.0 g, 4.7 mmol) and thiomorpholine (1.4 mL, 14 mmol) in THF (20 mL) was stirred at ambient temperature for 1 h. Then, the reaction mixture was poured into EtOAc (100 mL) and washed with 1N HCl (20 mL), $H_2O$ (20 mL), brine (20 mL), dried ($Na_2SO_4$) and concentrated under reduced pressure. Purification by chromatography (silica gel, 5 to 50% EtOAc in hexanes) gave methyl 2-thiomorpholinobenzoxazole-4-carboxylate (1.1 g, 84%) as a yellow solid. $^1$H NMR and MS consistent.

Step B: To methyl 2-thiomorpholinobenzoxazole-4-carboxylate (500 mg, 1.79 mmol) in $CH_3OH$ (10 mL) was added potassium peroxymonosulfate (1.95 g, 5.39 mmol) in $H_2O$ (10 mL). The yellow slurry was stirred at ambient temperature for 2 h and then concentrated under reduced pressure. The residue was taken up in $H_2O$ (30 mL) and extracted with chloroform (3×25 mL). The combined organic layers were washed with $H_2O$ (20 mL), brine (20 mL), dried ($Na_2SO_4$) and concentrated under reduced pressure to give methyl 2-(thiomorpholine 1,1-dioxide)benzoxazole-4-carboxylate (528 mg, 95%) as a yellow solid. $^1H$ NMR consistent.

Synthesis of lithium 2-(thiomorpholine 1,1-dioxide)benzoxazole-4-carboxylate: Following general procedure GP-B2, methyl 2-(thiomorpholine 1,1-dioxide)benzoxazole-4-carboxylate was converted to lithium 2-(thiomorpholine 1,1-dioxide)benzoxazole-4-carboxylate which was directly elaborated without purification.

Step C: Following general procedure GP-$C_1$, a mixture of lithium 2-(thiomorpholine 1,1-dioxide)benzoxazole-4-carboxylate and endo-3-amino-9-methyl-9-azabicyclo[3.3.1]nonane dihydrochloride were coupled except, after stirring at ambient temp for 12 h, the reaction mixture was heated in a 50° C. oil bath for 6 h. After the usual work-up, the residue was dissolved in $CH_2Cl_2$ (5 mL) and HCl (1 M solution in diethyl ether, 1.1 mL, 1.1 mmol) was added. The mixture was concentrated under reduced pressure. The residue was taken up in diethyl ether (10 mL) and a solid precipitated out of solution. The material was further purified by semi-preparative HPLC (Luna C18(2), 10% $CH_3CN$/0.05% TFA in $H_2O$/0.05% TFA to 100% $CH_3CN$/0.05% TFA over 30 min, l=223 nm). The desired fractions were combined and concentrated under reduced pressure. The residue was dissolved in $CH_2Cl_2$ (35 mL) and was washed with saturated $NaHCO_3$ (20 mL), $H_2O$ (20 mL), brine (20 mL), dried ($Na_2SO_4$) and concentrated under reduced pressure. To the residue was added an excess of HCl (1 M solution in diethyl ether) and the solution was concentrated under reduced pressure. The material was lyophilized from acetonitrile/$H_2O$ (1:1, 6 mL) to afford endo-N-(9-methyl-9-azabicyclo[3.3.1]nonan-3-yl)-2-(thiomorpholine 1,1-dioxide)benzoxazole-4-carboxamide hydrochloride. $^1H$ NMR and MS consistent.

EXAMPLE 83

Preparation of (S)—N-(quinuclidine-8-yl)-2-(ethyl (methyl)amino)benzoxazole-4-carboxamide Hydrochloride Step A: Following general procedure GP-A, methyl 2-chlorobenzoxazole-4-carboxylate and N-ethylmethanamine were converted to methyl 2-(ethyl(methyl)amino) benzoxazole-4-carboxylate except, the mixture was stirred at room temperature for 16 h and not heated. Also, the crude material was purified by column chromatography (silica gel, 40% EtOAc in hexane). MS consistent.

Step B: Lithium 2-(ethyl(methyl)amino)benzoxazole-4-carboxylate was synthesized by following general procedure GP-B2. MS consistent.

Step C: Following general procedure GP-$C_1$, a mixture of lithium 2-(ethyl(methyl)amino)benzoxazole-4-carboxylate and (S)-(−)-3-aminoquinuclidine dihydrochloride were coupled and to afford (S)—N-(quinuclidine-8-yl)-2-(ethyl (methyl)amino)benzoxazole-4-carboxamide, which was converted to the hydrochloride salt following general procedure GP-D1. $^1H$ NMR and MS consistent.

EXAMPLE 84

Preparation of Endo-N-(9-Methyl-9-azabicyclo [3.3.1]nonan-3-yl)-2-((S)-2-ethylpiperazine-1-yl) benzoxazole-4-carboxamide Hydrochloride Step A: 2-Benzylaminoethanol (3.45 g, 22.8 mmol) was added to solution of N-t-Boc-α-aminobutyric acid (4.0 g, 19.7 mmol) and carbonyldiimidazole (3.54 g, 21.8 mmol)) in THF (100 mL) and resulting mixture was stirred at room temperature for 17 h. The solvent was removed under vacuum and the residue purified by column chromatography (silica gel, from 0 to 100% EtOAc in hexanes) to afford (S)-tert-butyl 1-(benzyl(2-hydroxyethyl)amino)-1-oxobutan-2-yl-carbamate (3 g, 45%) as a clear oil. $^1H$ NMR consistent.

Step B: TFA(10 mL) was added to (S)-tert-butyl 1-(benzyl (2-hydroxyethyl)amino)-1-oxobutan-2-ylcarbamate (3 g, 8.92 mmol) in $CH_2Cl_2$ (50 mL) at 0° C. The mixture was stirred at 0° C. for 1.5 h, followed by solvent removal under reduced pressure. The residue was partitioned between $CH_2Cl_2$ (300 mL) and 25% aqueous sodium hydroxide (100 mL). The aqueous fraction was further extracted with $CH_2Cl_2$ (2×100 mL), and combined organic fraction was dried ($Na_2SO_4$), filtered and concentrated to afford (S)-2-amino-N-benzyl-N-(2-hydroxyethyl)butanamide as a yellow oil (1.84 g, 87%). $^1H$ NMR consistent.

Step C: Diisopropylazidodicarboxylate (1.82 g, 9.3 mmol) was added to solution of (S)-2-amino-N-benzyl-N-(2-hydroxyethyl)butanamide (1.84 g, 7.8 mmol) and triphenylphosphine (2.62 g, 10.0 mmol) in THF (50 mL). The reaction mixture was stirred at room temperature for 7 d. The solvent was removed under reduced pressure, and the residue was purified by column chromatography (silica gel, 10% $CH_3OH$ in EtOAc) to afford (S)-1-benzyl-3-ethylpiperazine-2-one (0.8 g, 47%) as clear oil. $^1H$ NMR consistent.

Step D: LiAlH4 (1 M solution in THF, 11 mL, 11.0 mmol) was added drop wise to solution of (S)-1-benzyl-3-ethylpiperazine-2-one (0.8 g, 3.66 mmol) in THF (30 mL) at 0° C. The reaction mixture was stirred at 65° C. for 17 h, then cooled 0° C. and quenched sequentially with $H_2O$ (0.7 mL), 10% NaOH (1 mL) and $H_2O$ (1.5 mL). Diethylether (100 mL) was added to the reaction mixture, and stirring was continued for 1.5 h. The solid was filtered off, the filtrate was concentrated and dried in vacuum to afford (S)-1-benzyl-3-ethylpiperazine (0.67 g, 87%) as an oily solid. $^1H$ NMR and MS consistent.

Step E: To a solution of (S)-1-benzyl-3-ethylpiperazine (650 mg, 3.22 mmol) in DME (10 mL) at room temperature, was added NaH (60% suspension in mineral oil, 144 mg, 3.50 mmol) and the mixture was stirred for 45 min. Methyl 2-chlorobenzoxazole-4-carboxylate (510 mg, 2.42 mmol) was added to the reaction mixture and the reaction was stirred at room temperature for 17 h. The reaction mixture was quenched with $CH_3OH$ (10 mL), silica gel (15 mL) was added, and solvent removed under reduced pressure. The mixture was purified by column chromatography (silica gel, 0 to 80% EtOAc in hexanes) to afford (S)-methyl 2-(4-benzyl-2-ethylpiperazine-1-yl)benzoxazole-4-carboxylate (0.87 g, 71%) as an oily solid. $^1H$ NMR and MS consistent.

Step F: 2-(4-benzyl-(S)-2-ethylpiperazine-1-yl)benzoxazole-4-carboxylic acid was synthesized by following general procedure GP-B3. MS consistent.

Step G: Following general procedure GP-$C_1$, a mixture of 2-(4-benzyl-(S)-2-ethylpiperazine-1-yl)benzoxazole-4-carboxylic acid and endo-3-amino-9-methyl-9-azabicyclo [3.3.1]nonane dihydrochloride were coupled to provide endo-N-(9-methyl-9-azabicyclo[3.3.1]nonan-3-yl)-2-((S)-2-ethyl-4-benzylpiperazin-1-yl)benzoxazole-4-carboxamide. $^1H$ NMR and MS consistent.

Step H: To a solution of endo-N-(9-methyl-9-azabicyclo [3.3.1]nonan-3-yl)-2-((S)-2-ethyl-4-benzylpiperazin-1-yl) benzoxazole-4-carboxamide (100 mg, 0.44 mmol) in 1,2- dichloroethane (10 mL) was added 1-chloroethylchloroformate (500 mg, 3.5 mmol) and $Cs_2CO_3$ (0.5 g, 2 mmol) and the mixture was stirred for 5 h at 55° C. Solvent was removed under vacuum, and the residue purified by column chromatography (silica gel, 10:1:0.1 $CH_2Cl_2$: $CH_3OH$:concentrated $NH_4OH$) to afford 31 mg (after during in vacuum) of clear oil with MS (ESI+) m/z 312 (M+H). The oil obtained was dissolved in $CH_2Cl_2$ (2 mL) and HCl (1 M solution in ether, 0.3 mL, 0.3 mmol) was added. The mixture was stirred at room temperature for 5 min then diluted with ethyl ether (40 mL). The solvent was removed under vacuum, and the residue was dissolved in $H_2O$/acetonitrile(1:1, 10 mL) and lyophilized to give endo-N-(9-methyl-9-azabicyclo [3.3.1]nonan-3-yl)-2-((S)-2-ethylpiperazine-1-yl)benzoxazole-4-carboxamide hydrochloride (20 mg, 21%) as a white powder. $^1H$ NMR and MS consistent.

EXAMPLE 85

Preparation of (S)—N-(quinuclidine-8-yl)-2-(isopropyl(methyl)amino)benzoxazole-4-carboxamide Hydrochloride Step A: Following general procedure GP-A, methyl 2-chlorobenzoxazole-4-carboxylate and N-methylpropan-2-amine were converted to methyl 2-(isopropyl(methyl)amino) benzoxazole-4-carboxylate except the mixture was stirred at room temperature for 16 h and not heated. MS consistent.

Step B: Lithium 2-(isopropyl(methyl)amino)benzoxazole-4-carboxylate was synthesized by following general procedure GP-B2. MS consistent.

Step C: Following general procedure GP-C1, a mixture of lithium 2-(isopropyl(methyl)amino)benzoxazole-4-carboxylate and (S)-(−)-3-aminoquinuclidine dihydrochloride were coupled to afford (S)—N-(quinuclidine-8-yl)-2-(isopropyl (methyl)amino)benzoxazole-4-carboxamide which was converted to the hydrochloride salt following general procedure GP-D1. $^1H$ NMR and MS consistent.

EXAMPLE 86

Preparation of Endo-N-(9-Methyl-9-azabicyclo [3.3.1]nonan-3-yl)-2-(3-oxopiperazine-1-yl)benzoxazole-4-carboxamide Hydrochloride Step A: A mixture of methyl 2-chlorobenzoxazole-4-carboxylate (750 mg, 3.54 mmol) and piperazin-2-one (780 mg, 7.79 mmol) in THF (60 mL) was stirred at ambient temperature overnight. The reaction mixture was diluted with EtOAc (150 mL) and 1 N HCl (25 ml). The aqueous layer was separated, basified with 1 N NaOH and extracted with EtOAc (6×50 mL). The combined organic extracts were dried ($Na_2SO_4$) and concentrated under reduced pressure to give methyl 2-(3-oxopiperazine-1-yl)benzoxazole-4-carboxylate (690 mg, 72%). $^1H$ NMR consistent.

Step B: Lithium 2-(3-oxopiperazine-1-yl)benzoxazole-4-carboxylate was synthesized by following general procedure GP-B2 which was directly elaborated without purification.

Step C: Following general procedure GP-C1, a mixture of lithium 2-(3-oxopiperazine-1-yl)benzoxazole-4-carboxylate and endo-3-amino-9-methyl-9-azabicyclo[3.3.1]nonane dihydrochloride were coupled to provide endo-N-(9-methyl-9-azabicyclo[3.3.1]nonan-3-yl)-2-(3-oxopiperazine-1-yl) benzoxazole-4-carboxamide except, the reaction mixture was stirred at 40° C. for 3 h. The material was purified by column chromatography (silica gel, 9:1 $CH_2Cl_2/CH_3OH$ to 90:9:1 $CH_2Cl_2/CH_3OH$/concentrated $NH_4OH$) followed by semi-prep HPLC (Luna C18(2), 10% $CH_3CN$/0.05% TFA in $H_2O$/0.05% TFA to 40% $CH_3CN$/0.05% TFA in $H_2O$/0.05% TFA over 30 min, 1=223 nm). The desired fractions were concentrated under reduced pressure to provide the TFA salt. The residue was dissolved in $CH_2Cl_2$ (25 mL) and washed with 1N NaOH (10 mL), H2O (10 mL), brine (10 mL) dried ($Na_2SO_4$), and concentrated under reduced pressure. The dried residue was converted to the hydrochloride salt following general procedure GP-D1 to afford endo-N-(9-methyl-9-azabicyclo[3.3.1]nonan-3-yl)-2-(3-oxopiperazine-1-yl)benzoxazole-4-carboxamide hydrochloride. $^1H$ NMR and MS consistent.

EXAMPLE 87

Preparation of Endo-N-(9-Methyl-9-azabicyclo [3.3.1]nonan-3-yl)-2-((3 S,5S)-3-ethyl-5-methylmorpholino)benzoxazole-4-carboxamide Hydrochloride Step A: A mixture of (S)-2-aminobutan-1-ol (14.5 g, 0.163 mmol), 1-hydroxypropan-2-one (13.3 mL, 0.195 mmol) and platinum(IV) oxide (100 mg, 0.440 mol) were stirred under a hydrogen atmosphere (1 atm). After 30.5 h, the reaction mixture was filtered through diatomaceous earth and the filtrate was concentrated under reduced pressure. The residue was purified by distillation to give (S)-2-(1-hydroxypropan-2-ylamino)butan-1-ol (17.5 g, 74%) as a colorless oil. $^1H$ NMR consistent.

Step B: To (S)-2-(1-hydroxypropan-2-ylamino)butan-1-ol (10.5 g, 0.071 mmol), in a 0° C. ice bath, was added concentrated $H_2SO_4$ (7 mL) in portions over 10 min. After 5 min the ice bath was removed and the reaction mixture was heated in a 180° C. oil bath. After 5.75 h, the reaction mixture was cooled to ambient temperature and then poured portion-wise into an ice-cold solution of potassium hydroxide (16 g) in $H_2O$ (100 mL). The resulting solids were removed by vacuum filtration. To the filtrate was added di-tert-butyl dicarbonate (15.5 g, 0.071 mol) and the mixture was allowed to stir at ambient temperature overnight. The reaction mixture was extracted with diethyl ether (3×100 mL) and the combined organic extracts were dried ($Na_2SO_4$) and concentrated under reduced pressure. The diastereomers were separated by column chromatography (silica gel, hexanes to 10% EtOAc in hexanes) to provide (3S,5S)-tert-butyl 3-ethyl-5-methylmorpholine-4-carboxylate (1.82 g, 11%); and (3R,5S)-tert-butyl 3-ethyl-5-methylmorpholine-4-carboxylate (1.32 g, 8.1%). $^1H$ NMR consistent.

Step C: (3S,5S)-tert-Butyl 3-ethyl-5-methylmorpholine-4-carboxylate (1.8 g, 7.8 mmol) was dissolved in ca. 10 M HCl in $CH_3OH$ and allowed to stir at ambient temperature. After 2.5 h, the solution was concentrated under reduced pressure. To the residue was added 1 N NaOH (20 mL) and this was extracted with $CH_2Cl_2$ (2×20 mL). The combined organics were dried ($Na_2SO_4$) and carefully concentrated under reduced pressure to give (3S,5S)-3-ethyl-5-methylmorpholine (1.0 g, quantitative). $^1H$ NMR consistent.

Step C: A mixture of methyl 2-chlorobenzoxazole-4-carboxylate (750 mg, 3.54 mmol) and (3S,5S)-3-ethyl-5-methylmorpholine (1.00 g, 7.75 mmol) in THF (40 mL) was stirred at ambient temperature overnight. Then the reaction mixture was heated in a 50° C. oil bath for 4.5 h. The reaction mixture was cooled to ambient temperature and most of the THF was removed under reduced pressure. The residue was dissolved in EtOAc (150 mL) and washed with 0.5 N HCl (25 ml), $H_2O$ (25 mL), brine (25 mL), dried ($Na_2SO_4$), and concentrated under reduced pressure. The crude material was purified by column chromatography (silica gel, hexanes to 10% EtOAc in hexanes) to give methyl 2-((3S,5S)-3-ethyl-5-methylmorpholino)benzoxazole-4-carboxylate (540 mg, 50%), as a colorless oil. $^1$H NMR consistent.

Step D: Lithium 2-((3S,5S)-3-ethyl-5-methylmorpholino) benzoxazole-4-carboxylate was synthesized by following general procedure GP-B2 which was directly elaborated without purification.

Step E: Following general procedure GP-C1, a mixture of 2-((3S,5S)-3-ethyl-5-methylmorpholino)benzoxazole-4-carboxylate and endo-3-amino-9-methyl-9-azabicyclo[3.3.1] nonane dihydrochloride were coupled to provide of endo-N-(9-methyl-9-azabicyclo[3.3.1]nonan-3-yl)-2-((3 S,5S)-3-ethyl-5-methylmorpholino)benzoxazole-4-carboxamide, which was converted to the hydrochloride salt following general procedure GP-D1. $^1$H NMR and MS consistent.

EXAMPLE 88

Preparation of Endo-N-(9-Methyl-3-oxa-9-azabicyclo[3.3.1]nonan-7-yl) 2-((3 S,5S)-3,5-dimethylmorpholino)benzoxazole-4-carboxamide Hydrochloride Step A: A mixture of methyl 2-chlorobenzoxazole-4-carboxylate (620 mg, 2.96 mmol) and (3S,5S)-3,5-dimethylmorpholine (341 mg, 2.96 mmol) and potassium carbonate (1.0 g, 7.4 mmol), in DMF (15 mL), was stirred in a 35° C. oil bath. After 17 h, the reaction mixture was cooled to ambient temperature, diluted with $H_2O$ (50 mL) and extracted with EtOAc (2×30 mL). The combined organic layers were washed with $H_2O$ (3×20 mL), brine (20 mL), dried ($Na_2SO_4$), and concentrated under reduced pressure. Methyl 2-((3 S,5S)-3,5-dimethylmorpholino)benzoxazole-4-carboxylate (770 mg, 89%) was obtained as an amber oil. $^1$H NMR consistent.

Step B: Lithium 2-((3S,5S)-3,5-dimethylmorpholino)benzoxazole-4-carboxylate was synthesized by following general procedure GP-B2 which was directly elaborated without purification.

Step C: Following general procedure GP-C$_1$, a mixture of 2-((3S,5S)-3,5-dimethylmorpholino)benzoxazole-4-carboxylate and endo-9-methyl-3-oxa-9-azabicyclo[3.3.1] nonan-7-amine dihydrochloride was converted to endo-N-(9-methyl-3-oxa-9-azabicyclo[3.3.1]nonan-7-yl) 2-((3 S,5S)-3,5-dimethylmorpholino)benzoxazole-4-carboxamide which was converted to the hydrochloride salt following general procedure GP-D1. $^1$H NMR and MS consistent.

EXAMPLE 89

Preparation of Endo-N-(9-Methyl-9-azabicyclo[3.3.1]nonan-3-yl)-2-(4-methoxypiperidin-1-yl)benzoxazole-4-carboxamide Hydrochloride Step A: To a solution of methyl 2-chlorobenzoxazole-4-carboxylate (210 mg, 0.99 mmol) in NMP (5 mL) was added 4-methoxypiperidine (230 mg, 1.98 mmol) in NMP (5 mL) at room temperature. NaH was added to the mixture in two portions in 5 min. The mixture was stirred at room temperature for 18 h. The reaction was quenched by adding 10 mL of $CH_3OH$ followed by concentration to dryness. The crude material was purified by column chromatography (silica gel, 50% EtOAc in hexane) to afford methyl 2-(4-methoxypiperidin-1-yl)benzoxazole-4-carboxylate (146 mg, 50%) as a yellow solid. MS consistent.

Step B: Lithium 2-(4-methoxypiperidin-1-yl)benzoxazole-4-carboxylate was synthesized by following general procedure GP-B2. MS consistent.

Step C: Following general procedure GP-C$_1$, a mixture of lithium 2-(4-methoxypiperidin-1-yl)benzoxazole-4-carboxylate and endo-3-amino-9-methyl-9-azabicyclo[3.3.1] nonane dihydrochloride were coupled to provide endo N-(9-methyl-9-azabicyclo[3.3.1]nonan-3-yl)-2-(4-methoxypiperidin-1-yl)benzoxazole-4-carboxamide, which was converted to the hydrochloride salt following general procedure GP-D1. $^1$H NMR and MS consistent.

EXAMPLE 90

Preparation (S)—N-(quinuclidine-8-yl)-2-((3S,5S)-3,5-Dimethylmorpholino)benzoxazole-4-carboxamide Hydrochloride Step A: Lithium 2-((3S,5S)-3,5-dimethylmorpholino)benzoxazole-4-carboxylate was synthesized by following general procedure GP-B2 which was directly elaborated without purification.

Step B: Following general procedure GP-C1,2-((3S,5S)-3,5-dimethylmorpholino)benzoxazole-4-carboxylate and (S)-(−)-3-aminoquinuclidine dihydrochloride were coupled to provide 2-((3S,5S)-3,5-dimethylmorpholino)-N-(quinuclidine-8-yl)benzoxazole-4-carboxamide, which was converted to the hydrochloride salt following general procedure GP-D1. $^1$H NMR and MS consistent.

EXAMPLE 91

Preparation of Endo-N-(9-Methyl-9-azabicyclo[3.3.1]nonan-3-yl)-2-(1,4-dioxa-8-azaspiro[4.5]decan-8-yl)benzoxazole-4-carboxamide Hydrochloride Step A: Following general procedure GP-A, methyl 2-chlorobenzoxazole-4-carboxylate and 1,4-dioxa-8-azaspiro[4.5]decane were converted to methyl 2-(1,4-dioxa-8-azaspiro[4.5]decan-8-yl)benzoxazole-4-carboxylate except the mixture was stirred at room temperature for 3 days and not heated. MS consistent.

Step B: Lithium 2-(1,4-dioxa-8-azaspiro[4.5]decan-8-yl) benzoxazole-4-carboxylate was synthesized by following general procedure GP-B2. MS consistent.

Step C: Following general procedure GP-C1, a mixture of lithium 2-(1,4-dioxa-8-azaspiro[4.5]decan-8-yl)benzoxazole-4-carboxylate and endo-3-amino-9-methyl-9-azabicyclo[3.3.1]nonane dihydrochloride were coupled to provide endo-N-(9-methyl-9-azabicyclo[3.3.1]nonan-3-yl)-2-(1,4-dioxa-8-azaspiro[4.5]decan-8-yl)benzoxazole-4-carboxamide, which was converted to the hydrochloride salt following general procedure GP-D1. $^1$H NMR and MS consistent.

EXAMPLE 92

Preparation of Endo-N-(9-methyl-9-azabicyclo[3.3.1]nonan-3-yl)-2-(4-oxopiperidin-1-yl)benzoxazole-4-carboxamide Hydrochloride Step A: Following general procedure GP-A, methyl 2-chlorobenzoxazole-4-carboxylate and 1,4-dioxa-8-azaspiro[4.5]decane were converted to methyl 2-(1,4-dioxa-8-azaspiro[4.5]decan-8-yl)benzoxazole-4-carboxylate except that the mixture was stirred at room temperature for 3 days and not heated. MS consistent.

Step B: Lithium 2-(1,4-dioxa-8-azaspiro[4.5]decan-8-yl) benzoxazole-4-carboxylate was synthesized by following general procedure GP-B2. MS consistent.

Step C: Following general procedure GP-C3, a mixture of lithium 2-(1,4-dioxa-8-azaspiro[4.5]decan-8-yl)benzoxazole-4-carboxylate and endo-3-amino-9-methyl-9-azabicyclo[3.3.1]nonane dihydrochloride were coupled to provide endo-N-(9-methyl-9-azabicyclo[3.3.1]nonan-3-yl)-2-(1,4-dioxa-8-azaspiro[4.5]decan-8-yl)benzoxazole-4-carboxamide. $^1$H NMR and MS consistent.

Step D: Endo-N-(9-methyl-9-azabicyclo[3.3.1]nonan-3-yl)-2-(1,4-dioxa-8-azaspiro[4.5]decan-8-yl)benzoxazole-4-carboxamide (100 mg, 0.23 mmol) and PPTS (85 mg, 0.34 mmol) were dissolved in acetone (1 mL) and H$_2$O (1 mL). The reaction mixture was subjected to microwave irradiation at 170° C. for 90 min. The solvent was removed under reduced pressure. The residual oil was diluted with CH$_2$Cl$_2$ (100 mL) and washed with H$_2$O (3×25 mL). The organic layer was dried (MgSO$_4$), filtered and concentrated to give the crude product. The crude product was purified by semi-prep HPLC (Luna C18(2), 10% CH$_3$CN/0.05% TFA in H$_2$O/0.05% TFA to 100% CH$_3$CN/0.05% TFA over 25 min, 1=223 nm) to afford Endo-N-(9-methyl-9-azabicyclo[3.3.1]nonan-3-yl)-2-(4-oxopiperidin-1-yl)benzoxazole-4-carboxamide which was converted to the hydrochloride salt following general procedure GP-D1. $^1$H NMR and MS consistent.

EXAMPLE 93

Preparation of (S)—N-(Quinulidin-8-yl)-2-aminobenzoxazole-4-carboxamide Hydrochloride Step A: To a solution of di (1H-imidazole-1-yl)methanamine (2.05 g, 12.26 mmol) in THF (60 mL) was added methyl-2-amino-3-hydroxybenzoate (1.98 g, 12.26 mmol) at room temperature and the resulting reaction mixture was heated to reflux for 17 h. The reaction mixture was cool to room temperature, diluted with EtOAc (100 mL) and washed with H$_2$O (3×100 mL), saturated ammonium chloride (2×100 mL), dried (Na$_2$SO$_4$), filtered and concentrated under reduced pressure. The crude material was purified by recrystallization from diethyl ether to afford methyl 2-aminobenzoxazole-4-carboxylate (1.10 g, 50%) as a brown solid. $^1$H NMR and MS consistent.

Step B: A mixture of the methyl 2-aminobenzoxazole-4-carboxylate (750 mg, 3.9 mmol), di-tert-butyldicarbonate (936 mg, 4.29 mmol) in CH$_2$Cl$_2$ (50 mL) was stirred at room temperature for 17 h. The reaction was quenched with a saturated NaHCO$_3$ (25 mL), and then extracted with CH$_2$Cl$_2$ (3×100 mL). The combined organic phase was washed with H$_2$O (2×75 µL), brine (1×50 mL), and dried (Na$_2$SO$_4$), filtered and concentrated under reduced pressure. The crude material was purified by column chromatography (silica gel, 9:1, CH$_2$Cl$_2$/CH$_3$OH) to afford methyl 2-(tert-butoxycarbonylamino-4-yl)benzoxazole-4-carboxylate (930 mg, 82%) as a light yellow solid. $^1$H NMR consistent.

Step C: 2-(tert-butoxycarbonylamino-4-yl)benzoxazole-4-carboxylic acid was synthesized by following general procedure GP-B1. $^1$H NMR and MS consistent.

Step D: Following general procedure GP-C1, 2-(tert-butoxycarbonylamino-4-yl)benzoxazole-4-carboxylic acid and, (S)-(−)-3-aminoquinuclidine dihydrochloride (199 mg, 1.0 mmol), 1-ethyl-3-(3-dimethylaminopropyl)carbodiimide hydrochloride were coupled to provide 4-(quinuclidine-8-ylcarbamoyl)benzoxazole-2-yl-carbamate (210 mg, 54%) as an off-white solid. MS consistent.

Step E: To a solution of tert-butyl 4-(quinuclidine-8-ylcarbamoyl)benzoxazole-2-yl-carbamate (0.210 g, 0.54 mmol), in CH$_2$Cl$_2$ (5 mL) was added TFA(2 mL) and the reaction mixture was stirred at room temperature for 5 h. The reaction mixture was concentrated and the crude material was treated with aqueous NaHCO$_3$ to adjust the pH to 7 and then extracted with CH$_2$Cl$_2$ (5×50 mL). The combined organic phase was concentrated and purified by preparative TLC (90:9:1 CH$_2$Cl$_2$/CH$_3$OH/concentrated NH$_4$OH) to afford (S)—N-(quinuclidine-8-yl)-2-aminobenzoxazole-4-carboxamide which was converted to the hydrochloride salt following general procedure GP-D1. $^1$H NMR and MS consistent.

EXAMPLE 94

Preparation of Endo-N-(9-Methyl-9-azabicyclo [3.3.1]nonan-3-yl)-2-((S)-3-(hydroxymethyl)morpholino)benzoxazole-4-carboxamide Hydrochloride Step A: To a solution of (R)-methyl-2-amino-3-hydroxypropanoate (33 g, 212 mmol) in 2 N NaOH solution (182 mL) was added benzaldehyde (32 mL, 318 mmol), the mixture stirred at room temperature for 30 min. and cooled to −5° C. Sodium borohydride (4.01 g, 106 mmol) was added in small portions over one hour, additional benzaldehyde (32 mL, 318 mmol) was added and the reaction mixture stirred at room temperature for 30 min, then cooled to −5° C. NaBH$_4$ (4.01 g, 106 mmol) was added in small portions over one hour and the reaction mixture stirred at room temperature for 12 h. The solution was extracted with diethyl ether (500 mL) and acidified with concentrated HCl to pH 1. The precipitate was filtered off and dried under vacuum to provide (R)-2-(benzylamino)-3-hydroxypropanoic acid hydrochloride (9.4 g, 23%) as a white solid. $^1$H NMR consistent.

Step B: To a solution of (R)-2-(benzylamino)-3-hydroxypropanoic acid hydrochloride (9.4 g, 48.2 mmol) and sodium hydroxide (2.57 g, 82.9 mmol) in H$_2$O (30 mL) at 0° C. was added drop wise chloroacetyl chloride (4.9 mL, 62.1 mL) while maintaining the temperature below 10° C. The reaction mixture was then warmed to room temperature and stirred for 2 hours. The reaction mixture was extracted with CH$_2$Cl$_2$ (2×250 mL) and the organic layer dried (MgSO$_4$), filtered and concentrated. The residue was purified by flash chromatography (silica gel, 10 to 30% CH$_3$OH in CH$_2$Cl$_2$ with 1% acetic acid) to provide (R)-2-(N-benzyl-2-chloroacetamido)-3-hydroxypropanoic acid (2.6 g, 20%) as a yellow foam. $^1$H NMR consistent.

Step C: To a solution of (R)-2-(N-benzyl-2-chloroacetamido)-3-hydroxypropanoic acid (1.53 g, 5.63 mmol) in tert-butanol was added potassium tert-butanolate and the reaction mixture heated to 110° C. for three h, then cooled to room temperature and concentrated to dryness. The residue was acidified with 1 N HCl to pH 1 and the aqueous solution extracted with EtOAc (3×250 mL). The organic layer was dried (MgSO$_4$), filtered and concentrated under reduced pressure. The residue was purified by flash chromatography (silica gel, 10 to 30% CH$_3$OH in CH$_2$Cl$_2$ with 1% acetic acid) to provide (R)-4-benzyl-5-oxomorpholine-3-carboxylic acid (780 mg, 59%) as a yellow foam. $^1$H NMR and MS consistent.

Step D: To a solution of (R)-4-benzyl-5-oxomorpholine-3-carboxylic acid (780 mg, 3.32 mmol) and triethylamine (567 mL, 4.08 mmol) in anhydrous THF (15 mL) at 0° C. was added borane dimethylsulfide complex over 15 min. The reaction mixture was warmed to room temperature and heated to reflux for 6 hours, then cooled in an ice bath. To this mixture was added H$_2$O (4 mL) drop wise over 30 min., then 2 N NaOH (6 mL) and the mixture concentrated to 30% of the volume. The residue was extracted with EtOAc (3×150 mL), the organic layer dried (MgSO$_4$) and concentrated. The residue was purified by flash chromatography (silica gel, 0 to 5%

CH₃OH in CH₂Cl₂) to provide (S)-(4-benzylmorpholine-3-yl)CH₃OH (470 mg, 68%) as a colorless oil. ¹H NMR and MS consistent.

Step E: A solution of (S)-(4-benzylmorpholine-3-yl) CH₃OH (450 mg, 2.17 mmol), tert-butylchlorodimethylsilane (392 mg, 2.60 mmol) and imidazole (370 mg, 5.42 mmol) in DMF (10 mL) was stirred at room temperature for 18 hours. The reaction mixture was diluted with CH₂Cl₂ (2×50 mL), washed with 5% NaHCO₃ solution (50 mL) and brine (3×20 mL) and the organic layer dried (MgSO₄) and concentrated. The residue was purified by flash chromatography (silica gel, 10 to 30% CH₃OH in CH₂Cl₂) to provide (R)-4-benzyl-3-((tert-butyldimethylsilyloxy)methyl)morpholine (576 mg, 82%) as a colorless foam. ¹H NMR and MS consistent.

Step F: A suspension of (R)-4-benzyl-3-((tert-butyldimethylsilyloxy)methyl)morpholine (576 mg, 1.79 mmol) and 10% palladium on carbon in EtOAc (20 mL) was placed in a Parr shaker and hydrogenated at 45 psi hydrogen pressure for 48 h. The heterogeneous mixture was filtered through a pad of diatomaceous earth, washed with CH₃OH (200 mL) and concentrated to provide (R)-3-((tert-butyldimethylsilyloxy)methyl)morpholine (414 mg, quant.) as a colorless oil. MS consistent.

Step G: Following general procedure GP-A, (R)-3-((tert-butyldimethylsilyloxy)-methyl)morpholine and -2-chlorobenzoxazole-4-carboxylate were converted to (R)-methyl 2-(3-((tert-butyldimethylsilyloxy)methyl)morpholino)benzoxazole-4-carboxylate. ¹H NMR and MS consistent.

Step H: To a solution of LiI (298 mg, 2.22 mmol) in refluxing anhydrous pyridine (50 mL) was added (R)-methyl 2-(3-((tert-butyldimethylsilyloxy)methyl)morpholino)benzoxazole-4-carboxylate (226 mg, 0.55 mmol) and the reaction mixture was refluxed for 24 h. The mixture was cooled to room temperature, concentrated to dryness and dried in vacuum to provide lithium (R)-2-(3-((tert-butyldimethylsilyloxy)methyl)morpholino)benzoxazole-4-carboxylate as a yellow oil which was used without further purification. MS consistent.

Step I: Following general procedure GP-C1, (R)-2-(3-((tert-butyldimethylsilyloxy)methyl)morpholino)benzoxazole-4-carboxylate and endo-3-amino-9-methyl-9-azabicyclo[3.3.1]nonane dihydrochloride were coupled to provide endo-N-(9-methyl-9-azabicyclo[3.3.1]nonan-3-yl)-2-((R)-3-((tert-butyldimethylsilyloxy)methyl)-morpholino)benzoxazole-4-carboxamide. ¹H NMR and MS consistent.

Step J: A solution of endo-N-(9-methyl-9-azabicyclo [3.3.1]nonan-3-yl)-2-((R)-3-((tert-butyldimethylsilyloxy) methyl)morpholino)benzoxazole-4-carboxamide (293 mg, 0.55 mmol) and tetrabutylammonium fluoride (1.7 mL, 1 M solution in THF) in anhydrous THF (80 mL) was stirred at room temperature for 12 hours. The reaction mixture was concentrated to dryness and the residue re-dissolved in CH₂Cl₂ (100 mL), washed with saturated ammonium chloride solution (2×25 mL), brine (25 mL), and the organic layer dried (MgSO₄) and concentrated. The crude material was purified by column chromatography (silica gel, 100% CH₂Cl₂ to 90:10:1 CH₂Cl₂/CH₃OH/concentrated NH₄OH) to afford endo-N-(9-methyl-9-azabicyclo[3.3.1]nonan-3-yl)-2-((S)-3-(hydroxymethyl)morpholino)benzoxazole-4-carboxamide which was converted to the hydrochloride salt following general procedure GP-D1. ¹H NMR and MS consistent.

EXAMPLE 95

Preparation of Endo-N-(9-Methyl-9-azabicyclo [3.3.1]nonan-3-yl)-2-(3-methylpiperazin-1-yl)benzoxazole-4-carboxamide Hydrochloride Step A: To a solution of tert-butyl 2-methylpiperazine-1-carboxylate (340 mg, 1.70 mmol) in THF (5 mL) was added sodium hydride (60%, 82 mg, 2.04 mmol). The reaction mixture was stirred at room temperature for 5 min, then methyl 2-chlorobenzoxazole-4-carboxylate (300 mg, 1.41 mmol) in THF (5 mL) was added to the reaction mixture. The reaction mixture was stirred at room temperature for 19 h. The mixture was concentrated under reduced pressure and the resulting residue was purified by column chromatography (silica gel, 20% EtOAc in hexane) to afford methyl 2-(4-(tert-butoxycarbonyl)-3-methylpiperazin-1-yl)benzoxazole-4-carboxylate (336 mg, 63%) as yellow solid. MS consistent.

Step B: Lithium 2-(4-(tert-butoxycarbonyl)-3-methylpiperazin-1-yl)benzoxazole-4-carboxylate was synthesized by following general procedure GP-B2. MS consistent.

Step C: Following general procedure GP-C₁, lithium 2-(4-(tert-butoxycarbonyl)-3-methylpiperazin-1-yl)benzoxazole-4-carboxylate and 9-methyl-9-azabicyclo[3.3.1]nonan-3-amine dihydrochloride were coupled to provide tert-butyl 2-methyl-4-(4-(9-methyl-9-azabicyclo[3.3.1]nonan-3-ylcarbamoyl)benzoxazol-2-yl)piperazine-1-carboxylate. MS consistent.

Step D: To a solution of provide tert-butyl 2-methyl-4-(4-(9-methyl-9-azabicyclo[3.3.1]nonan-3-ylcarbamoyl)benzoxazol-2-yl)piperazine-1-carboxylate (138 mg, 0.27 mmol) in CH₂Cl₂ (2 mL) was added TFA (2 mL) at 0° C. The reaction mixture was stirred at 0° C. for 1.5 h and concentrated to give the crude product. The crude product was purified by prep-TLC (silica gel, 80:19:1 chloroform/CH₃OH/concentrated NH₄OH) to afford endo-N-(9-methyl-9-azabicyclo[3.3.1] nonan-3-yl)-2-(3-methylpiperazin-1-yl)benzoxazole-4-carboxamide which was converted to the hydrochloride salt following general procedure GP-D1. ¹H NMR and MS consistent.

EXAMPLE 96

Preparation of Endo-N-(9-Methyl-9-azabicyclo [3.3.1]nonan-3-yl)-2-((S)-2-tert-butylpiperazin-1-yl) benzoxazole-4-carboxamide Hydrochloride Step A: Lithium aluminum hydride(1 M solution in THF, 40 mL, 40.0 mmol) was added drop wise to solution of (S)-2-tert-butylpiperazin-3,6-dione (1.5 g, 8.82 mmol) in THF (50 mL) at 0° C. The reaction mixture was stirred at room temperature for 7 days and at 65° C. for 17 h, then cooled to 0° C. and quenched sequentially with H₂O (1.7 mL), 10% NaOH (2.2 mL) and H₂O (3.4 mL). Ether (100 mL) was added to the reaction mixture, and stirring was continued for 1.5 h. The solid was filtered, the filtrate was concentrated and purified by column chromatography (silica gel, 33% EtOAc in hexanes) to afford (S)-2-tert-butylpiperazine (0.64 g, 52%) as a clear oil. ¹H NMR and MS consistent.

Step B: To (S)-2-tert-butylpiperazine (0.5 g, 3.49 mmol), in CH₂Cl₂ (15 mL) at room temperature was added triethylamine (0.5 mL, 3.59 mmol) followed by di-tert butyldicarbonate (0.83 g, 3.79 mmol) and the reaction mixture was allowed to stir at room temperature 17 h. The solvent was removed under vacuum, and the residue purified by column chromatography (silica gel, 10:1:0.1 $CH_2Cl_2/CH_3OH$/concentrated $NH_4OH$) to afford (S)-4-tert-butyloxycarbonyl-2-tert-butylpiperazine (0.59 g, 69%) as a clear oil. $^1H$ NMR consistent.

Step C: To (S)-4-tert-butyloxycarbonyl-2-tert-butylpiperazine (640 mg, 2.6 0 mmol) in DME (10 mL) at room temperature, was added NaH (60% suspension in mineral oil, 115 mg, 3.50 mmol) and the mixture was stirred for 45 min. Methyl 2-chlorobenzoxazole-4-carboxylate (780 mg, 3.69 mmol) was added to the reaction mixture and the reaction was stirred at room temperature for 3d and at 55° C. for 24 h. The reaction mixture was quenched with $CH_3OH$ (10 mL), silica gel (15 mL) was added, and solvent removed under reduced pressure. The residue was purified by column chromatography (silica gel, 33% EtOAc in hexanes) to afford (S)-methyl 2-(4-tert-butyloxycarbonyl-2-tert-butyl-piperazin-1-yl)benzoxazole-4-carboxylate (0.42 g, 39%) as a yellow solid. $^1H$ NMR and MS consistent.

Step D: Following general procedure GP-B3, (S)-methyl 2-(4-tert-butyloxycarbonyl-2-tert-butyl-piperazin-1-yl)benzoxazole-4-carboxylate was converted to (S)-2-(4-tert-butyloxycarbonyl-2-tert-butylpiperazin-1-yl)benzoxazole-4-carboxylic acid. MS consistent.

Step E: Following general procedure GP-$C_1$, (S)-2-(4-tert-butyloxycarbonyl-2-tert-butylpiperazin-1-yl)benzoxazole-4-carboxylic acid and endo-3-amino-9-methyl-9-azabicyclo[3.3.1]nonane dihydrochloride were coupled to afford endo-N-(9-methyl-9-azabicyclo[3.3.1]nonan-3-yl)-2-((S)-2-tert-butyl-4-tert-butyloxycarbonylpiperazin-1-yl)benzoxazole-4-carboxamide. MS consistent.

Step F: TFA(1 mL) was added to endo-N-(9-methyl-9-azabicyclo[3.3.1]nonan-3-yl)-2-((S)-2-tert-butyl-4-tert-butyloxycarbonylpiperazin-1-yl)benzoxazole-4-carboxamide (100 mg, 0.18 mmol) in $CH_2Cl_2$ (1 mL) and the mixture was stirred for 1 h at room temperature. The solvent was removed under vacuum, and the residue was neutralized by ion-exchange chromatography (SCX-2 column, 5 g) to afford 29 mg of clear oil. The oil obtained was converted to the hydrochloride salt following general procedure GP-D1 to give endo-N-(9-methyl-9-azabicyclo[3.3.1]nonan-3-yl)-2-((S)-2-tert-butylpiperazin-1-yl)benzoxazole-4-carboxamide hydrochloride. $^1H$ NMR and MS consistent.

EXAMPLE 97

Preparation of Endo-N-(9-Methyl-9-azabicyclo[3.3.1]nonan-3-yl)-2-((2S,6S)-4-benzyl-2,6-dimethyl-3-oxopiperazine-1-yl)benzoxazole-4-carboxamide Hydrochloride Step A: A mixture of methyl 2-chlorobenzoxazole-4-carboxylate (970 mg, 4.58 mmol) and (3S,5S)-1-benzyl-3,5-dimethylpiperazin-2-one (1.00 g, 4.58 mmol) in DMF (20 mL), was stirred in a 35° C. oil bath. After 16 h, the reaction mixture was heated to 55° C. After 3 h, potassium carbonate (630 mg, 4.58 mmol) was added. The reaction mixture was stirred for 2 h at 55° C. and then at ambient temperature for 17 h. The reaction mixture was diluted with $H_2O$ (50 mL) and extracted with EtOAc (2×50 mL). The combined organic layers were washed with 0.5 N HCl (25 mL), $H_2O$ (25 mL), brine (25 mL), dried ($Na_2SO_4$), and concentrated under reduced pressure. Purification by chromatography (silica gel, 10 to 80% EtOAc in hexanes) gave methyl 2-((2S,6S)-4-benzyl-2,6-dimethyl-3-oxopiperazine-1-yl)benzoxazole-4-carboxylate (1.08 g, 60%). $^1H$ NMR consistent.

Step B: Lithium 2-((2S,6S)-4-benzyl-2,6-dimethyl-3-oxopiperazine-1-yl)benzoxazole-4-carboxylate was synthesized by following general procedure GP-B2 which was directly elaborated without purification.

Step C: Following general procedure GP-C1, lithium 2-((2S,6S)-4-benzyl-2,6-dimethyl-3-oxopiperazine-1-yl)benzoxazole-4-carboxylate and endo-9-methyl-3-oxa-9-azabicyclo[3.3.1]nonan-7-amine dihydrochloride were coupled to provide endo-N-(9-methyl-9-azabicyclo[3.3.1]-nonan-3-yl)-2-((2S,6S)-4-benzyl-2,6-dimethyl-3-oxopiperazine-1-yl)benzoxazole-4-carboxamide which was converted to the hydrochloride salt following general procedure GP-D1. $^1H$ NMR and MS consistent.

EXAMPLE 98

Preparation of Endo-N-(9-Methyl-9-azabicyclo[3.3.1]nonan-3-yl)-2-((S)-2-methyl-3-oxopiperazine-1-yl)benzoxazole-4-carboxamide Hydrochloride Step A: A mixture of methyl 2-chlorobenzoxazole-4-carboxylate (370 mg, 1.75 mmol), (S)-3-methylpiperazin-2-one (200 mg, 1.75 mmol) and $K_2CO_3$ (605 mg, 4.38 mmol), in DMF (15 mL), was stirred at ambient temperature for 17 h. The reaction mixture was diluted with $H^2O$ (30 mL) and extracted with $CH_2Cl_2$ (2×50 mL). The combined organic layers were washed with $H_2O$ (3×20 mL), brine (20 mL), dried ($Na_2SO_4$). The material was concentrated under reduced pressure to give (S)-methyl 2-(2-methyl-3-oxopiperazine-1-yl)benzoxazole-4-carboxylate (500 mg, 73%) as a yellow oil. $^1H$ NMR consistent.

Step B: To (S)-methyl 2-(2-methyl-3-oxopiperazine-1-yl)benzoxazole-4-carboxylate (118 mg, 0.407 mmol) in THF (3 mL) was added potassium trimethylsilanolate (58 mg, 0.407 mmol). A yellow precipitate formed and after 1.5 h, additional potassium trimethylsilanolate (58 mg, 0.407 mmol) was added. After 1 h, the reaction mixture was heated at reflux. After 1.5 h, the reaction mixture was cooled to ambient temperature. The solid was collected by vacuum filtration and rinsed with diethyl ether to afford crude (S)-potassium 2-(2-methyl-3-oxopiperazine-1-yl)benzoxazole-4-carboxylate. $^1H$ NMR consistent.

Step C: Following general procedure GP-C1, a mixture of (S)-potassium 2-(2-methyl-3-oxopiperazine-1-yl)benzoxazole-4-carboxylate and endo-9-methyl-3-oxa-9-azabicyclo[3.3.1]nonan-7-amine dihydrochloride were coupled to provide endo-N-(9-methyl-9-azabicyclo[3.3.1]nonan-3-yl)-2-((S)-2-methyl-3-oxopiperazine-1-yl)benzoxazole-4-carboxamide hydrochloride following general procedure GP-D1. $^1H$ NMR and MS consistent.

EXAMPLE 99

Preparation of (S)—N-(Quinulidin-8-yl)-2-((2S,6S)-2,6-dimethylpiperazin-1-yl)benzoxazole-4-carboxamide Hydrochloride Step A: Lithium 2-((2S,6S)-4-(tert-butoxycarbonyl)-2,6-dimethylpiperazin-1-yl)benzoxazole-4-carboxylate was synthesized by following general procedure GP-B2. MS consistent.

Step B: Following general procedure GP-C1, lithium 2-((2S,6S)-4-(tert-butoxycarbonyl)-2,6-dimethylpiperazin-1-yl)benzoxazole-4-carboxylate and (S)-(−)-3-aminoquinuclidine dihydrochloride were coupled to provide (S)—N-(quinulidin-8-yl)-2-((2S,6S)-4-(tert-butoxycarbonyl)-2,6-dimethylpiperazin-1-yl)benzoxazole-4-carboxylate. $^1H$ NMR and MS consistent.

Step C: To solution of (S)—N-(quinulidin-8-yl)-2-((2S,6S)-4-(tert-butoxycarbonyl)-2,6-dimethylpiperazin-1-yl)benzoxazole-4-carboxylate (245 mg, 0.51 mmol) was added HCl (1.25 M solution in $CH_3OH$, 8.2 mL, 10.13 mmol) and the mixture was stirred at 35° C. for 17 h then concentrated under reduced pressure. The crude material was purified by column chromatography (silica gel, 100% 9:1 $CH_2Cl_2$/$CH_3OH$ to 100% 90:9:1 $CH_2Cl_2$/$CH_3OH$/concentrated $NH_4OH$) to afford (S)—N-(quinulidin-8-yl)-2-((2S,6S)-2,6-dimethylpiperazin-1-yl)benzoxazole-4-carboxamide which was converted to the hydrochloride salt following general procedure GP-D1. $^1H$ NMR and MS consistent.

EXAMPLE 100

Preparation of Endo-N-(9-Methyl-9-azabicyclo[3.3.1]nonan-3-yl)-2-(6,9-diazaspiro[4.5]decan-6-yl)benzoxazole-4-carboxamide Hydrochloride Step A: To a solution of tert-butyl 6,9-diazaspiro[4.5]decane-9-carboxylate (192 mg, 0.80 mmol) in DME (10 mL) was added NaH (60%, 96 mg, 2.4 mmol). The reaction mixture was stirred at room temperature for 10 min, followed by addition of methyl 2-chlorobenzoxazole-4-carboxylate (186 mg, 0.88 mmol). The reaction mixture was stirred at room temperature for 20 h. The reaction was quenched by adding 5 mL of $H_2O$ and extracted with EtOAc (2×30 mL). The organic layer was washed by brine, dried over $Na_2SO_4$, filtered, and concentrated under reduced pressure. The resulting residue was purified by column chromatography (silica gel, 50-100% chloroform in hexane) to afford methyl 2-(9-(tert-butoxycarbonyl)-6,9-diazaspiro[4.5]decan-6-yl)benzoxazole-4-carboxylate (61.4 mg, 18.5%) as yellow oil. MS consistent.

Step B: Following general procedure GP-B2, methyl 2-(9-(tert-butoxycarbonyl)-6,9-diazaspiro[4.5]decan-6-yl)benzoxazole-4-carboxylate was converted to lithium 2-(9-(tert-butoxycarbonyl)-6,9-diazaspiro[4.5]decan-6-yl)benzoxazole-4-carboxylate. MS consistent.

Step C: Following general procedure GP-$C_1$, lithium 2-(9-(tert-butoxycarbonyl)-6,9-diazaspiro[4.5]decan-6-yl)benzoxazole-4-carboxylate and endo-3-amino-9-methyl-9-azabicyclo[3.3.1]nonane dihydrochloride were coupled to provide tert-butyl 6-(4-(9-methyl-9-azabicyclo[3.3.1]nonan-3-ylcarbamoyl)benzoxazol-2-yl)-6,9-diazaspiro[4.5]decane-9-carboxylate (25 mg, 52%) as a yellow solid. MS consistent.

Step D: To tert-butyl 6-(4-(9-methyl-9-azabicyclo[3.3.1]nonan-3-ylcarbamoyl)benzoxazol-2-yl)-6,9-diazaspiro[4.5]decane-9-carboxylate (25 mg, 0.05 mmol) in $CH_2Cl_2$ (1 mL) was added TFA(1 mL) at 0° C. The reaction mixture was stirred at 0° C. for 30 min, then at room temperature for 30 min. The reaction mixture was concentrated under reduced pressure and the resulting residue was dissolved in $CH_2Cl_2$ (50 mL). The organic phase was with an aqueous saturated $NaHCO_3$ solution (25 mL). The organic layer was separated, dried over $MgSO_4$, filtered, and concentrated under reduced pressure to afford endo-N-(9-methyl-9-azabicyclo[3.3.1]nonan-3-yl)-2-(6,9-diazaspiro[4.5]decan-6-yl)benzoxazole-4-carboxamide which was converted to the hydrochloride salt following general procedure GP-D1. $^1H$ NMR and MS consistent.

EXAMPLE 101

Preparation of N-(8-Methyl-8-azabicyclo[3.2.1]octan-3-yl)-2-(3S,5S)-3,5-dimethylmorpholinobenzoxazole-4-carboxamide Hydrochloride Step A: Following general procedure GP-A, methyl 2-chlorobenzoxazole-4-carboxylate and (3S,5S)-3,5-dimethylmorpholine were converted to methyl 2-((3S,5S)-3,5-dimethylmorpholino)benzoxazole-4-carboxylate. $^1H$ NMR consistent.

Step B: 2-((3S,5S)-3,5-dimethylmorpholino)benzoxazole-4-carboxylic acid was synthesized by following general procedure GP-B3. MS consistent.

Step C: Following general procedure GP-C1, a mixture of 2-((3S,5S)-3,5-dimethylmorpholino)benzoxazole-4-carboxylic acid and 8-methyl-8-azabicyclo[3.2.1]octan-3-amine dihydrochloride were coupled to provide N-(8-methyl-8-azabicyclo[3.2.1]octan-3-yl)-2-(3 S,5S)-3,5-dimethylmorpholino)benzoxazole-4-carboxamide, which was converted to the hydrochloride salt following general procedure GP-D1. $^1H$ NMR and MS consistent.

EXAMPLE 102

Preparation of Endo-N-(9-Methyl-9-azabicyclo[3.3.1]nonan-3-yl)-2-(2,2-dimethylpiperazin-1-yl)benzoxazole-4-carboxamide Hydrochloride Step A: To an iced-cooled solution of 2,2-dimethylpiperazine (1.0 g, 8.76 mmol) in methanol (200 mL) was added di-tert-butyl dicarbonate (1.91 g, 8.76 mmol) and triethylamine (2.67 g, 26.27 mmol). The reaction mixture was stirred at room temperature for 20 h. The solvent was removed under reduced pressure and the residual oil was extracted with $CHCl_3$ (3×60 mL). The organic phase was concentrated under reduced pressure to afford tert-butyl 3,3-dimethylpiperazine-1-carboxylate (662 mg, 35%) as yellow oil. MS consistent.

Step B: Following general procedure GP-A, tert-butyl 3,3-dimethylpiperazine-1-carboxylate and methyl 2-chlorobenzoxazole-4-carboxylate were converted to methyl 2-(4-(tert-butoxycarbonyl)-2,2-dimethylpiperazin-1-yl)benzoxazole-4-carboxylate. $^1H$ NMR and MS consistent.

Step C: Lithium 2-(4-(tert-butoxycarbonyl)-2,2-dimethylpiperazin-1-yl)benzoxazole-4-carboxylate was synthesized by following general procedure GP-B2. MS consistent.

Step D: Following general procedure GP-$C_1$, lithium 2-(4-(tert-butoxycarbonyl)-2,2-dimethylpiperazin-1-yl)benzoxazole-4-carboxylate and endo-3-amino-9-methyl-9-azabicyclo[3.3.1]nonane dihydrochloride coupled to provide tert-butyl 3,3-dimethyl-4-(4-(9-methyl-9-azabicyclo[3.3.1]nonan-3-ylcarbamoyl)benzoxazol-2-yl)piperazine-1-carboxylate. MS consistent.

Step E: To a solution of tert-butyl 3,3-dimethyl-4-(4-(9-methyl-9-azabicyclo[3.3.1]nonan-3-ylcarbamoyl)benzoxazol-2-yl)piperazine-1-carboxylate (63 mg, 0.12 mmol) in $CH_2Cl_2$ (1 mL) was added TFA (1 mL) at 0° C. The reaction mixture was stirred at 0° C. for 30 min, then at room temperature for 30 min. The reaction mixture was concentrated under reduced pressure and the resulting residue was dissolved in $CH_2Cl_2$ (50 mL) and washed with an aqueous saturated $NaHCO_3$ solution (25 mL). The organic layer was separated, dried over $MgSO_4$, filtered, and concentrated under reduced pressure to afford endo-N-(9-Methyl-9-azabicyclo[3.3.1]nonan-3-yl)-2-(2,2-dimethylpiperazin-1-yl)benzoxazole-4-carboxamide (28.5 mg, 56%) as a white solid, which was

EXAMPLE 103

Preparation of (S)—N-(Quinulidin-8-yl)-2-amino-6-chlorobenzoxazole-4-carboxamide Hydrochloride Step A: To a solution of di(1H-imidazole-1-yl)methanamine (1.74 g, 10.83 mmol) in tetrahydrofuran (50 mL) was added methyl-2-amino-3-chloro-3-hydroxybenzoate (1.75 g, 8.66 mmol) at room temperature and the resulting reaction mixture was heated to reflux for 17 h. The reaction mixture was cooled to room temperature and concentrated under reduced pressure. The residue was dissolved in $CH_2Cl_2$ (100 mL) and washed with $H_2O$ (1×100 mL), saturated aqueous $NH_4Cl$ (3×100 mL), brine (1×100 mL), dried over $Na_2SO_4$, filtered, and concentrated under reduced pressure. The crude material was purified by trituration from EtOAc to afford methyl 2-amino-6-chlorobenzoxazole-4-carboxylate (1.05 g, 54%) as a light brown solid. $^1$H NMR and MS consistent.

Step B: A mixture of methyl 2-amino-6-chlorobenzoxazole-4-carboxylate (1.05 g, 4.65 mmol) and di-tert-butyldicarbonate (3.15 g, 3.25 mmol) in $CH_2Cl_2$ (50 mL) was stirred at room temperature for 17 h. The reaction was concentrated under reduced pressure. The crude material was purified by column chromatography (99:1, $CH_2Cl_2/CH_3OH$) to afford methyl 2-(tert-butoxycarbonylamino)-6-chlorobenzoxazole-4-carboxylate (720 mg, 36%) as a light yellow solid. $^1$H NMR and MS consistent.

Step C: Following general procedure GP-B3, methyl 2-(tert-butoxycarbonylamino)-6-chlorobenzoxazole-4-carboxylate was converted to 2-(tert-butoxycarbonylamino-4-yl)benzoxazole-4-carboxylic acid. MS consistent Step D: Following general procedure GP-C1, 2-(tert-butoxycarbonylamino-4-yl)benzoxazole-4-carboxylic acid and (S)-(−)-3-aminoquinuclidine dihydrochloride coupled to provide tert-butyl 6-chloro-4-(quinuclidine-8-yl-carbamoyl)benzoxazole-2-yl-carbamate. MS consistent.

Step E: To a solution of tert-butyl 6-chloro-4-(quinuclidine-8-yl-carbamoyl)benzoxazole-2-yl-carbamate (71 mg, 0.17 mmol) in $CH_2Cl_2$ (1 mL) was added TFA (1 mL). The reaction mixture stirred at room temperature for 3 h. The reaction mixture was concentrated under reduced pressure and the crude material was treated with concentrated ammonium hydroxide to adjust the pH to 7. The mixture was concentrated under reduced pressure and the crude material was purified by preparative TLC (90:9:1 $CH_2Cl_2/CH_3OH$/concentrated $NH_4OH$) to afford (S)—N-(quinuclidine-8-yl)-2-amino-6-chlorobenzoxazole-4-carboxamide (21 mg, 38%) as a white solid, which was converted to the hydrochloride salt following general procedure GP-D1. $^1$H NMR and MS consistent.

EXAMPLE 104

Preparation of (S)—N-(Quinulidin-8-yl)-2-ethylaminobenzoxazole-4-carboxamide Hydrochloride Step A: Following general procedure GP-A, methyl 2-chlorobenzoxazole-4-carboxylate and ethylamine converted to methyl 2-(ethylamino)benzoxazole-4-carboxylate. $^1$H NMR and MS consistent.

Step B: Lithium 2-(4-(tert-butoxycarbonyl)-2,2-dimethylpiperazin-1-yl)benzoxazole-4-carboxylate was synthesized by following general procedure GP-B3. MS consistent.

Step C: Following general procedure GP-C1, 2-(ethylamino)benzoxazole-4-carboxylic acid and (S)-(−)-3-aminoquinuclidine dihydrochloride were coupled to provide (S)—N-(quinulidin-8-yl)-2-ethylaminobenzoxazole-4-carboxamide, which was converted to the hydrochloride salt following general procedure GP-D1. $^1$H NMR and MS consistent.

EXAMPLE 105

Preparation of Endo-N-(9-Methyl-9-azabicyclo[3.3.1]nonan-3-yl)-2-ethylbenzoxazole-4-carboxamide Hydrochloride Following general procedure GP-C1, 2-(ethylamino)benzoxazole-4-carboxylic acid and endo-3-amino-9-methyl-9-azabicyclo[3.3.1]nonane dihydrochloride were coupled to provide endo-N-(9-methyl-9-azabicyclo[3.3.1]nonan-3-yl)-2-ethylbenzoxazole-4-carboxamide, which was converted to the hydrochloride salt following general procedure GP-D1. $^1$H NMR and MS consistent.

EXAMPLE 106

Preparation of Endo-6-Chloro-N-(9-methyl-9-azabicyclo[3.3.1]nonan-3-yl)-2-((S)-3-methylmorpholino)benzoxazole-4-carboxamide Hydrochloride Step A: A solution of (S)-(+)-2-amino-1-propanol (5.0 g, 67.0 mmol) in toluene (60 mL) was added drop wise at 0° C. to a stirred suspension of NaH (60% in mineral oil, 6.2 g, 145 mmol) in toluene (150 mL). The cooling bath was removed and the reaction mixture was stirred at room temperature for 0.5 h. A solution of ethyl chloroacetate (8.0 mL, 73.8 mmol) in toluene (60 mL) was then added drop wise at room temperature and the resulting reaction mixture heated at reflux for 20 h. The reaction was cooled to room temperature and solid ammonium chloride (5 g, 96.7 mmol) added to the reaction. The reaction mixture was stirred for 20 min, filtered and the filtrate concentrated under reduced pressure to yield a yellow syrup. Purification by column chromatography (silica gel, 94.5:5:0.5 $CH_2Cl_2/CH_3OH/NH_4OH$) afforded (S)-5-methylmorpholine-3-one (6.5 g, 84%) as an off-white semi-solid. $^1$H NMR and MS consistent.

Step B: A solution of (S)-5-methylmorpholine-3-one (6.9 g, 59.9 mmol) in tetrahydrofuran (40 mL) was added drop wise at 0° C. to a solution of $LiAlH_4$ hydride (1.0 M solution in THF, 120.0 mL, 120 mmol) in tetrahydrofuran (40 mL). The ice bath was removed and the reaction mixture was heated at reflux for 18 h. The reaction was cooled in an ice-bath and excess hydride reagent was quenched by careful, drop wise addition of water (5 mL), 15% sodium hydroxide (5 mL) and water (15 mL). The resulting mixture was stirred at room temperature for 1 h and the reaction mixture was filtered through a pad of Celite and the pad rinsed with ethyl acetate (100 mL). The filtrate was washed with saturated brine solution, dried over $Na_2SO_4$, filtered and concentrated under reduced pressure to provide (S)-3-methylmorpholine as a red oil. Due to the products suspected high volatility, the (S)-3-methylmorpholine was used in the next step without further isolation or purification.

Step C: Following general procedure GP-A, 2,6-dichlorobenzoxazole-4-carboxylate and (S)-3-methylmorpholine hydrochloride converted to (S)-methyl 6-chloro-2-(3-methylmorpholino)-benz-oxazole-4-carboxylate. $^1$H NMR consistent.

Step D: To (S)-methyl 6-chloro-2-(3-methylmorpholino)benzoxazole-4-carboxylate (390 mg, 1.25 mmol) in tetrahydrofuran (20 mL) was added potassium trimethyl-silanolate (178 mg, 1.25 mmol). The reaction mixture was heated to reflux for 45 min. Then, additional potassium trimethylsilanolate (178 mg, 1.25 mmol) was added. After 30 min, the reaction mixture was cooled to ambient temperature. The solid was collected by vacuum filtration, rinsed with diethyl ether and dried to afford crude (S)-potassium 6-chloro-2-(3-methylmorpholino)benzoxazole-4-carboxylate (454 mg, quantitative) which was directly elaborated without purification. $^1$H NMR consistent.

Step E: Following general procedure GP-C2, (S)-potassium 6-chloro-2-(3-methylmorpholino)benzoxazole-4-carboxylate and endo-3-amino-9-methyl-9-azabicyclo[3.3.1]nonane dihydrochloride were coupled to provide 6-chloro-N-(9-methyl-9-azabicyclo[3.3.1]nonan-3-yl)-2-((S)-3-methylmorpholino)benzoxazole-4-carboxamide, which was converted to the hydrochloride salt following general procedure GP-D1. $^1$H NMR and MS consistent.

EXAMPLE 107

Preparation of Endo-N-(9-Methyl-9-azabicyclo[3.3.1]nonan-3-yl)-2-((2S,6S)-2,6-dimethylpiperazine-1-yl)-7-fluorobenzoxazole-4-carboxamide hydrochloride Step A: Methyl 2-((2S,6S)-4-(tert-butoxycarbonyl)-2,6-dimethylpiperazin-1-yl)-7-fluorobenzoxazole-4-carboxylate was synthesized by following general procedure GP-A. $^1$H NMR and MS consistent.

Step B: Following general procedure GP-B3, methyl 2-((2S,6S)-4-(tert-butoxycarbonyl)-2,6-dimethylpiperazin-1-yl)-7-fluorobenzoxazole-4-carboxylate converted to 2-((2S,6S)-4-(tert-butoxycarbonyl)-2,6-dimethylpiperazin-1-yl)-7-fluorobenzoxazole-4-carboxylic acid. MS consistent Step C: Following general procedure GP-C1,2-((2S,6S)-4-(tert-butoxycarbonyl)-2,6-dimethylpiperazin-1-yl)-7-fluorobenzoxazole-4-carboxylic acid and endo-3-amino-9-methyl-9-azabicyclo[3.3.1]nonane dihydrochloride were coupled to provide endo-N-(9-methyl-9-azabicyclo[3.3.1]nonan-3-yl)-2-((2S,6S)-2,6-dimethyl-4-tert-butoxycarbonyl-piperazin-1-yl)-7-fluorobenzoxazole-4-carboxamide. MS consistent.

Step D: Endo-N-(9-Methyl-9-azabicyclo[3.3.1]nonan-3-yl)-2-((2S,6S)-2,6-dimethyl-4-tert-butoxycarbonyl-piperazine-1-yl)-7-fluorobenzoxazole-4-carboxamide was dissolved in 3 ml of 50% TFA in CH$_2$Cl$_2$ and stirred for 3.5 h at ambient temperature. The solvent was removed under vacuum, and the residue was neutralized by ion-exchange chromatography (SCX-2 column, 5 g) to afford endo-N-(9-methyl-9-azabicyclo[3.3.1]nonan-3-yl)-2-((2S,6S)-2,6-dimethylpiperazine-1-yl)-7-fluorobenzoxazole-4-carboxamide hydrochloride (62 mg) as a clear oil, which was converted to the hydrochloride salt following general procedure GP-D1. $^1$H NMR and MS consistent.

EXAMPLE 108

Preparation of (S)—N-(quinuclidine-8-yl)-6-chloro-2-(dimethylamino)benzoxazole-4-carboxamide Hydrochloride Step A: Methyl 2-(dimethylamino)-6-chlorobenzoxazole-4-carboxylate was synthesized by following general procedure GP-A. MS consistent.

Step C: Lithium 2-(dimethylamino)-6-chlorobenzoxazole-4-carboxylate was synthesized by following general procedure GP-B2. MS consistent Step D: Following general procedure GP-C$_1$, lithium 2-(dimethylamino)-6-chlorobenzoxazole-4-carboxylate and (S)-(−)-3-aminoquinuclidine dihydrochloride were coupled to provide (S)—N-(quinuclidine-8-yl)-6-chloro-2-(dimethylamino)benzoxazole-4-carboxamide, which was converted to the hydrochloride salt following general procedure GP-D1. $^1$H NMR and MS consistent.

EXAMPLE 109

Preparation of (S)—N-(quinulidin-8-yl)-2-(2,2,2-trifluoroethylethylamino)benzoxazole-4-carboxamide Hydrochloride Step A: Methyl 2-(2,2,2-trifluoroethylamino)benzoxazole-4-carboxylate was synthesized by following general procedure GP-A. $^1$H NMR and MS consistent.

Step B: 2-(2,2,2-trifluoroethylamino)benzoxazole-4-carboxylic acid synthesized by following general procedure GP-B3. $^1$H NMR and MS consistent.

Step C: Following general procedure GP-C1,2-(2,2,2-trifluoroethylamino)benzoxazole-4-carboxylic acid and (S)-(−)-3-aminoquinuclidine dihydrochloride coupled to provide (S)—N-(quinulidin-8-yl)-2-(2,2,2-trifluoroethylethylamino)benzoxazole-4-carboxamide, which was converted to the hydrochloride salt following general procedure GP-D1. $^1$H NMR and MS consistent.

EXAMPLE 110

Preparation of Endo-N-(9-Methyl-9-azabicyclo[3.3.1]nonan-3-yl)-2-((2S,6S)-4-acetyl-2,6-dimethylpiperazin-1-yl)benzoxazole-4-carboxamide Hydrochloride Step A: To an ice-cold solution of (2S,6S)-2,6-dimethylpiperazine (712 mg, 6.24 mmol) in CH$_2$Cl$_2$ (28 mL) was added di-tert-butyl dicarbonate (1.50 g, 6.86 mmol), triethylamine (1.33 g, 13.09 mmol) and N,N-dimethylpyridin-4-amine (38.1 mg, 0.31 mmol). The reaction mixture was stirred at 0° C. for 15 min, then warmed to room temperature and stirred for 20 h. The solvent was removed under reduced pressure. The residue was dried to afford (3S,5S)-tert-butyl 3,5-dimethylpiperazine-1-carboxylate (1.79 g, 100%) as white solid. MS consistent.

Step B: Methyl 2-(4-(tert-butoxycarbonyl)-2S, 6S-dimethylpiperazin-1-yl)benzoxazole-4-carboxylate was synthesized by following general procedure GP-A. MS consistent.

Step C: To an ice-cold solution of methyl 2-(4-(tert-butoxycarbonyl)-2S, 6S-dimethylpiperazin-1-yl)benzoxazole-4-carboxylate (360.1 mg, 0.924 mmol) in CH$_2$Cl$_2$ (5 mL) was added TFA (0.343 mL, 4.62 mmol). The reaction stirred for 18 h under an atmosphere of nitrogen while gradually warming to room temperature. The reaction was quenched with saturated aqueous sodium bicarbonate solution (15 mL). The organic layer was separated, washed with brine (10 mL), dried (Na$_2$SO$_4$), filtered, and concentrated under reduced pressure to provide methyl 2-((2S,6S)-2,6-dimethylpiperazin-1-yl)benzoxazole-4-carboxylate as an oil (285 mg, >99%). This material was carried on to the next step without characterization.

Step D: To an ice-cold solution of methyl 2-((2S,6S)-2,6-dimethylpiperazin-1-yl)benzoxazole-4-carboxylate (273 mg, 0.943 mmol) in CH$_2$Cl$_2$ (5 mL) was added pyridine (0.114 mL, 1.41 mmol) followed by acetyl chloride (0.100 mL, 1.41 mmol) under an atmosphere of nitrogen. The mixture stirred for 18 h while gradually warming to room temperature. The reaction was diluted with $CH_2Cl_2$ (10 mL) and washed with saturated aqueous $NaHCO_3$ solution (10 mL), 1 N HCl solution (10 mL), and brine (10 mL). The organic layer was dried ($Na_2SO_4$), filtered, and concentrated under reduced pressure. The resulting residue was purified by column chromatography over silica gel (0% to 50%, 95:15:1.5, $CH_2Cl_2$/ $CH_3OH$/concentrated $NH_4OH$ in $CH_2Cl_2$) to give methyl 2-((2S,6S)-4-acetyl-2,6-dimethylpiperazin-1-yl)benzoxazole-4-carboxylate as an oil (62.1 mg, 20%). $^1H$ NMR and MS consistent.

Step E: Following general procedure GP-B2, methyl 2-((2S,6S)-4-acetyl-2,6-dimethylpiperazin-1-yl)benzoxazole-4-carboxylate was reacted with lithium hydroxide monohydrate to provide lithium 2-((2S,6S)-4-acetyl-2,6-dimethylpiperazin-1-yl)benzoxazole-4-carboxylate. $^1H$ NMR and MS consistent.

Step F: Following general procedure GP-C2, lithium 2-((2S,6S)-4-acetyl-2,6-dimethylpiperazin-1-yl)benzoxazole-4-carboxylate and 9-methyl-9-azabicyclo[3.3.1]nonan-3-amine dihydrochloride were coupled to provide endo-N-(9-Methyl-9-azabicyclo[3.3.1]nonan-3-yl)-2-((2S,6S)-4-acetyl-2,6-dimethylpiperazin-1-yl)benzoxazole-4-carboxamide, which was converted to the hydrochloride salt following general procedure GP-D1. $^1H$ NMR and MS consistent.

EXAMPLE 111

Preparation of Endo-2-amino-6-chloro-N-(9-Methyl-9-azabicyclo[3.3.1]nonan-3-yl)benzoxazole-4-carboxamide Hydrochloride Step A: 2-amino-6-chlorobenzoxazole-4-carboxylic acid was synthesized by following general procedure GP-B2. $^1H$ NMR and MS consistent.

Step B: Following general procedure GP-C1,2-amino-6-chlorobenzoxazole-4-carboxylic acid and 9-methyl-9-azabicyclo[3.3.1]nonan-3-amine dihydrochloride coupled to provide endo-2-amino-6-chloro-N-(9-methyl-9-azabicyclo[3.3.1]nonan-3-yl)benzoxazole-4-carboxamide, which was converted to the hydrochloride salt following general procedure GP-D1. $^1H$ NMR and MS consistent.

EXAMPLE 112

Preparation of (S)—N-(quinulidin-8-yl)-2-amino-7-fluorobenzoxazole-4-carboxamide Hydrochloride Step A: A mixture of methyl 2-chloro-7-fluoro-2,3-dihydrobenzoxazole-4-carboxylate (720 mg, 3.14 mmol), o-nitrophenol (660 mg, 4.71 mmol) and $K_2CO_3$ (0.96 g, 7.0 mmol), in THF (10 mL), was stirred at ambient for 2.5 h. The reaction mixture was filtered and gaseous ammonia was bubbled through the mother liquor for 10 min. The precipitate formed was filtered and washed with THF (20 mL). The combined THF fractions were concentrated, and the resulting residue crystallized from methanol to afford methyl 2-amino-7-fluorobenzoxazole-4-carboxylate (173 mg, 26%) as a pale yellow solid. $^1H$ NMR and MS consistent.

Step B: 2-amino-7-fluorobenzoxazole-4-carboxylic acid synthesized by following general procedure GP-B3. $^1H$ NMR and MS consistent.

Step C: Following general procedure GP-C1,2-amino-7-fluorobenzoxazole-4-carboxylic acid and (S)-(–)-3-aminoquinuclidine dihydrochloride were coupled to provide (S)—N-(quinulidin-8-yl)-2-amino-7-fluorobenzoxazole-4-carboxamide, which was converted to the hydrochloride salt following general procedure GP-D1. $^1H$ NMR and MS consistent.

EXAMPLE 113

Preparation of (S)—N-(quinulidin-8-yl)-2-methylaminobenzoxazole-4-carboxamide Hydrochloride Step A: Methyl 2-methylaminobenzoxazole-4-carboxylate was synthesized by following general procedure GP-A. $^1H$ NMR and MS consistent.

Step B: 2-methylaminobenzoxazole-4-carboxylic acid was synthesized by following general procedure GP-B3. $^1H$ NMR and MS consistent.

Step C: Following general procedure GP-C1, 2-methylaminobenzoxazole-4-carboxylic acid and (S)-(–)-3-aminoquinuclidine dihydrochloride were coupled to provide (S)—N-(quinulidin-8-yl)-2-methylaminobenzoxazole-4-carboxamide, which was converted to the hydrochloride salt following general procedure GP-D1. $^1H$ NMR and MS consistent.

EXAMPLE 114

Preparation of Endo-N-(9-methyl-9-azabicyclo[3.3.1]nonan-3-yl)-6-chloro-2-((2S,6S)-2,6-dimethylpiperazin-1-yl)benzoxazole-4-carboxamide Hydrochloride Step A: Methyl 2-((2S,6S)-4-(tert-butoxycarbonyl)-2,6-dimethylpiperazin-1-yl)-6-chlorobenzoxazole-4-carboxylate was synthesized by following general procedure GP-A. $^1H$ NMR and MS consistent.

Step B: Lithium 2-((2S,6S)-4-(tert-butoxycarbonyl)-2,6-dimethylpiperazin-1-yl)-6-chlorobenzoxazole-4-carboxylate was synthesized by following general procedure GP-B2. $^1H$ NMR and MS consistent.

Step C: Following general procedure GP-C1, lithium 2-((2S,6S)-4-(tert-butoxycarbonyl)-2,6-dimethylpiperazin-1-yl)-6-chlorobenzoxazole-4-carboxylate and endo-3-amino-9-methyl-9-azabicyclo[3.3.1]nonane dihydrochloride were coupled to provide endo-N-(9-methyl-9-azabicyclo[3.3.1]nonan-3-yl)-6-chloro-2-((2S,6S)-2,6-dimethylpiperazin-1-yl)benzoxazole-4-carboxamide. $^1H$ NMR and MS consistent.

Step D: To solution of endo-N-(9-methyl-9-azabicyclo[3.3.1]nonan-3-yl)-6-chloro-2-((2S,6S)-2,6-dimethylpiperazin-1-yl)benzoxazole-4-carboxamide (294 mg, 0.53 mmol) in $CH_2Cl_2$ (10 mL) was added TFA (3.0 mL, 38.90 mmol) and the mixture was stirred at room temperature for 2 h then concentrated under reduced pressure. The crude material was purified by preparative TLC (silica gel, 100% 9:1 $CH_2Cl_2$/ $CH_3OH$) to 100% 90:9:1 $CH_2Cl_2$/$CH_3OH$/concentrated $NH_4OH$) followed by semi-preparative HPLC (Luna C18(2), 10% $CH_3CN$/0.05% TFA in $H_2O$/0.05% TFA to 100% $CH_3CN$/0.05% TFA over 30 min, 1=223 nm). The desired fractions were first treated with 10% aqueous $K_2CO_3$ until pH=9 and then the aqueous phase was concentrated to ⅓ of it original volume under reduced pressure and the aqueous phase was extracted with ethyl acetate (2×25 mL). The combined organic phase was washed with brine (10 mL) dried ($Na_2SO_4$), and concentrated under reduced pressure to afford endo-N-(9-methyl-9-azabicyclo[3.3.1]nonan-3-yl)-6-chloro-2-((2S,6S)-2,6-dimethylpiperazin-1-yl)benzoxazole- 4-carboxamide which was converted to the hydrochloride salt following general procedure GP-D1. $^1$H NMR and MS consistent.

EXAMPLE 115

Preparation of (S)—N-(quinuclidine-8-yl)-2-diethylaminobenzoxazole-4-carboxamide Hydrochloride Step A: Lithium 2-(diethylamino)benzoxazole-4-carboxylate was synthesized by following general procedure GP-B2. $^1$H NMR and MS consistent Step B: Following general procedure GP-C2, lithium 2-(diethylamino)benzoxazole-4-carboxylate and (S)-(−)-3-aminoquinuclidine dihydrochloride were coupled to provide (S)—N-(quinuclidine-8-yl)-2-diethylaminobenzoxazole-4-carboxamide, which was converted to the hydrochloride salt following general procedure GP-D1. $^1$H NMR and MS consistent.

EXAMPLE 116

Preparation of (S)—N-(Quinulidin-8-yl)-2-amino-6-fluorobenzoxazole-4-carboxamide Hydrochloride Step A: To a solution of fuming nitric acid (18 mL) and glacial acetic acid (36 mL) preheated to 55° C. was added 3-fluoro-5-methoxybenzoic acid (3.00 g, 17.63 mmol) portion wise over 5 min. The mixture was maintained at 55° C. for an additional 90 min. The reaction was cooled to ambient temperature and poured onto ice-water (200 mL). The pH of the solution was adjusted to 2 using aqueous NaHCO$_3$ solution. The precipitate formed was filtered and washed with hexanes (100 mL) to afford 5-fluoro-3-methoxy-2-nitrobenzoic acid (2.52 g, 66%) as a white solid. $^1$H NMR and MS consistent.

Step B: 5-Fluoro-3-methoxy-2-nitrobenzoic acid (2.78 g, 12.92 mmol) was suspended in a mixture of 48% aqueous hydrobromic acid/glacial acetic acid (7:2, 90 mL) and the mixture heated at 135° C. for 41 h. The solvent was removed under reduced pressure, the crude 5-fluoro-3-hydroxy-2-nitrobenzoic acid (2.60 g) was directly elaborated without further characterization/purification. MS consistent.

Step C: Crude 5-fluoro-3-hydroxy-2-nitrobenzoic acid (2.60 g, 12.92 mmol), was suspended in CH$_3$OH (50 mL) and cooled to 0° C. Thionyl chloride (9.4 ml, 129.26 mmol) was added drop wise at 0° C. The mixture was allowed to warm to ambient temperature then heated to reflux for 17 h. The reaction mixture was allowed to cool to ambient temperature, and the solvent removed under reduced pressure. The crude material was purified by column chromatography (silica gel, 0 to 20% CH$_3$OH in CH$_2$Cl$_2$) to afford methyl 5-fluoro-3-hydroxy-2-nitrobenzoate (1.15 g, 41%) as a white solid. $^1$H NMR and MS consistent.

Step D: To a solution of methyl 5-fluoro-3-hydroxy-2-nitrobenzoate (1.15 g, 5.34 mmol) in a mixture of CH$_3$OH and glacial acetic acid (3:1, 40 mL) was added 10 wt % palladium on activated charcoal (0.20 g, 17 wt %). The suspension was placed in a Parr hydrogenation apparatus under a H$_2$ atmosphere at 50 psi for 1.5 h. The suspension was filtered through diatomaceous earth eluting with CH$_2$Cl$_2$/CH$_3$OH (9:1, 100 mL). Purification by column chromatography (silica gel, 5 to 100% EtOAc in hexanes) afforded methyl 2-amino-5-fluoro-3-hydroxybenzoate (0.80 g, 83%) as a white solid. $^1$H NMR and MS consistent.

Step E: To a solution of di-(1H-imidazole-1-yl)methanamine (1.05 g, 6.52 mmol) in THF (30 mL) was added methyl-2-amino-5-fluoro-3-hydroxybenzoate (0.96 g, 5.22 mmol) at room temperature and the resulting reaction mixture was heated to reflux for 6 h. The reaction mixture was cooled to room temperature and concentrated under reduced pressure. The residue was dissolved in EtOAc (200 mL) and washed with H$_2$O (4×100 mL), saturated aqueous ammonium chloride (2×100 mL), brine (2×100 mL), dried over Na$_2$SO$_4$, filtered, and concentrated under reduced pressure to afford methyl 2-amino-6-fluorobenzoxazole-4-carboxylate (0.95 g, 87%) as a yellow solid. $^1$H NMR and MS consistent.

Step F: 2-amino-6-fluorobenzoxazole-4-carboxylic acid was synthesized by following general procedure GP-B3. $^1$H NMR consistent Step G: Following general procedure GP-C1,2-amino-6-fluorobenzoxazole-4-carboxylic acid and (S)-(−)-3-aminoquinuclidine dihydrochloride were coupled to provide (S)—N-(quinulidin-8-yl)-2-amino-6-fluorobenzoxazole-4-carboxamide, which was converted to the hydrochloride salt following general procedure GP-D1. $^1$H NMR and MS consistent.

EXAMPLE 117

Preparation of Endo-N-(9-methyl-9-azabicyclo[3.3.1]nonan-3-yl)-2-((2S,6S)-4-benzoyl-2,6-dimethylpiperazin-1-yl)benzoxazole-4-carboxamide Hydrochloride Step A: A mixture of endo-N-(9-methyl-9-azabicyclo[3.3.1]nonan-3-yl)-2-((2S,6S)-2,6-dimethylpiperazin-1-yl)benzoxazole-4-carboxamide (81.4 mg, 0.19 mmol), benzoyl chloride (34 mL, 0.30 mmol) and triethylamine (55 mL, 0.40 mmol), in CH$_2$Cl$_2$ (5 mL) was stirred at ambient temperature for 6 h. The reaction mixture was quenched with saturated NaHCO$_3$ (10 mL) and extracted with CH$_2$Cl$_2$ (2×30 mL). The combined organic layers were washed successively with 1N HCl (30 mL) brine (25 mL), dried (Na$_2$SO$_4$) and concentrated under reduced pressure. Purification by column chromatography (silica gel, 9:1 CH$_2$Cl$_2$/CH$_3$OH to 90:9:1 CH$_2$Cl$_2$/CH$_3$OH/NH$_4$OH) afforded endo-N-(9-methyl-9-azabicyclo[3.3.1]nonan-3-yl)-2-(4-benzoyl-2,6-dimethylpiperazin-1-yl)benzoxazole-4-carboxamide (36 mg, 35%) as a white solid. $^1$H NMR and MS consistent.

Step B: Following general procedure GP-D1, endo-N-(9-methyl-9-azabicyclo[3.3.1]nonan-3-yl)-2-((2S,6S)-4-benzoyl-2,6-dimethylpiperazin-1-yl)benzoxazole-4-carboxamide was converted to the hydrochloride salt. $^1$H NMR and MS consistent.

EXAMPLE 118

Preparation of (S)—N-(Quinulidin-8-yl)-2-((2S,6S)-2,6-dimethylpiperazine-1-yl)-7-fluorobenzoxazole-4-carboxamide hydrochloride Step A: Following general procedure GP-C1, a mixture of 2-((2S,6S)-4-(tert-butoxycarbonyl)-2,6-dimethylpiperazin-1-yl)-7-fluorobenzoxazole-4-carboxylic acid and (S)-(−)-3-aminoquinuclidine dihydrochloride were coupled to provide (S)—N-(quinulidin-8-yl)-2-((2S,6S)-2,6-dimethyl-4-tert-butoxycarbonyl-piperazine-1-yl)-7-fluorobenzoxazole-4-carboxamide. The carboxamide was dissolved in 3 ml of 50% TFA in CH$_2$Cl$_2$ and stirred for 2 h at ambient temperature. The solvent was removed under vacuum, and the residue was neutralized by ion-exchange chromatography (SCX-2 column, 2 g) to afford a clear oil (15.4 mg). The hydrochloride salt was obtained following general procedure GP-D1. $^1$H NMR and MS consistent.

EXAMPLE 119

Preparation of Endo-N-(9-methyl-9-azabicyclo[3.3.1]nonan-3-yl)-2-((2S,6S)-4-(cyclopropylmethyl)-2,6-dimethylpiperazin-1-yl)benzoxazole-4-carboxamide Hydrochloride Step A: A mixture of endo-N-(9-methyl-9-azabicyclo[3.3.1]nonan-3-yl)-2-((2S,6S)-2,6-dimethylpiperazin-1-yl)benzoxazole-4-carboxamide (51 mg, 0.12 mmol), cyclopropane carboxaldehyde (28 mL, 0.37 mmol) and NaBH(OAc)$_3$ (79 mg, 0.37 mmol), in CH$_2$Cl$_2$/HOAc (100:1, 10.1 mL), was stirred at ambient temperature for 17 h. The reaction mixture was diluted with saturated NaHCO$_3$ (10 mL) and extracted with EtOAc/CH$_2$Cl$_2$ (1:1, 2×20 mL). The combined organic layers were washed with brine (25 mL), dried (Na$_2$SO$_4$) and concentrated under reduced pressure. Purification by preparative TLC (silica gel, 9:1 CH$_2$Cl$_2$/CH$_3$OH/NH$_4$OH) afforded endo-N-(9-methyl-9-azabicyclo[3.3.1]nonan-3-yl)-2-((2S,6S)-4-(cyclopropylmethyl)-2,6-dimethylpiperazin-1-yl)benzoxazole-4-carboxamide (35.8 mg, 62%) as a white foam: $^1$H NMR and MS consistent.

Step B: Following general procedure GP-D1, endo-N-(9-methyl-9-azabicyclo[3.3.1]nonan-3-yl)-2-((2S,6S)-4-(cyclopropylmethyl)-2,6-dimethylpiperazin-1-yl)benzoxazole-4-carboxamide was converted to the hydrochloride salt. $^1$H NMR and MS consistent.

EXAMPLE 120

Preparation of Endo-N-(9-methyl-9-azabicyclo[3.3.1]nonan-3-yl)-2-((2S,6S)-2,4,6-trimethyl-3-oxopiperazine-1-yl)benzoxazole-4-carboxamide Hydrochloride Step A: To a-30° C. solution of N-t-Boc-L-alanine (20.0 g, 0.106 mol) and triethylamine (16.8 mL, 0.119 mol) in THF (300 mL) was added isobutyl chloroformate (15.0 mL, 0.114 mol) drop wise. The reaction mixture was warmed to ambient temperature over 1.25 h and then stirred for 3.5 h. The reaction mixture was cooled to 0° C. and a solution of N-methylbenzylamine (14.3 mL, 0.111 mol) and triethylamine (18.8 mL, 0.134 mol) in THF (60 mL) was added drop wise. The reaction mixture was allowed to warm to ambient temperature. After 16 h, saturated NaHCO$_3$ (200 mL) was added and most of the THF was removed under reduced pressure. The remaining aqueous layer was extracted with EtOAc (2×250 mL). The combined organic layers were washed with brine (100 mL), dried (Na$_2$SO$_4$) and concentrated under reduced pressure. Purification by column chromatography (silica gel, 10% EtOAc in hexanes to 40% EtOAc in hexanes) gave (S)-tert-butyl 1-(benzyl(methyl)amino)-1-oxopropan-2-ylcarbamate (26.3 g, 85%) as a colorless oil. $^1$H NMR consistent.

Step B: To an ice-cold solution of (S)-tert-butyl 1-(benzyl(methyl)amino)-1-oxopropan-2-ylcarbamate (26.3 g, 0.090 mol) in CH$_2$Cl$_2$ (100 mL) was added TFA(100 mL) drop wise. The reaction mixture was warmed to ambient temperature. After 18.5 h, the reaction mixture was concentrated under reduced pressure. The residue was partitioned between CH$_2$Cl$_2$ (250 mL) and saturated NaHCO$_3$ (250 mL). The aqueous layer was separated and basified to pH=9-10 with 1 N NaOH and extracted again with CH$_2$Cl$_2$ (100 mL). The combined organic layers were washed with saturated NaHCO$_3$ (100 mL), H$_2$O (100 mL), brine (100 mL), dried (Na$_2$SO$_4$) and concentrated under reduced pressure to give (S)-2-amino-N-benzyl-N-methylpropanamide (14.7 g, 85%) as an amber oil. $^1$H NMR consistent.

Step C: To an ice-cold solution of (S)-2-amino-N-benzyl-N-methylpropanamide (1.70 g, 8.80 mmol) in THF (25 mL) was added lithium aluminum hydride (18 mL of a 1.0 M solution in THF, 17.6 mmol) drop wise. The reaction mixture was heated at reflux for 2 h. After cooling to 0° C., the reaction mixture was quenched by the drop wise addition of H$_2$O (0.7 mL), 15% sodium hydroxide (0.7 mL), and H$_2$O (2.1 mL). Diethyl ether (25 mL) was added during the quench. The mixture was filtered through Celite and the Celite pad was rinsed with diethyl ether. The filtrate was concentrated under reduced pressure to give (S)—N-1-benzyl-N-1-methylpropane-1,2-diamine (1.3 g, 82%) as a colorless oil: $^1$H NMR consistent.

Step D: To an ice-cold solution of (R)-(+)-lactate (0.91 g, 8.7 mmol) in CH$_2$Cl$_2$ (40 mL) was added Tf$_2$O (1.5 mL, 8.7 mmol). After 10 min a solution of 2,6-lutidine (1.2 mL, 10 mmol) in CH$_2$Cl$_2$ (3 mL) was added. After another 10 min, a solution of (S)—N-1-benzyl-N-1-methylpropane-1,2-diamine (1.3 g, 7.3 mmol) and triethylamine (1.6 mL, 12 mmol) in CH$_2$Cl$_2$ (10 mL) was added. The reaction mixture was allowed to warm to ambient temperature. After 15.25 h, the reaction mixture was partitioned between saturated NaHCO$_3$ (100 mL) and CH$_2$Cl$_2$ (100 mL). The aqueous layer was separated and extracted again with CH$_2$Cl$_2$ (20 mL). The combined organic layers were washed with H$_2$O (50 mL), brine (50 mL), dried (Na$_2$SO$_4$) and concentrated under reduced pressure. Purification by column chromatography (silica gel, EtOAc) gave (S)-methyl 2-((S)-1-(benzyl(methyl)-amino)propan-2-ylamino)propanoate (0.98 g, 50% which contains 2,6-lutidine, ca 2:1 product:2,6-lutidine). $^1$H NMR consistent.

Step E: (S)-Methyl 2-((S)-1-(benzyl(methyl)-amino)propan-2-ylamino)-propanoate (0.98 g, 3.7 mmol), concentrated HCl (mL) and 10% Pd on carbon (200 mg) were combined in ethanol (25 mL). The reaction mixture was shaken on a Parr apparatus under a hydrogen atmosphere (15 psi). After 16.75 h, the reaction mixture was filtered through Celite and the Celite pad was rinsed with CH$_3$OH and CH$_2$Cl$_2$. The filtrate was concentrated under reduced pressure to give (S)-methyl 2-((S)-1-(methylamino)propan-2-ylamino)propanoate which was used directly in the next reaction. MS consistent.

Step F: The crude (S)-methyl 2-((S)-1-(methylamino)propan-2-ylamino)propanoate was dissolved in ethanol (30 mL) and p-toluenesulfonic acid (175 mg) was added. The reaction mixture was heated to reflux for 18 h and then concentrated under reduced pressure. The residue was partitioned between CH$_2$Cl$_2$ (40 mL) and saturated NaHCO$_3$ (20 mL). The aqueous layer was separated and extracted again with CH$_2$Cl$_2$ (20 mL). The combined organic layers were dried (Na$_2$SO$_4$) and concentrated under reduced pressure to give (3S,5S)-1,3,5-trimethylpiperazin-2-one (230 mg, 43% which contains 2,6-lutidine, ca 2:1 product:2,6-lutidine) as an amber oil. $^1$H NMR consistent.

Synthesis of methyl 2-((2S,6S)-2,4,6-trimethyl-3-oxopiperazine-1-yl)benzoxazole-4-carboxylate: A mixture of methyl 2-chlorobenzoxazole-4-carboxylate (342 mg, 1.62 mmol), (3S,5S)-1,3,5-trimethylpiperazin-2-one (230 mg, 1.62 mmol) and potassium carbonate (670 mg, 4.85 mmol), in DMF (10 mL), was stirred at ambient temperature for 16 h. The reaction mixture was diluted with H$_2$O (20 mL) and extracted with EtOAc (2×40 mL). The combined organic layers were washed with 0.5 N HCl (10 mL), H$_2$O (10 mL), brine (10 mL), dried (Na$_2$SO$_4$), filtered, and concentrated under reduced pressure. The residue was triturated with diethyl ether and the solids were removed by filtration. The filtrate was concentrated and purified by column chromatography (silica gel, 10% CH$_2$Cl$_2$ in EtOAc to 100% EtOAc) to give methyl 2-((2S,6S)-2,4,6-trimethyl-3-oxopiperazine-1-yl)benzoxazole-4-carboxylate (98 mg, 19%): $^1$H NMR consistent.

Step G: Following general procedure GP-B3, A mixture of methyl 2-((2S,6S-2,4,6-trimethyl-3-oxopiperazine-1-yl)benzoxazole-4-carboxylate was converted to 2-((2S,6S-2,4,6-trimethyl-3-oxopiperazine-1-yl)benzoxazole-4-carboxylic acid which was directly elaborated directly without purification.

Step H: Following general procedure GP-C2,2-((2S,6S)-2,4,6-trimethyl-3-oxopiperazine-1-yl)benzoxazole-4-carboxylic acid and endo-3-amino-9-methyl-9-azabicyclo[3.3.1]-nonane dihydrochloride were coupled to provide endo-N-(9-methyl-9-azabicyclo[3.3.1]nonan-3-yl)-2-((2S,6S)-2,4,6-trimethyl-3-oxopiperazine-1-yl)benzoxazole-4-carboxamide hydrochloride, which was converted to the hydrochloride salt following general procedure GP-D1. $^1$H NMR and MS consistent.

EXAMPLE 121

Preparation of Endo-2-amino-6-fluoro-N-(9-Methyl-9-azabicyclo[3.3.1]nonan-3-yl)benzoxazole-4-carboxamide Hydrochloride Step A: To a solution of di(1H-imidazole-1-yl)methanamine (1.05 g, 6.52 mmol) in THF (30 mL) was added methyl-2-amino-5-fluoro-3-hydroxybenzoate (0.96 g, 5.22 mmol) at room temperature and the resulting reaction mixture was heated to reflux for 6 h. The reaction mixture was cooled to room temperature and concentrated under reduced pressure. The residue was dissolved in EtOAc (200 mL) and washed with H$_2$O (4×100 mL), saturated aqueous ammonium chloride (2×100 mL), brine (2×100 mL), dried over Na$_2$SO$_4$, filtered, and concentrated under reduced pressure to afford methyl 2-amino-6-fluorobenzoxazole-4-carboxylate (0.95 g, 87%). $^1$H NMR and MS consistent.

Step B: 2-amino-6-fluorobenzoxazole-4-carboxylic acid was synthesized by following general procedure GP-B3. $^1$H NMR and MS consistent.

Step C: Following general procedure GP-C1,2-amino-6-fluorobenzoxazole-4-carboxylic acid and endo-3-amino-9-methyl-9-azabicyclo[3.3.1]nonane dihydrochloride were coupled to provide endo-2-amino-6-fluoro-N-(9-methyl-9-azabicyclo[3.3.1]nonan-3-yl)benzoxazole-4-carboxamide, which was converted to the hydrochloride salt following general procedure GP-D1. $^1$H NMR and MS consistent.

EXAMPLE 122

Preparation of Endo-N-(9-methyl-9-azabicyclo[3.3.1]nonan-3-yl)-2-((2S,6S-2,4,6-trimethylpiperazin-1-yl)benzoxazole-4-carboxamide Hydrochloride A mixture of endo-N-(9-methyl-9-azabicyclo[3.3.1]nonan-3-yl)-2-((2S,6S)-2,6-dimethylpiperazin-1-yl)benzoxazole-4-carboxamide (80 mg, 0.19 mmol), formaldehyde 37% aqueous solution, 6.0 mL, 76.9 mmol) and NaCNBH$_3$ (25 mg, 0.39 mmol), in CH$_3$OH/HOAc 10:1, 5.5 mL), was stirred at ambient temperature for 24 h. The reaction mixture was concentrated, diluted with saturated ammonium chloride (5 mL), and extracted with CH$_2$Cl$_2$ (2×25 mL). The aqueous phase was adjusted to pH 8 and extracted with CH$_2$Cl$_2$ (2×25 mL) and the combined organic phase was washed with brine (10 mL), dried (Na$_2$SO$_4$) and concentrated under reduced pressure to provide endo-N-(9-methyl-9-azabicyclo[3.3.1] nonan-3-yl)-2-((2S,6S)-2,4,6-trimethylpiperazin-1-yl)benzoxazole-4-carboxamide, which was converted to the hydrochloride salt following general procedure GP-D1. $^1$H NMR and MS consistent.

EXAMPLE 123

Preparation of Endo-N-(9-methyl-9-azabicyclo[3.3.1]nonan-3-yl)-2-((3S,5S)/(3R,5R)-3,5-dimethylthiomorpholine 1,1-dioxide)benzoxazole-4-carboxamide Hydrochloride Step A: To solution of freshly distilled chloroacetone (31.0 g, 0.33 mol) in ethanol (335 mL) was added drop wise at 75° C. under N$_2$ a solution of Na$_2$S.9H$_2$O (40.2 g, 0.17 mol) in H$_2$O (110 mL). After addition was complete the reaction mixture was heated for a further 45 min before it was allowed to cool to ambient temperature. The reaction mixture was concentrated to approximately half volume under reduced pressure and then partitioned with EtOAc (400 mL) and brine (200 mL). The layers were separated and the organic layer washed with brine (200 mL) and dried over Na$_2$SO$_4$ before concentrating under reduced pressure. The residual orange oil was distilled under high vacuum (140° C., <1 mm Hg) to afford 1,1'-thiodipropan-2-one (10.3 g, 42%). $^1$H NMR and MS consistent.

Step B: To a stirred solution of diphenylmethanimine (2.36 mL, 13.7 mmol), HOAc (0.86 mL, 15.1 mmol), and potassium hydroxide (0.19 g, 3.4 mmol) in CH$_3$OH (25 mL) cooled to 0° C. was added a solution of 1,1'-thiodipropan-2-one (2.0 g, 13.7 mmol) in CH$_3$OH (10 mL). NaCNBH$_3$ (0.86 g, 13.7 mmol) was then added and the reaction mixture stirred at ambient temperature for 16 h. A further portion of NaCNBH$_3$ (0.43 g, 6.9 mmol) was added and the reaction mixture stirred for another 4 h. The reaction mixture was partitioned with EtOAc (150 mL) and H$_2$O (150 mL) and the layers separated. The organic layer was washed with H$_2$O (150 mL), brine (150 mL) then dried over Na$_2$SO$_4$. After concentration under reduced pressure, the resulting residue was purified by flash column chromatography (silica gel, 10-50% EtOAc in hexanes) to afford (3S,5S)/(3R,5R)-4-benzhydryl-3,5-dimethylthiomorpholine (0.52 g, 13%). $^1$H NMR consistent.

Step C: A mixture of(3S,5S)/(3R,5R)-4-benzhydryl-3,5-dimethylthiomorpholine (0.52 g, 1.75 mmol), triethylsilane (1.12 mL, 7.00 mmol) and TFA (20 mL) was heated at reflux for 20 h. After cooling to ambient temperature the reaction mixture was concentrated under reduced pressure and the residue partitioned with 1 N HCl (10 mL) and Et$_2$O (20 mL). The aqueous layer was separated and lyophilized to afford (3S,5S)/(3R,5R)-3,5-dimethylthiomorpholine hydrochloride (285 mg, 97%). $^1$H NMR and MS consistent.

Step D: A mixture of methyl 2-chlorobenzoxazole-4-carboxylate (360 mg, 1.70 mmol), (3S,5S)/(3R,5R)-3,5-dimethylthiomorpholine hydrochloride (270 mg, 1.62 mmol) and potassium carbonate (672 mg, 4.86 mmol), in DMF (5 mL), was stirred at ambient temperature for 6 h. The reaction was then heated at 55° C. for 2 h before it was diluted with H$_2$O (20 mL) and extracted with EtOAc (2×40 mL). The combined organic layers were washed with brine, dried (Na$_2$SO$_4$) and concentrated under reduced pressure. The crude methyl ester was retained for future purification. The remaining aqueous phase was then acidified to pH 5 by addition of 1 N HCl and extracted with CH$_2$Cl$_2$ (2×40 mL). The combined organic extracts were dried (Na$_2$SO$_4$) and concentrated under reduced pressure to afford crude (3S,5S)/(3R,5R)-3,5-dimethylthiomorpholino)benzoxazole-4-carboxylic acid (70 mg, 15%) which was directly elaborated without purification.

Step E: To a solution of (3S,5S)/(3R,5R)-3,5-dimethylthiomorpholino)benzoxazole-4-carboxylic acid (68 mg, 0.23 mmol) in $CH_3OH$ (3 mL) and dioxane (0.5 mL) was added a solution of Oxone (215 mg 0.35 mmol) in H2O (1.5 mL). The resulting slurry was stirred at ambient temperature for 2 h then partitioned with $CH_2Cl_2$ (50 mL) and $H_2O$ (50 mL). The layers were separated and the aqueous phase extracted further with $CH_2Cl_2$ (50 mL). The combined organic extracts were washed with brine, dried over $Na_2SO_4$ and concentrated under reduced pressure to afford crude 2-((3 S,5S)/(3R,5R)-3,5-dimethylthiomorpholine 1,1-dioxide)benzoxazole-4-carboxylic acid which was directly elaborated without purification. $^1H$ NMR consistent.

Step F: Following general procedure GP-C1,2-((3S,5S)/(3R,5R)-3,5-dimethylthiomorpholine 1,1-dioxide)benzoxazole-4-carboxylic acid and endo-9-methyl-3-oxa-9-azabicyclo[3.3.1]nonan-7-amine dihydrochloride were coupled to provide endo-N-(9-methyl-9-azabicyclo[3.3.1]nonan-3-yl)-2-((3 S,5S)/(3R,5R)-3,5-dimethylthiomorpholine 1,1-dioxide)benzoxazole-4-carboxamide, which was converted to the hydrochloride salt following general procedure GP-D1. $^1H$ NMR and MS consistent.

EXAMPLE 124

Preparation of N-(Quinuclidine-8-yl)-2-((2S,6S)-2,4, 6-trimethyl-3-oxopiperazine-1-yl)benzoxazole-4-carboxamide Hydrochloride Step A: Following general procedure GP-A, mixture of methyl 2-chlorobenzoxazole-4-carboxylate and (3S,5S)-1,3,5-trimethylpiperazin-2-one converted to methyl 2-((2S,6S)-2,4,6-trimethyl-3-oxopiperazine-1-yl)benzoxazole-4-carboxylate. $^1H$ NMR consistent.

Step B: 2-((2S,6S)-2,4,6-trimethyl-3-oxopiperazine-1-yl)benzoxazole-4-carboxylic acid Following general procedure GP-B3 which was directly elaborated without characterization.

Step C: Following general procedure GP-C2,2-((2S,6S)-2,4,6-trimethyl-3-oxopiperazine-1-yl)benzoxazole-4-carboxylic acid (237 mg, 0.78 mmol) and (S)-3-amino-9-methyl-9-azabicyclo[3.3.1]-nonane dihydrochloride were coupled to provide N-(quinuclidine-8-yl)-2-((2S,6S)-2,4,6-trimethyl-3-oxopiperazine-1-yl)benzoxazole-4-carboxamide, which was converted to the hydrochloride salt following general procedure GP-D1. $^1H$ NMR and MS consistent.

EXAMPLE 125

Preparation of Endo-(3S,5S)-Methyl 3,5-dimethyl-4-(4-(9-methyl-9-azabicyclo[3.3.1]nonan-3-ylcarbamoyl)benzoxazol-2-yl)piperazine-1-carboxylate Hydrochloride Step A: To an ice-cold mixture of endo-N-(9-methyl-9-azabicyclo[3.3.1]nonan-3-yl)-2-((2S,6S)-2,6-dimethylpiperazin-1-yl)benzoxazole-4-carboxamide (222.1 mg, 0.54 mmol), and triethylamine (82.1 mL, 0.59 mmol), in $CH_2Cl_2$ (5 mL) was added methyl chloroformate (45.1 mL, 0.59 mmol), the mixture was stirred and allowed to warm to ambient temperature and stirred for an additional 20 h. The reaction mixture was quenched with $CH_3OH$/brine (1:2, 15 mL) and extracted with $CH_2Cl_2$ (2×30 mL). The combined organic layers were washed successively with 1N aqueous HCl (30 mL), brine (25 mL), dried ($Na_2SO_4$) and concentrated under reduced pressure. Purification by column chromatography (silica gel, 9:1 $CH_2Cl_2/CH_3OH$ to 90:9:1 $CH_2Cl_2/CH_3OH/NH_4OH$) afforded (3S,5S)-methyl 3,5-dimethyl-4-(4-(9-methyl-9-azabicyclo[3.3.1]nonan-3-ylcarbamoyl)benzoxazol-2-yl)piperazine-1-carboxylate (51.2 mg, 20%) as an off-white solid. $^1H$ NMR and MS consistent Step B: 3,5-Dimethyl-4-(4-(9-methyl-9-azabicyclo[3.3.1] nonan-3-ylcarbamoyl)benzoxazol-2-yl)piperazine-1-carboxylate was converted to the hydrochloride salt following of general procedure GP-D1. $^1H$ NMR and MS consistent

EXAMPLE 126

Preparation of Endo-N-(9-Methyl-9-azabicyclo [3.3.1]nonan-3-yl)-2-((4aS,8aS)-octahydroquinoxalin-1(2H)-yl)benzoxazole-4-carboxamide Dihydrochloride Step A: To an ice-cold solution of(1S,2S)-(+)-1,2-diaminocyclohexane in $H_2O$ (120 mL) was added chloroacetic acid (3.31 g, 35.02 mmol) and $KHCO_3$ (3.51 g, 35.02 mmol). The mixture stirred at room temperature for 16 h then heated at 90° C. for 4 h. The mixture cooled to room temperature and was concentrated under reduced pressure to provide (4aS, 8aS)-octahydroquinoxalin-2(1H)-one (8.82 g, >99%).

Step B: A mixture of (4aS,8aS)-octahydroquinoxalin-2(1H)-one (8.82 g, 57.19 mmol), 2,4-dimethoxybenzaldehyde (9.50 g, 57.19 mmol), and sodium triacetoxyborohydride (36.31 g, 171.57 mmol) in 1% HOAc in $CH_2Cl_2$ (250 mL) was stirred at room temperature for 16 h. The mixture was neutralized with saturated aqueous $NaHCO_3$ solution (200 mL). The organic layer was separated and washed with $H_2O$ (100 mL), brine (100 mL), dried ($Na_2SO_4$), filtered, and concentrated under reduced pressure. Purification of the residue by column chromatography (silica gel, 0% to 100% 90:9:1 $CH_2Cl_2/CH_3OH/NH_4OH$ in $CH_2Cl_2$) afforded (4aS,8aS)-4-(2,4-dimethoxybenzyl)octahydroquinoxalin-2(1H)-one (1.10 g, 11.1% over two steps). $^1H$ NMR and MS consistent.

Step C: To an ice-cold 1.0M solution of $LiAlH_4$ in THF (4.10 mL, 4.10 mmol) was added a solution of (4aS,8aS)-4-(2,4-dimethoxybenzyl)octahydroquinoxalin-2(1H)-one (500 mg, 1.64 mmol) in THF (10 mL). The mixture was heated at reflux for 8 h. The reaction was cooled to 0° C. and carefully quenched with EtOAc (50 mL) and 1 N NaOH solution (20 mL). The mixture stirred for 30 min and the layers were separated. The organic layer was washed with brine (20 mL), dried ($Na_2SO_4$), filtered, and concentrated under reduced pressure. Purification of the residue by column chromatography (silica gel, 0% to 60% 90:9:1 $CH_2Cl_2/CH_3OH/NH_4OH$ in $CH_2Cl_2$) afforded (4aS,8aS)-1-(2,4-dimethoxybenzyl) decahydroquinoxaline (120.1 mg, 25.4%). $^1H$ NMR and MS consistent.

Step D: Following of general procedure GP-A, (4aS,8aS)-1-(2,4-dimethoxybenzyl)decahydroquinoxaline (120.1 mg, 0.41 mmol) and methyl 2-chlorobenzoxazole-4-carboxylate were converted to methyl 2-((4aS,8aS)-4-(2,4-dimethoxybenzyl)octahydroquinoxalin-1(2H)-yl)benzoxazole-4-carboxylate. $^1H$ NMR and MS consistent Step E: 2-((4aS,8aS)-4-(2,4-dimethoxybenzyl)octahydroquinoxalin-1(2H)-yl)benzoxazole-4-carboxylic acid was synthesized by following general procedure GP-B3. MS consistent.

Step F: Following general procedure GP-C2,2-((4aS,8aS)-4-(2,4-dimethoxybenzyl)octahydroquinoxalin-1(2H)-yl) benzoxazole-4-carboxylic acid and endo-3-amino-9-methyl-9-azabicyclo[3.3.1]nonane dihydrochloride were coupled to provide endo-2-((4aS,8aS)-4-(2,4-dimethoxybenzyl)octahydroquinoxalin-1(2H)-yl)-N-(9-methyl-9-azabicyclo[3.3.1]nonan-3-yl)benzoxazole-4-carboxamide. MS consistent.

Step G: A mixture of endo-2-((4aS,8aS)-4-(2,4-dimethoxybenzyl)octahydroquinoxalin-1(2H)-yl)-N-(9-methyl-9-azabicyclo[3.3.1]nonan-3-yl)benzoxazole-4-carboxamide (200 mg, 0.34 mmol) 10% palladium on carbon (25 mg, 0.04 mmol) in $CH_3OH$ (10 mL) was subjected to an atmosphere of hydrogen gas under a pressure of 30 psi at room temperature for 7 h. The mixture was filtered and the filter cake was rinsed with $CH_3OH$. The filtrate was concentrated under reduced pressure. Purification of the residue by column chromatography (silica gel, 0% to 100% 90:9:1 $CH_2Cl_2/CH_3OH/NH_4OH$ in $CH_2Cl_2$) afforded endo-N-(9-methyl-9-azabicyclo[3.3.1]nonan-3-yl)-2-((4aS,8aS)-octahydroquinoxalin-1(2H)-yl)benzoxazole-4-carboxamide (25.1 mg, 16.9%). $^1H$ NMR and MS consistent.

Step H: Following general procedure GP-D1 endo-N-(9-methyl-9-azabicyclo[3.3.1]nonan-3-yl)-2-((4aS,8aS)-octahydroquinoxalin-1(2H)-yl)benzoxazole-4-carboxamide was converted in the dihydrochloride salt. $^1H$ NMR and MS consistent.

EXAMPLE 127

Preparation of (S)—N-(quinulidin-8-yl)-2-amino-6-methylbenzoxazole-4-carboxamide Hydrochloride Step A: To a solution of methyl 2-amino-3-methoxybenzoate (13.0 g, 71.8 mmol) in DMF (30 mL) was added NBS (14.38 g, 80.8 mmol) at room temperature and the resulting reaction mixture was stirred for 17 h. The reaction mixture was filtered through Celite, and the filtrate was concentrated under reduced pressure. The resulting residue was purified by column chromatography (silica gel, 2% to 5% EtOAc in hexanes) to afford methyl 2-amino-5-bromo-3-methoxybenzoate (13.7 g, 73%). $^1H$ NMR consistent.

Step B: A mixture of methyl 2-amino-5-bromo-3-methoxybenzoate (6.50 g, 25 mmol), methylboronic acid (3.0 g, 50 mmol), potassium fluoride (5.8 g, 100 mmol) and tri-t-butylphosphonium tetrafluoroborte (0.87 g, 3.0 mmol) in THF (200 mL) was deoxygenated and then backfilled with argon. Tris(dibenzylideneacetone)dipalladium(0) (1.43 g, 1.5 mmol), was added and the mixture was heated at 70° C. for 17 h under an argon atmosphere. The reaction mixture was concentrated and the residue purified by column chromatography (silica gel, 0% to 5% EtOAc in hexanes) to afford methyl 2-amino-5-methoxy-3-methylbenzoate (3.55 g, 73%) $^1H$ NMR consistent.

Step C: A mixture of methyl 2-amino-5-methoxy-3-methylbenzoate (2.96 g, 15.21 mmol), 48% HBr (25 mL) and HOAc (2.5 mL) was heated at reflux for 8 h. The reaction mixture was cooled to room temperature to afford a slurry. The solid was isolated and dried under high vacuum to afford desired 2-amino-3-hydroxy-5-methylbenzoic acid hydrobromide (2.32 g, 61%). $^1H$ NMR consistent.

Step D: To a solution of 2-amino-3-hydroxy-5-methylbenzoic acid hydrobromide (2.65 g, 10.7 mmol) in anhydrous $CH_3OH$ (50 mL) was added thionyl chloride (3.9 mL, 53.4 mmol) at −78° C. The resulting reaction mixture was allowed to warm to room temperature and then heated to reflux for 17 h. The reaction mixture was cooled to room temperature and concentrated under reduced pressure. The residue was treated with a saturated aqueous $NaHCO_3$ solution to adjust pH to 7 and then extracted with EtOAc (4×100 mL). The combined organic phase was washed with $H_2O$, brine, dried ($Na_2SO_4$), filtered and concentrated under reduced pressure to afford methyl 2-amino-3-hydroxy-5-methylbenzoate (1.40 g, 72%): $^1H$ NMR consistent.

Step E: To a solution of di (1H-imidazole-1-yl)methanamine (1.56 g, 9.67 mmol) in THF (30 mL) was added methyl 2-amino-3-hydroxy-5-methylbenzoate (1.40 g, 7.73 mmol) at room temperature and the resulting reaction mixture was heated at reflux for 6 h. The reaction mixture was cooled to room temperature and concentrated under reduced pressure. The residue was dissolved in $CH_2Cl_2$ (100 mL), treated with saturated aqueous ammonium chloride (25 mL), and then extracted with $CH_2Cl_2$ (2×100 mL). The combined organic phase was washed with brine (2×100 mL), dried ($Na_2SO_4$), filtered, and concentrated under reduced pressure to afford a yellow solid. The solid was triturated from $CH_3OH$ to afford methyl 2-amino-6-methylbenzoxazole-4-carboxylate (0.717 g, 45%). $^1H$ NMR and MS consistent.

Step F: Following of general procedure GP-B3, methyl 2-amino-6-methylbenzoxazole-4-carboxylate was converted to 2-amino-6-methylbenzoxazole-4-carboxylic acid. $^1H$ NMR and MS consistent.

Step G: Following of general procedure GP-C1, 2-amino-6-methylbenzoxazole-4-carboxylic acid (0.35 g, 1.79 mmol) and (S)-(−)-3-aminoquinuclidine dihydrochloride were coupled to (S)—N-(quinulidin-8-yl)-2-amino-6-methylbenzoxazole-4-carboxamide, which was converted to the hydrochloride salt following general procedure GP-D1. $^1H$ NMR and MS consistent.

EXAMPLE 128

Preparation of Endo-N-(9-Methyl-9-azabicyclo[3.3.1]nonan-3-yl)-2-amino-5-fluorobenzoxazole-4-carboxamide Hydrochloride Step A: A solution of sodium persulfate (15.4 g, 64.5 mmol) in $H_2O$ (160 mL) was added dropwise to a solution of 2-amino-6-fluorobenzoic acid (10 g, 64.5 mmol) in 2 N NaOH(60 mL) over 3 h. The resulting black mixture was stirred for 2 days at ambient temperature, and extracted sequentially with ether (3 L) and EtOAc (IL). The aqueous layer was concentrated under reduced pressure and the resulting residue was suspended in $CH_3OH$ (1 L) and stirred overnight at ambient temperature. The precipitate was filtered off, the mother liquor was concentrated to ⅓ of initial volume, cooled to −78° C. and treated with $SOCl_2$ (15 mL, 128 mmol). The mixture was allowed to warm to room temperature then was heated at reflux for 16 h. The mixture was concentrated under reduced pressure and the resulting residue was suspended in EtOAc (1 L) and extracted with saturated aqueous $NaHCO_3$ (300 mL). The organic fraction was washed with brine, dried ($Na_2SO_4$), filtered, and concentrated under reduced pressure. The residue was purified by column chromatography (silica gel, 1:3 EtOAc/hexanes) to afford methyl 2-amino-6-fluoro-3-hydroxybenzoate (0.4 g, 3.3%). $^1H$ and MS consistent.

Step B: To a solution of methyl 2-amino-6-fluoro-3-hydroxybenzoate (0.4 g, 2.2 mmol) in THF (10 mL) was added di-(1H-imidazole-1-yl)methanamine (0.44 g, 2.75 mmol) at room temperature and the resulting reaction mixture was heated at reflux for 16 h. The reaction mixture cooled to room temperature and was concentrated under reduced pressure. The residue was dissolved in $CH_2Cl_2$ (100 mL), and the solution was treated with saturated aqueous ammonium chloride (25 mL). The organic layer was separated and the aqueous layer was extracted with additional $CH_2Cl_2$ (2×100 mL). The combined organic phase was washed with brine (2×100 mL), dried (Na$_2$SO$_4$), filtered, and concentrated under reduced pressure to afford a yellow solid. The solid was triturated from ether to afford methyl 2-amino-5-fluorobenzoxazole-4-carboxylate. MS consistent.

Step C: 2-amino-5-fluorobenzoxazole-4-carboxylic acid was synthesized by following of general procedure GP-B3. MS consistent Step D: Following general procedure GP-C1, mixture of 2-amino-5-fluorobenzoxazole-4-carboxylic acid and endo-3-amino-9-methyl-9-azabicyclo[3.3.1]nonane dihydrochloride were coupled to provide endo-N-(9-methyl-9-azabicyclo[3.3.1]nonan-3-yl)-2-amino-5-fluorobenzoxazole-4-carboxamide, which was converted to the hydrochloride salt following general procedure GP-D1. $^1$H NMR and MS consistent.

EXAMPLE 129

Preparation of Endo-2-amino-6-methyl-N-(9-Methyl-9-azabicyclo[3.3.1]nonan-3-yl)benzoxazole-4-carboxamide Hydrochloride Following of general procedure GP-C-1,2-amino-6-methylbenzoxazole-4-carboxylic acid and endo-3-amino-9-methyl-9-azabicyclo[3.3.1]nonane dihydrochloride were coupled to provide endo-2-amino-6-methyl-N-(9-methyl-9-azabicyclo[3.3.1]nonan-3-yl)benzoxazole-4-carboxamide, which was converted to the hydrochloride salt following general procedure GP-D1. $^1$H NMR and MS consistent.

EXAMPLE 130

Preparation of Endo-N-(9-methyl-9-azabicyclo[3.3.1]nonan-3-yl)-2-((2S,6S)-2,6-dimethyl-4-pivaloylpiperazin-1-yl)benzoxazole-4-carboxamide Hydrochloride Following general procedure GP-E, endo-N-(9-methyl-9-azabicyclo[3.3.1]nonan-3-yl)-2-((2S,6S)-2,6-dimethylpiperazin-1-yl)benzoxazole-4-carboxamide and pivaloyl chloride were coupled to provide endo-N-(9-methyl-9-azabicyclo[3.3.1]nonan-3-yl)-2-((2S,6S)-2,6-dimethyl-4-pivaloylpiperazin-1-yl)benzoxazole-4-carboxamide, which was converted to the hydrochloride salt following general procedure GP-D1. $^1$H NMR and MS consistent.

EXAMPLE 131

Preparation of Endo-N-(9-methyl-9-azabicyclo[3.3.1]nonan-3-yl)-2-((2S,6S-2,6-dimethyl-4-(methylsulfonyl)piperazin-1-yl)benzoxazole-4-carboxamide Hydrochloride Following general procedure GP-E, endo-N-(9-methyl-9-azabicyclo[3.3.1]nonan-3-yl)-2-((2S,6S)-2,6-dimethylpiperazin-1-yl)benzoxazole-4-carboxamide and methane sulfonyl chloride were coupled to provide endo-N-(9-methyl-9-azabicyclo[3.3.1]nonan-3-yl)-2-((2S,6S)-2,6-dimethyl-4-(methylsulfonyl)piperazin-1-yl)benzoxazole-4-carboxamide, which was converted to the hydrochloride salt following general procedure GP-D1. $^1$H NMR and MS consistent.

EXAMPLE 132

Preparation of Endo-N-(9-methyl-9-azabicyclo[3.3.1]nonan-3-yl)-2-((2S,6S)-4-(cyclohexanecarbonyl)-2,6-dimethylpiperazin-1-yl)benzoxazole-4-carboxamide Hydrochloride Following general procedure GP-E, endo-N-(9-methyl-9-azabicyclo[3.3.1]nonan-3-yl)-2-((2S,6S)-2,6-dimethylpiperazin-1-yl)benzoxazole-4-carboxamide and cyclohexanoyl chloride were coupled to provide endo-N-(9-methyl-9-azabicyclo[3.3.1]nonan-3-yl)-2-((2S,6S)-4-(cyclohexanecarbonyl)-2,6-dimethylpiperazin-1-yl)benzoxazole-4-carboxamide, which was converted to the hydrochloride salt following general procedure GP-D1. $^1$H NMR and MS consistent

EXAMPLE 133

Preparation of Endo-N-(9-methyl-9-azabicyclo[3.3.1]nonan-3-yl)-2-((2S,6S-4-(cyclopentanecarbonyl)-2,6-dimethylpiperazin-1-yl)benzoxazole-4-carboxamide Hydrochloride Following general procedure GP-E, endo-N-(9-methyl-9-azabicyclo[3.3.1]nonan-3-yl)-2-((2S,6S)-2,6-dimethylpiperazin-1-yl)benzoxazole-4-carboxamide and cyclopentanyl chloride were coupled to provide endo-N-(9-methyl-9-azabicyclo[3.3.1]nonan-3-yl)-2-((2S,6S)-4-(cyclopentanecarbonyl)-2,6-dimethylpiperazin-1-yl)benzoxazole-4-carboxamide, which was converted to the hydrochloride salt following general procedure GP-D1. $^1$H NMR and MS consistent.

EXAMPLE 134

Preparation of Endo-N-(9-methyl-9-azabicyclo[3.3.1]nonan-3-yl)-2-((2S,6S)-2,6-dimethyl-4-propionylpiperazin-1-yl)benzoxazole-4-carboxamide Hydrochloride Following general procedure GP-E, endo-N-(9-methyl-9-azabicyclo[3.3.1]nonan-3-yl)-2-((2S,6S)-2,6-dimethylpiperazin-1-yl)benzoxazole-4-carboxamide and propionyl chloride were coupled to provide endo-N-(9-methyl-9-azabicyclo[3.3.1]nonan-3-yl)-2-((2S,6S)-2,6-dimethyl-4-propionylpiperazin-1-yl)benzoxazole-4-carboxamide, which was converted to the hydrochloride salt following general procedure GP-D1. $^1$H NMR and MS consistent.

EXAMPLE 135

Preparation of Endo-N-(9-methyl-9-azabicyclo[3.3.1]nonan-3-yl)-2-((2S,6S)-4-isobutyryl-2,6-dimethylpiperazin-1-yl)benzoxazole-4-carboxamide Hydrochloride Following general procedure GP-E, endo-N-(9-methyl-9-azabicyclo[3.3.1]nonan-3-yl)-2-((2S,6S)-2,6-dimethylpiperazin-1-yl)benzoxazole-4-carboxamide and isobutyryl chloride were coupled to provide endo-N-(9-methyl-9-azabicyclo[3.3.1]nonan-3-yl)-2-((2S,6S)-2,6-dimethyl-4-isobutyrylpiperazin-1-yl)benzoxazole-4-carboxamide, which was converted to the hydrochloride salt following general procedure GP-D1. $^1$H NMR and MS consistent.

EXAMPLE 136

Preparation of Endo-N-(9-methyl-9-azabicyclo [3.3.1]nonan-3-yl)-2-((2S,6S)-2,6-dimethyl-4-(dimethylcarbamoyl)piperazin-1-yl)benzoxazole-4-carboxamide Hydrochloride Step A: To a solution of methyl 2-((2S,6S)-2,6-dimethyl-4-piperazin-1-yl)benzoxazole-4-carboxylate (235 mg, 0.81 mmol) and diisopropylethylamine (339 mL, 1.95 mmol) in $CH_2Cl_2$ (5 mL) was added 1-dimethylcarbamoylcarbonyl chloride (163 ml, 1.79 mmol). The reaction mixture was stirred at ambient temperature for 90 min then partitioned with $CH_2Cl_2$ (50 mL) and 0.5 M citric acid (20 mL). The organic layer was washed with brine, dried ($Na_2SO_4$), filtered, and concentrated under reduced pressure. The crude material was purified by column chromatography (silica gel, dichloromethane then 90:9:1 $CH_2Cl_2/CH_3OH$/concentrated $NH_4OH$) to afford methyl 2-((2S,6S)-2,6-dimethyl-4-(dimethylcarbamoyl)piperazin-1-yl)benzoxazole-4-carboxylate as a colorless oil (270 mg, 92%). $^1H$ NMR and MS consistent.

Step B: To a solution of methyl 2-((2S,6S)-2,6-dimethyl-4-(dimethylcarbamoyl)piperazin-1-yl)benzoxazole-4-carboxylate (265 mg, 0.74 mmol) in pyridine (5 mL) was added LiI (984 mg, 7.35 mmol). The mixture was heated at 110° C. for 14 h and allowed to cool to ambient temperature. The reaction was partially concentrated under reduced pressure before partitioning with 9:1 $CH_2Cl_2$/2-propanol (50 mL) and 1 N HCl (20 mL). The organic layer was washed with brine, dried ($Na_2SO_4$) and concentrated under reduced pressure to afford crude 2-((2S,6S)-2,6-dimethyl-4-(dimethylcarbamoyl)piperazin-1-yl)benzoxazole-4-carboxylic acid as an orange oil which was directly elaborated without purification.

Step C: Following general procedure GP-C1,2-((2S,6S)-2,6-dimethyl-4-(dimethylcarbamoyl)piperazin-1-yl)benzoxazole-4-carboxylic acid and endo-3-amino-9-methyl-9-azabicyclo[3.3.1]nonane dihydrochloride were coupled to provide endo-N-(9-methyl-9-azabicyclo[3.3.1]nonan-3-yl)-2-((2S,6S)-2,6-dimethyl-4-(dimethylcarbamoyl)piperazin-1-yl)benzoxazole-4-carboxamide, which was converted to the hydrochloride salt following general procedure GP-D1. $^1H$ NMR and MS consistent.

EXAMPLE 137

Preparation of Endo-N-(9-methyl-9-azabicyclo [3.3.1]nonan-3-yl)-2-((2S,6S)-2,6-dimethyl-4-(2,2,2-trifluoroethyl)piperazin-1-yl)benzoxazole-4-carboxamide Hydrochloride To a mixture of endo-N-(9-methyl-9-azabicyclo[3.3.1]nonan-3-yl)-2-((2S,6S)-2,6-dimethylpiperazin-1-yl)benzoxazole-4-carboxamide (150 mg, 0.36 mmol), and pyridine (65 mL, 0.80 mmol) in N,N-dimethylformamide (10 mL) was added 2,2,2-trifluoroethyl trifluoromethanesulfonate (115 mL, 0.80 mmol) and the mixture was heated to 110° C. for 20 h. The reaction was quenched with saturated ammonium chloride (10 mL) and extracted with $CH_2Cl_2$ (2×30 mL). The combined organic layers were washed successively with $NaHCO_3$ (10 mL) and brine (25 mL), and then dried ($Na_2SO_4$), filtered, and the solution concentrated under reduced pressure. Purification by column chromatography (silica gel, 9:1 $CH_2Cl_2/CH_3OH$ to 90:9:1 $CH_2Cl_2/CH_3OH$/ $NH_4OH$) afforded endo-N-(9-methyl-9-azabicyclo[3.3.1] nonan-3-yl)-2-((2S,6S)-2,6-dimethyl-4-(2,2,2-trifluoroethyl)piperazin-1-yl)benzoxazole-4-carboxamide (52 mg, 29%) which was converted to the hydrochloride salt following general procedure GP-D1. $^1H$ NMR and MS consistent.

EXAMPLE 138

Preparation of Endo-N-(9-methyl-9-azabicyclo [3.3.1]nonan-3-yl)-2-((2S,6S)-4-(isobutoxycarbonyl)-2,6-dimethylpiperazin-1-yl)benzoxazole-4-carboxamide Hydrochloride Step A: To a solution of lithium iodide (185 mg, 1.38 mmol) in refluxing anhydrous pyridine (10 mL) was added methyl 2-((2S,6S)-2,6-dimethylpiperazin-1-yl)benzoxazole-4-carboxylate (100 mg, 0.346 mmol) and the reaction mixture was refluxed for 24 hours. The mixture was cooled to room temperature, concentrated to dryness and dried in vacuo to provide lithium 2-((2S,6S)-2,6-dimethylpiperazin-1-yl)benzoxazole-4-carboxylate as a solid which was used without further purification: MS consistent Step B: To a vigorously stirred suspension of lithium 2-((2S,6S)-2,6-dimethylpiperazin-1-yl)benzoxazole-4-carboxylate (97 mg, 0.346 mmol) and $NaHCO_3$ (87 mg, 1.037 mmol) in chloroform (6 mL) and $H_2O$ (6 mL) was added dropwise isobutyl chloroformate (54 mL, 0.415 mmol). The reaction mixture was stirred at room temperature for 2 h, then neutralized with 1N aqueous HCl, and concentrated under reduced pressure to provide 2-((2S,6S)-4-(isobutoxycarbonyl)-2,6-dimethylpiperazin-1-yl)benzoxazole-4-carboxylic acid. MS consistent.

Step C: Following general procedure GP-C1, a mixture of 2-((2S,6)-4-(isobutoxycarbonyl)-2,6-dimethylpiperazin-1-yl)benzoxazole-4-carboxylic acid and endo-3-amino-9-methyl-9-azabicyclo[3.3.1]nonane dihydrochloride were coupled to provide endo-N-(9-methyl-9-azabicyclo[3.3.1] nonan-3-yl)-2-((2S,6S)-4-(isobutoxycarbonyl)-2,6-dimethylpiperazin-1-yl)benzoxazole-4-carboxamide which was converted to the hydrochloride salt following general procedure GP-D1. $^1H$ NMR and MS consistent.

EXAMPLE 139

Preparation of (S)—N-(quinulidin-8-yl)-2-amino-5-fluorobenzoxazole-4-carboxamide Hydrochloride Following the general procedure GP-C2,2-amino-5-fluorobenzoxazole-4-carboxylic acid and (S)-(−)-3-aminoquinuclidine dihydrochloride were coupled to (S)—N-(quinulidin-8-yl)-2-amino-5-fluorobenzoxazole-4-carboxamide which was converted to the hydrochloride salt following general procedure GP-D1. $^1H$ NMR and MS consistent.

EXAMPLE 140

Preparation of Endo-N-(9-methyl-9-azabicyclo [3.3.1]nonan-3-yl)-2-((2S,6S)-2,6-dimethyl-4-(pyrrolidine-1-carbonyl)piperazin-1-yl)benzoxazole-4-carboxamide hydrochloride Step A: Following of general procedure GP-E, methyl 2-((2S,6S)-2,6-dimethyl-4-piperazin-1-yl)benzoxazole-4-carboxylate and 1-pyrrolidinecarbonyl chloride were coupled to provide methyl 2-((2S,6S)-2,6-dimethyl-4-(pyrrolidine-1-carbonyl)piperazin-1-yl)benzoxazole-4-carboxylate. $^1H$ NMR and MS consistent.

Step B: To a solution of methyl 2-((2S,6S)-2,6-dimethyl-4-(pyrrolidine-1-carbonyl)piperazin-1-yl)benzoxazole-4-carboxylate (200 mg, 0.52 mmol) in pyridine (2 mL) was added lithium iodide (550 mg, 4.11 mmol). The mixture was heated at 110° C. for 18 h and allowed to cool to ambient temperature before partitioning with 9:1 mixture of dichloromethane and isopropanol (100 mL) and 1 N HCl (50 mL). The non-homogenous organic layer was washed with brine and concentrated under reduced pressure. The residue was treated with 9:1 toluene/methanol (100 mL) and concentrated in vacuo to afford crude 2-((2S,6S)-2,6-dimethyl-4-(pyrrolidine-1-carbonyl)piperazin-1-yl)benzoxazole-4-carboxylic acid as a brown solid which was directly elaborated without purification.

Step C: Following general procedure GP-C1, mixture of 2-((2S,6S)-2,6-dimethyl-4-(pyrrolidine-1-carbonyl)piperazin-1-yl)benzoxazole-4-carboxylic acid and endo-3-amino-9-methyl-9-azabicyclo[3.3.1]nonane dihydrochloride were coupled to provide endo-N-(9-methyl-9-azabicyclo[3.3.1]nonan-3-yl)-2-((2S,6S)-2,6-dimethyl-4-(pyrrolidine-1-carbonyl)piperazin-1-yl)benzoxazole-4-carboxamide except that reaction mixture was extracted with $CH_2Cl_2$/2-propanol (9/1). The carboximide was converted to the dihydrochloride salt following general procedure GP-D1. $^1$H NMR and MS consistent.

EXAMPLE 141

Preparation of Endo-N-(9-methyl-9-azabicyclo [3.3.1]nonan-3-yl)-2-((2S,6S)-2,6-dimethyl-4-(piperidine-1-carbonyl)piperazin-1-yl)benzoxazole-4-carboxamide hydrochloride Step A: Following general procedure GP-E, methyl 2-((2S,6S)-2,6-dimethyl-4-piperazin-1-yl)benzoxazole-4-carboxylate and 1-piperidinecarbonyl chloride were coupled to provide methyl 2-((2S,6S)-2,6-dimethyl-4-(piperidine-1-carbonyl)piperazin-1-yl)benzoxazole-4-carboxylate. $^1$H NMR and MS consistent.

Step B: To a solution of methyl 2-((2S,6S)-2,6-dimethyl-4-(piperidine-1-carbonyl)piperazin-1-yl)benzoxazole-4-carboxylate (200 mg, 0.52 mmol) in pyridine (2 mL) was added lithium iodide (495 mg, 3.70 mmol). The mixture was heated at 110° C. for 18 h and allowed to cool to ambient temperature before partitioning with 9:1 dichloromethane/2-propanol (100 mL) and 1 N HCl (50 mL). The non-homogenous organic layer was washed with brine and concentrated in vacuo. The residue was treated with 9:1 mixture of toluene and methanol (100 mL) and concentrated under reduced pressure to afford crude 2-((2S,6S)-2,6-dimethyl-4-(piperidine-1-carbonyl)piperazin-1-yl)benzoxazole-4-carboxylic acid as a brown solid which was directly elaborated without purification.

Step C: Following the general procedure GP-C1, a mixture of 2-((2S,6S)-2,6-dimethyl-4-(piperidine-1-carbonyl)piperazin-1-yl)benzoxazole-4-carboxylic acid and endo-3-amino-9-methyl-9-azabicyclo[3.3.1]nonane dihydrochloride were coupled to provide endo-N-(9-methyl-9-azabicyclo[3.3.1]nonan-3-yl)-2-((2S,6S)-2,6-dimethyl-4-(piperidine-1-carbonyl)piperazin-1-yl)benzoxazole-4-carboxamide except that the reaction mixture was extracted with 9:1 $CH_2Cl_2$/2-propanol (9/1). The carboxamide was converted to the hydrochloride salt following general procedure GP-D1. $^1$H NMR and MS consistent.

EXAMPLE 142

Preparation of (S)—N-(quinuclidine-8-yl) 2-((2S, 6S)-4-benzyl-2,6-dimethyl-3-oxopiperazine-1-yl) benzoxazole-4-carboxamide Hydrochloride Step A: 2-((2S,6S)-4-benzyl-2,6-dimethyl-3-oxopiperazine-1-yl)benzoxazole-4-carboxylic acid was synthesized by following general procedure GP-B3. $^1$H NMR consistent.

Step B: Following the general procedure GP-C2, a mixture of 2-((2S,6S)-4-benzyl-2,6-dimethyl-3-oxopiperazine-1-yl) benzoxazole-4-carboxylic acid and (S)-(−)-3-aminoquinuclidine dihydrochloride were coupled to provide (S)—N-(quinuclidine-8-yl) 2-((2S,6S)-4-benzyl-2,6-dimethyl-3-oxopiperazine-1-yl)benzoxazole-4-carboxamide which was converted to the hydrochloride salt following general procedure GP-D1. $^1$H NMR and MS consistent.

EXAMPLE 143

Preparation of Endo-N-(9-methyl-9-azabicyclo [3.3.1]nonan-3-yl)-2-((2S,6S)-4-(isopropoxycarbonyl)-2,6-dimethylpiperazin-1-yl)benzoxazole-4-carboxamide Hydrochloride Step A: To a vigorously stirred suspension of lithium 2-((2S,6S)-2,6-dimethylpiperazin-1-yl)benzoxazole-4-carboxylate (208 mg, 0.743 mmol) and $NaHCO_3$ (187 mg, 2.23 mmol) in chloroform (12 mL) and $H_2O$ (2 mL) was added dropwise isopropylchloroformate (1M solution in toluene, 892 mL, 0.891 mmol). The reaction mixture was stirred at room temperature for 2 h, then neutralized with 1N aqueous HCl. The mixture was concentrated under reduced pressure to provide lithium 2-((2S,6S)-4-(isopropoxycarbonyl)-2,6-dimethylpiperazin-1-yl)benzoxazole-4-carboxylate. MS consistent.

Step B: Following general procedure GP-C1, lithium 2-((2S,6)-4-(isopropoxycarbonyl)-2,6-dimethylpiperazin-1-yl)benzoxazole-4-carboxylate and endo-3-amino-9-methyl-9-azabicyclo[3.3.1]nonane dihydrochloride were coupled to provide endo-N-(9-methyl-9-azabicyclo[3.3.1]nonan-3-yl)-2-((2S,6S)-4-(isopropoxycarbonyl)-2,6-dimethylpiperazin-1-yl)benzoxazole-4-carboxamide which was converted to the hydrochloride salt following general procedure GP-D1. $^1$H NMR and MS consistent.

EXAMPLE 144

Preparation of Endo-N-(9-methyl-9-azabicyclo [3.3.1]nonan-3-yl)-2-((2S,6S)-4-(ethoxycarbonyl)-2, 6-dimethylpiperazin-1-yl)benzoxazole-4-carboxamide Hydrochloride Step A: To a vigorously stirred suspension of methyl 2-((2S,6S)-2,6-dimethylpiperazin-1-yl)benzoxazole-4-carboxylate (208 mg, 0.743 mmol) and $NaHCO_3$ (187 mg, 2.23 mmol) in chloroform (12 mL) and $H_2O$ (2 mL) was added dropwise ethylchloroformate (85 mL, 0.891 mmol). The reaction mixture was stirred at room temperature for 2 h, then neutralized with 1N aqueous HCl, and concentrated under reduced pressure to provide lithium 2-((2S,6S)-4-(ethoxycarbonyl)-2,6-dimethylpiperazin-1-yl)benzoxazole-4-carboxylate. MS consistent.

Step B: Following general procedure GP-C1, lithium 2-((2S,6S)-4-(ethoxycarbonyl)-2,6-dimethylpiperazin-1-yl) benzoxazole-4-carboxylate and endo-3-amino-9-methyl-9-azabicyclo[3.3.1]nonane dihydrochloride were coupled to provide endo-N-(9-methyl-9-azabicyclo[3.3.1]nonan-3-yl)-2-((2S,6S)-4-(ethoxycarbonyl)-2,6-dimethylpiperazin-1-yl)benzoxazole-4-carboxamide which was converted to the hydrochloride salt following general procedure GP-D1. $^1$H NMR and MS consistent.

EXAMPLE 145

Preparation of N-((4-methyl-1H-imidazol-5-yl)methyl)-2-amino-6-chlorobenzoxazole-4-carboxamide Step A: A solution of 5-(chloromethyl)-4-methyl-1-trityl-1H-imidazole (1.00 g, 2.68 mmol) in ammonia (7 N in CH$_3$OH, 4 mL, 28 mmol) was heated to 50° C. in a sealed tube for 16 h. The reaction mixture was concentrated under reduced pressure and the crude material purified by column chromatography (silica gel, 100% CH$_2$Cl$_2$ to 50% CH$_3$OH) to provide (4-methyl-1-trityl-1H-imidazol-5-yl)methanamine (250 mg, 26%). $^1$H NMR consistent.

Step B: A solution of (4-methyl-1-trityl-1H-imidazol-5-yl)methanamine (250 mg, 0.07 mmol) in glacial acetic acid (50 mL) was heated to reflux for 2 h. The reaction mixture was cooled to room temperature and concentrated to dryness to provide (4-methyl-1H-imidazol-5-yl)methanamine (79 mg, quant.). $^1$H NMR and MS consistent.

Step C: Following general procedure GP-C1, 2-amino-6-chlorobenzoxazole-4-carboxylic acid and (4-methyl-1H-imidazol-5-yl)methanamine were coupled to provide N-((4-methyl-1H-imidazol-5-yl)methyl)-2-amino-6-chlorobenzoxazole-4-carboxamide which was converted to the hydrochloride salt following general procedure GP-D1. $^1$H NMR and MS consistent.

EXAMPLE 146

Preparation of Endo-N-(9-azabicyclo[3.3.1]nonan-3-yl)-2-((2S,6S)-2,6-dimethyl-4-(pyrrolidine-1-carbonyl)piperazin-1-yl)benzoxazole-4-carboxamide hydrochloride Endo-N-(9-azabicyclo[3.3.1]nonan-3-yl)-2-((2S,6S)-2,6-dimethyl-4-(pyrrolidine-1-carbonyl)piperazin-1-yl)benzoxazole-4-carboxamide was unexpectedly isolated as a side product from the coupling of 2-((2S,6S)-2,6-dimethyl-4-(pyrrolidine-1-carbonyl)piperazin-1-yl)benzoxazole-4-carboxylic acid and endo-3-amino-9-methyl-9-azabicyclo[3.3.1]nonane dihydrochloride (see Example 141) following general procedure GP-C1 except that reaction mixture was extracted with CH$_2$Cl$_2$/2-propanol (9/1). The carboxamide was converted to the hydrochloride salt following general procedure GP-D1. $^1$H NMR and MS consistent.

EXAMPLE 147

Preparation of Endo-N-(9-Methyl-9-azabicyclo[3.3.1]nonan-3-yl)-2-((2S*,5R*)-4-allyl-2,5-dimethylpiperazin-1-yl)benzoxazole-4-carboxamide Dihydrochloride Step A: Following general procedure GP-A, methyl 2-chlorobenzoxazole-4-carboxylate and (±) trans-1-allyl-2,5-dimethylpiperazine were converted methyl 2-((2S*,5R*)-4-allyl-2,5-dimethylpiperazin-1-yl)benzoxazole-4-carboxylate. $^1$H NMR and MS consistent.

Step B: 2-((2S*,5R*)-4-allyl-2,5-dimethylpiperazin-1-yl)benzoxazole-4-carboxylic acid was synthesized by following general procedure GP-B3 which was subsequently used without further purification. MS consistent.

Step C: 2-((2S*,5R*)-4-allyl-2,5-dimethylpiperazin-1-yl)benzoxazole-4-carboxylic acid and endo-3-amino-9-methyl-9-azabicyclo[3.3.1]nonane dihydrochloride were coupled following general procedure GP-D1 to afford endo-N-(9-methyl-9-azabicyclo[3.3.1]nonan-3-yl)-2-((2S*,5R*)-4-allyl-2,5-dimethylpiperazin-1-yl)benzoxazole-4-carboxamide. $^1$H NMR and MS consistent.

Step D: Following general procedure GP-D1, endo-N-(9-methyl-9-azabicyclo[3.3.1]nonan-3-yl)-2-((2S*,5R*)-4-allyl-2,5-dimethylpiperazin-1-yl)benzoxazole-4-carboxamide was converted to endo-N-(9-methyl-9-azabicyclo[3.3.1]nonan-3-yl)-2-((2S*,5R*)-4-allyl-2,5-dimethylpiperazin-1-yl)benzoxazole-4-carboxamide dihydrochloride except that the product was isolated from an aqueous solution by lyophilization. $^1$H NMR and MS consistent.

EXAMPLE 148

Preparation of Endo-N-(9-methyl-9-azabicyclo[3.3.1]nonan-3-yl)-2-((2S,6S)-4-benzyl-2,6-dimethylpiperazin-1-yl)benzoxazole-4-carboxamide Hydrochloride Step A: Following general procedure GP-A, methyl 2-chlorobenzoxazole-4-carboxylate was treated with potassium carbonate and (3S,5S)-1-benzyl-3,5-dimethylpiperazine-4 in N,N-dimethylformamide at 40° C. for 60 h to provide methyl 2-((2S,6S-4-benzyl-2,6-dimethylpiperazin-1-yl)benzoxazole-4-carboxylate. $^1$H NMR and MS consistent.

Step B: Lithium 2-((2S,6S)-4-benzyl-2,6-dimethylpiperazin-1-yl)benzoxazole-4-carboxylate was synthesized by following general procedure GP-B2. $^1$H NMR consistent Step C: Following general procedure GP-C1, lithium 2-((2S,6S)-4-benzyl-2,6-dimethylpiperazin-1-yl)benzoxazole-4-carboxylate and endo-3-amino-9-methyl-9-azabicyclo[3.3.1]-nonane dihydrochloride coupled to provide endo-N-(9-methyl-9-azabicyclo[3.3.1]nonan-3-yl)-2-((2S,6S)-4-benzyl-2,6-dimethylpiperazin-1-yl)benzoxazole-4-carboxamide, which was converted to the hydrochloride salt following general procedure GP-D1. $^1$H NMR and MS consistent.

EXAMPLE 151

Preparation of Endo-N-(9-Methyl-9-azabicyclo[3.3.1]nonan-3-yl)-2-((R)-3-ethyl morpholino)-benzoxazole-4-carboxamide Hydrochloride Step A: To an ice cold, stirred suspension of sodium hydride (60% in oil, 2.1 g, 52.0 mmol) in toluene (65 mL) was added dropwise a solution of (R)-2-aminobutan-1-ol (2.0 g, 22.0 mmol) in toluene (48 mL). After the addition was completed, the reaction mixture was warmed to room temperature and a solution of ethyl chloroacetate (3.0 g, 25.0 mmol) in toluene (12 mL) was added in a dropwise manner. The resulting mixture was then stirred at reflux for 20 h, cooled to room temperature, and solid ammonium chloride (2.7 g, 52.0 mmol) added to the reaction. The mixture was stirred for 20 min and then concentrated under reduced pressure. The crude material was purified by column chromatography (silica gel, 95:5 dichloromethane/methanol) to give (R)-5-ethylmorpholine-3-one (2.0 g, 70%) as a light yellow solid. To ice-cold tetrahydrofuran (10 mL) was added lithium aluminum hydride (1.0 M solution in tetrahydrofuran, 31.0 mL, 31.0 mmol). Once the addition was complete, a solution of (R)-5- ethylmorpholine-3-one (2.0 g, 16 mmol) in tetrahydrofuran (10 mL) was added dropwise over 20 min. Once the addition was completed, the ice bath was removed and the reaction mixture stirred at reflux for 20 h. The reaction was cooled in an ice-bath and tot his was slowly added water (1.3 mL), then a 15% solution of sodium hydroxide (1.3 mL), and then water (1.3 mL). The resulting mixture was stirred at room temperature for 1.5 h and then filtered washing the solid with ethyl acetate (50 mL). The filtrate was concentrated at room temperature under reduced pressure to provide (R)-3-ethylmorpholine (1.6 g, 90%) as a light yellow oil. $^1$H NMR and MS consistent.

Step B: (R)-Methyl-2-(3-ethylmorpholino)benzoxazole-4-carboxylate was synthesized by following general procedure GP-A. MS consistent.

Step C: (R)-2-(3-Ethylmorpholino)benzoxazole-4-carboxylic acid was synthesized following general procedure GP-B3. MS consistent.

Step D: Following general procedure GP-C2, (R)-2-(3-ethylmorpholino)benzoxazole-4-carboxylic acid and endo-3-amino-9-methyl-9-azabicyclo[3.3.1]nonane dihydrochloride Were coupled to provide endo-N-(9-methyl-9-azabicyclo[3.3.1]nonan-3-yl)-2-((R)-3-ethylmorpholino)-benzoxazole-4-carboxamide which was converted to the hydrochloride salt following general procedure GP-D1. $^1$H NMR and MS consistent.

EXAMPLE 152

Preparation of Endo-N-(9-Methyl-9-azabicyclo [3.3.1]nonan-3-yl)-2-((R)-3-isopropylmorpholino) benzoxazole-4-carboxamide Hydrochloride Step A: To an ice cold, stirred suspension of sodium hydride (60% in oil, 1.6 g, 40.0 mmol) in toluene (52 mL) was added dropwise a solution of (R)-2-amino-3-methylbutan-1-ol (1.8 g, 17.0 mmol) in toluene (38 mL). After the addition was completed, the reaction mixture was warmed to room temperature and a solution of ethyl chloroacetate (2.3 g, 19.0 mmol) in toluene (8 mL) was added in a dropwise manner. The resulting mixture was then stirred at reflux for 20 h, cooled to room temperature, and solid ammonium chloride (2.1 g, 40.0 mmol) added to the reaction. The mixture was stirred for 20 min and then concentrated under reduced pressure. The crude material was purified by column chromatography (silica gel, 95:5 dichloromethane/methanol) to give (R)-5-isopropylmorpholin-3-one (1.7 g, 68%) as a light yellow solid.

To ice-cold tetrahydrofuran (8.0 mL) was added lithium aluminum hydride (1.0 M solution in tetrahydrofuran, 23.0 mL, 23.0 mmol). Once the addition was complete, a solution of (R)-5-isopropylmorpholin-3-one (1.7 g, 12.0 mmol) in tetrahydrofuran (8 mL) was added dropwise over 20 min. Once the addition was completed, the ice bath was removed and the reaction mixture stirred at reflux for 20 h. The reaction was cooled in an ice-bath and to this was slowly added water (1.0 mL), then a 15% solution of sodium hydroxide (1.0 mL), and then water (1.0 mL). The resulting mixture was stirred at room temperature for 1.5 h and then filtered washing the solid with ethyl acetate (50 mL). The filtrate was concentrated at room temperature under reduced pressure to provide (R)-3-isopropylmorpholine (1.4 g, 93%) as a light yellow oil. $^1$H NMR consistent.

Step B: (R)-Methyl-2-(3-isopropylmorpholino)benzoxazole-4-carboxylate was synthesized following general procedure GP-A. MS consistent.

Step C: (R)-2-(3-Isopropylmorpholino)benzoxazole-4-carboxylic acid was synthesized following general procedure GP-B3. MS consistent.

Step D: Following general procedure GP-C2, (R)-2-(3-isopropylmorpholino)benzoxazole-4-carboxylic acid and endo-3-amino-9-methyl-9-azabicyclo[3.3.1]nonane dihydrochloride were coupled to provide endo-N-(9-methyl-9-azabicyclo[3.3.1]nonan-3-yl)-2-((R)-3-isopropylmorpholino)-benzoxazole-4-carboxamide which was converted to the hydrochloride salt following general procedure GP-D1. $^1$H NMR and MS consistent.

In other embodiments where $R^2$ is not hydrogen or halogen, the method of preparation of the foregoing is similar to those presented in U.S. Patent Application 2006/183769, the entire contents of which are herein incorporated by reference. In situations where an inconsistency in nomenclature between the foregoing application and the present application may exist, the nomenclature and definitions of the present application take precedence.

Compound Affinity for the human 5-HT3 Receptor (Assay A)

Compounds were tested by MDS Pharma Services—Taiwan Ltd., 158 Li-The Road, Peitou, Taipei, Taiwan 112 R.O.C. In order to evaluate the relative affinity of the various compounds for the human 5-HT3 receptor, N1E-155 cell lines were developed to express the target protein. For binding, these cells were homogenized, centrifuged and washed with buffer (20 mM HEPES, 150 mM NaCl, pH 7.4) then suspended in 0.5 mL of buffer and [3H]-GR65630 added at a concentration of 3.5×10-10 M. An initial single concentration of 10-7 M of the test compound was then added. Incubation was carried out at room temperature for 60 minutes at 25° C. then was terminated by rapid removal of the incubation medium. Radioactivity was assessed using liquid scintillation spectrophotometry after exposure to scintillation cocktail for at least three hours. Compounds displaying greater than 75% inhibition of radioligand binding at 10-7 M were then resubmitted to the above protocol using the following range of test compound concentrations: 10-9 M, 10-8 M, 3×10-8 M, 10-7 M, 3×10-7 M and 10-6 M. Competition curves were then plotted and IC50 determinations made using non-linear regression analysis. Ki values were then calculated from the Cheng-Prusoff equation. In all of the above binding studies the non-specific determinant was MDL-72222 (1.0 µM).

Compound Affinity for the human 5-HT3 Receptor (Assay B)

The relative affinity of the various compounds for the human 5-HT3 receptor was measured in a radioligand binding assay, using a scintillation proximity assay (SPA) format. Test compounds were dissolved to 10 mM in 100% DMSO, then serially diluted at 10× assay concentrations in 100% DMSO in 96-well polypropylene plates and further diluted to 4× assay concentrations with the assay buffer. Samples were incubated in 50 mM Tris-HCl, pH 7.5, 3 mM MgCl2, 1, mM EDTA and 10% DMSO with 10 nM [9-methyl-3H]BRL-43694 (Perkin Elmer), 3 µg of human 5-HT3 receptor membranes (Perkin Elmer) and 0.5 mg/mL SPA beads (WGA PVT, Amersham Biosciences) in a final volume of 0.2 mL. Binding reactions were set up in wells of PicoPlates-96 (Perkin Elmer) by adding consecutively 50 µL of each competing compound or buffer, SPA beads, the radioligand and 5-HT3 receptor membranes. After 60-min incubation at room temperature on a Nutator mixer, plates were centrifuged for 15 min at 1,500 rpm, followed by incubation in the dark for 30 min. Radioactivity was counted in the TopCount microplate counter (Perkin Elmer) for 5 min. Total binding control contained buffer only; nonspecific binding was determined in the presence of 30 μM MDL-72222. Specific binding was determined by subtracting nonspecific binding from total binding. All experiments were performed in duplicate using ten concentrations of a competing ligand, with ondansetron included as a control in every run. IC50 values were determined from specific binding data using XLfit4.1 curve fitting software from IDBS Ltd. Ki values were then calculated from the Cheng-Prusoff equation.

Compound Affinity for the mouse 5-HT3 Receptor (Assay C)

Compounds were tested by Novoscreen Biosciences Corporation, 7170 Standard Drive, Hanover, Md. in a radioligand binding assay using the mouse 5-HT3 receptor derived from mouse neuroblastoma cells and [3H]-GR65630 (ligand). The non-specific binding determinant was MDL 72222. Compounds were tested at a single concentration of 100 nM in duplicate. Percent inhibition is reported. In order to evaluate the relative affinity of the various compounds for the 5-HT3 receptor, N1E-155 cell lines were developed to express the target protein. For binding, these cells were homogenized, centrifuged and washed with buffer (20 mM BEPES, 150 mM NaCl, pH 7.4) then suspended in 0.5 mL of buffer and [3H]-GR65630 added at a concentration of 3.5×10-10 M. An initial single concentration of 10-7 M of the test compound was then added. Incubation was carried out at room temperature for 60 minutes at 25° C. then was terminated by rapid removal of the incubation medium. Radioactivity was assessed using liquid scintillation spectrophotometry after exposure to scintillation cocktail for at least three hours. Compounds displaying greater than 75% inhibition of radioligand binding at 10-7 M were then resubmitted to the above protocol using the following range of test compound concentrations: 10-9 M, 10-8 M, 3×10-8 M, 10-7 M, 3×10-7 M and 10-6 M. Competition curves were then plotted and IC50 determinations made using non-linear regression analysis. Ki values were then calculated from the Cheng-Prusoff equation. In all of the above binding studies the non-specific determinant was MDL-72222 (1.0 μM).

In the table below, the assay in which the data were obtained is shown (as A, B or C) along with the data. The data presented was obtained by method B unless otherwise annotated.

| Structure | Ex. | NMR and MS data | 5-HT$_3$ K$_i$ (nM) |
|---|---|---|---|
| 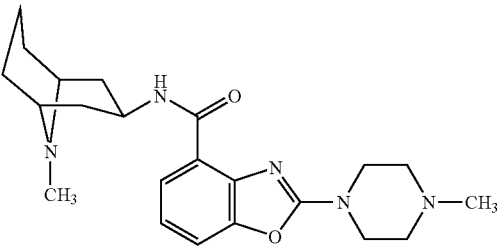 | 1 | $^1$H NMR (500 MHz, DMSO-d$_6$) δ 11.49 (br s, 1H), 10.48 (br s, 0.4H), 9.71 (br s, 0.6H), 9.11 (d, J = 5.5 Hz, 0.4H), 8.86 (d, J = 5.5 Hz, 0.6H), 7.81-7.77 (m, 1H), 7.69-7.65 (m, 1H), 7.23-7.18 (m, 1H), 4.60-4.50 (m, 0.6H), 4.38-4.25 (m, 2.4H), 3.72 (t, J = 12.5 Hz, 2H), 3.63 (d, J = 9.5 Hz, 1H), 3.58-3.50 (m, 3H), 3.30-3.18 (m, 2H), 2.86-2.75 (m, 6H), 2.72-2.58 (m, 2H), 2.25 (d, J = 6.0 Hz, 1 H), 2.18-2.05 (m, 2H), 1.85-1.70 (m, 3H), 1.60-1.42 (m, 2H); MS (ESI +) m/z 398 (M = H). | 85 |
| 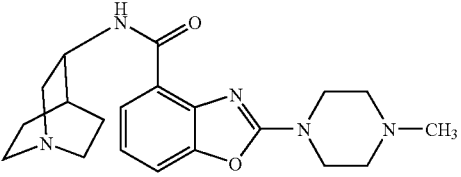 | 2 | $^1$H NMR (500 MHz, DMSO-d$_6$) δ 11.56 (br s, 1H), 10.39 (br s, 1H), 9.23 (d, J = 6.5 Hz, 1H), 7.77 (dd, J = 8.0, 1.0 Hz, 1H), 7.69 (dd, J = 8.0, 1.0 Hz, 1H), 7.21 (t, J = 8.0 Hz, 1H), 4.45-4.36 (m, 1H), 4.30 (d, J = 14.0 Hz, 2H), 3.78-3.63 (m, 3H), 3.54 (d, J = 11.5 Hz, 2H), 3.40-3.31 (m, 1H), 3.30-3.18 (m, 6H), 2.80 (s, 3H), 2.23 (dd, J = 6.0, 3.0 Hz, 1H), 2.10-2.02 (m, 1H), 1.98-1.85 (m, 3H); MS (ESI +) m/z 370 (M + H) | 382 |
| 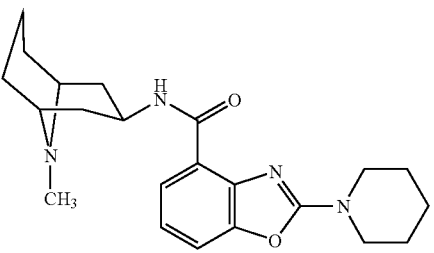 | 3 | $^1$H NMR (500 MHz, DMSO-d$_6$) δ 10.37 (br s, 0.4H), 9.70 (br s, 0.6H), 9.28 (d, J = 6.0 Hz, 0.4H), 9.03 (d, J = 6.0 Hz, 0.6H), 7.76-7.72 (m, 1H), 7.59-7.57 (m, 1H), 7.13-7.09 (m, 1H), 4.64-4.45 (m, 0.6H), 4.38-4.30 (m, 0.4H), 3.68 (br s, 4H), 3.63-3.50 (m, 2H), 2.85-2.82 (m, 3H), 2.72-2.60 (m, 2H), 2.32-2.08 (m, 3H), 1.85-1.72 (m, 3H), 1.65 (br s, 6H), 1.51 (t, J = 11.0 Hz, 2H); MS (ESI +) m/z 383 (M + H). | 10.4 |
| 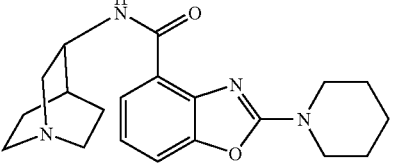 | 4 | $^1$H NMR (500 MHz, DMSO-d$_6$) δ 10.34 (br s, 1H), 9.42 (d, J = 6.5 Hz, 1H), 7.71 (dd, J = 9.0, 1.0 Hz, 1H), 7.60 (dd, J = 9.0, 1.0 Hz, 1H), 7.12 (t, J = 8.0 Hz, 1H), 4.40-4.32 (m, 1H), 3.74 (t, J = 12.5 Hz, 1H), 3.68 (br s, 4H), 3.29 (t, J = 8.0 Hz, 2H), 3.23 (t, J = 8.0 Hz, 2H), 3.12 (dd, J = 13.5, 4.0 Hz, 1H), 2.27-2.22 (m, 1H), 2.14-2.08 (m, 1H), 1.98-1.88 (m, 3H), 1.66 (br s, 6H); MS (ESI +) m/z 355 (M + H). | 34.2 |

-continued

| Structure | Ex. | NMR and MS data | 5-HT₃ K$_i$ (nM) |
|---|---|---|---|
| 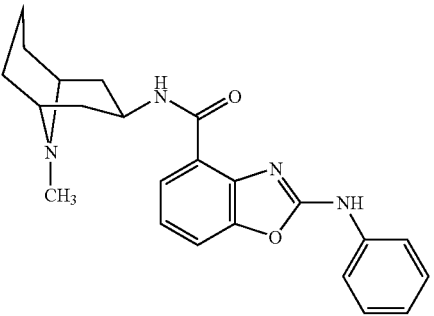 | 5 | ¹H NMR (500 MHz, DMSO-d₆) δ 11.15 (s, 0.8H), 11.10 (s, 0.2H), 10.29 (br s, 0.2H), 9.47 (br s, 0.8H), 9.04 (d, J = 6.0 Hz, 0.2H), 9.00 (d, J = 6.0 Hz, 0.8H), 7.85-7.65 (m, 4H), 7.45-7.38 (m, 2H), 7.24 (t, J = 8.0 Hz, 1H), 7.13 (t, J = 8.0 Hz, 1H), 4.69-4.62 (m, 0.8H), 4.41-4.35 (m, 0.2H), 3.70 (d, J = 9.5 Hz, 1.6H), 3.61 (d, J = 9.5 Hz, 0.4H), 2.88-2.82 (m, 3H), 2.78-2.60 (m, 2H), 2.16-1.97 (m, 3H), 1.80-1.70 (m, 2H), 1.68-1.40 (m, 3H); MS (ESI +) m/z 391 (M + H). | 6.25 |
| 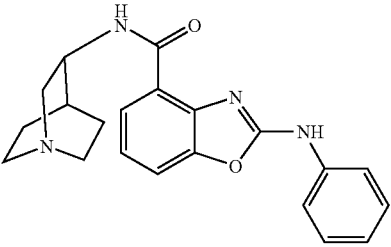 | 6 | ¹H NMR (500 MHz, DMSO-d₆) δ 11.14 (s, 1H), 10.24 (br s, 1H), 9.23 (d, J = 6.0 Hz, 1H), 7.79 (dd, J = 8.0, 1.0 Hz, 1H), 7.72 (dd, J = 8.0, 1.0 Hz, 3H), 7.43 (dd, J = 8.5, 7.5 Hz, 2H), 7.26 (t, J = 8.0 Hz, 1H), 7.13 (t, J = 7.5 Hz, 1H), 4.45-4.35 (m, 1H), 3.79 (t, J = 11.5 Hz, 1H), 3.30-3.12 (m, 5H), 2.31-2.28 (m, 1H), 2.20-2.10 (m, 1H), 2.02-1.85 (m, 3H); MS (ESI +) m/z 363 (M + H). | 8.1 |
| 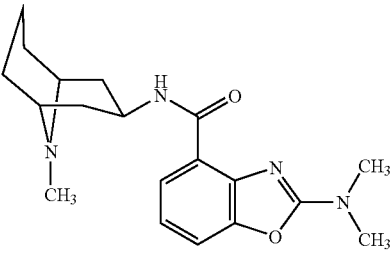 | 7 | ¹H NMR (500 MHz, DMSO-d₆) δ 10.27 (br s, 0.4H), 9.61 (br s, 0.6H), 9.32 (d, J = 6.0 Hz, 0.4H), 9.09 (d, J = 6.0 Hz, 0.6H), 7.76-7.72 (m, 1H), 7.60-7.58 (m, 1H), 7.12-7.08 (m, 1H), 4.55-4.47 (m, 0.6H), 4.38-4.30 (m, 0.4H), 3.67-3.52 (m, 2H), 3.25-3.18 (m, 6H), 2.86-2.83 (m, 3H), 2.75-2.60 (m, 2H), 2.30-2.08 (m, 3H), 1.83-1.72 (m, 3H), 1.60-1.44 (m, 2H); MS (ESI +) m/z 343 (M + H). | 6.1 |
| 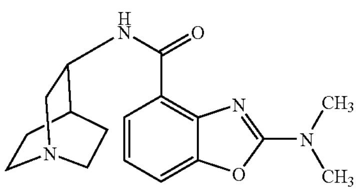 | 8 | ¹H NMR (500 MHz, DMSO-d₆) δ 10.06 (br s, 1H), 9.51 (d, J = 6.5 Hz, 1H), 7.72 (dd, J 8.0, 1.0 Hz, 1H), 7.61 (dd, J = 8.0, 1.0 Hz, 1H), 7.11 (t, J = 8.0 Hz, 1H), 4.42-4.37 (m, 1H), 3.75 (t, J = 11.5 Hz, 1H), 3.35-3.20 (m, 10H), 3.13 (d, J = 13.0 Hz, 1H), 2.28-2.21 (m, 1H), 2.18-2.08 (m, 1H), 1.98-1.88 (m, 3H); MS (ESI +) m/z 315 (M + H). | 18.1 |
| 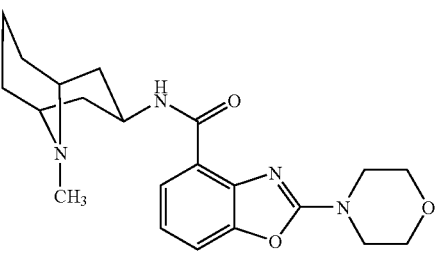 | 9 | ¹H NMR (500 MHz, DMSO-d₆) δ 10.53 (br s, 0.4H), 9.80 (br s, 0.6H), 9.20 (d, J = 5.8 Hz, 0.4H), 8.94 (d, J = 6.6 Hz, 0.6H), 7.78-7.74 (m, 1H), 7.65-7.60 (m, 1H), 7.18-7.12 (m, 1H), 4.56-4.50 (m, 0.6H), 4.30-4.25 (m, 0.4H), 3.80-3.75 (m, 4H), 3.72-3.66 (m, 4H), 3.65-3.60 (m, 1.2H), 3.55-3.50 (m, 0.8H), 2.85-2.80 (m, 3H), 2.70-2.65 (m, 2H), 2.30-2.20 (m, 1H), 2.15-2.05 (m, 2H), 1.85-1.72 (m, 3H), 1.55-1.45 (m, 2H); MS (ESI +) m/z 385 (M + H). | 42 |
| 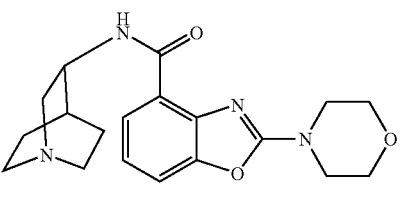 | 10 | ¹H NMR (500 MHz, DMSO-d₆) δ 12.64 (br s, 1H), 9.36 (d, J = 7.2 Hz, 1H), 7.74 (dd, J = 8.0, 1.0 Hz, 1H), 7.64 (dd, J = 8.0, 1.0 Hz, 1H), 7.16 (t, J = 7.9 Hz, 1H), 4.42-4.35 (m, 1H), 3.78-3.70 (m, 4H), 3.78-3.65 (m, 4H), 3.35-3.32 (m, 5H), 3.12 (dd, J = 14.1, 4.2 Hz, 1H), 2.30-2.20 (m, 1H), 2.18-2.10 (m, 1H), 2.00-1.90 (m, 3H); MS (ESI +) m/z 357 (M + H). | 164 |

-continued

| Structure | Ex. | NMR and MS data | 5-HT$_3$ K$_i$ (nM) |
|---|---|---|---|
| 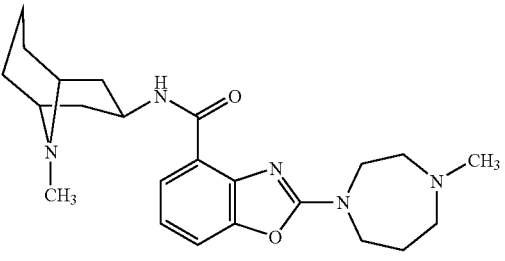 | 11 | $^1$H NMR (500 MHz, DMSO-d$_6$) δ 11.10 (br s, 0.6H), 10.98 (br s, 0.4H), 10.34 (br s, 0.4H), 9.61 (br s, 0.6H), 9.19 (br s, 0.4H), 8.98 (d, J = 3.5 Hz, 0.6H), 7.79-7.63 (m, 2H), 7.17-7.13 (m, 1H), 4.58-4.47 (m, 0.6H), 4.38-4.30 (m, 0.4H), 4.22-4.10 (m, 1H), 4.00-3.75 (m, 3H), 3.65-3.55 (m, 2H), 3.40-3.25 (m, 3H), 3.05-2.95 (m, 1H), 2.85-2.75 (m, 6H), 2.72-2.60 (m, 3H), 2.30-2.15 (m, 2H), 2.14-2.05 (m, 2H), 1.82-1.70 (m, 3H), 1.60-1.42 (m, 2H); MS (ESI +) m/z 412 (M + H). | 89.6 |
| 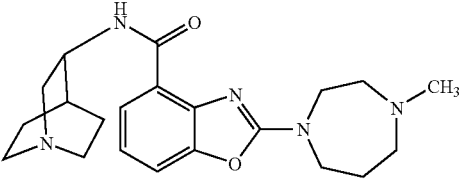 | 12 | $^1$H NMR (500 MHz, DMSO-d$_6$) δ 11.26 (br s, 1H), 10.35 (br s, 1H), 9.39 (br s, 1H), 7.75 (d, J = 8.0 Hz, 1H), 7.66 (d, J = 8.0 Hz, 1H), 7.16 (t, J = 8.0 Hz, 1H), 4.45-4.32 (m, 1H), 4.28-4.10 (m, 1H), 4.00-3.70 (m, 4H), 3.55-2.98 (m, 9H), 2.80-2.70 (m, 4H), 2.30-1.85 (m, 6H); MS (ESI +) m/z 384 (M + H). | 317 |
| 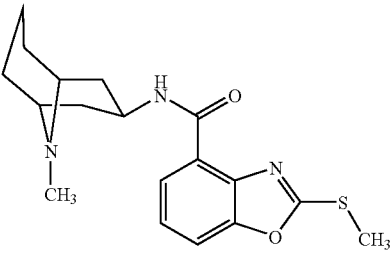 | 13 | $^1$H NMR (500 MHz, DMSO-d$_6$) δ 10.20 (br s, 0.3H), 9.45 (br s, 0.7H), 8.95 (d, J = 6.5 Hz, 0.3H), 8.74 (d, J = 6.5 Hz, 0.7H), 7.92-7.86 (m, 2H), 7.47-7.42 (m, 1H), 4.63-4.55 (m, 0.7H), 4.40-4.32 (m, 0.3H), 3.70-3.52 (m, 2H), 2.88-2.82 (m, 6H), 2.72-2.54 (m, 2H), 2.20-2.04 (m, 3H), 1.85-1.75 (m, 3H), 1.60-1.42 (m, 2H); MS (ESI +) m/z 346 (M + H). | 4.6(A) |
| 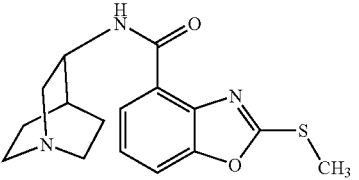 | 14 | $^1$H NMR (500 MHz, DMSO-d$_6$) δ 10.11 (br s, 1H), 9.12 (d, J = 6.5 Hz, 1H), 7.90-7.86 (m, 2H), 7.46 (t, J = 8.0 Hz, 1H), 4.45-4.36 (m, 1H), 3.74 (t, J = 11.0 Hz, 1H), 3.30-3.16 (m, 5H), 2.85 (s, 3H), 2.30-2.27 (m, 1H), 2.20-2.10 (m, 1H), 1.98-1.85 (m, 3H); MS (ESI +) m/z 318 (M + H). | 2.6(A) |
| 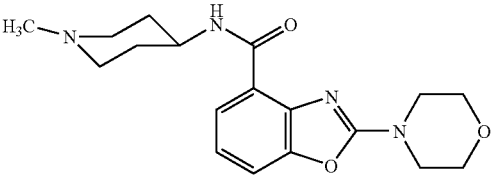 | 15 | $^1$H NMR (500 MHz, DMSO-d$_6$) δ 10.27 (br s, 0.2H), 10.12 (br s, 0.8H), 9.10 (br s, 0.2H), 8.95 (d, J = 7.0 Hz, 0.8H), 7.74 (d, J = 7.5 Hz, 1H), 7.61 (d, J = 7.5 Hz, 1H), 7.14 (t, J = 7.5 Hz, 1H), 4.21-4.18 (m, 0.2H), 4.09-4.00 (m, 0.8H), 3.79-3.75 (m, 4H), 3.70-3.65 (m, 4H), 3.45 (d, J = 11.5 Hz, 2H), 3.12 (t, J = 11.5 Hz, 2H), 2.75 (s, 3H), 2.18 (d, J = 12.5 Hz, 2H), 1.85-1.75 (m, 2H); MS (ESI +) m/z 345 (M + H). | 87 (C) |
| 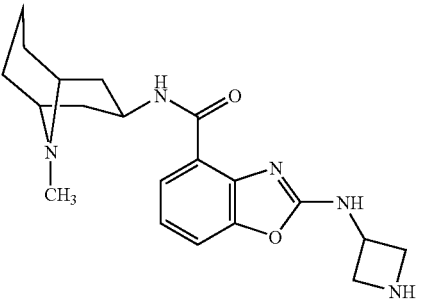 | 16 | $^1$H NMR (500 MHz, DMSO-d$_6$) δ 9.52 (br s, 1.2H), 9.50-9.40 (m, 1H), 9.16 (br s, 0.8H), 9.07 (d, J = 6.0 Hz, 0.4H), 8.89 (d, J = 6.0 Hz, 0.6H), 7.76-7.73 (m, 1H), 7.65-7.60 (m, 1H), 7.19-7.15 (m, 1H), 5.05-4.51 (m, 2H), 4.38-4.02 (m, 4H), 3.70-3.62 (m, 2H), 3.10-2.93 (m, 1H), 2.85-2.80 (m, 3H), 2.75-2.60 (m, 3H), 2.18-2.02 (m, 2H), 1.90-1.72 (m, 3H), 1.65-1.50 (m, 2H); MS (ESI +) m/z 370 (M + H). | 179 |

-continued

| Structure | Ex. | NMR and MS data | 5-HT$_3$ K$_i$ (nM) |
|---|---|---|---|
| 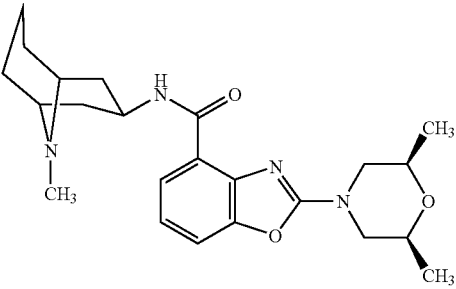 | 17 | $^1$H NMR (500 MHz, DMSO-d$_6$) δ 10.32 (br s, 0.4H), 9.69 (br s, 0.6H), 9.23 (d, J = 6.0 Hz, 0.4H), 9.02 (d, J = 6.0 Hz, 0.6H), 7.79-7.74 (m, 1H), 7.61-7.60 (m, 1H), 7.16-7.12 (m, 1H), 4.53-4.45 (m, 0.6H), 4.38-4.30 (m, 0.4H), 4.10-4.00 (m, 2H), 3.70-3.69 (m, 2H), 3.65-3.50 (m, 2H), 2.95-2.80 (m, 5H), 2.72-2.60 (m, 2H), 2.35-2.05 (m, 3H), 1.86-1.70 (m, 3H), 1.60-1.45 (m, 2H), 1.20-1.13 (m, 6H); MS (ESI +) m/z 413 (M + H). | 54.2 |
| 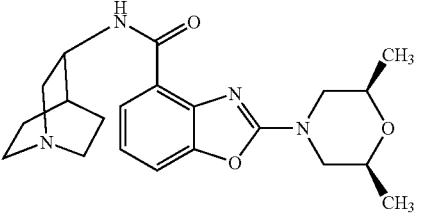 | 18 | $^1$H NMR (500 MHz, DMSO-d$_6$) δ 10.11 (br s, 1H), 9.39 (d, J = 7.0 Hz, 1H), 7.73 (dd, J = 8.0, 1.0 Hz, 1H), 7.62 (dd, J = 8.0, 1.0 Hz, 1H), 7.16 (t, J = 8.0 Hz, 1H), 4.42-4.37 (m, 1H), 4.08-4.01 (m, 2H), 3.78-3.70 (m, 3H), 3.35-3.22 (m, 4H), 3.15 (dd, J = 13.5, 4.5 Hz, 1H), 2.97-2.88 (m, 2H), 2.28-2.21 (m, 1H), 2.18-2.08 (m, 1H), 1.98-1.89 (m, 3H), 1.17 (d, J = 6.0 Hz, 6H); MS (ESI +) m/z 385 (M + H). | 443 |
| 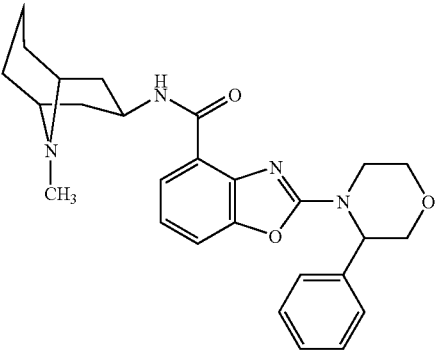 | 19 | $^1$H NMR (500 MHz, DMSO-d$_6$) δ 10.12 (br s, 0.4H), 9.47 (br s, 0.6H), 9.10 (d, J = 6.0 Hz, 0.4H), 8.88 (d, J = 6.0 Hz, 0.6H), 7.79-7.74 (m, 1H), 7.68-7.60 (m, 1H), 7.50-7.30 (m, 5H), 7.19-7.12 (m, 1H), 5.40-5.35 (m, 1H), 4.53-4.45 (m, 1H), 4.38-4.25 (m, 1H), 4.10-3.95 (m, 3H), 3.80-3.69 (m, 1H), 3.65-3.45 (m, 3H), 2.85-2.78 (m, 3H), 2.70-2.55 (m, 2H), 2.12-1.93 (m, 3H), 1.80-1.52 (m, 3H), 1.47-1.37 (m, 2H); MS (ESI +) m/z 461 (M + H). | 17 |
| 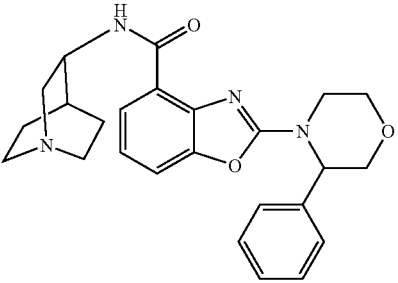 | 20 | $^1$H NMR (500 MHz, DMSO-d$_6$) δ 10.10 (br s, 1H 9.27-9.23 (m, 1H) 7.74 (d, J = 8.0 Hz 1H), 7.65 (d, J = 8.0 Hz, 1H), 7.50-7.28 (m, 5H), 7.20-7.14 (m, 1H), 5.40-5.33 (m, 1H), 4.45-4.27 (m, 2H), 4.10-3.96 (m, 3H), 3.80-3.52 (m, 3H), 3.25-3.00 (m, 5H), 2.25-2.03 (m, 1H), 1.93-1.62 (m, 4H); MS (ESI +) m/z 433 (M + H). | 34.4 |
| 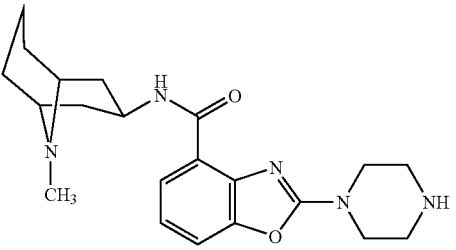 | 21 | $^1$H NMR (500 MHz, DMSO-d$_6$) δ 10.48 (br s, 0.4H), 9.72 (br s, 0.6H), 9.56 (br s, 2H), 9.11 (d, J = 5.5 Hz, 0.4H), 8.86 (d, J = 5.5 Hz, 0.6H), 7.80-7.74 (m, 1H), 7.68-7.62 (m, 1H), 7.22-7.15 (m, 1H), 4.60-4.51 (m, 0.6H), 4.38-4.30 (m, 0.4H), 3.98-3.88 (m, 4H), 3.63 (d, J = 9.0 Hz, 2H), 3.35-3.27 (m, 4H), 2.85-2.80 (m, 3H), 2.75-2.60 (m, 2H), 2.40-2.05 (m, 3H), 1.85-1.72 (m, 3H), 1.60-1.45 (m, 2H); MS (ESI +) m/z 384 (M + H). | 74.6 |

-continued

| Structure | Ex. | NMR and MS data | 5-HT$_3$ K$_i$ (nM) |
|---|---|---|---|
| 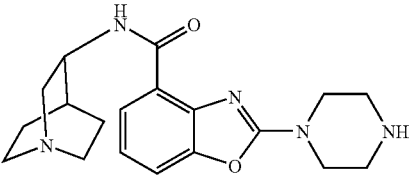 | 22 | $^1$H NMR (500 MHz, DMSO-d$_6$) δ 10.35 (br s, 1H), 9.59 (br s, 2H), 9.25 (d, J = 6.5 Hz, 1H), 7.76 (d, J = 8.0 Hz, 1H), 7.66 (dd, J = 8.0, 1.0 Hz, 1H), 7.19 (t, J = 8.0 Hz, 1H), 4.42-4.37 (m, 1H), 3.94 (t, J = 5.0 Hz, 4H), 3.74 (t, J = 11.6 Hz, 1H), 3.36-3.20 (m, 8H), 3.15 (dd, J = 13.4, 4.2 Hz, 1H), 2.27-2.20 (m, 1H), 2.10 2.02 (m, 1H), 1.98-1.83 (m, 3H); MS (ESI +) m/z 356 (M + H). | 321 |
| 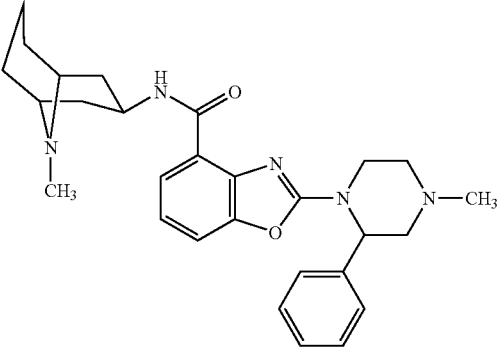 | 23 | $^1$H NMR (500 MHz, DMSO-d$_6$) δ 11.67 (br s, 0.2H), 10.52 (br s, 0.4H), 10. 109.56 (m, 1.4H), 9.03-8.52 (m, 1H), 7.88-7.61 (m, 2H), 7.48-7.29 (m, 5H), 7.20-7.15 (m, 1H), 5.94 (br s, 0.8H), 5.55-5.37 (m, 0.2H), 4.60-4.26 (m, 3H), 3.82-3.25 (m, 6H), 2.98-2.80 (m, 6H), 2.76-2.52 (m, 2H), 2.07-1.90 (m, 3H), 1.81-1.20 (m, 5H); MS (ESI +) m/z 474 (M + H). | 25.2 |
| 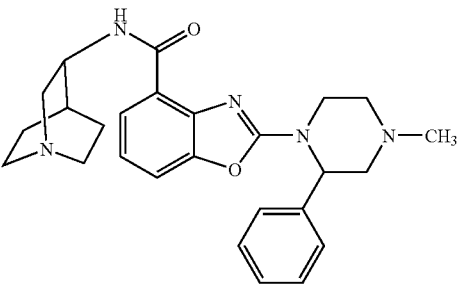 | 24 | $^1$H NMR (500 MHz, DMSO-d$_6$) δ 11.81 (brs, 0.2H), 10.70-10.45 (m, 1H), 10.17 (br s, 0.8H), 9.20-8.97 (m, 1H), 7.80-7.73 (m, 2H), 7.42-7.23 (m, 5H), 7.18-7.08 (m, 1H), 6.02-5.50 (m, 1H), 4.71-4.15 (m, 3H), 3.84-3.20 (m, 5H), 3.18-2.81 (m, 8H), 2.18-1.45 (m, 5H); MS (ESI +) m/z 446 (M + H). | 103 |
| 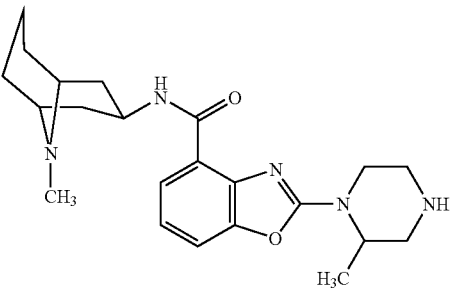 | 25 | $^1$H NMR (500 MHz, DMSO-d$_6$) δ 10.58 (br s, 0.4H), 9.85 (br s, 1.6H), 9.49 (br s, 1H), 9.11 (d, J = 7.0 Hz, 0.4H), 8.89 (d, J = 7.0 Hz, 0.6H), 7.80-7.74 (m, 1H), 7.68-7.62 (m, 1H), 7.22-7.15 (m, 1H), 4.65-4.58 (m, 1H), 4.55-4.47 (m, 0.6H), 4.38-4.28 (m, 0.4H), 4.20-4.12 (m, 1H), 3.68-3.60 (m, 2H), 3.52-3.25 (m, 4H), 3.18-3.08 (m, 1H), 2.85-2.80 (m, 3H), 2.75-2.60 (m, 2H), 2.32-2.05 (m, 3H), 1.80-1.72 (m, 3H), 1.60-1.45 (m, 5H); MS (ESI +) m/z 398 (M + H). | 27.5 |
| 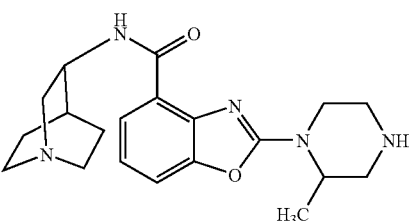 | 26 | $^1$H NMR (500 MHz DMSO-d$_6$) δ 10.49 (br s, 1H) 9.91 (d, J = 100 Hz, 1H), 9.53 (d, J = 9.0 Hz, 1H), 9.29 (d, J = 6.5 Hz, 1H), 7.76 (d, J = 8.0 Hz, 1H), 7.66 (d, J = 8.0 Hz, 1H), 7.17 (t, J 8.0 Hz, 1H), 4.68-4.59 (m, 1H), 4.41-4.32 (m, 1H), 4.18 (d, J = 14.0 Hz, 1H), 3.72 (t, J = 12.0 Hz, 1H), 3.61 (t, J = 12.0 Hz, 1H), 3.40 3.05 (m, 9H), 2.27-2.20 (m, 1H), 2.10-2.02 (m, 1H), 1.98-1.83 (m, 3H), 1.50-1.45 (m, 3H); MS (ESI +) m/z 370 (M + H). | 241 |

-continued

| Structure | Ex. | NMR and MS data | 5-HT$_3$ K$_i$ (nM) |
|---|---|---|---|
| 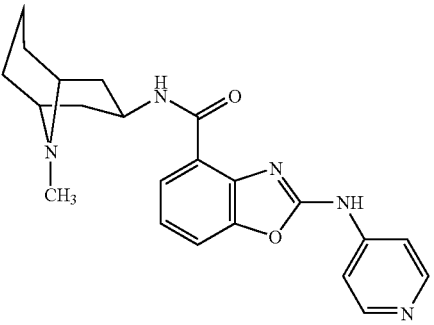 | 27 | $^1$H NMR (500 MHz, DMSO-d$_6$) δ 10.38 (br s, 0.2H), 9.54 (br s, 0.8H), 8.72 (d, J = 6.5 Hz, 2.2H), 8.61 (d, J = 6.5 Hz, 0.8H), 8.18-8.05 (m, 2H), 7.88-7.80 (m, 2H), 7.43-7.36 (m, 1H), 4.73-4.63 (m, 0.8H), 4.42-4.38 (m, 0.2H), 3.72-3.55 (m, 2H), 2.87-2.82 (m, 3H), 2.78-2.53 (m, 3H), 2.20-2.05 (m, 3H), 1.86-1.45 (m, 5H); MS (ESI +) m/z 392 (M + H). | 4.5 |
| 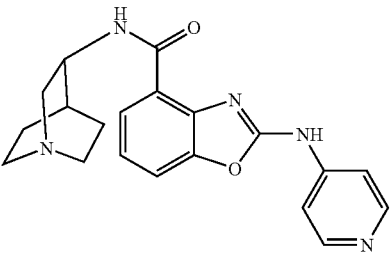 | 28 | $^1$H NMR (500 MHz, DMSO-d$_6$) δ 10.48 (br s, 1H), 8.89 (d, J = 6.0 Hz, 1H), 8.80 (d, J = 7.0 Hz, 2H), 8.17 (d, J = 7.0 Hz, 2H), 7.89 (dd, J = 8.0, 1.0 Hz, 1H), 7.84 (dd, J = 8.0, 1.0 Hz, 1H), 7.43 (t, J = 8.0 Hz, 1H), 4.42 (d, J = 5.5 Hz, 1H), 3.78 (t, J = 11.0 Hz, 1H), 3.38-3.15 (m, 6H), 2.38-2.34 (m, 1H), 2.20-2.10 (m, 1H), 2.01-1.87 (m, 3H); MS (ESI +) m/z 364 (M + H). | 5.3 |
| 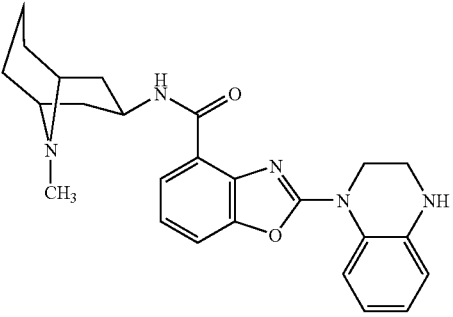 | 29 | $^1$H NMR (500 MHz, DMSO-d$_6$) δ 10.70 (br s, 0.3H), 9.77 (br s, 0.7H), 9.17 (d, J = 5.5 Hz, 0.3H), 9.01 (d, J = 7.0 Hz, 0.7H), 7.84 (d, J 8.0 Hz, 1H), 7.79 (d, J = 7.5 Hz, 1H), 7.69 (d, J = 7.5 Hz, 1H), 7.21 (t, J = 8.0 Hz, 1H), 6.96 (t, J = 7.5 Hz, 1H), 6.73 (d, J = 8.0 Hz, 1H), 6.63 (d, J = 7.5 Hz, 1H), 4.65-4.55 (m, 0.7H), 4.40-4.30 (m, 0.3H), 4.08-4.40 (m, 2H), 3.64 (d, J = 9.0 Hz, 1.3H), 3.60-3.50 (m, 0.7H), 3.48-3.42 (m, 2H), 2.86-2.80 (m, 3H), 2.70-2.58 (m, 2H), 2.20-1.96 (m, 3H), 1.80-1.60 (m, 2H), 1.56-1.50 (m, 1H), 1.48-1.36 (m, 2H); MS (ESI +) m/z 432 (M + H). | 3.6 |
| 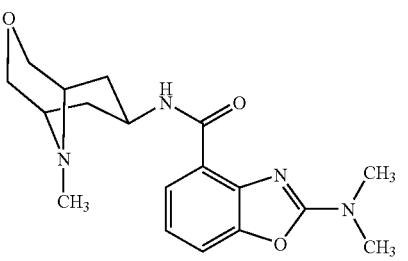 | 30 | $^1$H NMR (500 MHz, DMSO-d$_6$) δ 11.26 (br s, 0.7H), 10.80 (br s, 0.3H), 9.80 (d, J = 9.6 Hz, 1H), 7.75 (d, J = 7.9 Hz, 1H), 7.54 (dd, J 7.9, 0.9 Hz, 1H), 7.08-7.04 (m, 1H), 4.75-4.65 (m, 1H), 4.28-4.20 (m, 2H), 4.04 (d, J = 12.9 Hz, 1.4H), 3.86 (d, J = 12.9 Hz, 0.6H), 3.48 3.40 (m, 2H), 3.20 (s, 6H), 3.01 (d, J = 5.0 Hz, 1H), 2.88 (d, J = 5.0 Hz, 2H), 2.85-2.80 (m, 0.6H), 2.72-2.62 (m, 1.4H), 1.97 (m, 0.6H), 1.75 (m, 1.4H); MS (ESI +) m/z 345 (M + H). | 79 |
| 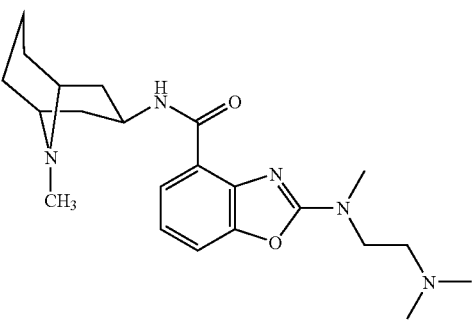 | 31 | $^1$H NMR (500 MHz, DMSO-d$_6$) δ 11.02 10.96 (m, 1H), 10.79 (br s, 0.3H), 9.85 (br s, 0.7H), 9.08 (br s, 0.3H), 8.81 (br s, 0.7H), 7.78-7.75 (m, 1H), 7.62 (dd, J = 7.9, 0.8 Hz, 1H), 7.15-7.12 (m, 1H), 5.95 (br s, 3H), 4.69 4.62 (m, 0.7H), 4.38-4.35 (m, 0.3H), 4.07 4.00 (m, 2H), 3.65-3.62 (m, 1.5H), 3.56-3.52 (m, 0.5H), 3.47-3.42 (m, 2H), 3.25 (s, 3H), 2.85-2.82 (m, 9H), 2.69-2.57 (m, 2H), 2.31-2.05 (m, 3H), 1.82-1.73 (m, 3H), 1.53-1.48 (m, 3H); MS (ESI +) m/z 400 (M + H). | 107 |

| Structure | Ex. | NMR and MS data | 5-HT$_3$ K$_i$ (nM) |
|---|---|---|---|
| 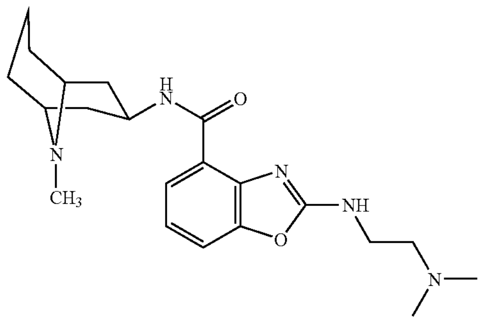 | 32 | $^1$H NMR (500 MHz, DMSO-d$_6$) δ 10.95 (br s, 0.7H), 10.86 (br s, 0.3H), 10.50 (br s, 0.3H), 9.72 (br s, 0.7H), 9.15 (br s, 0.3H), 8.93-8.90 (m, 1.7H), 7.76-7.73 (m, 1H), 7.60-7.58 (m, 1H), 7.16-7.12 (1H), 4.64-4.55 (m, 0.8H), 4.36-4.32 (m, 0.2H), 4.21 (br s, 6H), 3.87-3.77 (m, 2H), 3.65-3.62 (m, 1.4H), 3.55-3.52 (m, 0.6H), 3.40-3.35 (m, 2H), 2.84-2.82 (m, 9H), 2.69-2.57 (m, 2H), 2.29-2.05 (m, 3H), 1.84-1.71 (m, 2.6H), 1.57-1.49 (m, 2.4H); MS (ESI +) m/z 386 (M + H). | 234 |
| 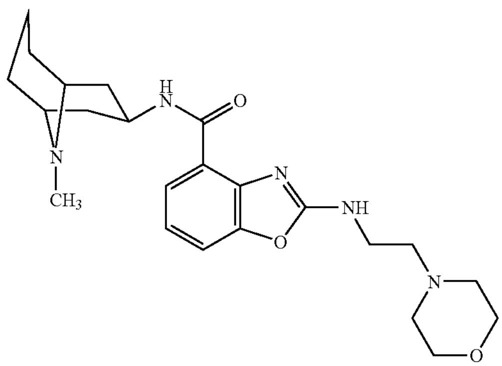 | 33 | $^1$H NMR (500 MHz, DMSO-d$_6$) δ 11.45 (br s, 0.7), 11.18 (br s, 0.3H), 10.32 (br s, 0.3H), 9.57 (br s, 0.7H), 9.16 (br s, 0.3H), 8.93-8.90 (m 1.7H) 7.76-7.73 (m, 1H) 7.59 (d, J = 7.9 Hz, 1H), 7.16-7.12 (m, 1H), 4.61-4.52 (m, 0.6H), 4.35-4.31 (m, 0.4H), 3.99-3.84 (m, 3.5H), 3.66-3.43 (m, 3.5H), 3.17-3.13 (m, 1H), 2.85-2.81 (m, 3H), 2.67-2.59 (m, 3H), 2.22-2.05 (m, 3H), 1.87-1.71 (m, 4H), 1.56 1.50 (m, 2H), 0.89-0.62 (m, 2H); MS (ESI +) m/z 428 (M + H). | 168 |
| 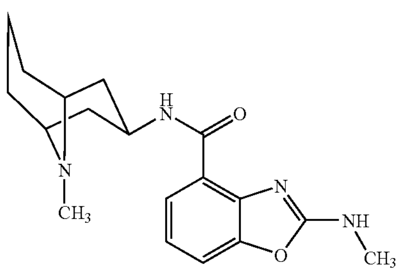 | 34 | $^1$H NMR (500 MHz, DMSO-d$_6$) δ 10.46 (br s, 0.4H), 9.81 (br s, 0.6H), 9.42 (d, J = 5.9 Hz, 0.4H), 9.17 (d, J = 6.5, Hz, 0.6H), 8.55-8.45 (m, 1H), 7.75-7.66 (m, 1H), 7.57-7.50 (m, 1H), 7.10-7.04 (m, 1H), 4.55-4.45 (m, 1.2H), 4.35-4.25 (m, 0.8H), 3.65-3.57 (m, 1.2H), 3.55-3.50 (m, 0.8H), 3.02-2.94(m, 3H), 2.88-2.80 (m,3H), 2.74-2.70 (m, 2H), 2.30-2.20 (m, 1H), 2.15-2.05 (m, 2H), 1.84-1.72 (m, 3H), 1.60-1.45 (m, 2H); MS (ESI +) m/z 329 (M + H). | 5.3 |
| 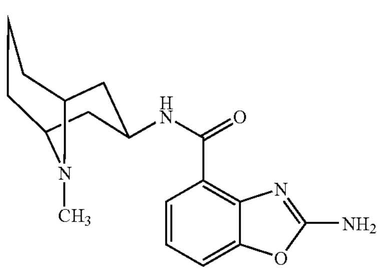 | 35 | $^1$H NMR (500 MHz, DMSO-d$_6$) δ 10.54 (br s, 0.3H), 9.81 (br s, 0.7H), 9.37 (d, J = 5.5 Hz, 0.3H), 9.03 (d, J = 7.1 Hz, 0.7H), 8.30 (br s, 1.4H), 8.18 (br s, 0.6H), 7.78-7.70 (m, 1H), 7.60-7.50 (m, 1H), 7.15-7.05 (m, 1H), 4.65-4.55 (m, 0.7H), 4.35-4.25 (m, 0.3H), 3.70 3.50 (m, 2H), 2.90-2.80 (m, 3H), 2.72-2.55 (m, 2H), 2.15-2.05 (m, 3H), 1.90-1.70 (m, 3H), 1.54-1.45 (m, 2H); MS (ESI +) m/z 315 (M + H). | 9.1 |
| 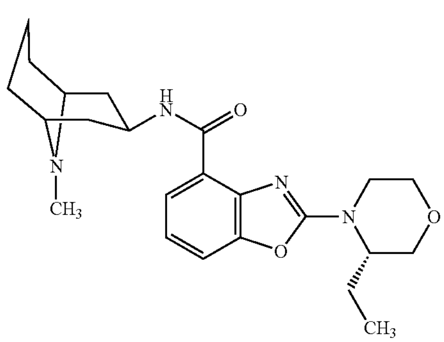 | 36 | $^1$H NMR (500 MHz, DMSO-d$_6$) δ 10.69 (br s, 0.4H), 9.89 (br s, 0.6H), 9.15-9.14 (m, 0.4H), 8.96-8.95 (m, 0.6H), 7.77-7.74 (m, 1H), 7.61-7.59 (m, 1H), 7.15-7.11 (m, 1H), 4.57-4.53 (m, 0.6H), 4.34-4.33 (m, 0.4H), 4.04-4.03 (m, 1H), 3.94-3.84 (m, 3H), 3.68-3.46 (m, 5H), 2.83-2.81 (m, 3H), 2.68-2.62 (m, 2H), 2.27 2.25 (m, 1H), 2.12-2.10 (m, 2H), 1.91-1.74 (m, 5H), 1.53-1.47 (m, 2H), 0.93-0.86 (m, 3H); MS (ESI +) m/z 413 (M + H). | 4.7 |

-continued

| Structure | Ex. | NMR and MS data | 5-HT$_3$ K$_i$ (nM) |
|---|---|---|---|
| 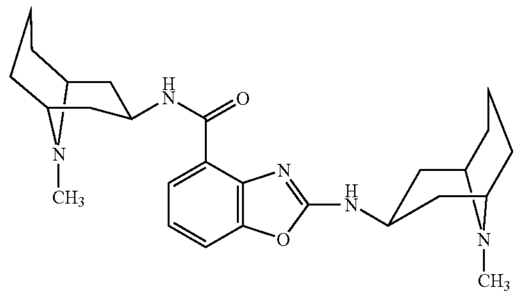 | 37 | $^1$H NMR (500 MHz, DMSO-d$_6$) δ 11.35-11.15 (m, 0.8H), 10.96-10.85 (m, 0.2H), 10.62 (s, 0.2H), 10.00-9.60 (m, 0.8H), 9.18-9.06 (m, 0.5H), 8.98 (d, J = 7.0 Hz, 0.5H), 8.74-8.66 (m, 1H), 7.80-7.70 (m, 1H), 7.60-7.54 (m, 1H), 7.18-7.12 (m, 1H), 4.96-4.82 (m, 1H), 4.68-4.60 (m, 0.6H), 4.40-4.24 (m, 0.4H), 3.66-3.50 (m, 4H), 2.90-2.74 (m, 6H), 2.70-2.60 (m, 3H), 2.36-2.20 (m, 2H), 2.16-2.00 (m, 5H), 1.94-1.88 (m, 1H), 1.86-1.70 (m, 2H), 1.68-1.46 (m, 5H); MS (ESI +) m/z 452 (M + H). | 243 |
| 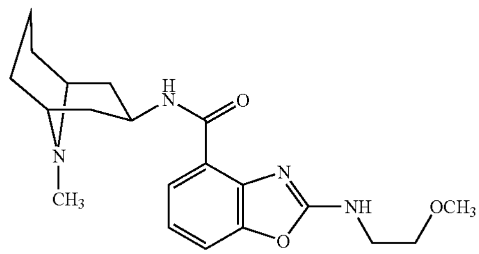 | 38 | $^1$H NMR (500 MHz, DMSO-d$_6$) δ 10.77 (s, 0.4H), 10.05 (s, 0.6H), 9.30 (d, J = 5.5 Hz, 0.4H), 9.12 (d, J = 6.5 Hz, 0.6H), 8.77 (s, 1H), 8.30-7.80 (br s, 1H), 7.74-7.71 (m, 1H), 7.55 (dd J = 8.0, 1.0 Hz, 1H), 7.10 (app t, J = 8.0 Hz, 1H), 4.56-4.48 (m, 0.6H), 4.38-4.30 (m, 0.4H), 3.64-3.50 (m, 6H), 3.30 (d, J = 3.5 Hz, 3H), 2.84-2.80 (m, 3H), 2.74-2.62 (m, 2H), 2.38-2.24 (m, 1.2H), 2.11 (d, J = 6.5 Hz, 1.8H), 1.82-1.70 (m, 3H), 1.50-1.46 (m, 2H); MS (ESI +) m/z 373 (M + H). | 7.5 |
| 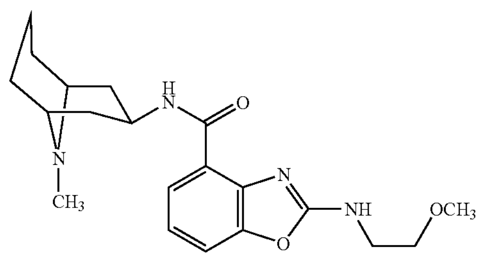 | 39 | $^1$H NMR (500 MHz, DMSO-d$_6$) δ 10.70 (s, 0.4H), 9.99 (s, 0.6H), 9.34 (d, J = 5.5 Hz, 0.4H), 9.16 (d, J = 6.5 Hz, 0.6H), 8.73-8.66 (m, 1H), 7.90-7.50 (br s, 1H), 7.80-7.66 (m, 1H), 7.56-7.53 (m, 1H), 7.09 (app t, J = 8.0 Hz, 1H), 4.56-4.50 (m, 0.6H), 4.36-4.30 (m, 0.4H), 3.61 (d, J = 9.0 Hz, 1H), 3.53 (br s, 1H), 3.46-3.38 (m, 4H), 3.23 (d, J = 1.0 Hz, 3H), 2.82 (dd, J = 8.5, 5.0 Hz, 3H), 2.75-2.62 (m, 2H), 2.16-2.08 (m, 1.2H), 2.12 (d, J = 7.0 Hz, 1.8H), 1.92-1.82 (m, 2H), 1.80-1.70 (m, 3H), 1.60-1.44 (m, 2H); MS (ESI +) m/z 387 (M + H). | 13.2 |
| 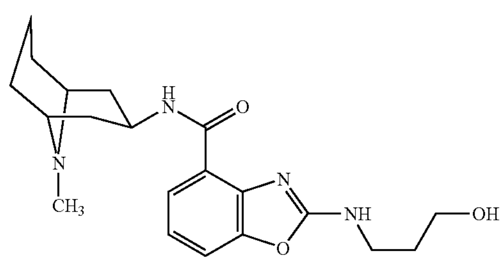 | 40 | $^1$H NMR (500 MHz, DMSO-d$_6$) δ 10.76 (s, 0.4H), 10.03 (s, 0.6H), 9.36 (d, J = 6.0 Hz, 0.4H), 9.20 (d, J = 6.0 Hz, 0.6H), 8.70-8.62 (m, 1H), 7.90-7.50 (br s, 1H), 7.80-7.70 (m, 1H), 7.60-7.52 (m, 1H), 7.10 (app t, J = 8.0 Hz, 1H), 4.60-4.50 (m, 0.6H), 4.40-4.30 (m, 0.4H), 3.61 (d, J = 9.0 Hz, 1H), 3.54-3.50 (m, 2H), 3.49-3.40 (m, 2H), 2.85-2.80 (m, 2H), 2.74-2.60 (m, 2H), 2.38-2.28 (m, 1H), 2.16-2.08 (m, 2H), 1.82-1.70 (m, 4H), 1.60-1.46 (m, 2H); MS (ESI +) m/z 373 (M + H). | 7.8 |
| 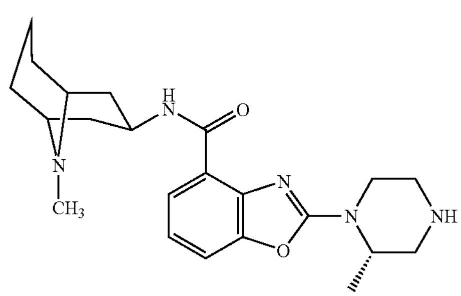 | 41a | $^1$H NMR (500 MHz, DMSO-d$_6$) δ 10.47 (br s, 0.4H), 9.50-9.57 (m, 1.6H), 9.41 (br s, 1H), 9.10 (s, 0.4H), 8.89 (s, 0.6H), 7.88-7.72 (m, 1H), 7.65 (s, 1H), 7.32-7.06 (m, 1H), 4.64 (br s, 1H), 4.54-4.49 (m, 1H), 4.27-4.09 (m, 1H), 3.75-3.56 (m, 2H), 3.53 (s, 1H), 3.34-3.22 (m, 3H), 3.22-3.01 (m, 1H), 2.84 (s, 3H), 2.72-2.60 (m, 2H), 2.26 (s, 1H), 2.11 (s, 2H), 1.93-1.64 (m, 3H), 1.63-1.33 (m, 5H); MS (ESI +) m/z 398 (M + H). | 14.2 |

-continued

| Structure | Ex. | NMR and MS data | 5-HT₃ K$_i$ (nM) |
|---|---|---|---|
| 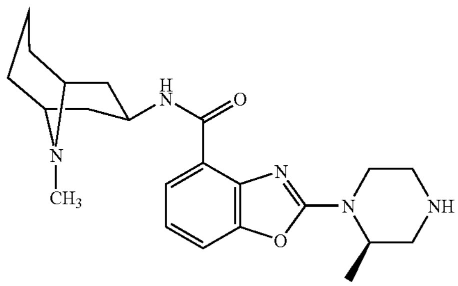 | 41b | ¹H NMR (500 MHz, DMSO-d₆) δ 10.47 (br s, 0.4H), 9.50-9.57 (m, 1.6H), 9.41 (br s, 1H), 9.10 (s, 0.4H), 8.89 (s, 0.6H), 7.88-7.72 (m, 1H), 7.65 (s, 1H), 7.32-7.06 (m, 1H), 4.64 (br s, 1H), 4.54-4.49 (m, 1H), 4.27-4.09 (m, 1H), 3.75-3.56 (m, 2H), 3.53 (s, 1H), 3.34-3.22 (m, 3H), 3.22-3.01 (m, 1H), 2.84 (s, 3H), 2.72-2.60 (m, 2H), 2.26 (s, 1H), 2.11 (s, 2H), 1.93-1.64 (m, 3H), 1.63-1.33 (m, 5H); MS (ESI +) m/z 398 (M + H). | 125 |
| 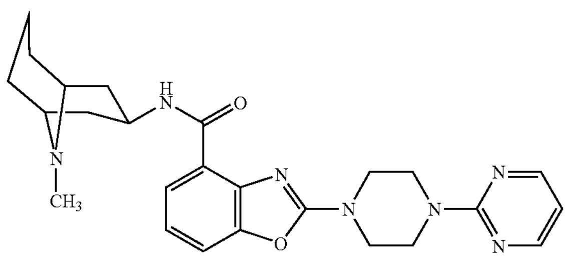 | 42 | ¹H NMR (500 MHz, CD₃OD) δ 8.41 (s, 2H), 7.84 (s, 1H), 7.62-7.47 (m, 1H), 7.28-7.05 (m, 1H), 6.81-6.61 (m, 1H), 4.66-4.29 (m, 1H), 4.17-3.97 (m, 4H), 3.96-3.78 (m, 4H), 3.78-3.58 (m, 2H), 3.08-2.91 (m, 3H), 2.91-2.62 (m, 2H), 2.37-2.11 (m, 3H), 2.11-1.91 (m, 2.5H), 1.80-1.59 (m, 2.5H); MS (ESI +) m/z 462 (M + H). | 11 |
| 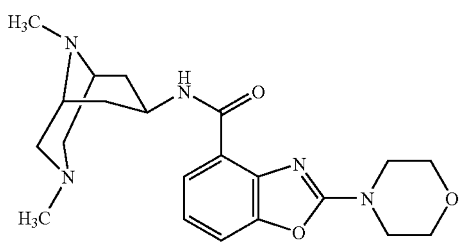 | 43 | ¹H NMR (500 MHz, DMSO-d₆) δ 9.14-8.93 (m, 0.5H), 7.85-7.65 (m, 0.8H), 7.65-7.53 (m, 0.8H), 7.25-6.99 (m, 0.9H), 5.39-5.00 (m, 1H), 4.74-3.98 (m, 6H), 3.86-3.39 (m, 9H), 3.29-2.58 (m, 6H), 2.48-1.93 (m, 5H); MS (ESI +) m/z 400 (M + H). | 480 |
| 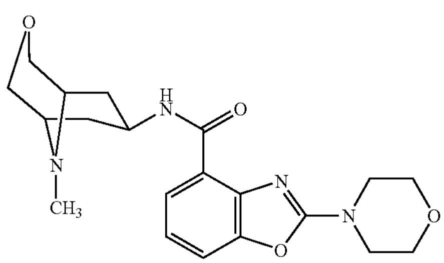 | 44 | ¹H NMR (500 MHz, CD₃OD) δ10.21 (br s, 1H), 7.94-7.68 (m, 1H), 7.56-7.38 (m, 1H), 7.26-6.96 (m, 1H), 4.81-4.63 (m, 1H), 4.11-3.89 (m, 2H), 3.88-3.70 (m, 10H), 2.85-2.67 (m, 2H), 2.68-2.48 (m, 5H), 1.71-1.51 (m, 2H); MS (ESI +) m/z 387 (M + H). | 323 |
| 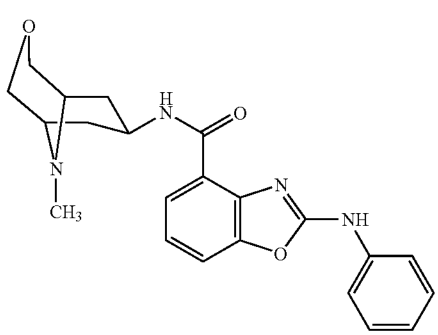 | 45 | ¹H NMR (500 MHz, DMSO-d₆) δ 10.91-10.88 (m, 0.6H), 10.86-10.53 (m, 0.4H), 10.53-10.10 (m, 0.2H), 9.42-9.13 (m, 0.8H), 7.98-7.79 (m, 1H), 7.79-7.60 (m, 3.9H), 7.58-7.34 (m, 2H), 7.34-7.17 (m, 1H), 7.15-6.98 (m, 1H), 4.79-4.51 (m, 1H), 4.35-4.12 (m, 0.9H), 4.12-3.90 (m, 2.4H), 3.90-3.65 (m, 1H), 3.65-3.40 (m, 2.3H), 3.10-2.96 (m, 1.3H), 2.96-2.84 (m, 1.8H), 2.84-2.62 (m, 2.4H), 2.17-1.97 (m, 0.8H), 1.95-1.73 (m, 1.2H); MS (ESI +) m/z 393 (M + H). | 22.6 |

| Structure | Ex. | NMR and MS data | 5-HT$_3$ K$_i$ (nM) |
|---|---|---|---|
| 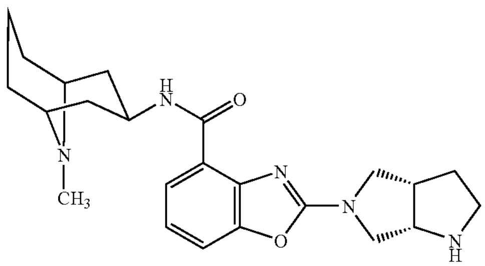 | 46 | $^1$H NMR (500 MHz, DMSO-d$_6$) δ 10.56 (br s, 0.5H), 10.07 (s, 0.5H), 10.01 (s, 0.5H), 9.52 (s, 1H), 9.22 (d, J = 5.5 Hz, 0.4H), 8.99 (d, J = 5.5 Hz, 0.6H 7.78 (t, J = 7.5 Hz, 1H), 7.67 (d, J = 8.0 Hz, 1H), 7.19-7.16 (m, 1H), 4.91 (s, 0.5H), 4.87 (s, 0.5H), 4.34-4.31 (d, J = 10.5 Hz, 1H), 3.79-3.76 (m, 1H), 3.62-3.59 (m, 1H), 3.52 (s, 1H), 3.42 (s, 1H), 3.34-3.32 (m, 1H), 2.89 01502.83 (m, 3H), 2.78-2.62 (m, 2H), 2.30-2.23 (m, 2H), 2.17-2.08 (m, 1H), 2.05 (d, J = 10.0 Hz, 1H), 1.83-1.78 (m, 3H), 1.63-1.58 (m, 1H), 1.51-1.49 (m, 1H); MS (ESI +) m/z 396 (M + H). | 284 |
| 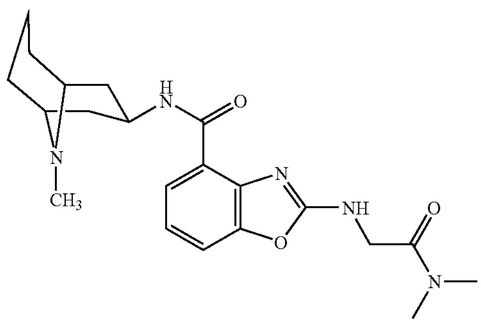 | 47 | $^1$H NMR (500 MHz, DMSO-d$_6$) δ 10.40 (br s, 1H), 9.62 (br s, 1H), 9.21-9.20 (m, 0.3H), 9.08-9.06 (m, 0.7H), 8.75 (br s, 0.7H), 8.67-8.65 (m, 0.3H), 7.74-7.71 (m, 1H), 7.58 (d, J = 7.8 Hz, 1H), 7.13-7.09 (m, 1H), 4.80 (br s, 4H), 4.31 (m, 2.5H), 3.65-3.63 (m, 1.5H), 3.54 (br s, 0.5H), 3.03 (s, 3H), 3.00 (s, 1H), 2.87-2.80 (m, 6H), 2.70-2.59 (m, 2H), 2.20 (br s, 0.8H), 2.11-2.09 (m, 2.2H), 1.78-1.74 (m, 3H), 1.53-1.45 (2.5H); MS (ESI +) m/z 400 (M + H). | 137 |
| 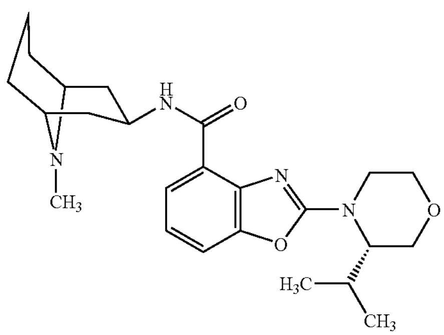 | 48 | $^1$H NMR (500 MHz, DMSO-d$_6$) δ 10.77 (br s, 0.4H), 9.98 (br s, 0.6H), 9.14-9.13 (m, 0.4H), 8.98-8.97 (m, 0.6H), 7.77-7.74 (m, 1H), 7.60-7.58 (m, 1H), 7.14-7.10 (m, 1H), 4.58-4.51 (m, 0.6H), 4.34-4.33 (m, 0.4H), 4.04-3.91 (m, 3H), 3.76-3.71 (m, 1H), 3.68-3.44 (m, 5H), 2.83-2.77 (m, 3H), 2.73-2.64 (m, 2H), 2.46-2.35 (m, 1H), 2.32-2.18 (m, 1H), 2.12-2.08 (m, 2H), 1.80-1.73 (m, 3H), 1.54-1.45 (m, 2H), 1.07-0.99 (m, 3H), 0.91-0.81 (m, 3H); MS (ESI +) m/z 427 (M + H). | 6.0 |
| 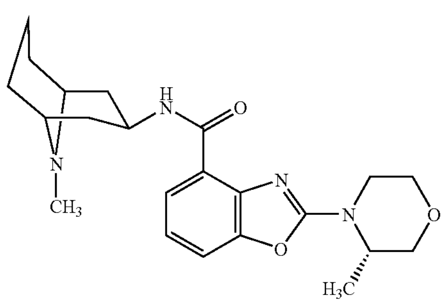 | 49 | $^1$H NMR (500 MHz, DMSO-d$_6$) δ 10.59 (br s, 0.4H), 9.89 (br s, 0.6H), 9.18-9.17 (m, 0.4H), 8.98-8.98 (m, 0.6H), 7.77-7.74 (m, 1H), 7.62-7.61 (m, 1H), 7.16-7.12 (m, 1H), 5.50-5.00 (br s, 4H), 4.57-4.53 (m, 0.6H), 4.34-4.33 (m, 0.4H), 4.04-4.03 (m, 1H), 3.95 (m, 1H), 3.86 (m, 1H), 3.74-3.72 (m, 2H), 3.60-3.51 (m, 4H), 2.83-2.81 (m, 3H), 2.68-2.62 (m, 2H), 2.27-2.25 (m, 1H), 2.12-2.10 (m, 2H), 1.80-1.78 (m, 3H), 1.53-1.47 (m, 2H), 1.36-1.34 (m, 3H); MS (ESI +) m/z 399 (M + H). | 10.9 |
| 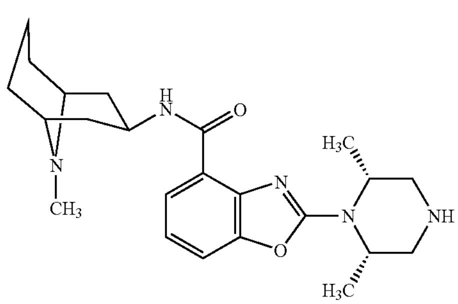 | 50 | $^1$H NMR (500 MHz, DMSO-d$_6$) δ 10.70 (s, 0.4H), 10.49 (s, 1H), 9.99 (s, 0.6H), 9.80-9.60 (m, 1H), 9.07 (d, J = 5.5 Hz, 0.5H), 8.98 (d, J = 6.0 Hz, 0.5H), 7.78 (dd, J = 11.0, 8.0 Hz, 1H), 7.67 (d, J = 8.0 Hz, 1H), 7.17 (app. t, J = 8.0 Hz, 1H), 4.60-4.55 (m, 3H), 4.54-4.49 (m, 1.5H), 4.38-4.28 (m, 0.5H), 3.66-3.58 (m, 1.2H), 3.56-3.48 (m, 0.8H), 3.38-3.22 (m, 4H), 2.88-2.78 (m, 3H), 2.74-2.64 (m, 2H), 2.38-2.18 (m, 1.2H), 2.16-2.06 (m, 1.8H), 1.82-1.72 (m, 3H), 1.60-1.46 (m, 6H); MS (ESI +) m/z 412 (M + H). | 13.6 |

-continued

| Structure | Ex. | NMR and MS data | 5-HT₃ K$_i$ (nM) |
|---|---|---|---|
| 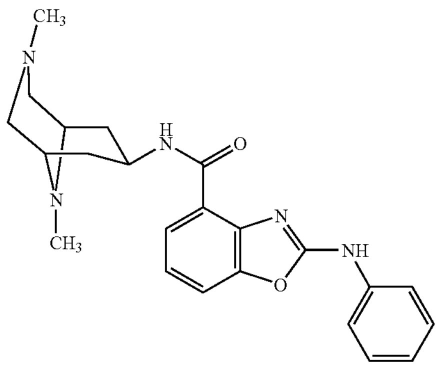 | 51 | ¹H NMR (500 MHz, DMSO-d₆) δ 11.0-10.71 (m, 1H), 10.39 (br s, 0.8H), 10.01-9.73 (m, 0.8H), 7.89-7.56 (m, 4H), 7.56-7.36 (m, 2H), 7.26-7.17 (m, 1H), 7.17-6.98 (m, 1H), 4.62-4.33 (m, 1H), 3.60-3.35 (m, 2.5H), 3.32-3.10 (m, 1H), 2.98-2.73 (m, 5.5H), 2.73-2.62 (m, 1.6H), 2.62-2.53 (m, 2H), 2.09-1.59 (m, 4.8H); MS (ESI +) m/z 406 (M + H). endo | 212 |
| 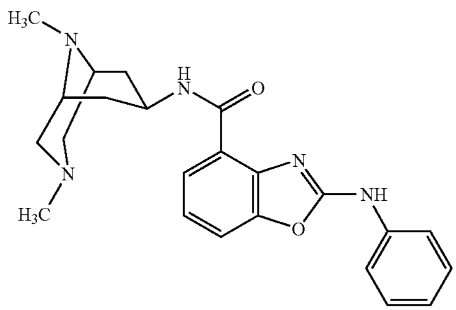 | 52 | ¹H NMR (500 MHz, DMSO-d₆) δ 11.30-11.00 (m, 1H), 10.68 (br s, 0.5H), 8.81 (br s, 0.5H), 8.97-8.66 (m, 1H), 7.93-7.63 (m, 4H), 7.62-7.37 (m, 2H), 7.34-7.19 (m, 1H), 7.19-7.02 (m, 1H), 5.47-5.10 (m, 1H), 3.85-3.62 (m, 3H), 3.27-3.03 (m, 2H), 3.03-2.86 (m, 4H), 2.86-2.61 (m, 2H), 2.43-1.93 (m, 6H); MS (ESI +) m/z 406 (M + H). exo | 27.6 |
| 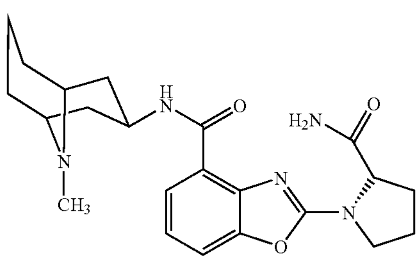 | 53 | ¹H NMR (500 MHz, DMSO-d₆) δ 10.15 (br s, 0.3H), 9.40 (br s, 0.7H), 9.14 (br s, 1H), 7.76-7.73 (m, 1H), 7.69 (s, 1H), 7.63 (d, J = 6.3 Hz, 1H), 7.22 (br s, 1H), 7.14-7.09 (m, 1H), 4.54-4.32 (m, 4H), 3.83-3.54 (m, 4H), 2.84-2.82 (m, 3H), 2.73-2.52 (m, 2H), 2.38-2.30 (m, 1H), 2.12-1.95 (m, 5H), 1.80-1.68 (m, 2H), 1.55-1.45 (m, 2H); MS (ESI +) m/z 412 (M + H). | 212 |
| 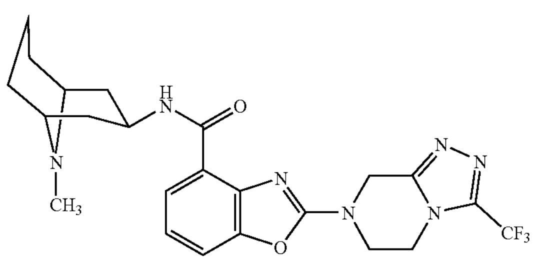 | 54 | ¹H NMR (500 MHz, DMSO-d₆) δ 10.32 (s, 0.4H), 9.63 (s, 0.6H), 9.07 (d, J = 6.0 Hz, 0.4H), 8.88 (d, J = 6.0 Hz, 0.6H), 7.78 (dd, J = 8.0, 1.0 Hz, 1H), 7.70 (d, J = 8.0 Hz, 1H), 7.24-7.18 (m, 1H) 5.20 (d, J = 12.0 Hz, 2H), 4.58-4.50 (m, 0.6H), 4.40-4.34 (m, 2.4H), 4.25-4.20 (m, 2H), 3.64 (d, J = 9.0 Hz, 2H), 2.85-2.84 (m, 3H), 2.73-2.60 (m, 2H), 2.32-2.22 (m, 1H), 2.20-2.08 (m, 2H), 1.90-1.78 (m, 2H), 1.60-1.46 (m, 2H); MS (ESI +) m/z 490 (M + H). | 118 |
| 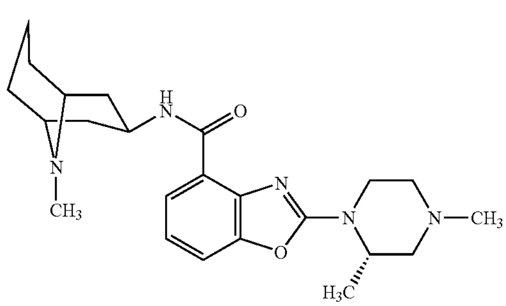 | 55 | ¹H NMR (500 MHz, DMSO-d₆) δ 11.02-10.84 (m, 0.7H), 10.29-10.17 (m, 0.3H), 9.61-9.46 (m, 0.5H), 9.10-9.00 (m, 0.4H), 8.90-8.80 (m, 0.6H), 7.84-7.71 (m, 1H), 7.71-7.58 (m, 1H), 7.26-7.07 (m, 1H), 4.79-4.65 (m, 1H), 4.59-4.44 (m, 0.7H), 4.39-4.20 (m, 1.5H), 3.79-3.59 (m, 2.5H), 3.59-3.45 (m, 3H), 3.26-3.09 (m, 1.2H), 2.88-2.78 (m, 6.3H), 2.75-2.57 (m, 2.5H), 2.29-2.15 (m, 1.5H), 2.14-2.01 (m, 2H), 1.86-1.68 (m, 3H), 1.59-1.40 (m, 4H); MS (ESI +) m/z 412 M + H). | 28.8 |

| Structure | Ex. | NMR and MS data | 5-HT$_3$ K$_i$ (nM) |
|---|---|---|---|
| 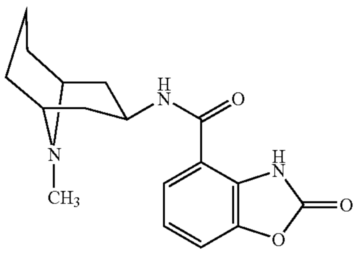 | 56 | $^1$H NMR (500 MHz, DMSO-d$_6$) δ 11.7-8.47 (br m, 2.5H), 7.70 (d, J = 8.1 Hz, 1H), 7.44 (d, J = 7.8 Hz, 1H), 7.16 (t, J = 8.0 Hz, 1H), 4.73-4.12 (br m, 1H), 3.60 (d, J = 9.0 Hz, 2H), 3.17 (s, 1H), 2.81 (s, 3H), 2.42 (br s, 2H), 2.25-2.07 (m, 3H), 1.87 (t, J = 11.9 Hz, 2H), 1.70-1.35 (m, 3H); MS (ESI +) m/z 316 (M + H). | 72 |
| 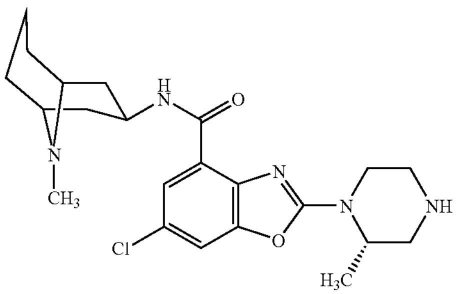 | 57 | $^1$H NMR (500 MHz, DMSO-d$_6$) δ 10.43-10.14 (m, 0.3H), 9.86-9.63 (m, 0.7H), 9.60-9.48 (m, 0.5H), 9.48-9.16 (m, 0.8H), 9.07-8.94 (m, 0.4H), 8.85-8.62 (m, 0.7H), 7.94-7.81 (s, 1H), 7.80-7.53 (s, 1H), 4.71-4.56 (m, 1H), 4.56-4.43 (m, 0.7H), 4.40-4.37 (m, 0.5H), 4.27-4.02 (m, 1H), 3.76-3.58 (m, 2.5H), 3.58-3.45 (m, 1H), 3.21-3.03 (m, 1.4H), 2.95-2.76 (m, 3.4H), 2.76-2.56 (m, 2.7H), 2.32-1.98 (m, 3.4H), 1.98-1.64 (m, 3H), 1.63-1.34 (m, 6H); MS (ESI +) m/z 432 (M + H). | 11.4 |
| 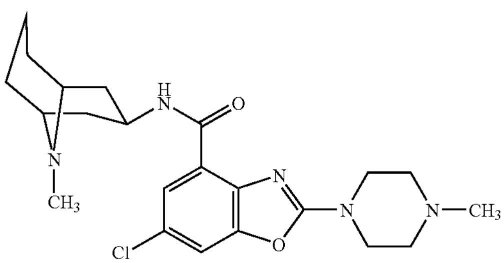 | 58 | $^1$H NMR (500 MHz, DMSO-d$_6$) δ 10.54-10.34 (m, 0.3H), 9.79-9.53 (m, 0.6H), 9.11-8.94 m, 0.4H), 8.87-8.62 (m, 0.6H), 7.95-7.81 (s, 1H), 7.80-7.67 (s, 1H), 4.66-4.44 (m, 0.6H), 4.44-4.10 (m, 2.4H), 3.83-3.49 (m, 6H), 3.28-3.09 (m, 2.5H), 2.91-2.75 (m, 6H), 2.74-2.54 (m, 2.5H), 2.35-2.17 (m, 1H), 2.17-1.97 (m, 2H), 1.87-1.71 (m, 3H), 1.60-1.41 (m, 2H); MS (ESI +) m/z 432 (M + H). | 11.9 |
| 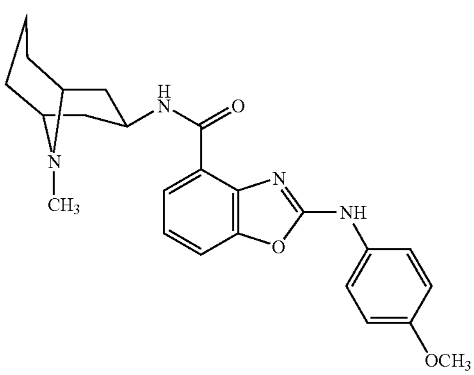 | 59 | $^1$H NMR (500 MHz, DMSO-d$_6$) δ 11.01-10.91 (m, 0.7H), 10.91-10.84 (m, 0.2H), 10.34-10.08 (m, 0.2H), 9.60-9.40 (m, 0.7H), 9.16-9.00 (m, 1H), 7.86-7.50 (m, 4H), 7.31 7.16 (m, 1H), 7.06-6.85 (m, 2H), 4.72-4.49 (m, 0.7H), 4.48-4.26 (m, 0.2H), 3.87-3.72 (m, 3H), 3.72-3.52 (m, 2H), 2.94-2.78 (m, 3H), 2.78-2.59 (m, 1.5H), 2.23-1.89 (m, 3H), 1.89-1.32 (m, 5H); MS (ESI +) m/z 421 (M + H). | 7.6 |
| 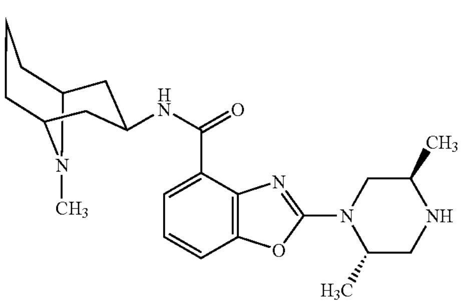 | 60 | $^1$H NMR (500 MHz, DMSO-d$_6$) δ 10.63 (s, 0.4H), 9.87 (br s, 1.6H), 9.67 (d, J = 10.0 Hz, 1H), 9.07 (d, J = 6.5 Hz, 0.4H), 8.90 (d, J = 6.5 Hz, 0.6H) 7.79-7.75 (m, 1H), 7.65 (d, J = 8.5 Hz, 1H), 7.19-7.16 (m, 1H), 4.57-4.50 (m, 1.6H), 4.34-4.32 (m, 0.4H), 3.91-3.79 (m, 2H), 3.70-3.62 (m, 2H), 3.53-3.45 (m, 2H), 3.16-3.13 (m, 1H), 2.83 (t, J = 5.2 Hz, 3H), 2.73-2.61 (m, 2H), 2.30-2.23 (m, 1H), 2.18-2.06 (m, 2H), 1.79-1.68 (m, 3H), 1.56-1.42 (m, 5H), 1.37-1.34 (m, 3H). MS (ESI +) m/z 412 (M + H). | 10.5 |

-continued

| Structure | Ex. | NMR and MS data | 5-HT$_3$ K$_i$ (nM) |
|---|---|---|---|
| 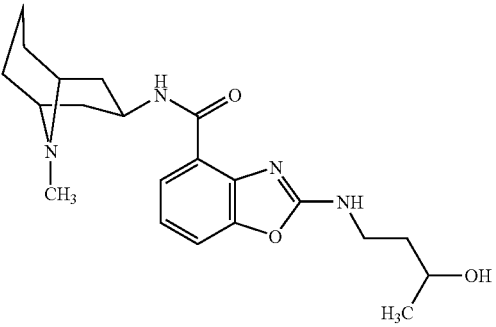 | 61 | $^1$H NMR (500 MHz, DMSO-d$_6$) δ 10.25-10.03 (m, 0.5H), 9.52-9.09 (m, 1H), 9.30-9.09 (m, 0.5H), 8.66-8.47 (m, 1H), 7.79-7.65 (m, 1H), 7.65-7.46 (m, 1H), 7.15-7.03 (m, 1H), 4.61-4.41 (m, 1H), 4.41-4.25 (m, 0.5H), 3.84-3.61 (m, 2H), 3.61-3.52 (m, 1H), 3.25-3.03 (m, 0.75H), 2.94-2.78 (m, 2.75H), 2.78-2.55 (m, 2H), 2.35-1.94 (m, 3H), 1.90-1.62 (m, 5H), 1.62-1.37 (m, 3H), 1.37-1.21 (m 0.5H), 1.19-0.99 (m, 3H), 0.99-0.82 (m, 0.5H); MS (ESI +) m/z 387 (M + H). | 19.9 |
| 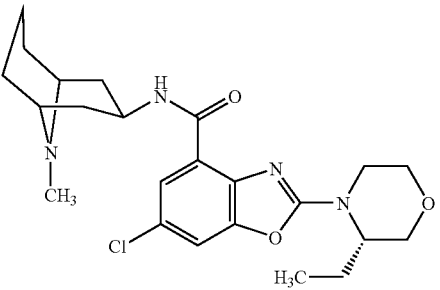 | 62 | $^1$H NMR (500 MHz, DMSO-d$_6$) δ 10.43 (br s, 0.35H), 9.65 (br s, 0.65H), 9.05-9.04 (m, 0.35H), 8.85-8.83 (m, 0.65H), 7.81 (apt s, 1H), 7.71-7.64 (m, 1H), 4.58-4.50 (m, 0.7H), 4.35-4.32 (m, 0.3H), 4.03-4.00 (m, 1H), 3.95-3.80 (m, 3H), 3.72-3.44 (m, 5H), 2.83-2.82 (m, 3H), 2.71-2.54 (m, 2H), 2.24-2.17 (m, 1H), 2.13-2.01 (m, 2H), 1.93-1.74 (m, 5H), 1.58-1.44 (m, 2H), 0.94-0.86 (m, 3H); MS (ESI +) m/z 447 (M + H). | 6.3 |
| 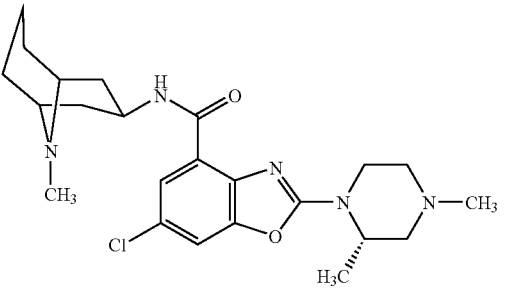 | 63 | $^1$H NMR (500 MHz, DMSO-d$_6$) δ 9.58-8.62 (m, 1H), 7.94-7.77 (m, 1H), 7.77-7.58 (m, 1H), 4.81-4.58 (m, 0.3H), 4.56-4.06 (m, 2H), 4.06-3.83 (m, 0.8H), 3.83-3.59 (m, 1.5H), 3.55-3.39 (m, 2H), 2.92-2.79 (m, 4.5H), 2.79-2.56 (m, 3.5H), 2.40-1.93 (m, 7.3H), 1.86-1.65 (m, 2.8H), 1.61-1.17 (m, 5.5H); MS (ESI +) m/z 446 (M + H). | 16.1 |
| 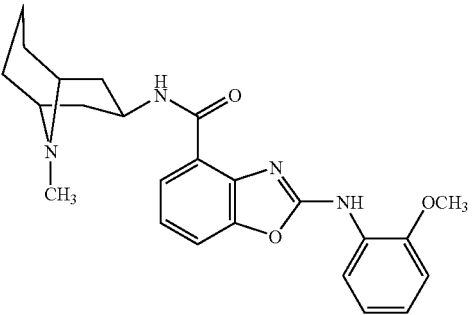 | 64 | $^1$H NMR (500 MHz, DMSO-d$_6$) δ 10.32-10.24 (m, 1H), 10.09-9.89 (m, 0.25H), 9.38-9.20 (m, 0.75H), 9.20-9.10 (m, 0.25H), 9.10-8.91 (m, 0.75H), 8.09-7.95 (m, 0.75H), 7.87-7.59 (m, 1.25H), 7.72-7.60 (m, 1H), 7.31-7.08 (m, 3H), 7.08-6.86 (m, 1H), 4.71-4.45 (m, 0.75H), 4.41-4.22 (m, 0.25H), 3.97-3.79 (m, 3H), 3.76-3.59 (m, 1.5H), 2.92-2.79 (m, 3H), 2.74-2.53 (m, 2H), 2.20-1.78 (m, 3H), 1.78-1.19 (m, 5H); MS (ESI +)m/z 421 (M + H). | 16.2 |
| 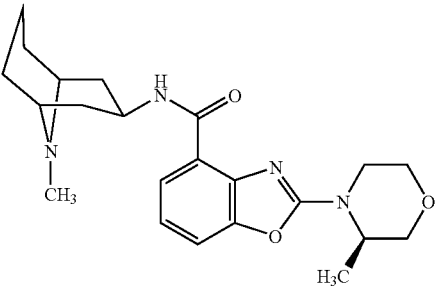 | 65 | $^1$H NMR (500 MHz, DMSO-d$_6$) δ 10.59 (br s, 0.4H), 9.89 (br s, 0.6H), 9.18-9.17 (m, 0.4H), 8.98-8.98 (m, 0.6H), 7.77-7.74 (m, 1H), 7.62-7.61 (m, 1H), 7.16-7.12 (m, 1H), 4.60-4.20 (m, 2H), 3.95 (m, 1H), 3.74-3.72 (m, 1H), 3.56-3.46 (m, 4H), 2.83-2.81 (m, 3H), 2.68-2.62 (m, 2H), 2.27-2.25 (m, 2H), 2.12-2.10 (m, 2H), 1.80-1.78 (m, 3H), 1.53-1.47 (m, 3H), 1.36-1.34 (m, 3H); MS (ESI +) m/z 399 (M + H). | 89 |

| Structure | Ex. | NMR and MS data | 5-HT$_3$ K$_i$ (nM) |
|---|---|---|---|
| 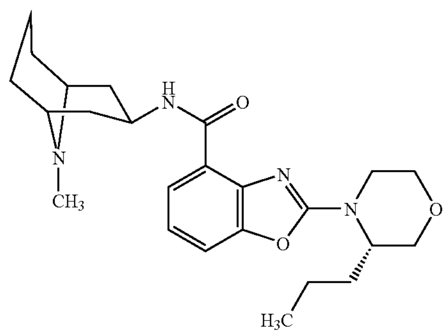 | 66 | $^1$H NMR (500 MHz, DMSO-d$_6$) δ 10.66 (br s, 0.35H), 9.81 (br s, 0.65H), 9.14-9.12 (m, 0.35H), 8.92-8.90 (m, 0.65H), 7.77-7.74 (m, 1H), 7.61-7.59 (m, 1H), 7.14-7.11 (m, 1H), 4.61-4.53 (m, 0.65H), 4.36-4.32 (m, 0.35H), 4.17-4.14 (m, 1H), 3.94-3.89 (m, 2H), 3.85-3.81 (m, 1H), 3.69-3.47 (m, 5H), 2.83-2.78 (m, 3H), 2.73-2.61 (m, 2H), 2.32-2.17 (m, 1H), 2.14-2.02 (m, 2H), 1.92-1.70 (m, 5H), 1.55-1.22 (m, 4H), 0.96-0.89 (m, 3H); MS (ESI +) m/z 427 (M + H). | 4.1 |
| 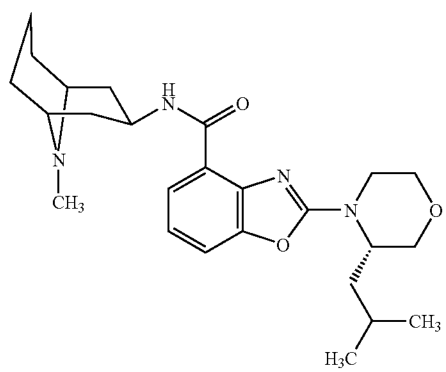 | 67 | $^1$H NMR (500 MHz, DMSO-d$_6$) δ 10.67 (br s, 0.3H), 9.73 (br s, 0.7H), 9.10-9.09 (m, 0.3H), 8.82-8.81 (m, 0.7H), 7.77-7.72 (m, 1H), 7.61-7.59 (m, 1H), 7.15-7.11 (m, 1H), 4.63-4.60 (m, 0.7H), 4.37-4.35 (m, 0.3H), 4.27-4.20 (m, 1H), 3.94-3.90 (m, 2H), 3.83-3.78 (m, 1H), 3.71-3.64 (m, 2H), 3.60-3.49 (m, 3H), 2.87-2.77 (m, 3H), 2.74-2.54 (m, 2H), 2.36-2.17 (m, 1H), 2.13-2.00 (m, 2H), 1.86-1.37 (m, 8H), 1.02-0.89 (m, 6H); (ESI +) m/z 441 (M + H). | 3.9 |
| 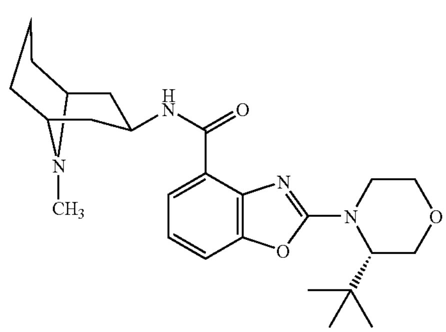 | 68 | $^1$H NMR (500 MHz, DMSO-d$_6$) δ 10.76 (br s, 0.35H), 9.87 (br s, 0.65H), 9.13-9.12 (m, 0.35H), 8.98-8.97 (m, 0.65H), 7.79-7.70 (m, 1H), 7.63-7.59 (m, 1H), 7.16-7.09 (m, 1H), 4.61-4.59 (m, 0.65H), 4.38-4.33 (m, 0.35H), 4.25-4.14 (m, 1H), 4.13-4.02 (m, 1H), 3.95-3.77 (m, 2H), 3.72-3.36 (m, 5H), 2.87-2.78 (m, 3H), 2.77-2.58 (m, 2H), 2.41-1.95 (m 3H), 1.77-1.70 (m, 3H), 1.56-1.36 (m, 2H), 1.09-1.08 (m, 9H); MS (ESI +) m/z 441 (M + H). | 2.0 |
| 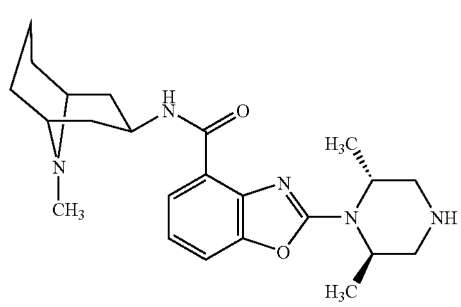 | 69 | $^1$H NMR (500 MHz, DMSO-d$_6$) δ 10.79 (br s, 0.2H), 10.20-9.95 (m, 2H), 9.05-8.90 (m, 0.8H), 7.84-7.77 (m, 1H), 7.72-7.65 (m, 1H), 7.15-7.05 (m, 1H), 6.80 (br s, 1H) 4.60-4.45 (m, 0.5H), 4.41-4.32 (m, 2H), 3.60-3.40 (m, 4.5H), 3.39-3.17 (m, 2H), 2.82 (s, 3H), 2.73-2.62 (m, 2H), 2.28-2.22 (m, 0.6H), 2.20-2.00 (m, 2H), 1.80-1.62 (m, 2.4H), 1.60-1.20 (m, 8H); MS (ESI +) m/z 412 (M + H). | 32.7 |

-continued

| Structure | Ex. | NMR and MS data | 5-HT$_3$ K$_i$ (nM) |
|---|---|---|---|
| 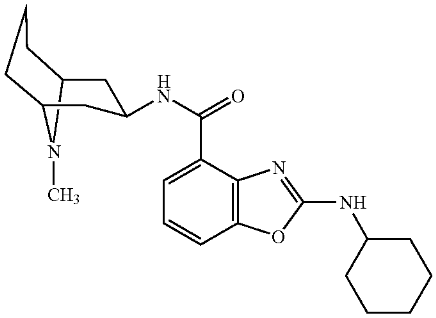 | 70 | $^1$H NMR (500 MHz, DMSO-d$_6$) δ 10.56 (s, 0.4H), 9.79 (s, 0.6H), 9.25 (d, J = 5.5 Hz, 0.4H), 9.21 (d, J = 5.5 Hz, 0.6H), 8.60-8.53 (m, 1H), 7.73-7.68 (m, 1H), 7.55-7.50 (m, 1H), 7.07 (app t, J = 8.0 Hz, 1H), 4.54-4.50 (m, 1H), 3.60-3.52 (m, 3H), 2.90-2.80 (m, 3H), 2.75-2.65 (m, 2H), 2.27 (s, 1H), 2.22-1.97 (m, 4H), 1.75-1.60 (m, 5H), 1.57-1.46 (m, 4H), 1.37-1.26 (m, 4H; MS (ESI +) m/z 397 (M + H). | 19.2 |
| 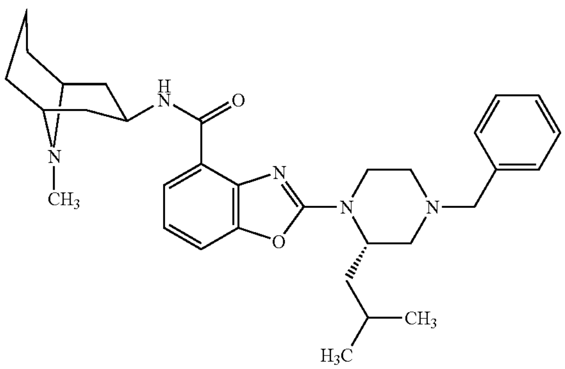 | 71 | $^1$H NMR (500 MHz, DMSO-d$_6$) δ 10.40 (s, 0.3H), 9.52 (s, 0.7H), 8.96 (s, 0.4H), 8.61 (s, 0.6H), 7.78 (d, J = 7.5 Hz, 1H), 7.69 (br s, 2H), 7.63 (d, J = 7.5 Hz, 1H), 7.44 (br.s, 3H), 7.36 (s, 1H), 7.18-7.15 (m, 1H), 4.71-4.52 (m, 1H), 4.50-4.38 (m, 1H), 4.34-4.27 (m, 2H), 3.84-3.70 (m, 1H), 3.65 (d, J = 9.0 Hz, 2H), 3.54 (br.s, 1H), 3.32-3.30 (m, 1H), 3.25 3.11 (m, 1H), 2.84-2.82 (m, 3H), 2.75-2.62 (m, 1H), 2.60-2.52 (m, 2H), 2.30-2.14 (m, 1H), 2.11-2.06 (m, 3H), 1.91-1.80 (m, 1H), 1.72-1.62 (m, 3H), 1.53-1.35 (m, 3H), 1.30 1.23 (m, 1H), 0.95-0.89 (m, 6H); (ESI +) m/z 530 (M + H). | 48.6 |
| 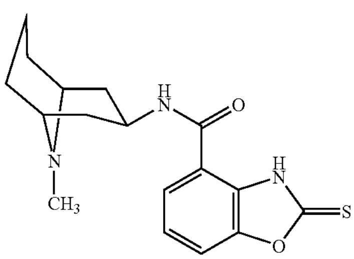 | 72 | $^1$H NMR (500 MHz, DMSO-d$_6$) δ 9.59-7.91 (br m, 2H), 7.58-7.49 (m, 1H), 7.26 (d, J = 7.6 Hz, 1H), 6.95 (t, J = 7.8 Hz, 1H), 5.76-4.52 (br m, 1H), 3.62 (br s, 2H), 3.32 (br s, 1H), 2.82 (br s, 3H), 2.57 (br s, 2H), 2.09 (br s, 3H), 1.72 (br s, 2H), 1.55 (br s, 3H); MS (ESI +) m/z 332 (M + H). | 30.8 |
| 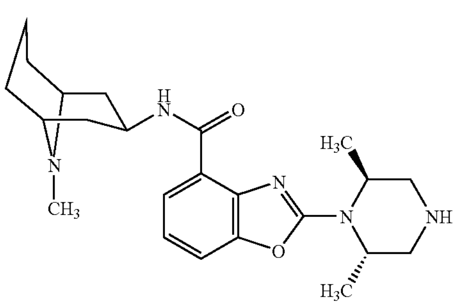 | 73 | $^1$H NMR (500 MHz, DMSO-d$_6$) δ 10.69 (br s, 0.2H), 10.00-9.70 (m, 2H), 9.10-8.90 (m, 0.8H), 7.84-7.76 (m, 1H), 7.70-7.68 (m, 1H), 7.20-7.14 (m, 1H), 5.20 (br s, 1H) 4.60-4.45 (m, 0.6H), 4.41-4.32 (m, 2.4H), 3.66-3.42 (m, 4H), 3.32-3.20 (m, 2H), 2.85 (s, 3H), 2.80-2.60 (m, 2H), 2.30-2.00 (m, 3H), 1.80-1.62 (m, 2H), 1.60-1.20 (m, 9H); MS (ESI +) m/z 412 (M + H). | 2.2 |

| Structure | Ex. | NMR and MS data | 5-HT$_3$ K$_i$ (nM) |
|---|---|---|---|
| 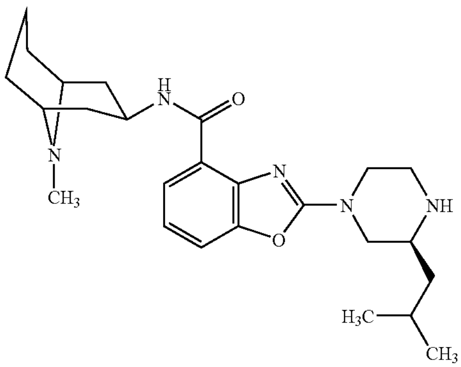 | 74 | $^1$H NMR (500 MHz, DMSO-d$_6$) δ 10.35 (s, 0.4H) 9.85-9.78 (m, 1H), 9.61-9.56 (m, 1.6H), 9.05 (d, J = 5.8 Hz, 0.4H), 8.85 (d, J = 7.1 Hz, 0.6H), 7.80-7.77 (m, 1H), 7.67-7.64 (m, 1H), 7.21-7.15 (m, 1H), 4.63-4.56 (m, 0.7H), 4.40-4.56 (m, 1H), 4.23 (t, J = 9.2 Hz, 1.3H), 3.73-3.64 (m, 3H), 3.56 (br. s, 1H), 3.52-3.35 (m, 9H), 3.27-3.23 (m, 1H), 2.84-2.80 (m, 3H), 2.73-2.63 (m, 1H), 2.62-2.58 (m, 2H), 2.28-2.22 (m, 1H), 1.87-1.72 (m, 4H), 1.61-1.51 (m, 3H), 1.45 (t, J = 12.0 Hz, 2H), 0.95-0.93 (m, 6H); (ESI +) m/z 440 (M + H). | 72.9 |
| 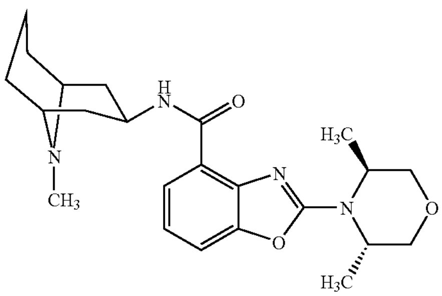 | 75 | $^1$H NMR (500 MHz, CD$_3$OD) δ 7.89-7.84 (m, 1H), 7.57-7.55 (m, 1H), 7.23-7.20 (m, 1H), 4.60-4.45 (m, 1H), 4.19-4.15 (m, 2H), 3.97-3.93 (m, 2H), 3.76-3.65 (m, 2H), 3.64-3.60 (m, 2H), 3.02 (s, 0.75H), 2.98 (s, 2.25H), 2.90-2.70 (m, 2H), 2.30-2.10 (m, 3H), 1.97-1.86 (m, 2.5H), 1.73-1.60 (m, 2.5H), 1.49-1.46 (m, 6H); MS (ESI +) m/z 413 (M + H). | 0.59 |
| 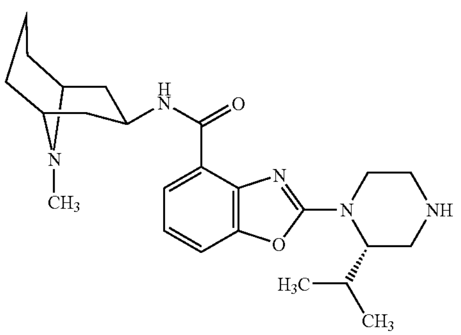 | 76 | $^1$H NMR (500 MHz, DMSO-d$_6$) δ 10.50 (s, 0.3H), 9.75 (s, 0.7H), 9.76 (d, J = 5.0 Hz, 1H) 9.53-9.43 (m, 1H), 9.04 (d, J = 5.5 Hz, 0.4H), 8.91 (d, J = 5.5 Hz, 0.6H), 7.80-7.75 (m, 1H), 7.64-7.62 (m, 1H), 7.18-7.14 (m, 1H), 4.57-4.52 (m, 0.6H), 4.40-4.22 (m, 1.4H), 4.08 (dd, J = 10.0, 3.0 Hz, 0.7 H), 4.04 (dd, J = 10.0, 3.0 Hz, 0.3 H), 3.81-3.61 (m, 5H), 3.66-3.48 (m, 3H), 3.34-3.22 (m, 2H), 3.20-3.08 (m, 1H), 2.87-2.82 (m, 3H), 2.75-2.62 (m, 3H), 2.25-2.21 (m, 1H), 2.18-2.14 (m, 1H), 1.81-1.72 (m, 2H), 1.55-1.45 (m, 2H), 1.07-1.03 (m, 3H), 0.89-0.86 (m, 3H); MS (ESI +) m/z 426 (M + H). | 9.8 |
| 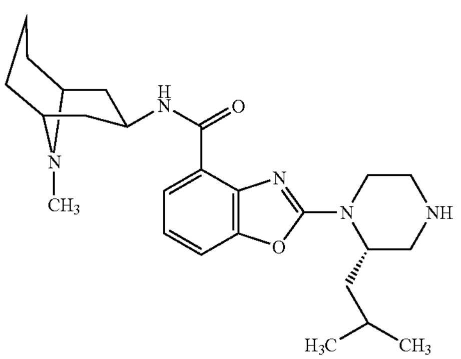 | 77 | $^1$H NMR (500 MHz, DMSO-d$_6$) δ 10.56 (s, 0.4H) 9.82 (d, J = 7.5 Hz, 1H), 9.68 (m, 0.7H), 9.42 (d, J = 7.5 Hz, 1H), 9.00 (d, J = 6.0 Hz, 0.3H), 8.75 (d, J = 7.0 Hz, 0.6H), 7.79-7.77 (m, 1H), 7.65-7.63 (m, 1H), 7.17 (t, J = 8.0 Hz, 1H), 4.64-4.61 (m, 1H), 4.55 (s, 0.5H), 4.35 (s, 0.5H), 4.24-4.19 (m, 1H), 3.70-3.53 (m, 3H), 3.40-3.28 (m, 2H), 3.18-3.05 (m, 1H), 2.80 (s, 3H), 2.75-2.65 (m, 1H), 2.62-2.55 (m, 2H), 2.35-2.20 (m, 1H), 2.15-1.98 (m, 2H), 1.97-1.78 (m, 2H), 1.75-1.63 (m, 2H), 1.60-1.50 (m, 2H), 1.56 (t, J = 13.5 Hz, 2H), 1.00-0.86 (m, 6H); MS (ESI +) m/z 440 (M + H). | 6.4 |

-continued

| Structure | Ex. | NMR and MS data | 5-HT₃ K$_i$ (nM) |
|---|---|---|---|
| 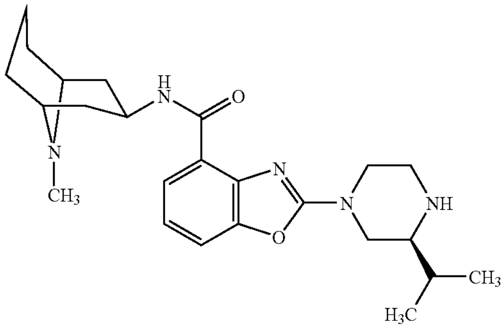 | 78 | $^1$H NMR (500 MHz, DMSO-d$_6$) δ 10.30 (s, 0.3H) 9.70-9.52 (m, 1H), 9.44 (br s, 0.7H), 9.35 (s, 1H), 9.03 (d, J = 6.0 Hz, 0.3H), 8.87 (d, J = 6.0 Hz, 0.7H), 7.80-7.77 (m, 1H), 7.70-7.64 (m, 1H), 7.21-7.17 (m, 1H), 4.64-4.56 (m, 0.7H), 4.42-4.37 (m, 1H), 4.26 (d, J = 12.5 Hz, 1.3H), 3.72-3.62 (m, 2H), 3.51 (br. s, 1H), 3.48-3.41 (m, 2H), 3.40-3.25 (m, 2H), 2.88 (s, 3H), 2.72-2.64 (m, 1H), 2.62-2.54 (m, 1H), 2.28-2.18 (m, 1H), 2.10-1.97 (m, 3H), 1.82-1.65 (m, 2H), 1.58-1.49 (m, 1H), 1.42 (t, J = 15.0 Hz, 2H), 1.21-0.95 (m, 6H); MS (ESI +) m/z 426 (M + H). | 25.8 |
| 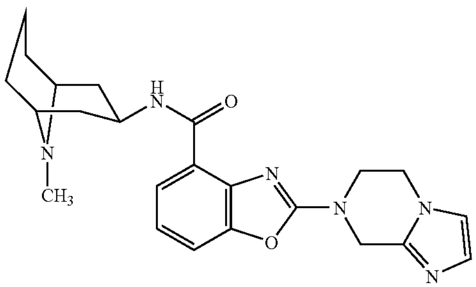 | 79 | $^1$H NMR (500 MHz, DMSO-d$_6$) δ 10.40 (s, 0.4H), 9.60 (s, 0 6H), 9.08 (d, J = 5.5 Hz, 0.4H), 8.86 (d, J = 5.5 Hz, 0.6H), 7.85-7.78 (m, 1H), 7.75-7.66 (m, 3H), 7.26-7.20 (m, 1H), 5.25-5.15 (m, 2H), 4.62-4.50 (m, 0.7H), 4.40-4.30 (m, 2.3H), 4.25-4.15 (m, 2H), 3.72-3.64 (m, 1.5H), 3.60-3.48 (m, 1H), 2.85 (s, 3H), 2.80-2.62 (m, 2.5H), 2.32-2.24 (m, 1H), 2.15-2.05 (m, 2H), 1.88-1.80 (m, 2.7H), 1.64 1.54 (m, 2.3H); MS (ESI +) m/z 421 (M + H). | 29.3 |
| 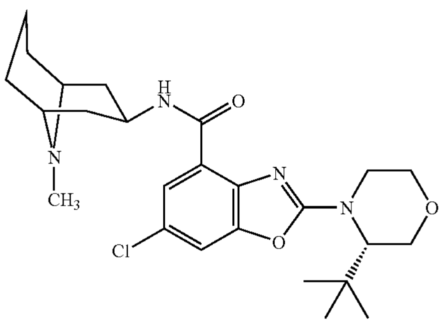 | 80 | $^1$H NMR (500 MHz, DMSO-d$_6$) δ 10.68-9.74 (br m, 1H), 9.02-8.86 (br m, 1H), 7.82-7.80 (m, 1H), 7.69-7.67 (m, 1H), 4.59 (br s, 1H), 4.18 (d, J = 12.4 Hz, 2H), 4.07 (br s, 1H), 3.95 (d, J = 9.3 Hz, 1H), 3.72-3.55 (m, 5H), 2.82 (d, J = 4.3 Hz, 3H), 2.73-2.59 (m, 2H), 2.29-2.23 (m, 1H), 2.15-2.05 (m, 2H), 1.80-1.65 (m, 3H), 1.55-1.53 (m, 1H), 1.47-1.40 (m, 1H), 1.31-1.18 (m, 1H), 1.10-1.07 (m, 8H); MS (ESI +) m/z 475 (M + H). | 29.4 |
| 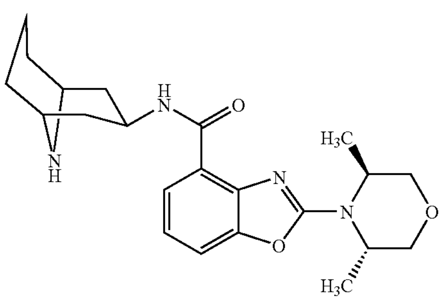 | 81 | $^1$H NMR (500 MHz, CD$_3$OD) δ 7.86-7.84 (m, 1H), 7.57-7.56 (m, 1H), 7.21 (app t, J = 8.0 Hz, 1H), 4.44-4.35 (m, 1H), 4.19-4.16 (m, 2H), 3.96-3.90 (m, 4H), 3.64-3.60 (m, 2H), 2.69-2.61 (m, 2H), 2.17-2.06 (m, 1H), 1.96-1.90 (m, 2H), 1.79-1.67 (m, 5H), 1.49 (d, J = 6.5 Hz, 6H); MS (ESI +) m/z 399 (M + H). | 16.8 |
| 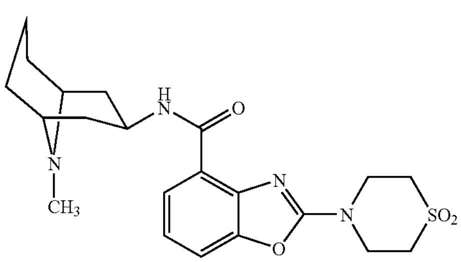 | 82 | $^1$H NMR (500 MHz, CD$_3$OD) δ 7.88-7.84 (m, 1H), 7.58-7.56 (m, 1H), 7.23-7.19 (m, 1H), 4.57-4.51 (m, 0.7H), 4.47-4.43 (m, 0.3H), 4.31-4.29 (m, 4H), 3.74-3.67 (m, 2H), 3.36-3.32 (m, 4H), 3.00-2.98 (m, 3H), 2.88-2.80 (m, 0.6H), 2.77-2.70 (m, 1.4H), 2.43-2.14 (m, 3H), 2.03-1.93 (m, 2.5H), 1.70-1.62 (m, 2.5H); MS (ESI +) m/z 433 (M + H). | 132 |

-continued

| Structure | Ex. | NMR and MS data | 5-HT$_3$ K$_i$ (nM) |
|---|---|---|---|
| 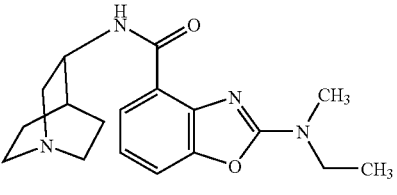 | 83 | $^1$H NMR (500 MHz, DMSO-d$_6$) δ 10.39 (br s, 1H), 9.52 (d, J = 6.6 Hz, 1H), 7.73-7.71 (m, 1H), 7.61-7.60 (m, 1H), 7.11 (t, J = 7.9 Hz, 1H), 4.37 (br s, 1H), 3.78-3.70 (m, 1H), 3.65-3.60 (m, 2H), 3.29 (t, J = 8.1 Hz, 2H), 3.23 (t, J = 8.1 Hz, 2H), 3.20 (s, 3H), 3.12-3.07 (m, 1H), 2.25-2.23 (m, 1H), 2.18-2.06 (m, 1H), 1.97-1.90 (m, 3H), 1.23 (t, J = 7.1 Hz, 3H); MS (ESI +) m/z 329 (M + H). | 6.8 |
| 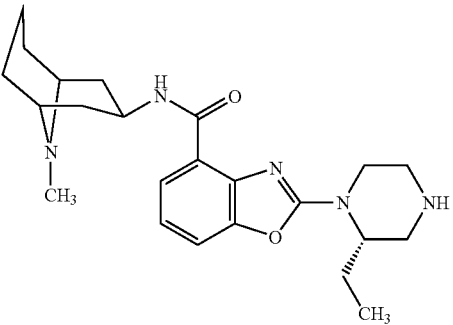 | 84 | $^1$H NMR (500 MHz, DMSO-d$_6$) δ 10.74 (s, 0.4H) 9.93-9.87 (m, 1.6H), 9.59-9.53 (m, 1H), 9.06 d, J = 5.5 Hz, 0.4 H), 8.88 (d, J = 5.5 Hz, 0.6H), 7.76 (t, J = 8.0 Hz, 1H), 7.64 (d, J = 7.5 Hz, 1H), 4.62-4.42 (m, 4H), 4.41-4.25 (m, 2H), 4.23 (t, J = 13.0 Hz, 1H), 3.70-3.48 (m 3H), 3.42-3.22 (m, 3H), 3.20-3.05 (m, 1H), 2.83-2.81 (m, 3H), 2.72-2.61 (m, 2H), 2.32-2.27 (m, 1H), 2.20-2.01 (m, 3H), 2.00-1.86 (m, 1H), 1.85-1.65 (m, 3H), 1.60-1.40 (m, 2H), 0.93-0.88 (m, 3H); MS (ESI +) m/z 412 (M + H). | 11.3 |
| 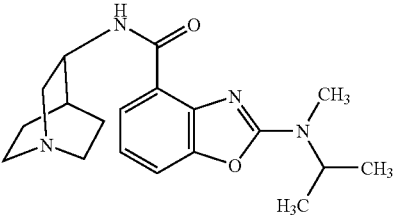 | 85 | $^1$H NMR (500 MHz, DMSO-d$_6$) δ 10.44 (br s, 1H), 9.52 (d, J = 6.6 Hz, 1H), 7.72-7.7 1 (m, 1H), 7.61-7.59 (m, 1H), 7.11 (t, J = 7.9 Hz, 1H), 4.52-4.43 (m, 1H), 4.40-4.32 (m, 1H), 3.77-3.72 (m, 1H), 3.29 (t, J = 8.0 Hz, 2H), 3.23 (t, J = 7.9 Hz, 2H), 3.08 (s, 3H), 2.25-2.23 (m, 1H), 2.16-2.08 (m, 1H), 1.97-1.94 (m, 3H), 1.28-1.26 (m, 6H), 0.99 (s, 1H); MS (ESI +) m/z 343 (M + H). | 28.9 |
| 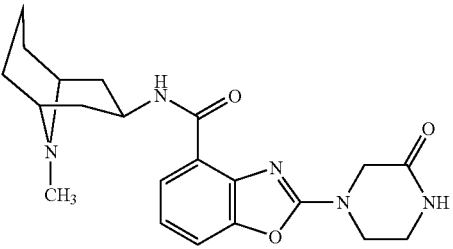 | 86 | $^1$H NMR (500 MHz, CD$_3$OD) δ 7.88-7.84 (m, 1H), 7.58-7.56 (m, 1H), 7.21-7.18 (m, 1H), 4.73-4.46 (m, 1H), 4.38 (s, 2H), 4.35 (s, 1H), 4.01-3.97 (m 2H) 3.74-3.71 (m 1.4H) 3.69-3.65 (m, 0.6H), 3.55-3.53 (m, 2H), 3.01 (s, 1H), 2.99 (s, 2H), 2.89-2.81 (m, 0.6H), 2.78-2.72 (m, 1.4H), 2.49-2.56 (m, 0.3H), 2.30-2.14 (m, 2.7H), 2.05-1.96 (m, 2.5H), 1.75-1.64 (m, 2.5H); MS (ESI +) m/z 398 (M + H). | 66.2 |
| 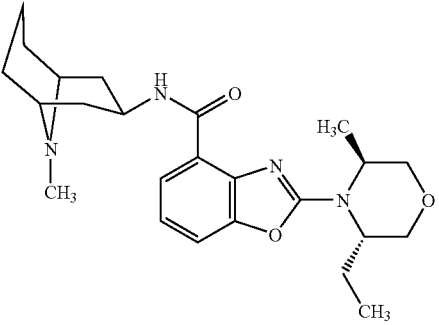 | 87 | $^1$H NMR (500 MHz, CD$_3$OD) δ 7.89-7.83 (m, 1H), 7.57-7.53 (m, 1H), 7.23-7.16 (m, 1H), 4.64-4.49 (m, 1H), 4.09-4.03 (m, 2H), 4.01-3.93 (m, 1H), 3.91-3.89 (m, 2H), 3.77-3.73 (m, 2H), 3.55-3.48 (m, 1H), 3.02 (s, 0.6H), 2.97 (s, 2.4H), 2.90-2.68 (m, 2H), 2.30-1.68 (m, 9H), 1.57-1.52 (m, 4H), 1.01-0.94 (m, 3H); MS (ESI +) m/z 427 (M + H). | 1.0 |

-continued

| Structure | Ex. | NMR and MS data | 5-HT₃ K$_i$ (nM) |
|---|---|---|---|
| (structure) | 88 | $^1$H NMR (500 MHz, CD$_3$OD) δ 9.96 (br s, 1H), 7.89 (dd, J = 8.0, 0.9 Hz, 1H), 7.52 (dd, J = 8.0, 0.9 Hz, 1H), 7.17 (appt t, J = 8.0 Hz, 1H), 4.44-4.30 (m, 1H), 4.24-4.19 (m, 3H), 4.12-4.05 (m, 1H), 4.02-3.93 (m, 3H), 3.60 (dd, J = 11.6, 5.4 Hz, 2H), 3.56-3.48 (m, 2H), 3.20-3.02 (m, 3H), 2.90-2.70 (m, 2H), 2.24-2.22 (m, 1H < 2.02-2.00 (m, 1H), 1.44 (dd, J = 6.5 Hz, 6H); MS (ESI +) m/z 415 (M + H). | 19.9 |
| (structure) | 89 | $^1$H NMR (500 MHz, DMSO-d$_6$) δ 10.61-9.92 (br m, 1H), 9.26-9.00 (br m, 1H), 7.76-7.73 (m, 1H), 7.60-7.58 (m, 1H), 7.14-7.10 (m, 1H), 4.52-4.33 (m, 1H), 3.92-3.86 (m, 2H), 3.61 (d, J = 8.5 Hz, 1H), 3.57-3.49 (m, 4H), 3.30 (s, 3H), 2.84-2.81 (m, 3H), 2.72-2.64 (m, 2H), 2.29 (d, J = 6.3 Hz, 1H), 2.18-2.08 (m, 2H), 1.99-1.95 (m, 2H), 1.84-1.75 (m, 3H), 1.64-1.57 (m, 2H), 1.53-1.48 (m, 2H); MS (ESI +) m/z 413 (M + H). | 36.9 |
| (structure) | 90 | $^1$H NMR (500 MHz, DMSO-d$_6$) δ 10.0 (br s, 1H), 9.30 (d, J = 6.4 Hz, 1H), 7.77 (dd, J = 8.0, 0.8 Hz, 1H), 7.68 (dd, J = 8.0, 0.7 Hz, 1H), 7.21 (appt t J = 8.0 Hz, 1H), 4.41-4.35 (m, 1H), 4.11-4.08 (m, 2H), 3.90 (dd, J = 11.6, 3.6 Hz, 2H), 3.80-3.74 (m, 1H), 3.56 (dd, J = 11.6, 5.4 Hz, 2H), 3.30-3.23 (m, 4H), 3.18-3.12 (m, 1H), 2.21-2.19 m, 1H), 2.12-2.05 (m, 1H), 1.97-1.88 (m, 3H), 1.38 (dd, J = 6.5 Hz, 6H); MS (ESI +) m/z 385 (M + H). | 6.8 |
| (structure) | 91 | $^1$H NMR (500 MHz, DMSO-d$_6$) δ 10.52-9.84 (br m, 1H), 9.24-8.99 (m, 1H), 7.76-7.73 (m, 1H), 7.60-7.58 (m, 1H), 7.14-7.11 (m, 1H), 4.52-4.33 (m, 1H), 3.95 (s, 3H), 3.79-3.76 (m, 4H), 3.61 (d, J = 8.5 Hz, 1H), 3.53-3.46 (m, 5H), 2.83 (t, J = 5.5 Hz, 2H), 2.73-2.63 (m, 2H), 2.28-2.26 (m, 1H), 2.15-2.08 (m, 1H), 1.83-1.77 (m, 6H), 1.54-1.47 (m, 2H); MS (ESI +) m/z 441 (M + H). | 14.5 |
| (structure) | 92 | $^1$H NMR (500 MHz, DMSO-d$_6$) δ 10.37-9.69 (br m, 1H), 9.24-8.99 (m, 1H), 7.79-7.76 (m, 1H), 7.66-7.64 (m, 1H), 7.18-7.14 (m, 1H), 4.53-4.34 (m, 1H), 4.05-4.01 (m, 4H), 3.62 (d, J = 8.5 Hz, 1H), 3.49 (br s, 1H), 3.32 (s, 1H), 2.83 (t, J = 4.4 Hz, 3H), 2.72-2.58 (m, 6H), 2.36-2.22 (m, 1H), 2.17-2.08 (m, 2H), 1.85-1.75 (m, 2H), 1.53-1.49 (m, 2H) MS (ESI +) m/z 397 (M + H). | 21.2 |
| (structure) | 93 | $^1$H NMR (500 MHz, DMSO-d$_6$) δ 10.33 (s, 1H), 9.50 (d, J = 6.6 Hz, 1H), 8.09, (br, s, 2H), 7.69 (d, J = 7.9 Hz, 1H), 7.54 (d, J = 7.9 Hz, 1H), 7.09 (t, J = 7.9 Hz, 1H), 4.40-4.35 (m, 1H), 3.74 (t, J = 11.4 Hz, 1H), 3.31-3.20 (m, 4H), 3.10-3.03 (m, 1H), 2.25-2.16 (m, 2H), 1.97-1.85 (m, 3H); MS (ESI +) m/z 287 (M + H). | 12.1 |

-continued

| Structure | Ex. | NMR and MS data | 5-HT₃ Kᵢ (nM) |
|---|---|---|---|
| 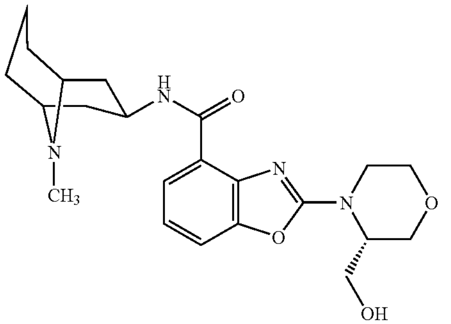 | 94 | ¹H NMR (500 MHz, DMSO-d₆) δ 9.20 (br s, 0.5H), 8.85 (br s, 1H), 7.73 (d, J = 7.9 Hz, 1H), 7.56 (d, J = 7.9Hz, 1H), 7.11 (d, J = 7.9 Hz, 1H), 5.09-4.96 (m, 1H), 4.53-4.22 (m, 1H), 4.21-4.02 (m, 2H), 4.02-3.81 (m, 3H), 3.81-3.39 (m, 5H), 3.26-3.14 (m, 1.5H), 3.13-2.87 (m, 1.5H), 2.48-2.22 (m, 3H), 2.22-0.75 (m, 8H); MS (ESI +) m/z 415 (M + H). | 27.5 |
| 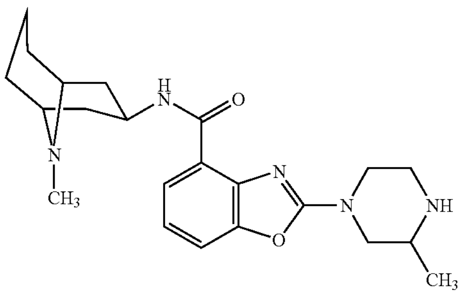 | 95 | ¹H NMR (500 MHz, DMSO-d₆) δ 8.96 (br s, 1H), 7.74 (dd, J = 8.0, 0.8 Hz, 1H), 7.58 (dd, J = 7.9, 0.8 Hz, 1H), 7.12 (t, J = 8.0 Hz, 1H), 4.38-4.32 (m, 1H), 4.07 (d, J = 9.9 Hz, 2H), 3.38-3.20 (m, 7H), 3.13 (d, J = 12.4 Hz, 1H), 2.99 (d, J = 7.7 Hz, 2H), 2.98-2.85 (m, 1H), 2.60 (br s, 3H), 2.15-2.02 (m, 3H), 1.58-1.45 (m, 3H), 1.35-1.20 (m, 2H), 1.13 (d, J = 5.3 Hz, 3H); MS (ESI +) m/z 398 (M + H). | 52.4 |
| 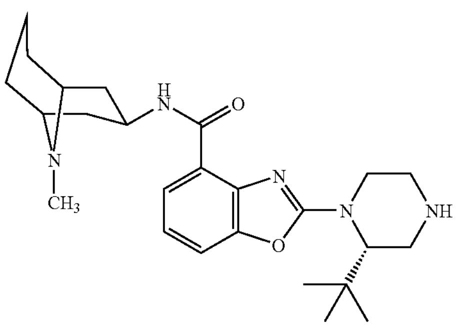 | 96 | ¹H NMR (500 MHz, DMSO-d₆) δ 10.49 (s, 0.4H) 9.64 (br s, 1.6H), 9.15 (s, 1H), 9.00 (s, 0.3 H), 8.93 (d, J = 5.0 Hz, 0.7H), 7.83-7.75 (m, 1H), 7.67-7.63 (m, 1H), 7.23-7.14 (m, 1H), 4.67-4.57 (m, 1H), 4.41-4.25 (m, 2H), 3.68-3.63 (m, 2H), 3.56 (s, 1H), 3.48-3.32 (m, 2H), 3.26 (br s, 2H), 2.83 (s, 3H), 2.75-2.61 (m, 2H), 2.27-2.18 (m, 1H), 2.15-2.01 (m, 2H), 1.82-1.62 (m, 3H), 1.58-1.53 (m, 1H), 1.50-1.38 (m, 1H), 1.04-0.99 (m, 9H); MS (ESI +) m/z 440 (M + H). | 7.5 |
| 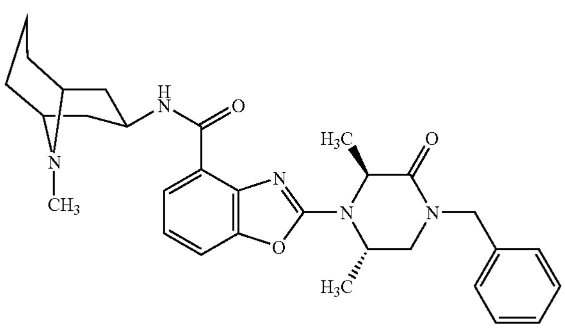 | 97 | ¹H NMR (500 MHz, CD₃OD) δ 7.85-7.83 (m, 1H), 7.56-7.54 (m, 1H), 7.38-7.31 (m, 5H), 7.18 (app t J = 8.0 Hz, 1H), 4.76-4.63 (m, 3H), 4.52-4.47 (m, 2H), 3.91 (dd, J = 13.7, 3.5 Hz, 1H), 3.64-3.61 (m, 2H), 3.41-3.37 (m, 1H), 2.92 (s, 3H), 2.82-2.71 (m, 2H), 2.23-2.19 (m, 3H), 1.90-1.88 (m, 2H), 1.73-1.60 (m, 6H), 1.13 (d, J = 6.5 Hz, 3H); MS (ESI +) m/z 516 (M + H). | 0.40 |
| 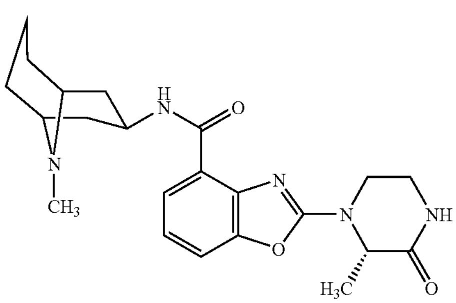 | 98 | ¹H NMR (500 MHz, CD₃OD) δ 7.87-7.83 (m, 1H), 7.56-7.54 (m, 1H), 7.20-7.16 (m, 1H), 4.79-4.76 (m, 1H), 4.54-4.41 (m, 1H), 4.30-4.25 (m, 1H), 3.78-3.65 (m, 3H), 3.62-3.55 (m, 1H), 3.48-3.42 (m, 1H), 3.01-2.99 (m, 3H), 2.90-2.80 (m, 0.7H), 2.80-2.72 (m, 1.3H), 2.50-2.37 (m, 0.3H), 2.30-2.14 (m, 2.7H), 2.04-1.94 (m, 2.5H), 1.75-1.61 (m, 5.5H); MS (ESI +) m/z 412 (M + H). | 14.6 |

-continued

| Structure | Ex. | NMR and MS data | 5-HT₃ K$_i$ (nM) |
|---|---|---|---|
| 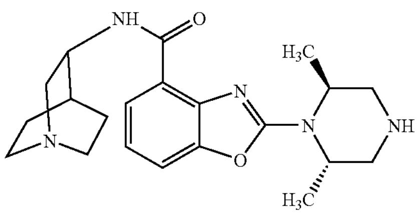 | 99 | ¹H NMR (500 MHz, DMSO-d₆) δ 9.70 (br s, 2H), 9.33 (d, J = 6.5 Hz, 1H), 7.76 (d, J = 8.0 Hz, 1H), 7.67 (d, J = 8.0 Hz, 1H), 7.18 (app t, J = 8.0 Hz, 1H), 4.40-4.30 (m, 3H), 3.76-3.73 (m, 1H), 3.42-3.00 (m, 10H), 2.20 (br s, 1H), 2.18-2.05 (m, 3H), 1.48 (d, J=6.5 Hz, 3H), 1.44 (d, J=6.5 Hz, 3H); MS (ESI +) m/z 384 (M + H). | 13.2 |
| 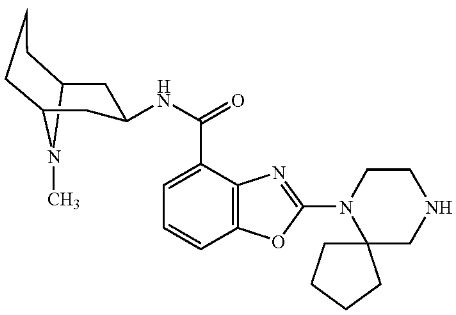 | 100 | ¹H NMR (500 MHz, DMSO-d₆) δ 10.39-9.56 (br m, 1H), 8.87-8.65 (m, 1H), 7.81-7.78 (m, 1H), 7.71-7.66 (m, 1H), 7.24-7.19 (m, 1H), 4.72-4.37 (m, 1H), 4.00-3.98 (m, 2H), 3.68 3.58 (m, 2H), 3.28-3.25 (m, 4H), 3.17 (s, 1H), 2.85-2.83 (m, 3H), 2.75-2.54 (m, 2H), 2.46-2.27 (m, 2H), 2.23-2.10 (m, 3H), 2.07 (s, 1H), 2.03-1.94 (m, 1H), 1.91-1.84 (m, 2H), 1.72-1.62 (m, 4H), 1.59-1.53 (m, 1H), 1.45 (d, J = 13.8 Hz, 2H); MS (ESI +) m/z 438 (M + H). | 11.4 |
| 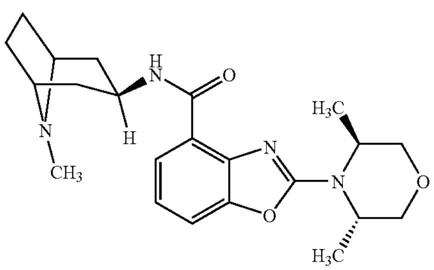 | 101 | ¹H NMR (500 MHz, DMSO-d₆) δ 10.89 (s, 1H), 8.95 (d, J = 7.0 Hz, 1H), 7.76 (d, J = 8.0 Hz, 1H), 7.63 (d, J = 8.0 Hz, 1H), 7.18 (t, J = 8.0 Hz, 1H), 4.37-4.33 (m, 1H), 4.15-4.08 (m, 2H), 3.90 (br s, 2H), 3.86 (dd, J = 11.5, 0.5 Hz, 2H), 3.57-3.52 (m, 2H), 3.33 (br s, 3H), 2.66 (d, J = 5.0 Hz, 1H), 2.28-2.21 (m, 2H), 2.20-2.10 (m, 4H), 2.04-1.99 (m, 2H), 1.41-1.39 (m, 6H); MS (ESI +) m/z 399 (M + H). | 2.6 |
| 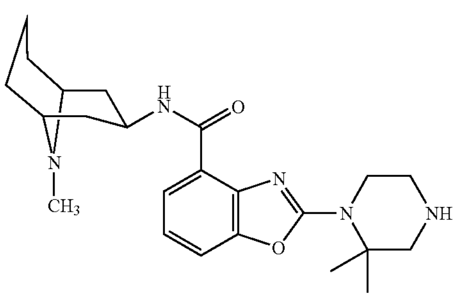 | 102 | ¹H NMR (500 MHz, DMSO-d₆) δ 8.94-8.89 (br m, 1H), 7.78 (dd, J = 7.9, 0.6 Hz, 1H), 7.66 (dd, J = 7.9, 0.7 Hz, 1H), 7.20 (t, J = 8.0 Hz, 1H), 4.52 (br s, 1H) 38.7 (t, J = 5.4 Hz, 2H) 3.58-3.52 (m, 2H), 3.31 (br s, 3H), 3.22 (t, J = 5.4 Hz, 2H), 3.11 (br s, 2H), 2.78 (br s, 3H), 2.67-2.61 (m, 2H), 2.12-2.01 (m, 3H), 1.65 (s, 6H), 1.61-1.52 (m, 2H), 1.50-1.40 (m, 2H); MS (ESI +) m/z 412 (M + H). | 15.8 |
| 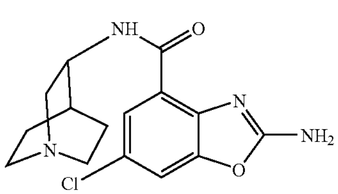 | 103 | ¹H NMR (500 MHz, DMSO-d₆) δ 10.22 (s, 1H), 9.38 (d, J = 6.7 Hz, 1H), 8.27, (br, s, 2H), 7.76 (d, J = 2.0 Hz, 1H), 7.62 (d, J = 2.0 Hz, 1H), 4.37-4.33 (m, 1H), 3.73 (t, J = 11.4 Hz, 1H), 3.30-3.20 (m, 4H), 3.10-3.06 (m, 1H), 2.22-2.12 (m, 2H), 1.97-1.85 (m, 3H); MS (ESI +) m/z 321 (M + H). | 5.1 |
| 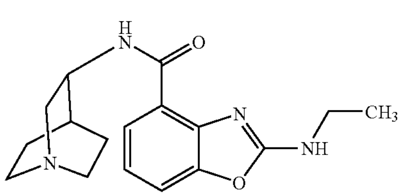 | 104 | ¹H NMR (500 MHz, DMSO-d₆) δ 10.51 (s, 1H), 9.57 (d, J = 7.0 Hz, 1H), 8.71-8.69 (m, 1H), 7.69 (dd, J = 7.0, 1.0 Hz, 1H); 7.56 (dd, J = 7.0, 0.7 Hz, 1H), 7.10 (t, J = 8.0 Hz, 1H), 4.75 (br s, 2H), 4.37 (s, 1H), 3.74 (t, J = 6.0 Hz, 1H), 3.42-3.38 (m, 2H), 3.33-3.23 (m, 2H), 3.21-3.17 (m, 2H), 3.09 (d, J = 12.0 Hz, 1H), 2.24-2.22 (m, 1H), 3.18-3.08 (m, 1H), 1.97-1.94 (m, 3H), 1.24 (t, J = 7.5 Hz, 3H); (ESI +) m/z 315 (M + H). | 13.5 |

-continued

| Structure | Ex. | NMR and MS data | 5-HT$_3$ K$_i$ (nM) |
|---|---|---|---|
| 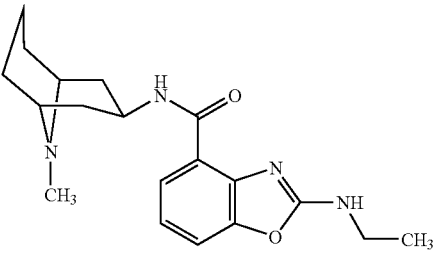 | 105 | $^1$H NMR (500 MHz, DMSO-d$_6$) δ 10.30 (s, 04H), 9.65 (s, 0.6H), 9.35 (d, J = 6.0 Hz, 0.4H), 9.17 (d, J = 6.0 Hz, 0.6H), 8.60-8.58 (m, 1H), 7.73-7.68 (m, 1H), 7.55 (d, J = 7.5 Hz, 1H), 7.10-7.05 (m, 1H), 4.60-4.48 (m, 1.5H), 4.40-4.30 (m, 0.5H), 3.70-3.60 (m, 1H), 3.59-3.52 (m, 1H), 3.45-3.33 (m, 2H), 2.83 (s, 3H), 2.80-2.60 (m, 2H), 2.30-2.20 (m, 1H), 2.18-2.05 (m, 2H), 1.60-1.40 (m, 3H), 1.28-1.15 (m, 3H) (ESI +) m/z 343 (M + H). | 3.3 |
| 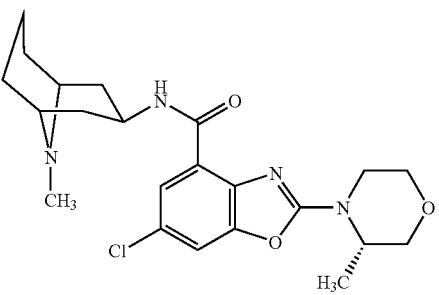 | 106 | $^1$H NMR (500 MHz, DMSO-d$_6$) δ 9.67 (br s, 0.35H), 9.18 (br s, 0.65H), 9.07 (d, J = 5.3 Hz, 0.35H), 8.84 (d, J = 6.7 Hz, 0.65H), 7.83 (d, J = 2.0 Hz, 1H), 7.70-7.67 (m, 1H), 4.49-4.25 (m, 2H), 3.98-3.95 (m, 1H), 3.85-3.52 (m, 7H), 2.86-2.83 (m, 3H), 2.72-2.52 (m, 2H), 2.14-2.05 (m, 3H), 1.82-1.78 (m, 3H), 1.53-1.47 (m, 2H), 1.36-1.33 (m, 3H); MS (ESI +) m/z 433 (M + H). | 12.6 |
| 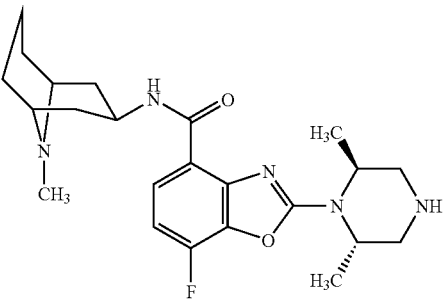 | 107 | $^1$H NMR (500 MHz, DMSO-d$_6$) δ 10.38 (s, 3H), 9.86 (s, 2H), 9.58 (s, 0.7H), 8.83 (d, J = 5.5 Hz, 0.4H), 8.75 (d, J = 5.5 Hz, 0.6H); 7.82-7.77 (m, 1H), 7.16-7.12 (m, 1H), 4.60-4.52 (m, 0.7H) 4.45-4.40 (m, 2H) 4.36 (br s, 0.3H), 3.66-3.62 (m, 1H), 3.55 (br s, 1H), 3.52-3.43 (m, 2H), 3.28-3.22 (m, 3H), 2.86 (s, 3H), 2.76-2.71 (m, 1H), 2.70-2.58 (m, 1H), 2.28-2.00 (m, 3H), 1.82-1.65 (m, 3H), 1.60-1.39 (m, 8H); (ESI +) m/z 430 (M + H). | 14.2 |
| 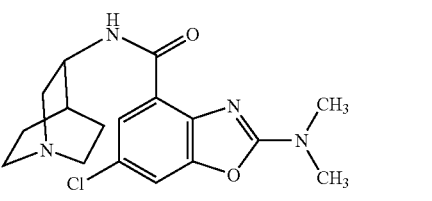 | 108 | $^1$H NMR (500 MHz, DMSO-d$_6$) δ 10.68-9.74 (br m, 1H), 9.02-8.86 (br m, 1H), 7.82-7.80 (m, 1H), 7.69-7.67 (m, 1H), 4.59 (br s, 1H), 4.18 (d, J = 12.4 Hz, 2H), 4.07 (br s, 1H), 3.95 (d, J = 9.3 Hz, 1H), 3.72-3.55 (m, 5H), 2.82 (d, J = 4.3 Hz, 3H), 2.73-2.59 (m, 2H), 2.29 2.23 (m, 1H), 2.15-2.05 (m, 2H), 1.80-1.65 (m, 3H), 1.55-1.53 (m, 1H), 1.47-1.40 (m, 1H), 1.31-1.18 (m, 1H), 1.10-1.07 (m, 8H); MS (ESI +) m/z 349 (M+H) | 14.4 |
| 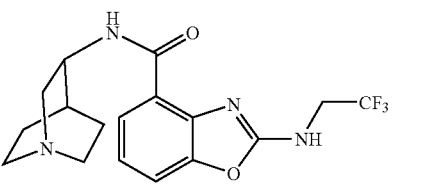 | 109 | $^1$H NMR (500 MHz, DMSO-d$_6$) δ 10.33 (br s, 1H), 9.50-9.39 (m, 1H), 9.33 (d, J = 6.7, 1H), 7.75 (dd, J = 8.2, 0.8 Hz, 1H), 7.65 (dd, J = 8.0, 0.8 Hz, 1H), 7.19 (t, J = 8.0 Hz, 1H), 4.47-4.07 (m, 3H), 3.72 (t, J = 11.0 Hz, 1H), 3.28 (t, J = 8.4Hz, 2H), 3.24 (t, J = 8.4 Hz, 2H), 3.19-3.10 (m, 1H), 2.24-2.22 (m, 1H), 2.17-2.06 (m, 1H), 1.97-1.93 (m, 2H), 1.92-1.82 (m, 1H); MS (ESI +) m/z 369 (M + H). | 47.9 |

-continued

| Structure | Ex. | NMR and MS data | 5-HT₃ $K_i$ (nM) |
|---|---|---|---|
| 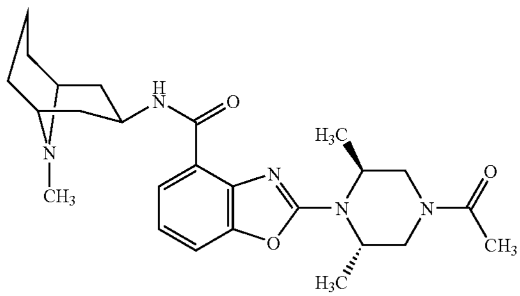 | 110 | ¹H NMR (300 MHz, DMSO-d₆) δ 9.90 (br m, 0.4H), 9.16 (br m, 0.6H), 7.78 (dd, J = 7.9, 0.6 Hz, 1H), 7.66 (d, J = 7.9, 1H), 7.16 (t, J = 8.0 Hz, 1H), 4.39 (bm, 3H), 3.89 (m, 2H), 3.68-3.34 (m, 4H), 2.86 (m, 3H), 2.85-2.51 (m, 3H), 2.12-2.08 (m, 3H), 1.48-1.23 (m, 8H); MS (ESI +) m/z 454 (M + H). | 2.2 |
| 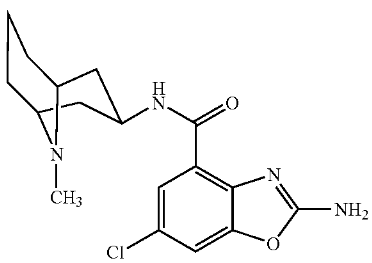 | 111 | ¹H NMR (500 MHz, DMSO-d₆) δ 10.30 (br s, 0.25H), 9.58 (br s, 0.75H), 9.26 (d, J = 5.8 Hz, 0.25H), 8.91 (d, J = 5.8 Hz, 0.75H), 8.28 (br s, 2H), 7.75 (d, J = 2.0Hz, 1H), 7.63 (d, J = 2.0 Hz, 1H), 4.64-4.59 (m, 0.75H), 4.35-4.25 (m, 0.25H), 3.64 (d, J = 9.2 Hz, 1.2H), 3.60-3.55 (m, 0.25H), 2.85-2.80 (m, 3H), 2.72-2.54 (m, 2H), 2.27-2.10 (m, 3H), 2.85-2.65 (m, 3H), 1.60-1.42 (m, 2H); MS (ESI +) m/z 349 (M + H). | 2.0 |
| 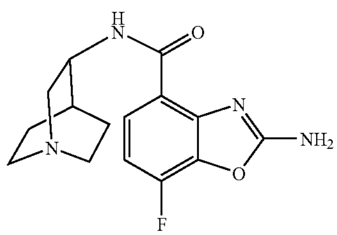 | 112 | ¹H NMR (500 MHz, DMSO-d₆) δ 10.00 (s, 1H), 9.30 (d, J = 6.6 Hz, 1H), 8.32 (s, 2H), 7.71-7.68 (m, 1H), 7.04 (t, J = 8.0 Hz, 1H), 4.40-4.28 (m, 1H), 3.80-3.70 (m, 1H), 3.35-3.26 (m, 2H), 3.25-3.20 (m, 2H), 3.10-3.02 (m, 1H), 2.28-2.22 (m, 1H), 2.18-2.10 (m, 1H), 1.98-1.92 (m, 3H); MS (ESI +) m/z 305 (M + H). | 33.3 |
| 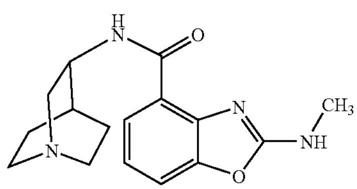 | 113 | ¹H NMR (500 MHz, DMSO-d₆) δ 10.33 (br s, 1H), 9.61 (d, J = 6.8 Hz, 1H), 8.55-8.52 (m, 1H), 7.70 (dd, J = 8.1, 0.9 Hz, 1H), 7.65 (dd, J = 8.1, 1.0 Hz, 1H), 7.10 (t,J = 8.0 Hz, 1H), 4.39-4.37 (m, 1H), 3.75 (t, J = 11.4 Hz, 1H), 3.31 (t, J = 7.3 Hz, 2H), 3.24 (t, J = 8.8 Hz, 2H), 3.15-3.11 (m, 1H), 2.97 (s, 3H), 2.24-2.23 (m, 1H), 2.21-2.16 (m, 1H), 1.97-1.90 (m, 3H); MS (ESI +) m/z 301 (M + H). | 14.5 |
| 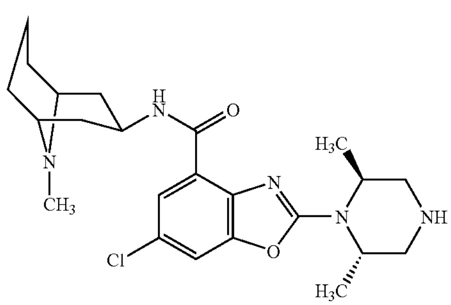 | 114 | ¹H NMR (500 MHz, CD₃OD) δ 9.15 (d, J = 6.0 Hz, 0.3H), 9.08 (d, J = 6.0 Hz, 0.3H), 7.84-7.82 (m, 1H), 7.66 (d, J = 1.5 Hz, 1H), 4.62-4.46 (m, 3H), 3.82-3.60 (m, 4H), 3.44-3.38 (m, 2H), 3.01-2.97 (m, 3H), 2.92-2.70 (m, 2H), 2.32-2.16 (m, 3H), 2.00-1.82 (m, 3H), 1.72-1.64 (m, 1H), 1.63 (d, J = 3.6 Hz, 6H); MS (ESI +) m/z 446 (M + H). | 6.6 |
| 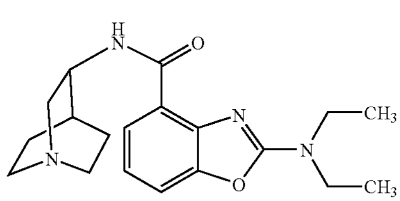 | 115 | ¹H NMR (300 MHz, DMSO-d₆) δ 9.55 (br m, 1H), 7.73 (d, J = 7.9 Hz, 1H), 7.62 (d, J = 7.9 Hz, 1H), 7.12 (t, J = 7.9 Hz, 1H), 4.29 (br m, 1H), 3.65 (m, 5H), 3.12 (m, 4H), 2.99 (m, 1H), 2.15 (m, 2H), 1.87 (m, 3H), 1.23 (t, J = 3.6 Hz, 6H); MS (ESI +) m/z 343 (M + H). | 4.8 |

-continued

| Structure | Ex. | NMR and MS data | 5-HT₃ K$_i$ (nM) |
|---|---|---|---|
| 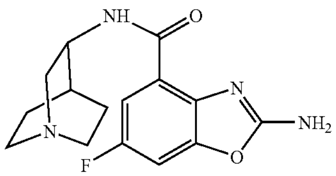 | 116 | ¹H NMR (300 MHz, DMSO-d₆) δ 9.39 (d, J = 7.2 Hz, 1H), 8.10, (br, s, 2H), 7.60 (dd, J = 8.1, 2.7 Hz, 1H), 7.40 (dd, J = 8.1, 2.7 Hz, 1H), 4.23-4.06 (m, 1H), 3.55-3.45 (m, 1H), 3.09-2.95 (m, 4H), 2.79 (dd, J = 13.5, 4.5 Hz, 1H), 2.10-1.90 (m, 2H), 1.82-1.64 (m, 3H); MS (ESI +) m/z 305 (M + H). | 9.4 |
| 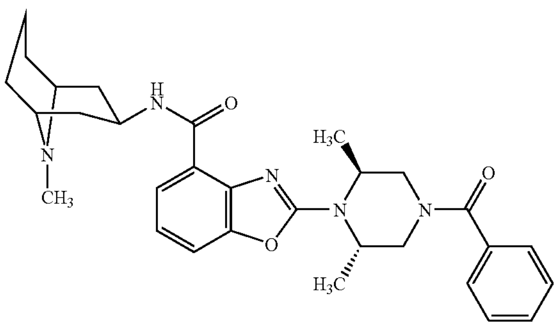 | 117 | ¹H NMR (500 MHz, DMSO-d₆) δ 9.90-9.80 (m, 0.25H), 9.40-9.00 (m, 1.5H), 7.74 (d, J = 8.0 Hz, 1H), 7.65 (d, J = 8.0 Hz, 1H), 7.55-7.48 (m, 5H), 7.13 (d, J = 8.0 Hz, 1H), 4.53-4.20 (m, 2H), 4.05-3.85 (m, 3H), 370-342 (m, 2H), 2.85-2.75 (m, 2.5H), 2.70-2.40 (m, 4.25H), 2.16-1.90 (m, 3H), 1.88-1.62 (m, 2.5H), 1.60-1.40 (m, 5H), 1.28-1.20 (m, 4H); MS (ESI +) m/z 516 (M + H). | 2.3 |
| 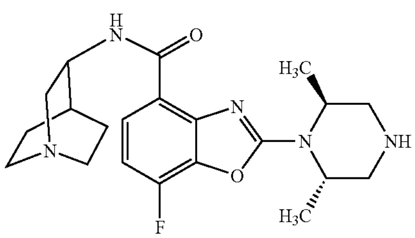 | 118 | ¹H NMR (500 MHz, DMSO-d₆) δ 10.08-9.90 (br s, 1H), 9.78-9.60 (br s, 2H), 9.10 (d, J = 6.8 Hz, 1H), 7.80-7.77 (m, 1H), 7.17-7.13 (m, 1H), 4.44-4.40 (m, 3H), 3.80-3.75 (m, 1H), 3.51-3.47 (m, 2H), 3.38-3.20 (m, 6H), 3.17-3.08 (m, 1H), 2.62-2.60 (m, 0.5H), 2.38-2.36 (m, 0.5H), 2.19-2.18 (m, 1H), 2.10-2.00 (m, 1H), 1.98-1.85 (m, 3H), 1.52-1.49 (m, 6H). (ESI +) m/z 402 (M + H). | 26.8 |
| 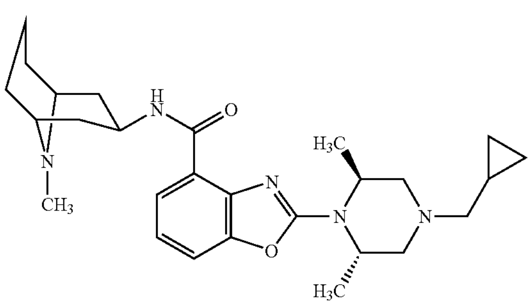 | 119 | ¹H NMR (500 MHz, DMSO-d₆) δ 11.20 11.00 (m, 1H), 10.32 (br s, 0.3H), 9.50 (s, 0.7H), 9.00-8.90 (m, 1H), 7.86-7.80 (m, 1H), 7.72-7.68 (m, 1H), 7.26-7.18 (m, 1H), 4.86-4.74 (m, 1H), 4.68-4.58 (m, 0.7H), 4.40-4.32 (m, 0.3H), 4.28-4.20 (m, 1H), 3.70-3.56 (m, 4H), 3.20-3.00 (m, 3H), 2.86 (s, 3H), 2.40 1.92 (m, 3H), 1.80-1.72 (m, 6H), 1.70-1.54 (m, 4H), 1.50-1.40 (m, 2H), 1.30-1.18 (m, 1H), 0.70-0.60 (m, 2H), 0.50-0.30 (m, 2H); MS (ESI +) m/z 466 (M + H). | 6.6 |
| 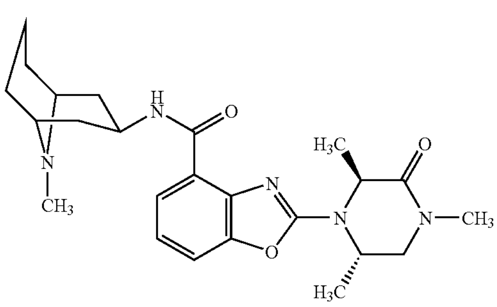 | 120 | ¹H NMR (500 MHz, DMSO-d₆, mixture of rotomers) δ 9.95 (br s, 0.35H), 9.34 (br s, 0.65 H), 9.08 (d, J = 5.4 Hz, 0.35H), 9.01 (d, J = 6.9 Hz, 0.65H), 7.80-7.66 (m, 2H), 7.19-7.14 (m, 1H), 4.55-4.34 (m, 3H), 3.97-3.93 (m, 1H), 3.67-3.58 (m, 2H), 3.39-3.36 (m, 1H), 3.00 (s, 3H), 2.285 (d, J = 4.6 Hz, 3H), 2.73-2.61 (m, 2H), 2.15-2.06 (m, 3H), 1.80-1.69 (m, 3H), 1.59-1.46 (m, 5H), 1.30-1.23 (m, 3H). MS (ESI +) m/z 440 (M + H). | 1.9 |

-continued

| Structure | Ex. | NMR and MS data | 5-HT$_3$ K$_i$ (nM) |
|---|---|---|---|
| 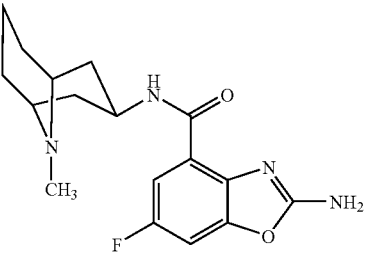 | 121 | $^1$H NMR (500 MHz, DMSO-d$_6$) δ 10.30 (br s, 0.25H), 9.58 (br s, 0.75H), 9.26 (d, J = 5.8 Hz, 0.25H), 8.91 (d, J = 5.8 Hz, 0.75H), 8.28 (br s, 2H), 7.75 (d, J = 2.0 Hz, 1H), 7.63 (d, J = 2.0 Hz, 1H), 4.64-4.59 (m, 0.75H), 4.35-4.25 (m, 0.25H), 3.64 (d, J = 9.2 Hz, 1.2H), 3.60-3.55 (m, 0.25H), 2.85-2.80 (m, 3H), 2.72-2.54 (m, 2H), 2.27-2.10 (m, 3H), 2.85-2.65 (m, 3H), 1.60-1.42 (m, 2H) MS (ESI +); m/z 333 (M + H). | 9.0 |
| 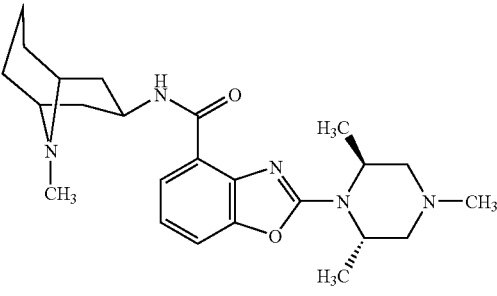 | 122 | $^1$H NMR (500 MHz, DMSO-d$_6$) δ 11.20-11.00 (m, 1H), 10.36 (br s, 0.25H), 9.51 (br s, 0.75H), 7.82-7.76 (m, 1H), 7.70-7.68 (m, 1H), 7.25-7.20 (m, 1H), 4.76-4.70 (m, 1H), 4.62-4.58 (m, 0.7H), 4.40-4.30 (m, 0.3H), 4.20-4.10 (m, 1H), 3.70-3.45 (m, 2H), 3.10-3.02 (m, 1H), 2.95-2.85 (m, 5H), 2.75-2.50 (m, 7H), 2.30-1.85 (m, 3H), 1.80-1.38 (m, 10H); MS (ESI +) m/z 426 (M + H). | 2.3 |
| 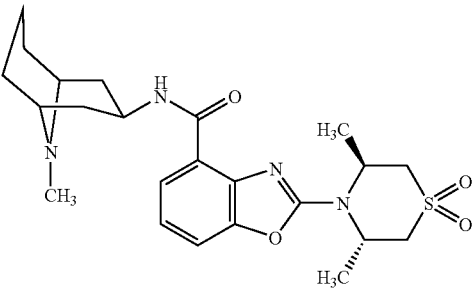 | 123 | $^1$H NMR (500 MHz, CD$_3$OD) δ 7.85-7.92 (m, 1H), 7.59 (d, J = 7.8 Hz, 1H), 7.24 (t, J = 8.0 Hz, 1H), 4.47-4.60 (m, 1H), 3.68-3.77 (m, 2H), 3.40-3.58 (m, 6H), 3.12 (s, 0.75H), 2.97 (s, 2.25), 2.72-2.86 (m, 2H), 2.08-2.37 (m, 3H), 1.60-2.00 (m, 12H); MS (ESI +) m/z 461 (M + H). | 57 |
| 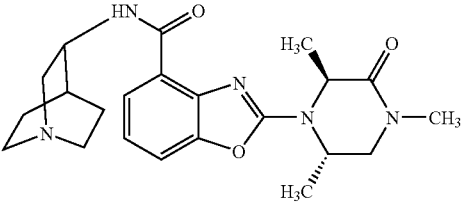 | 124 | $^1$H NMR (500 MHz, DMSO-d$_6$) δ 10.22 (br s, 1H), 9.39 (d, J = 6.9 Hz, 1H), 7.76 (dd, J = 7.9, 0.9 Hz, 1H), 7.69 (dd, J = 7.9, 0.9 Hz, 1H), 7.17 (app t, J = 7.9 Hz, 1H), 4.49-4.40 (m, 3H), 3.93 (dd, J = 13.7, 3.3 Hz, 1H), 3.76-3.72 (m, 1H), 3.39-3.36 (m, 1H), 3.34-3.30 (m, 2H), 3.26-3.23 (m, 2H), 3.19-3.15 (m, 1H), 3.01 (s, 3H), 2.22-2.20 (m, 1H), 2.19-2.15 (m, 1H), 1.98-1.91 (m, 3H), 1.53 (d, J = 6.9 Hz, 3H), 1.28 (d, J = 6.5 Hz, 3H); MS (ESI +) m/z 412 (M + H). | 17.7 |
| 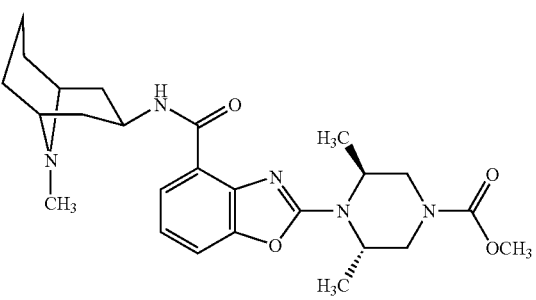 | 125 | $^1$H NMR (500 MHz, DMSO-d$_6$) δ 9.89 (m, 0.3H), 9.23 (m, 0.7H), 7.78 (m, 1H), 7.63 (m, 1H), 7.15 (m, 1H), 4.52 (m, 0.3H), 4.44 (m, 2.7H), 3.87-3.52 (m, 9H), 2.90 (s, 3H), 2.77-2.65 (m, 2H), 2.36-2.10 (m, 3H), 1.87-1.31 (m, 11H); MS (ESI +) m/z 470 (M + H). | 2.1 |

-continued

| Structure | Ex. | NMR and MS data | 5-HT$_3$ K$_i$ (nM) |
|---|---|---|---|
| 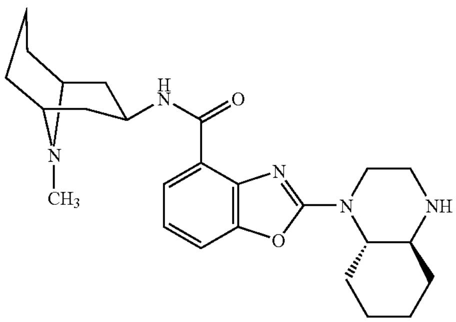 | 126 | $^1$H NMR (500 MHz, DMSO-d$_6$) δ 9.85-9.30 (m, 2H), 9.00-8.85 (m, 1H), 7.80 (m, 1H), 7.68 (m, 1H), 7.16 (m, 1H), 4.61 (m, 0.8H), 4.33 (m, 0.2H), 4.16 (m, 1H), 3.96-3.40 (m, 6H), 2.84 (s, 3H), 2.72-2.56 (m, 3H), 2.39-1.41 (m, 19H); MS (ESI +) m/z 438 (M + H). | 16.5 |
| 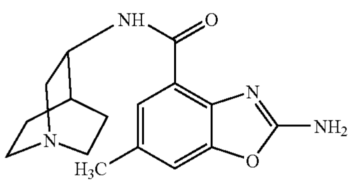 | 127 | $^1$H NMR (500 MHz, DMSO-d$_6$) δ 10.31 (br s, 1H), 9.44 (d, J = 6.7 Hz, 1H), 7.97, (br, s, 2H), 7.51 (s, 1H), 7.39 (s, 1H), 4.40-4.30 (m, 1H), 3.74 (t, J = 11.6 Hz, 1H), 3.55-3.20 (m, 4H), 3.05-3.01 (m, 1H), 2.37 (s, 3H), 2.22-2.12 (m, 2H), 1.95-1.85 (m, 3H); MS (ESI +) m/z 301 (M + H). | 20.0 |
| 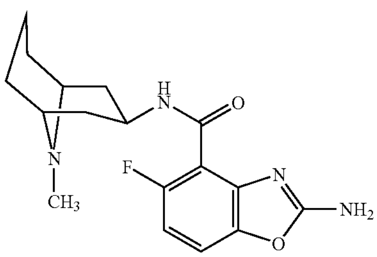 | 128 | $^1$H NMR (500 MHz, DMSO-d$_6$) δ 10.20 (s, 0.2H), 9.42 (s, 0.8H), 8.93 (dJ = 7.5 Hz, 0.2H), 8.65 (d, J = 7.5 Hz, 0.8H), 7.85 (s, 2H), 7.43-7.39 (m, 1H), 6.84-6.79 (m, 1H), 4.61-4.44 (m, 0.8H), 4.31-4.18 (m, 0.2H), 3.63-3.55 (m, 2H), 2.82-2.81 (m, 3H), 2.66-2.54 (m, 1H), 2.47-2.42 (m, 1H), 2.19-1.92 (m, 3H), 1.74-1.68 (m, 3H), 1.58-1.49 (m, 1H); 1.47-1.36 (m, 2H); (ESI +) m/z 333 (M + H). | 124 |
| 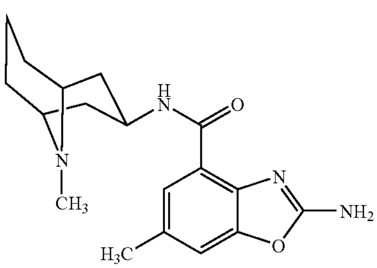 | 129 | $^1$H NMR (500 MHz, DMSO-d$_6$) δ 10.30 (br s, 0.3H), 9.42 (br s, 0.7H), 9.32 (d, J = 5.7 Hz, 0.3H), 8.95 (d, J = 5.7 Hz, 0.7H), 7.88 (br s, 1.4H), 7.86 (s, 0.6H), 7.52 (s, 0.7H), 7.51 (s, 0.3H), 7.37 (s, 1H), 4.60-4.55 (m, 0.7H), 4.35-4.25 (m, 0.3H), 3.65 (d, J = 8.9 Hz, 1.4H), 3.60-3.55 (m, 0.3H), 2.85-2.80 (m, 3H), 2.75-2.55 (m, 2H), 2.37 (s, 3H), 2.20-2.00 (m, 3H), 1.85-1.65 (m, 3H), 1.60-1.40 (m, 2H); MS (APCI) m/z 329 (M + H). | 10.7 |
| 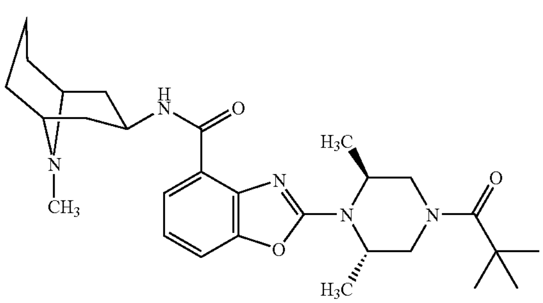 | 130 | $^1$H NMR (500 MHz, DMSO-d$_6$) δ 10.20-10.10 (m, 0.4H), 9.50-9.40 (m, 0.6H), 9.18-9.06 (m, 1H), 7.84-7.74 (m, 1H), 7.66 (d, J = 8.0 Hz, 1H), 7.13 (dt, J = 8.0, 2.0 Hz, 1H), 4.54-4.50 (m, 0.7H), 4.42-4.30 (m, 2.3H), 3.96-3.86 (m, 2H), 3.82-3.68 (m, 2H), 3.64-3.50 (m, 2H), 2.85 (m, 3H), 2.76-2.52 (m, 2H), 2.12-1.90 (m, 2H), 1.82-1.42 (m, 5H), 1.40-1.30 (m, 6H), 1.25 (s, 9H); MS (ESI +) m/z 496 (M + H). | 2.8 |

-continued

| Structure | Ex. | NMR and MS data | 5-HT$_3$ K$_i$ (nM) |
|---|---|---|---|
| 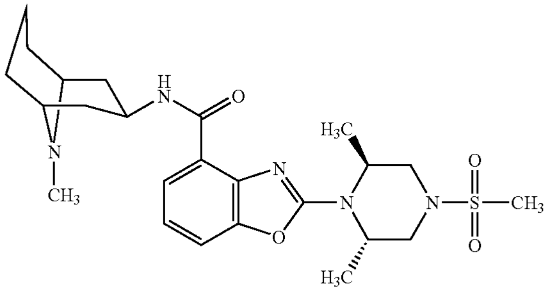 | 131 | $^1$H NMR (500 MHz, DMSO-d$_6$) δ 10.40 (s, 0.4H), 9.64 (s, 0.6H), 9.12-9.00 (m, 1H), 7.82-7.74 (m, 1H), 7.65 (dd, J = 8.0, 2.0 Hz, 1H) 7.17 (app t, J = 8.0 Hz, 1H), 4.60-4.54 (m, 0.6H), 4.42-4.32 (m, 2.4H), 3.70-3.36 (m, 8H), 3.02 (s, 3H), 2.84 (s, 1H), 2.80-2.58 (m, 2H), 2.30-1.98 (m, 2H), 1.80-1.68 (m, 2H), 1.60-1.52 (m, 1H), 1.50-1.38 (m, 7H); MS (ESI +) m/z 490 (M + H). | 1.0 |
| 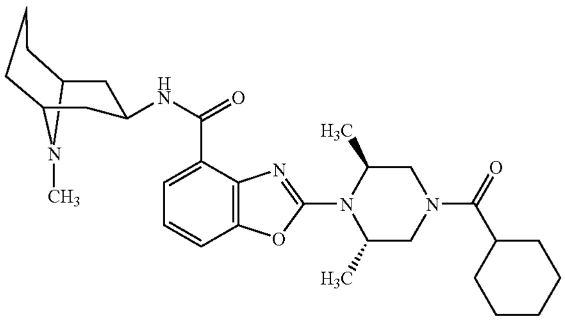 | 132 | $^1$H NMR (500 MHz, DMSO-d$_6$) δ 10.30-10.10 (m, 0.4H), 9.80-9.30 (m, 0.6H), 7.75 (d, J = 8.0 Hz, 1H), 7.64 (d, J = 8.0 Hz, 1H), 7.13 (app t, J = 8.0 Hz, 1H), 4.60-4.30 (m, 3H), 3.96-3.90 (m, 2H), 3.86-3.78 (m, 1H), 3.60-3.46 (m, 3H), 2.80 (s, 3H), 2.64-2.55 (m, 3H), 2.30-2.00 (m, 3H), 1.80-1.60 (m, 7H), 1.60-1.10 (m, 14H); MS (ESI +) m/z 522 (M + H). | 1.9 |
| 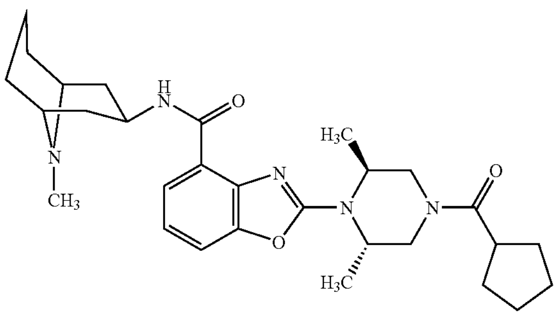 | 133 | $^1$H NMR (500 MHz, DMSO-d$_6$) δ 9.60-9.30 (m, 0.2H), 9.20-9.02 (m, 0.8H), 7.75 (d, J = 7.5 Hz, 1H), 7.64 (d, J = 8.0 Hz, 1H), 7.13 (app t, J = 8.0, Hz, 1H), 4.54-4.30 (m, 3H), 4.00-3.82 (m, 3H), 3.70-3.40 (m, 2H), 3.38-3.26 (m, 6H), 3.02-2.96 (m, 1H), 2.90-2.50 (m, 4H), 2.40-1.90 (m, 3H), 1.88-1.40 (m, 10H), 1.40-1.30 (m, 6H); MS (ESI +) m/z 508 (M + H). | 1.8 |
| 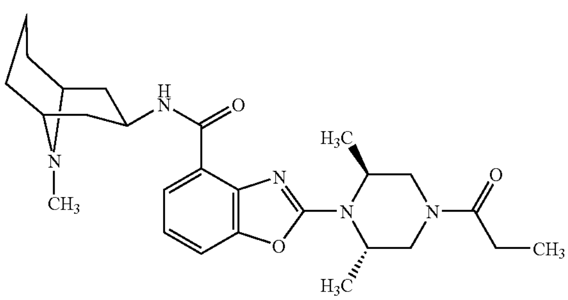 | 134 | $^1$H NMR (500 MHz, DMSO-d$_6$) δ 10.05 (s, 1H), 7.76 (d, J = 8.0 Hz, 1H), 7.62 (d, J = 8.0, 2.0 Hz, 1H), 7.12 (app t, J = 8.0 Hz, 1H), 4.50-4.34 (m, 3H), 3.96 (dd, J = 13, 1.5 Hz, 1H), 3.88 (dd, J = 13.5, 4.0 Hz, 1H), 3.73 (dd, J = 13, 1.5Hz, 1H), 3.51 (dd, J = 13.5, 4.0 Hz, 1H), 3.32-3.27 (m, 5H), 2.60-2.30 (m, 3H), 2.15-1.85 (m, 3H), 1.60-1.30 (m, 9H), 1.15-1.05 (m, 3H); MS (ESI +) m/z 468 (M + H). | 1.7 |
| 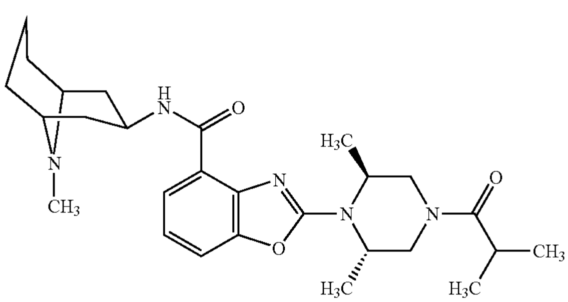 | 135 | $^1$H NMR (500 MHz, DMSO-d$_6$) δ 9.16-8.96 (m, 1H), 7.75 (d, J = 8.0 Hz, 1H), 7.63 (d, J = 8.0 Hz, 1H), 7.12 (app t, J = 8.0 Hz, 1H), 4.50-4.30 (m, 2H), 3.96-3.90 (m, 2H), 3.86-3.80 (m, 1H), 3.60-3.46 (m, 2H), 3.30-3.26 (s, 6H), 2.96-2.80 (m, 2H), 2.20-1.90 (m, 3H), 1.70-1.20 (m, 9H), 1.16-1.08 (m, 6H). MS (ESI +) m/z 482 (M + H). | 2.0 |

-continued

| Structure | Ex. | NMR and MS data | 5-HT₃ K$_i$ (nM) |
|---|---|---|---|
| 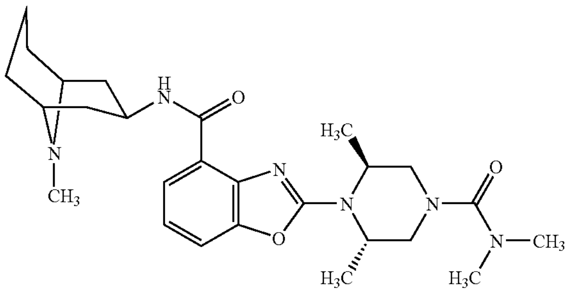 | 136 | ¹H NMR (500 MHz, CD₃OD) δ 7.80-7.87 (m, 1H), 7.55-7.61 (m, 1H), 7.17-7.25 (m, 1H), 4.44-4.69 (m, 3H), 3.90-3.97 (m, 2H), 3.67-3.77 (m, 2H), 3.42-3.47 (m, 2H), 2.97-3.03 (m, 3H), 2.89 (s, 6H), 2.69-2.82 (m, 2H), 2.15-2.42 (m, 3H), 1.87-2.02 (m, 2.5H), 1.59-1.75 (m, 2.5H), 1.47-1.53 (m, 6H); MS (ESI +) m/z 483 (M + H). | 2.6 |
| 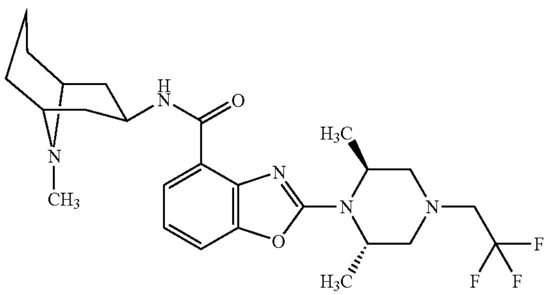 | 137 | ¹H NMR (500 MHz, DMSO-d₆) δ 8.96-8.80 (s, 1H), 7.76 (d, J = 8.0 Hz, 1H), 7.62 (d, J = 8.0 Hz, 1H), 7.18 (app t, J = 8.0 Hz, 1H), 4.40-4.24 (m, 1H), 4.20-4.14 (m, 2H), 3.36-3.22 (m, 6H), 3.16-2.88 (m, 3H), 2.72-2.62 (m, 2H), 2.60-2.34 (m, 3H), 2.12-1.88 (m, 3H), 1.60-1.40 (m, 8H), 1.38-0.88 (m, 3H); ¹⁹F {¹H}NMR (282 MHz, DMSO-d₆), δ- 64.02; MS (ESI +) m/z 494 (M + H). | 1.8 |
| 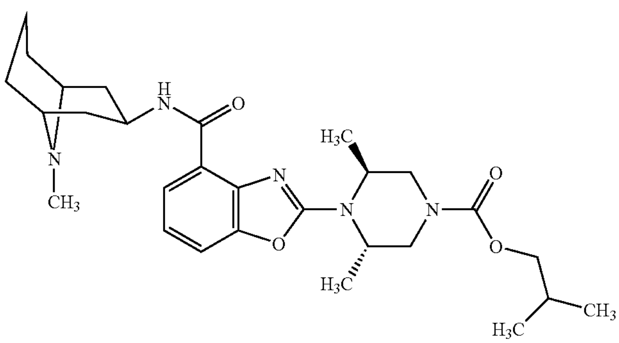 | 138 | ¹H NMR (500 MHz, CD₃OD) δ 7.90-7.72 (m, 1H), 7.59-7.45 (m, 1H), 7.25-7.03 (m, 1H), 4.59-4.34 (m, 3H), 4.07-3.88 (m, 2H), 3.88-3.67 (m, 4H), 3.50-3.36 (m, 2H), 2.83-2.54 (m, 5H), 2.22-2.06 (m, 3H), 2.06-1.87 (m, 1H), 1.80-1.58 (m, 3H), 1.58-1.36 (m, 8H), 1.08-0.91 (m, 6H); MS (ESI +) m/z 513 (M + H). | 2.4 |
| 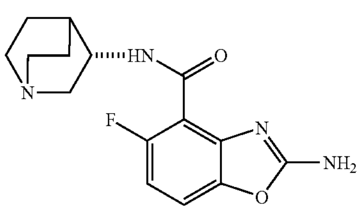 | 139 | ¹H NMR (500 MHz, DMSO-d₆) δ 10.24 (s, 1H), 9.04 (d, J = 6.5 Hz, 1H), 7.93 (s, 2H), 7.45-7.42 (m, 1H), 6.85-6.81 (m, 1H), 4.33-4.31 (m, 1H), 3.69-3.65 (m, 1H), 3.25-3.19 (m, 4H), 3.06-2.98 (m, 2H), 2.24-2.08 (m, 2H), 1.92-1.89 (m, 2H), 1.81-1.71 (m, 1H); MS (ESI +) m/z 305 (M + H). | 67.4 |
| 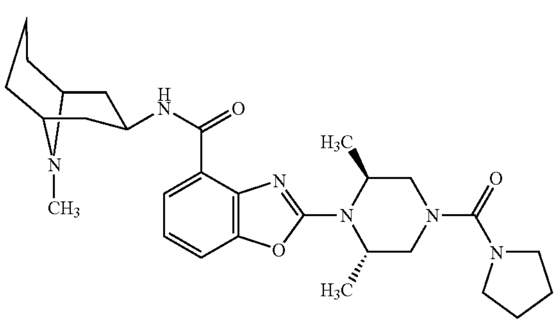 | 140 | ¹H NMR (500 MHz, CD₃OD) δ 7.82-7.87 (m, 1H), 7.55-7.61 (m, 1H), 7.16-7.24 (m, 1H), 4.45-4.63 (m, 3H), 3.92 (dd, J = 13.0, 3.3 Hz, 1H), 3.67-3.78 (m, 2H), 3.49-3.56 (m, 4H), 3.30-3.38 (m, 2H), 3.02 (s, 1H), 2.97 (s, 2H), 2.72-2.91 (m, 2H), 2.15-2.43 (m, 3H), 1.60-2.02 (m, 9H), 1.47-1.53 (m, 6H); MS (ESI +) m/z 509 (M + H). | 2.2 |

| Structure | Ex. | NMR and MS data | 5-HT$_3$ K$_i$ (nM) |
|---|---|---|---|
| 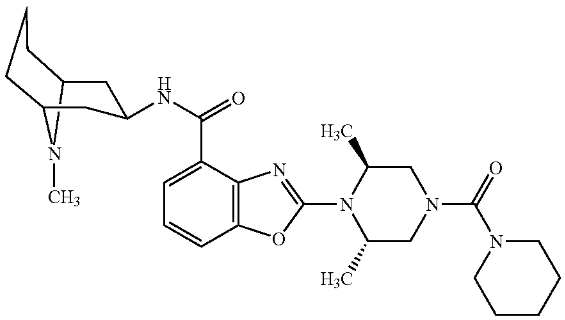 | 141 | $^1$H NMR (500 MHz, CD$_3$OD) δ 7.82-7.87 (m, 1H), 7.53-7.57 (m, 1H), 7.15-7.20 (m, 1H), 4.43-4.58 (m, 3H), 3.90-3.96 (m, 2H), 3.67-3.78 (m, 2H), 3.44 (dd, J = 13.1, 2.3 Hz, 2H), 3.17-3.25 (m, 2 H), 3.02 (s, 0.75 H), 2.97 (s, 2.25 H), 2.72-2.92 (m, 2H), 2.13-2.42 (m, 3H), 1.86-2.02 (m, 2H), 1.46-1.75 (14H); MS (ESI +) m/z 523 (M + H). | 1.8 |
| 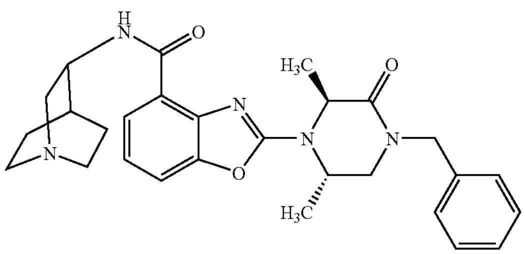 | 142 | $^1$H NMR (500 MHz, CD$_3$OD) δ 7.84 (dd, J = 8.0, 1.0 Hz, 1H), 7.57 (dd, J = 8.0, 0.9 Hz, 1H), 7.39-7.32 (m, 5H), 7.19 (app t, J = 8.0 Hz, 1H), 4.77-4.65 (m, 3H), 4.55-4.45 (m, 2H), 3.93-3.89 (m, 2H), 3.48-3.38 (m, 5H), 3.30-3.25 (m, 1H), 2.38-2.36 (m, 2H), 2.17-2.12 (m, 3H), 1.67 (d, J = 7.0 Hz, 3H), 1.12 (d, J = 6.5 Hz, 3H); MS (ESI +) m/z 488 (M + H). | 11.5 |
| 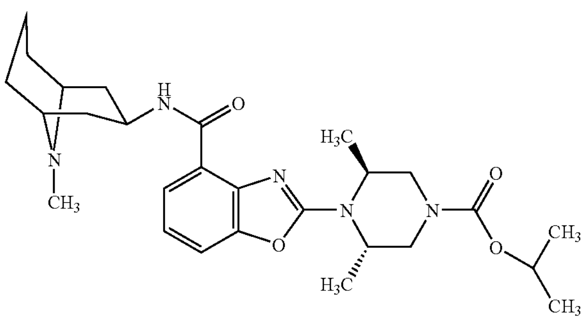 | 143 | $^1$H NMR (500 MHz, CD$_3$OD) δ 7.90-7.78 (m, 1H), 7.57-7.49 (m, 1H), 7.21-7.12 (m, 1H), 5.04-489 (m, 1H), 4.58-4.41 (m, 3H), 3.87-3.66 (m, 6H), 3.00 (s, 3H), 2.92-2.65 (m, 2H), 2.47-1.58 (m, 8H), 1.53-1.43 (m, 6H), 1.36-1.22 (m, 6H). MS (ESI +) m/z 498 (M + H). | 1.4 |
| 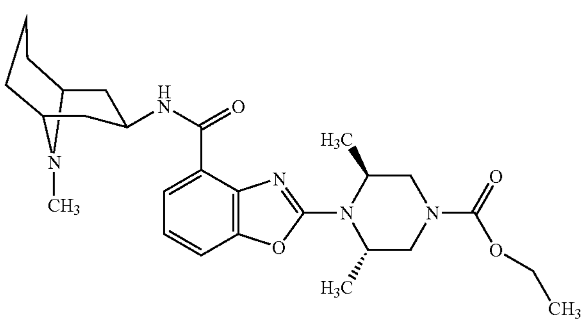 | 144 | $^1$H NMR (500 MHz, CD$_3$OD) δ 7.89-7.80 (m, 1H), 7.60-7.49 (m, 1H), 7.20-7.12 (m, 1H), 4.61-4.41 (m, 3H), 4.30-4.16 (m, 2H), 3.91-3.63 (m, 6H), 3.06-2.95 (m, 3H), 2.90-2.69 (m, 2H), 2.38-1.53 (m, 8H), 1.53-1.36 (m, 6H), 1.36-1.23 (m, 3H); MS (ESI +) m/z 484 (M + H). | 1.0 |
| 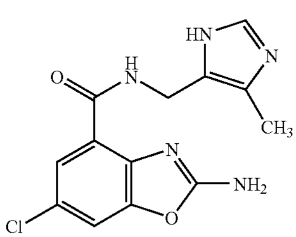 | 145 | $^1$H NMR (500 MHz, CD$_3$OD) δ 8.20 (s, 1H), 7.76 (s, 1H), 7.48 (s, 1H), 4.61 (s, 2H), 2.35 3H); MS (ESI +) m/z 306 (M + H). | 127 |

-continued

| Structure | Ex. | NMR and MS data | 5-HT$_3$ K$_i$ (nM) |
|---|---|---|---|
| 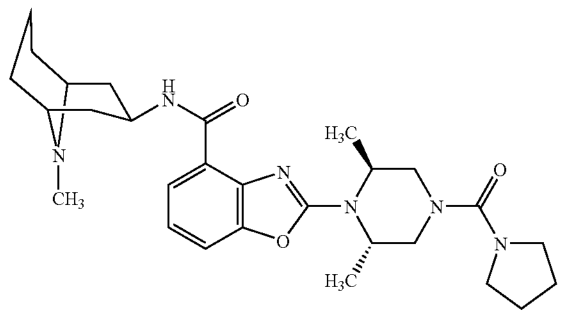 | 146 | $^1$H NMR (500 MHz, CD$_3$OD) δ 7.82 (d, J = 8.0 Hz, 1H), 7.54 (d, J = 7.9 Hz, 1H), 7.15 (t, J = 8.0 Hz, 1H), 4.43-4.52 (m, 2H), 4.33-4.42 (m, 1H), 3.88-3.93 (m, 4H), 3.48-3.55 (m, 4H), 3.30-3.35 (m, 2H), 2.62-2.72 (m, 2H), 2.10-2.22 (m, 1H), 1.65-2.02 (m, 11H), 1.52 (d, J = 6.7 Hz, 6H); MS (ESI +) m/z 495 (M + H). | 32.2 |
| 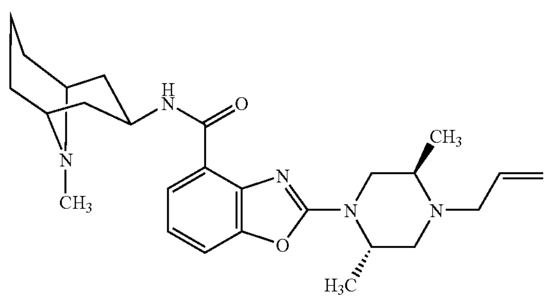 | 147 | $^1$H NMR (500 MHz, DMSO-d$_6$) δ 10.40-10.30 (m, 0.4H), 9.60-9.53 (m, 0.6H), 9.10-9.00 (m, 0.4H), 8.89-8.83 (d, J = 6.0 Hz, 0.6H), 7.80-7.76 (m, 1H), 7.65 (d, J = 10 Hz, 1H), 7.20-7.17 (m, 1H), 6.26-6.16 (m, 0.8H), 6.07-6.02 (m, 0.2H), 5.61-5.50 (m, 2H), 4.68 (d, J = 6.0 Hz, 1H), 4.60-4.48 (m, 1H), 4.32-4.30 (m, 0.5H), 4.16-4.05 (m, 1H), 4.02-3.98 (m, 1H), 3.60-3.54 (m, 2H), 3.52-3.48 (m, 1H), 3.46-3.16 (m, 5H), 2.85 (s, 3H), 2.75-2.55 (m, 2H), 2.27-2.18 (m, 1H), 2.12-2.05 (m, 2H), 1.78-1.68 (m, 3H), 1.60-1.40 (m, 2H), 1.30-1.22 (m, 3H); (ESI +) m/z 452 (M + H). | 10.8 |
| 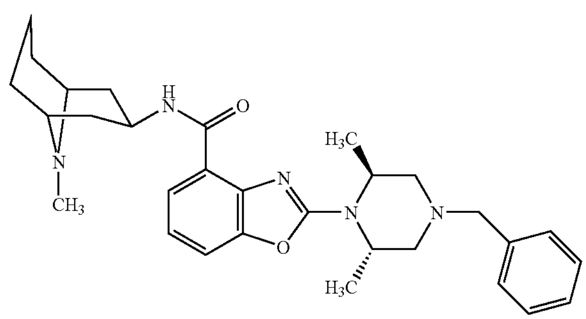 | 148 | $^1$H NMR (500 MHz, DMSO-d$_6$) δ 11.62-11.44 (m, 1H), 10.40-10.32 (m, 0.3H), 9.58-9.50 (m, 0.7H), 8.96-8.78 (m, 1H), 7.84-7.64 (m, 4H), 7.54-7.30 (m, 3H), 7.22-7.18 (m, 1H), 4.80-4.72 (m, 1H), 4.68-4.58 (m, 1H), 4.56-4.46 (m, 1H), 4.40-4.22 (m, 2H), 3.90-3.50 (3H), 3.42-3.30 (m, 1H), 3.22-3.12 (m, 2H), 2.86 (s, 3H), 2.78-2.62 (m, 2H), 2.20-1.90 (m, 3H), 1.76-1.60 (m, 5H), 1.56-1.44 (m, 6H); MS (ESI +) m/z 502 (M + H). | 1.6 |
| 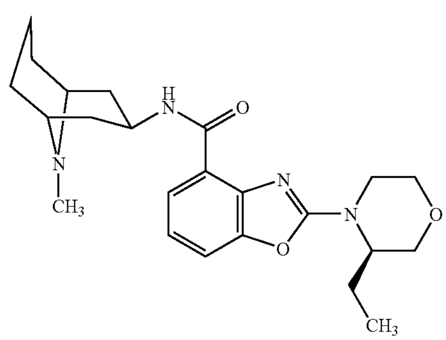 | 151 | $^1$H NMR (500 MHz, DMSO-d$_6$) □ 10.66 (br s, 0.4H), 9.86 (br s, 0.6H), 9.16-9.15 (m, 0.4H), 8.96-8.95 (m, 0.6H), 7.77-7.72 (m, 1H), 7.61-7.57 (m, 1H), 7.15-7.11 (m, 1H), 4.59-4.51 (m, 0.6H), 4.36-4.31 (m, 0.4H), 4.06-4.03 (m 1H), 3.95-3.84 (m, 3H), 3.68-3.46 (m, 5H), 2.83-2.81 (m, 3H), 2.75-2.62 (m, 2H), 2.31-2.19 (m, 1H), 2.11-2.09 (m, 2H), 1.94-1.74 (m, 5H), 1.58-1.45 (m, 2H), 0.93-0.87 (m, 3H); MS (ESI +) m/z 413 (M + H) | 34 |

-continued

| Structure | Ex. | NMR and MS data | 5-HT$_3$ K$_i$ (nM) |
|---|---|---|---|
| (structure) | 152 | $^1$H NMR (500 MHz, DMSO-d$_6$) □ 10.66 (br s, 0.4H), 9.84 (br s, 0.6H), 9.14-9.13 (m, 0.4H), 8.98-8.97 (m, 0.6H), 7.77-7.73 (m, 1H), 7.60-7.58 (m, 1H), 7.14-7.10 (m, 1H), 4.58-4.50 (m, 0.6H), 4.36-4.31 (m, 0.4H), 4.04-3.91 (m, 3H), 3.76-3.71 (m, 1H), 3.63-3.44 (m, 5H), 2.83-2.81 (m, 3H), 2.73-2.62 (m, 2H), 2.46-2.36 (m, 1H), 2.26-2.18 (m, 1H), 2.12-2.01 (m, 2H), 1.81-1.73 (m, 3H), 1.54-1.45 (m, 2H), 1.09-0.99 (m, 3H), 0.95-0.85 (m, 3H); MS (ESI +) m/z | 75 |

Bezold-Jarisch Assay in vivo. In order to demonstrate functional antagonism of 5-HT$_3$ receptors, compounds (see below) were evaluated for their ability to inhibit serotonin induced bradycardia in vivo in the mouse [Saxena, P. R. and Lawang, A. A comparison of cardiovascular and smooth muscle effects of 5-hydroxytryptamine and 5-carboxamidotryptamine, a selective agonist of 5-HT$_1$ receptors. Arch. Int. Pharmacodyn. 277: 235-252, 1985]. Test substances and vehicle [2% Tween 80] were each administered orally (0.3 to 3 mg/kg) to a group of 5 male or female CD-1(Crl.) mice each weighing 24±2 g. A dosing volume of 10 mL/kg was used. Sixty minutes later, 5-HT (0.1 mg/kg IV)-induced bradycardia was recorded in urethane (2225-2500 mg/kg IP, given 10 minutes before 5-HT)-anesthetized animals.

In vivo 5-HT$_3$ Antagonism in the mouse (Bradycardia Reflex)

| Compound | Example | % Inhibition @ dose of test substance (p.o.) |
|---|---|---|
| (structure) | 8 | 83% @ 0.3 mg/kg |
| (structure) | 49 | 86% @ 1 mg/kg |
| (structure) | 75 | 98% @ 1 mg/kg |

-continued

| Compound | | % Inhibition @ dose of Example test substance (p.o.) |
|---|---|---|
| 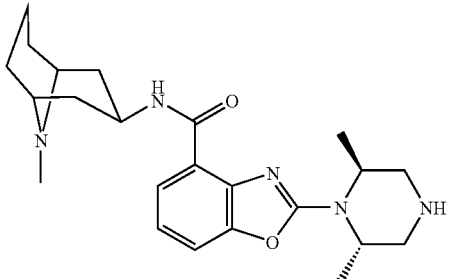 | 50 | 80% @ 3 mg/kg |
| 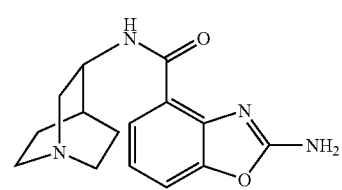 | 93 | 85% @ 3 mg/kg |
| 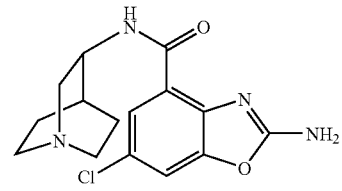 | 103 | 97% @ 3 mg/kg |
| 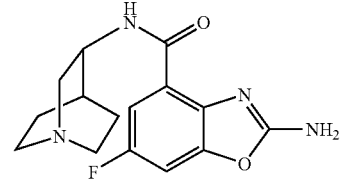 | 116 | 97% @ 3 mg/kg |

The compounds of the invention may be administered orally or via injection at a dose from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

While it may be possible for the compounds of formulas I and II to be administered as the raw chemical, it is preferable to present them as a pharmaceutical composition. According to a further aspect, the present invention provides a pharmaceutical composition comprising a compound of formula I or II or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula I or II or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation. Preferred unit dosage formulations are those containing an effective dose or an appropriate fraction thereof, of the active ingredient.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a waterin-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions, which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

It should be understood that in addition to the ingredients particularly mentioned above, the formulations of this invention may include other agents conventional in the art having regard to the type of formulation in question, for example those suitable for oral administration may include flavoring agents.

Although the foregoing invention has been described in some detail for purposes of illustration, it will be readily apparent to one skilled in the art that changes and modifications may be made without departing from the scope of the invention described herein.

What is claimed is:

1. A compound of formula I, II or III:

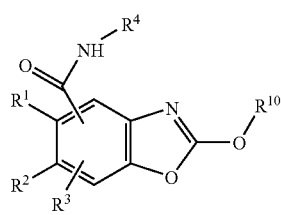

I

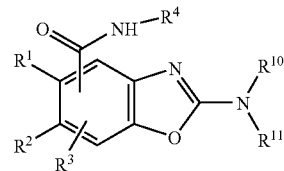

II

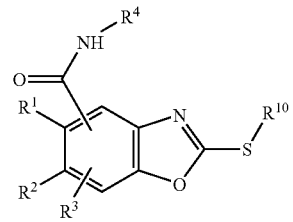

III wherein $R_1$, $R_2$ and $R_3$ are independently selected from hydrogen, halogen, cyano, alkyl or aryl sulfoxide, alkyl or aryl sulfone, amino, alkylamino, dialkylamino, acylamino, morpholinyl, —O-loweralkyl, hydroxy, loweralkyl, fluoroloweralkyl, O lowerfluoroalkyl, methylenedioxy, ethylenedioxy, alkoxy-loweralkyl and hydroxyloweralkyk;$R_4$ is a group chosen from:

(i) a saturated nitrogen heterocycle or methyl-substituted saturated nitrogen heterocycle, in which said nitrogen is tertiary, said heterocycle containing at least one 5 or 6-membered ring; and (ii) an imidazolylalkyl residue wherein the imidazole of said imidazolylalkyl is optionally substituted with up to three groups chosen from halogen, $(C_1$-$C_4)$alkyl, substituted $(C_1$-$C_4)$alkyl and $NH_2$; and $R_{10}$ is chosen from the group consisting of (i) hydrogen;

(ii) $(C_1$-$C_{10})$alkyl;

(iii) substituted $(C_1$-$C_{10})$alkyl;

(iv) heterocyclyl;

(v) substituted heterocyclyl;

(vi) aryl; and (vii) substituted aryl;

$R_{11}$ is chosen from the group consisting of hydrogen and $(C_1$-$C_{10})$alkyl; or taken together $R_{10}$, $R_{11}$ and the nitrogen to which they are attached form a nitrogenous heterocyle or substituted nitrogenous heterocycle, with the proviso that, when $R_{10}$, $R_{11}$ and nitrogen form a morpholine ring, the compound is not endo-N-(3,9-dimethyl-3,9-diazabicyclo[3.3.1]nonan-7-yl)-2morpholinobenzoxazole-4-carboxamide.

2. A compound according to claim 1 of formula Ia or Ib:

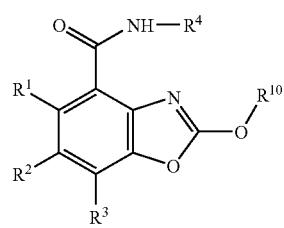

Ia

-continued

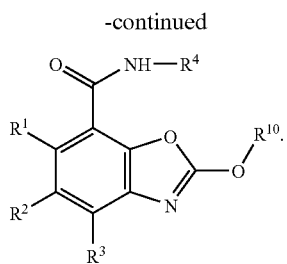
Ib

3. A compound according to claim 1 of formula IIa or IIb:

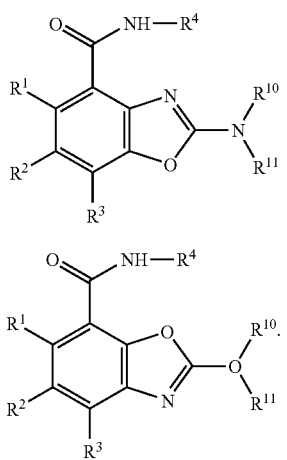
IIa

IIb

4. A compound according to claim 1 of formula IIIa or IIIb:

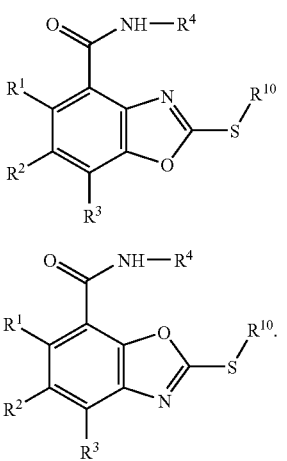
IIIa

IIIb

5. A compound according to claim 1 wherein R4 is chosen from:

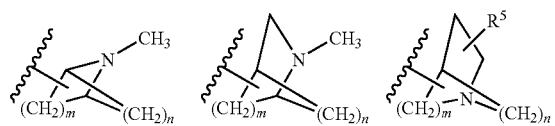

-continued

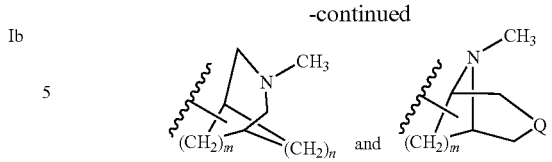
and and
wherein
m is 1, 2, 3 or 4;
n is 0, 1, 2, 3 or 4;
Q is $N(CH_3)$ or —O—; and
$R_5$ is hydrogen or methyl.

6. A compound according to claim 1 wherein $R_4$ is chosen from quinuclidine, tropane, azabicyclo[3.3.1]nonane, methyl azabicyclo[3.3.1]nonane, dimethyl diazabicyclo[3.3.1] nonane, methylpiperidine and methyl-3-oxa-9-azabicyclo [3.3.1]nonane.

7. A compound according to claim 1 wherein $R_1$, $R_2$ and $R_3$ are hydrogen.

8. A compound according to claim 1 wherein one of $R_1$, $R_2$ and $R_3$ is halogen.

9. A compound according to claim 1 wherein $R_{10}$ is chosen from the group consisting of hydrogen and ($C_1$ to $C_3$)alkyl.

10. A compound according to claim 3 wherein $R_{11}$ is H or $CH_3$.

11. A compound according to claim 1, wherein $R_{10}$ is chosen from the group consisting of phenyl, substituted phenyl, ($C_1$-$C_6$)alkyl, 4 to 7-membered monocyclic nitrogenous heterocycle, 4 to 10 carbon bicyclic nitrogenous heterocycle, 4 to 7-membered monocyclic nitrogenous heterocycle substituted with one or more ($C_1$-$C_6$)alkyl, 4 to 10 carbon bicyclic nitrogenous heterocycle substituted with one or more ($C_1$-$C_6$) alkyl, dimethylamino($C_1$-$C_6$)alkyl, 4 to 7-membered monocyclic nitrogenous heterocyclyl($C_1$-$C_6$)alkyl, ($C_1$-$C_6$) alkoxy($C_1$-$C_6$)alkyl, hydroxy($C_1$-$C_6$)alkyl, and dialkylaminocarbonyl($C_1$-$C_6$)alkyl.

12. A compound according to claim 3, wherein $R_{10}$ and $R_{11}$, taken together, form a nitrogenous heterocycle or substituted nitrogenous heterocycle.

13. A compound according to claim 10, wherein $R_{10}$ and $R_{11}$, taken together, form a morpholine, piperazine, piperidine, diazepam, tetrahydroquinoxaline, triazolopyrazine, azabicyclo[3.3.1]nonane, diazabicyclo[2.2.1]heptane, or any of the foregoing substituted with one, two or three substituents chosen independently from ($C_1$-$C_6$)alkyl, ($C_1$-$C_6$)haloalkyl, ($C_1$-$C_6$)alkoxy phenyl and heteroaryl.

14. A pharmaceutical composition comprising a pharmaceutically acceptable carrier and a therapeutically effective amount of a compound according to claim 1.

15. A pharmaceutical composition according to claim 14 additionally comprising a second antiemetic agent.

16. A pharmaceutical composition according to claim 15, wherein said second antiemetic agent is a neurokinin antagonist.

17. A pharmaceutical composition according to claim 14 additionally comprising a corticosteroid.

18. A method of treating irritable bowel syndrome, emesis, post-operative nausea or vomiting, a psychological disorder, obesity, substance abuse disorders, dementia associated with a neurodegenerative disease, cognition deficits, pain or pain management, fibromyalgia syndrome, chronic fatigue syndrome, bronchial asthma, bulimia nervosa, sleep apnea, pruritis, radiation-induced nausea and vomiting, or epilepsy, which comprises administering to a patient in need of such treatment a therapeutically effective amount of a compound according to claim 1.

19. A method according to claim 18, wherein said disorder is irritable bowel syndrome.

20. A method according to claim 18 for treating emesis.

21. A method according to claim 18 for treating postoperative nausea or vomiting.

22. A method according to claim 18 for treating a psychological disorder.

23. A method according to claim 22, wherein said psychological disorder is chosen from depression, psychosis, schizophrenia, anxiety and appetite disorder.

24. A method according to claim 18 for treating obesity.

25. A method according to claim 18 for treating substance abuse disorders.

26. A method according to claim 25, wherein said substance abuse disorder is chosen from chemical dependency, cocaine addiction, alcohol dependence and amphetamine addiction.

27. A method according to claim 18 for treating dementia associated with a neurodegenerative disease.

28. A method according to claim 18 for treating cognition deficits.

29. A method according to claim 18 for treating pain or for pain management.

30. A method according to claim 18 for treating fibromyalgia syndrome.

31. A method according to claim 18 for treating chronic fatigue syndrome.

32. A method according to claim 18 for treating or preventing bronchial asthma.

33. A method according to claim 18 for treating bulimia nervosa.

34. A method according to claim 18 for treating sleep apnea.

35. A method according to claim 18 for treating pruritis.

36. A method according to claim 18 for treating radiation-induced nausea and vomiting.

37. A method according to claim 18 for treating epilepsy.

* * * * *